(12) United States Patent
Flynn

(10) Patent No.: US 9,221,805 B2
(45) Date of Patent: Dec. 29, 2015

(54) PREPARATION AND METHODS OF USE FOR ORTHO-ARYL 5-MEMBERED HETEROARYL-CARBOXAMIDE CONTAINING MULTI-TARGETED KINASE INHIBITORS

(71) Applicant: Gary A. Flynn, Oro Valley, AZ (US)
(72) Inventor: Gary A. Flynn, Oro Valley, AZ (US)
(73) Assignee: Spacefill Enterprises LLP, Oro Valley, AZ (US)
(*) Notice: Subject to any disclaimer, the term of this patent is extended or adjusted under 35 U.S.C. 154(b) by 0 days.

(21) Appl. No.: 14/173,125
(22) Filed: Feb. 5, 2014
(65) Prior Publication Data
US 2014/0228367 A1    Aug. 14, 2014

Related U.S. Application Data

(63) Continuation-in-part of application No. PCT/US2012/049559, filed on Aug. 3, 2012.
(60) Provisional application No. 61/515,434, filed on Aug. 5, 2011.

(51) Int. Cl.

| | |
|---|---|
| C07D 413/12 | (2006.01) |
| C07D 403/12 | (2006.01) |
| C07D 401/14 | (2006.01) |
| C07D 405/14 | (2006.01) |
| C07D 413/14 | (2006.01) |
| C07D 401/12 | (2006.01) |
| C07D 405/12 | (2006.01) |
| C07D 417/12 | (2006.01) |
| C07D 417/14 | (2006.01) |
| C07D 471/04 | (2006.01) |
| C07D 495/04 | (2006.01) |
| A61K 31/4155 | (2006.01) |
| A61K 31/422 | (2006.01) |
| A61K 31/427 | (2006.01) |
| C07D 487/04 | (2006.01) |

(52) U.S. Cl.
CPC .......... *C07D 413/12* (2013.01); *A61K 31/4155* (2013.01); *A61K 31/422* (2013.01); *A61K 31/427* (2013.01); *C07D 401/12* (2013.01); *C07D 401/14* (2013.01); *C07D 403/12* (2013.01); *C07D 405/12* (2013.01); *C07D 405/14* (2013.01); *C07D 413/14* (2013.01); *C07D 417/12* (2013.01); *C07D 417/14* (2013.01); *C07D 471/04* (2013.01); *C07D 487/04* (2013.01); *C07D 495/04* (2013.01)

(58) Field of Classification Search
CPC .. C07D 413/12; C07D 401/12; C07D 401/14; C07D 403/12; C07D 405/12; C07D 405/14; C07D 413/14; C07D 417/12; C07D 417/14; C07D 471/04; C07D 487/04; C07D 495/04; A61K 31/4155; A61K 31/422; A61K 31/427
USPC ........................................ 546/274.4; 514/341
See application file for complete search history.

(56) References Cited

U.S. PATENT DOCUMENTS 6,187,797 B1    2/2001    Pruitt et al.

| | | |
|---|---|---|
| 2007/0072862 A1 | 3/2007 | Dimauro et al. |
| 2010/0330069 A1 | 12/2010 | Wrasidlo et al. |
| 2011/0159111 A1 | 6/2011 | Curry et al. |

FOREIGN PATENT DOCUMENTS

| | | |
|---|---|---|
| WO | 98/28282 A2 | 7/1998 |
| WO | 01/53274 A1 | 7/2001 |
| WO | 03/028641 A2 | 4/2003 |
| WO | WO 03028641 A2 * | 4/2003 |
| WO | WO 2007125330 A1 * | 11/2007 |
| WO | 2008/058037 A1 | 5/2008 |
| WO | WO 2008058037 A1 * | 5/2008 |
| WO | WO 2009077990 A1 * | 6/2009 |

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
J.M. Fevig et al., 11 Bioorganic and Medicinal Chemistry Letters, 641-645 (2001).*
CAS Registry No. Abstracts 1002046-03-8, and 1061583-38-7 (Entered STN 2008).*
CAS Registry No. Abstracts 1181502-59-9, 1135141-96-6, and 1171529-69-3 (Entered STN 2009).*
CAS Registry No. Abstract 1215821-19-4 (Entered STN 2010).*
CAS Registry No. Abstracts 956514-87-7, 957047-35-7, 956733-18-9, and 958576-36-8 (Entered STN 2007).*
J. Dietrich et al., Bioorganic & Medicinal Chemistry, 292-304 (2010).*
D.S. Ermolat'ev et al., 50 Tetrahedron Letters, 5218-5220 (2009).*
H. Steenackers et al., 54 Journal of Medicinal Chemistry, 472-484 (2011).*
CAS Registry No. Abstract 1323603-46-8 (Entered STN 2011).*
CAS Registry No. Abstract 1323344-92-8 (Entered STN 2011).*
Dietrich, J. et al. "Application of a Novel [3+2] Cycloaddition Reaction to Prepare Substituted Imidazoles and their use in the Design of Potent DFG-Out Allosteric B-Raf Inhibitors," Bioorganic & Medicinal Chemistry, Pergamon, GB, vol. 18, No. 1, Jan. 1, 2010, pp. 292-304.
Supplementary European Search Report, Application No. EP12822808, Dated Dec. 4, 2014.
Written Opinion of the International Searching Authority, International Application No. PCT/US12/49559; International Filing Date: Aug. 3, 2012; Date of Mailing: Oct. 4, 2012.
Zuccotto, F., et al., "Through the 'Gatekeeper Door': Exploiting the Active Kinase Conformation", Journal of Medicinal Chemistry, 2010, vol. 53, No. 7, pp. 2681-2694.

* cited by examiner

*Primary Examiner* — Alexander R Pagano
(74) *Attorney, Agent, or Firm* — McCarter & English LLP; Jonathan M. Sparks; Michael J. DeGrazia

(57) ABSTRACT

The present disclosure relates to compounds of the Formula (I):

and pharmaceutically acceptable salts, as kinase modulators, compatible with the Type-II inhibition of kinases.

10 Claims, 17 Drawing Sheets

A) Hinge--Linker--Gatekeeper-

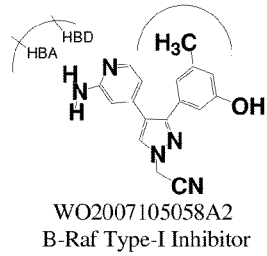

WO2007105058A2
B-Raf Type-I Inhibitor

B) Hinge--Linker--Gatekeeper--Bridge--Selectivity Sites

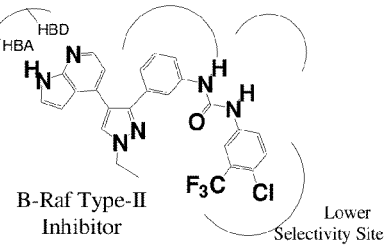

B-Raf Type-II Inhibitor

C) Hinge--Linker--Gatekeeper-

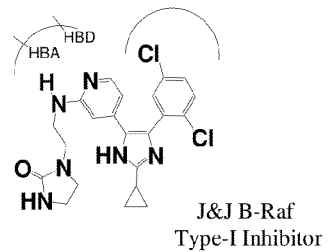

J&J B-Raf Type-I Inhibitor

D) Hinge--Linker--Gatekeeper--Bridge--Selectivity Sites

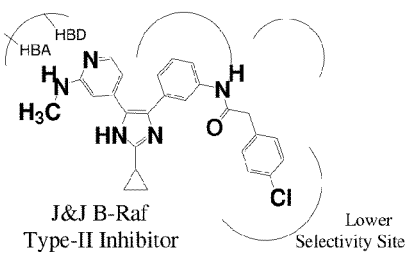

J&J B-Raf Type-II Inhibitor

E) Hinge--Linker--Gatekeeper-

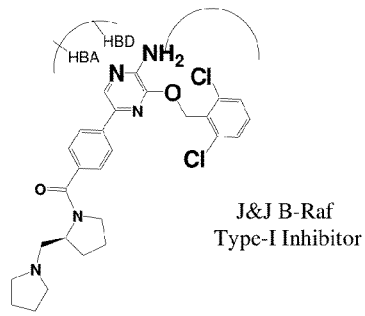

J&J B-Raf Type-I Inhibitor

F) Hinge--Linker--Gatekeeper--Bridge--Selectivity Sites

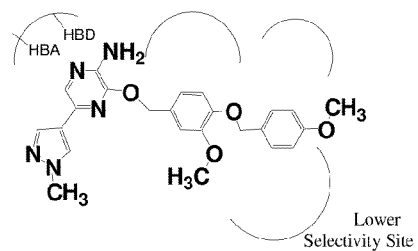

Figure 3

Substitute azole scaffold for substituted benzamide ere mutation driven aberrant kinase activations are particularly significant. Applications for kinase inhibitors in cancer therapy continues to evolve and these utilities have been extensively reviewed (Zhang J., *Nat. Rev. Cancer* (2009) 9(1): 28-39). However, strong links exist between cancer progression and a pro-growth inflammatory environment have been established (Rakoff-Nahoum S., *Yale J. Biol. Med.* (2006), 79:123-130; Schmid M. C., *Cancer Cell*, (2011) 19(6): 715-727). In addition, a diverse set of kinases participate in chronic inflammatory diseases, such as rheumatoid arthritis, psoriatic arthritis, inflammatory bowel disease, and chronic obstructive pulmonary disease, which are highly debilitating diseases that affect a large segment of our population. Moreover, it has become apparent that metabolic diseases such as type 2 diabetes, neuro-degenerative disorders such as Alzheimers, and cardiovascular diseases such as atherosclerosis, also have a strong inflammatory component involving overactive kinase pathways. Therefore, selective inhibition of key kinases and their compensatory mechanisms continues to be pursued as a promising strategy for therapeutic intervention. (Garuti L., *Current Medicinal Chemistry* (2010) 17: 2804-2821).

PREPARATION AND METHODS OF USE FOR ORTHO-ARYL 5-MEMBERED HETEROARYL-CARBOXAMIDE CONTAINING MULTI-TARGETED KINASE INHIBITORS

RELATED APPLICATIONS

This application is a continuation-in-part of PCT/US2012/049559, filed Aug. 3, 2012, which claims the benefit of U.S. Provisional Application No. 61/515,434, filed Aug. 5, 2011. The entire contents of each of these applications are expressly incorporated herein by reference.

FIELD OF THE INVENTION

The present disclosure is directed to novel kinase inhibitors, processes for their preparation, pharmaceutical compositions containing these inhibitors, and their use in the treatment of various diseases and conditions.

BACKGROUND

Roles and Actions of Kinases

Receptor protein kinases coupled with complex downstream kinase and phosphatase mediated cascades and feedback loops play critical roles in signal transduction from the cell exterior into the nucleus where transcriptional regulation takes place. Upon receptor activation, this signal transduction is performed by the act of phosphate transfer to the serine, threonine, and tyrosine residues of proteins that results in enzyme activation or inactivation, changes in conformation, increased or decreased affinity for other proteins, appropriate localization, and in some cases targeting of proteins for degradation by the proteosome. Understandably, these processes are tightly regulated and balanced through control of external receptor ligands as well as expression of receptors, receptor antagonists, decoy receptors, and through redundancies or crosstalk between signaling pathways. Thus, it is accepted that kinases perform essential functions in regulating cell growth and proliferation, differentiation and cell development, cell division and aberrant mitogenesis. Kinases also mediate and regulate cell adhesion, angiogenesis, stress responses, cell-cell or cell-matrix interactions, and short range contact-mediated axional guidance. Mechanistically similar non-protein kinases, such as PI3Ks and SPK1, can also phosphorylate other ligands that contribute to the regulatory process (Brown J. R., *BMC Evolutionary Biology* (2011) 11(4): 1471-2148; Alvarez S. E., *Nature* (2010) 465: 1084-1088). Therefore, diseases and conditions where aberrant kinase activity plays a role are plentiful. However, the complexities of the systems biology combined with the structural homology of the kinase sites in the over 500 members of the human kinome presents a significant challenge for disease specific intervention by kinase inhibitors.

The Therapeutic Utility of Kinase Inhibitors:

With the advent of Imatinib (Deininger M., *Blood* (2005) 105 (7):2640-2653) the primary focus for kinase inhibitor development has been for the targeted treatment of specific cancers wh Due to the complexity of signal transduction pathways, compensatory mechanisms often confound the initial therapeutic benefits seen with highly selective targeted kinase inhibitors. Conversely, undesired off-target effects can introduce significant toxicity. The ongoing challenge in the development of kinase inhibitors, particularly for chronic administration, is achieving the balance between efficacy and safety. Since, the aberrant activity of kinases is fundamental to many chronic diseases and cancers, much effort continues to be expended to understand their diverse and complex roles in basic physiology.

Kinases in Inflammatory Diseases:

Mitogen-activated protein (MAP) kinases are known to play key roles in the transmission of signals from cell surface receptors to transcription factors which up-regulate the expression of pro-inflammatory cytokines. The MAP kinase p38-α is participant in one pathway that regulates the production of the pro-inflammatory cytokines TNF-α, IL-1, IL-6 and IL-8, as well as the enzymes COX-2, MMP-1 and MMP-3. It has also been demonstrated that inhibiting p38-α kinase delays the onset of joint disease in animal models of arthritis (Mihara K., *British Journal of Pharmacology* (2008) 154: 153-164) by arresting the over production of these pro-inflammatory cytokines (Schindler J. F. *J. Dental Res.* (2007), 86(9): 800-811). However, high hopes for p38 inhibitors as a single target therapy for chronic inflammation have not been realized in clinical studies which demonstrated these effects to be short lived, presumably by activation of compensatory mechanisms (Sweeney S. E., *Nature Reviews Rheumatology* (2009) 5: 475-477). However, recent reports of phase-II data in osteoarthritic patients using a sustained release formulations of p38 inhibitor, FX005, delivered intra-articularly to the knee look promising for both relief of pain and inflammation. More recently, redundant and non-redundant functions of the JNK isoforms JNK1 and JNK2 in the immune system and arthritis have been described (Guma M., *Proc Natl Acad Sci USA.* (2010), 107(51):22122-7; Hommes D., *Gastroenterology.* (2002), 122(1):7-14.; Stambe C., *Kidney Int* (2003), 64:2121-2132; Ma F. Y., *Laboratory Investigation* (2009) 89: 470-484). Additionally, inhibitors of Janus family kinases (JAK1, JAK2, and JAK3) have demonstrated anti-inflammatory effects in animal models (Stump K L., *Arthritis Research and Therapy* (2011) 13:R68; Meyer D M., *J. Inflammation* (2010) 7(41):1-12). Consequently, interest in small-molecule therapeutics that target p38, JAK, and JNK isoforms for inflammatory diseases remains high (Liu C., *J. Med. Chem.* (2010) 53(18): 6629-6639).

Encouraging anti-inflammatory preclinical and clinical results with Imatinib, the well-known anti-cancer kinase inhibitor with Abl, PDGFR, c-KIT, and c-Raf activities, (Deininger M., *Blood* (2005) 105 (7):2640-2653.) has rekindled interest in the development of kinase inhibitors as anti-inflammatory agents (Iyoda M., *Kidney International* (2009), 75(10):1060-70; Ghofrani H. A., *J Am Coll Cardiol* (2009) 54:108-117; Louvet C, *Proc. Natl. Acad. Sci. USA* (2008) 105:18895-18900). Both protein and lipid kinases are now seen as potential targets for the attenuation of the inflammatory response. Macrophage colony stimulating factor receptor (CSF-1R or FMS) along with KIT, FLT3, and PDGFR-a/b, are members of the type-III receptor tyrosine kinase family which have enjoyed much attention as potential kinase targets (Tamura T. and Koch A., *Anti-Inflamm Anti-Allergy Agents in Med. Chem.* (2007) 6: 47-60). CSF-1R and its ligand (CSF-1) have been implicated in a range of macrophage and osteoclast related pathological processes, including rheumatoid arthritis, osteo-arthritis, progression of atherosclerotic plaques, and bone metastasis (Ohno H. et al., *Mol. Cancer. Ther.* (2006) 5(11): 2634-2643). c-Kit, the receptor of stem cell factor (SCF), plays a key role in modulation of histamine release from mast cells and influences cell migration and adhesion to the extracellular matrix. Inhibition of c-Kit mediates signaling in cynovial tissue from patients with rheumatoid arthritis and induced apoptosis of mast cells. The platelet derived growth factor (PDGF) receptor, which is structurally related to both CSF-1R and KIT, is important for the proliferation and migration of mesenchymal cells and is thought to play a role in the airway remodeling in asthma patients, inflammation in arthritis, and psoriasis. Additionally, Raf-1(c-Raf) inhibition has been shown to suppress smoke-induced airway hyperresponsiveness in mice (Lie Y. et al., *Respiratory. Res.* (2008) 9(71): 1-10) and has been associated with clinical remission is severe Crohn's disease (Lowenberg M. et al., *J. Immunol.* (2005) 175:2293-2300).

Additionally, inhibition of the neurotrophin/Trk pathway using NGF antibodies or non-selective small molecule inhibitors of Trk A, B and C has been reported to be effective in treatment of pre-clinical models of inflammatory diseases such as asthma, interstitial cystitis, inflammatory bowel disease, atopic dermatitis and psoriasis (Freund-Michel V., *Pharmacology & Therapeutics* (2008), 117(1): 52-76; Hu V., *The Journal of Urology* (2005), 173(3): 1016-21; Di MoIa F. F., *Gut* (2000), 46(5), 670-678; Dou Y-C., *Archives of Dermatological Research* (2006) 298(1):31-37.; Raychaudhuri S. P., *Investigative Dermatology* (2004), 122(3): 812-819). PI3K-γ and PI3K-δ have been strongly implicated as a major player in inflammatory conditions (Ruckle T., *Nat. Rev. Drug Disc.* (2006) 5:903-918; Hawkins P. T., *Science* (2007) 318: 64-66; Barberis L., *Thromb Haemost* (2008) 99: 279-285.) and tumor growth in a model of colitis-associated cancer (Gonzalez-Garcia A., *Gastroenterology* (2010) 138:1374-1383). The links between inflammation and proliferative diseases also points to the potential of anti-inflammatory agents as an adjunct to cancer therapy (Karin M., *Proc. Am. Thor. Soc.* (2005) 2: 368-390; Rakoff-Nahoum s., *J. Biol. Med.* (2006), 79:123-130; Gust T. C., *Anti-Inflammatory & Anti-Allergy Agents in Medicinal Chemistry*, (2007), 6:19-27; Schmid M. C., *Cancer Cell* (2011) 19, 715-727). PI3Kγ-deficient mice phenotypes suggest a wide variety of potential therapeutic applications for a selective inhibitor, including: allergic hyper-responsiveness, anaphylaxis, thrombosis, rheumatoid arthritis, glomerulonephritis, systemic lupus erythematosus (SLE), lung injury and airway inflammation related conditions such as COPD, pancreatitis, reduced contractility due to heart failure and ischaemia, and hypertension. Due to system redundancies and the lack of involvement of PI3Kγ in metabolism and house keeping functions, effects induced by PI3Kγ inhibition, which may involve inhibition of chemotaxis and cell specific functions, are seen as soft methods of intervention where undesirable side effects may be minimized (Ruckle T., *Nat. Rev. Drug Disc.* (2006) 5:903-918).

Neurodegenrative Diseases:

Several kinases are believed to play a role in the pathogenesis of many neurodegenerative disorders. For example, the active form of c-Raf (also termed Raf-1) is upregulated in the brains of Alzheimer's patients and in transgenic Alzheimer's mouse models. The persistent activation of cRaf-1 can activate NFκB and consequently, upregulate the expression of several of its downstream factors such as the amyloid precursor protein (APP), Cox-2 and iNOS. These factors have been found upregulated in numerous neurodegenerative conditions including Alzheimer's, epilepsy, brain trauma, and psychological stress (Burgess S., *CNS Neurol Disord Drug Targets.* (2010) 1:120-7). In addition, the neurotrophin/Trk pathway, particularly through BDNF/TrkB signaling, has been linked to the etiology of neurodegenerative diseases including Parkinson's disease, multiple sclerosis, and Alzheimer's Disease (AD) (Sohrabji F., *Frontiers in Neuroendocrinology* (2006), 27(4), 404-414). Several kinases thought to be involved in the underlying inflammatory cause of AD, including GSK3, DAPK1, MAP-kinase, MLCK, and ROCK-1, have been studied. (Villar-Cheda B., *Neurobiol Dis.* 2012 47(2):268-79) and recently inhibitors of cytokin production in the brain have shown success in models of this disease (Bachstetter A. D., *J. Neuroscience*, 25 Jul. 2012, 32(30): 10201-10210). Parkinson's Disease (PD) has links to some of the se kinases but the over expression and mutations in LRRK2 has stimulated efforts to inhibit this kinase as a primary target (Kramer T, *ACS Chem. Neurosci.*, (2012), 3(3), 151-160).

Infectious Disease:

The TrkA receptor kinase has been reported to be critical to the disease process in the parasitic infection of *Trypanosoma cruzi* (Chagas disease) in human hosts (de Melo-Jorge M., *Cell Host & Microbe* (2007) 1(4):251-261).). Furthermore, a recent study demonstrated in mice that administration of the broad-spectrum receptor tyrosine kinase inhibitor sunitinib blocked the vascular remodeling and progressive splenomegaly associated with experimental visceral leishmaniasis (Dalton J. E., *J Clin Invest.* (2010) 120(4):1204-1216). In addition, sunitinib treatment restored the integrity of the splenic microarchitecture. While this treatment alone was insufficient to cause a reduction in tissue parasite burden, sunitinib proved to be successful as an adjunct therapy by providing dose-sparing effects when combined with an immune-dependent anti-leishmanial drug. These data suggest, therefore, that multi-targeted tyrosine kinase inhibitors may prove clinically useful as agents in the treatment of parasitic infections and perhaps other infectious diseases.

Diabetes:

Imatinib and other TKIs counteract diabetes not only in non-obese diabetic mice, but also in streptozotocin diabetic mice, db/db mice, high-fat treated rats and humans with Type-2 diabetes (T2D). In the later stages of T2D, β-cells are damaged. The molecular events leading to cytokine-induced β-cell dysfunction and death have been linked to the activation of the transcription factors NF-κB (nuclear factor KB) and STATs (signal transducers and activators of transcription). The MAPKs (mitogen-activated protein kinases), such as JNK (c-Jun N-terminal kinase) and p38 MAPK, in response to both cytokines and oxidative stress, play a central role in this chain of events (Eizirik M., *Diabetologia* (2001) 44(12):2115-2133). Although the mechanisms of protection need to be investigated further, the effects of imatinib and other TKIs in human T2D and the rapidly growing findings from animal models of Type 1 diabetes (T1D) and T2D are encouraging and give hope to improved treatment of this disease (Dariush, 2010). In addition to NF-βB and p38 pathway involvement, PI3K pathways have been implicated as a signaling pathway involved in LPS induced TNF-alpha production in human adipocytes (Hoareau L., *Journal of Inflammation*(2010) 7:1-12).

Cardiovascular Disease:

Atherosclerosis has also been linked to DDR1 and DDR2 expression. Neointimal thickening is a major cause of restenosis and atherosclerosis and smooth muscle cells (SMCs) are the predominant cell type contributing to its formation after arterial injury. Collagen synthesis by the SMCs after arterial injury acts as an important regulator of the arterial repair through DDR1 and DDR2 activation. In non-human primate hypercholesterolemic diet studies, both DDRs were found to be highly expressed by smooth muscle cells (SMCs) in the fibrous cap of atherosclerotic plaques (Ferri N, *Am J Pathol,* 2004, 164:1575-1585). Shyu et al demonstrated in balloon injury rat carotid artery model that DDR2 directly promoted the migration and proliferation of vascular smooth muscle cells which contributed to the development of neointimal formation in restenosis and accelerated the arteriopathy. Their study demonstrated that siRNA-mediated inhibition of DDR2 protein expression at the time of balloon injury reduced the neointimal lesion area significantly (Shyu K G, *Arterioscler Thromb Vase Biol.* 2008; 28:1447-1453). Furthermore, DDR1 null mice had much less severe collagen accumulation in atherosclerotic plaques than wild type mice which was attributed to their considerably lower expression of MMP2 and decreased SMC proliferation and migration (Hou G, *J Clin Invest.* 2001, 107(6):727; Hou G, *Circ. Res* 2002, 90:1147-1149).

Several growth factors and growth factor RTKs have been implicated in the abnormal proliferation and migration of pulmonary arterial smooth muscle cells, including PDGF, EGF, FGF, and VEGF (Pullamsetti S. S., *PVRIReview* (2009), 1(2): 124-128; Hassoun P. M., *JACC* Vol. 54, No. 1, Suppl S, (2009) S10-19.). Neointimal hyperplasia contributes to atherosclerosis, restenosis after percutaneous coronary intervention, and venous bypass graft disease. Vascular injury in each of these conditions results in the release of mitogenic growth factors and hormones, which contribute to pathological vascular growth. Many of these molecules contribute to neointimal hyperplasia by activating PI3-kinase in vascular smooth muscle cells (Sanada F., *Circ. Res.* (2009), 105; 667-675) and selective inhibition of PI3K-δ and -γ confers interesting anti-inflammatory effects (Williams O., *Chem. & Biol.* (2010), 17:123-134). The protein serine/threonine kinases related to ERK-1 and -2 transduce signals to the nucleus not in response to growth factors and other mitogens but in response to cellular stresses such as inflammatory cytokines (IL-1β and TNF). Ischemia kinases (JNKs) and p38 likely play critical roles in the genetic response of many components of the cardiovascular system disease processes (Force T., *Circulation Research*. (1996) 78:947-953) and have been suggested as targets for cardiovascular disease therapies (Force T., *Circulation*, (2004) 109(10): 1196). The Rho-ROCK pathway also has an important role in mediating various cardiac cell functions, including contraction, actin cytoskeleton organization, cell adhesion and motility, proliferation, cytokinesis and gene expression, all of which are involved in the pathogenesis of cardiovascular disease. Abnormal activation of this pathway is associated with the pathogenesis of various cardiovascular diseases such as hypertension, coronary and cerebral vasospasm, restenosis, atherosclerosis, stroke and heart failure, although the roles of the ROCK isoforms (ROCK1 and ROCK2) remain to be elucidated (Shimokawa H., *Trends in Pharmacological Sciences*, (2007), 28(6):296-302).

Rheumatoid Arthritis (RA):

RA is characterized by leukocyte infiltration, synoviocyte hyperplasia and osteoclastogenesis. Tyrosine kinases have key roles in the signaling pathways that regulate these processes (D'Aura Swanson C., *Nat. Rev. Rheumatol.* (2009) 5:317-324) Inhibition of receptor tyrosine kinases (RTK) such as platelet-derived growth factor receptors (PDGFR), vascular endothelial growth factor receptors (VEGFR) and Tie receptors have been shown to reduce synovial hyperplasia and angiogenesis (Irvine K. M., *FASEB* 20 (2006) E-1 to E-12). Non-RTKs are also important in RA. For example, signaling through Burton's tyrosine kinase results in B-cell and T-cell activation while more-specific inhibitors of Janus kinases and Syk, have already shown efficacy in the treatment of RA. Src inhibition is expected to reduce monocyte maturation and osteoclastogenesis. In addition, blocking Kit activation may induce mast cell apoptosis, thereby reducing the production of inflammatory cytokines and degradative molecules in the synovium. The status of current approaches to kinase inhibitor based therapy for RA has been reviewed recently (Muller S., *Exprt. Opin. Drug Disco*. (2010), 5(9): 867-881).

Discoidin Domain Receptors 1 and 2 (DDR1 and DDR2) are collagen receptors with protein tyrosine kinase activity that control fundamental cell processes including cell proliferation, adhesion, migration, and extracellular matrix remodeling (Vogel W, *Cellular Signalling,* 2006, 18:1108-1116). These RTKs are important in embryonic development, skeletal growth, tissue repair and injury-induced remodeling of blood vessels and the liver (Olaso E, *J Clin Invest.* 2001, 108:1369-1378; Zhang X H, *Arch Med. Res.* 2010, 41(8):586-92; Ali B R, *Hum Mol Gen,* 2010, 19(11):2239-2250; Hou G, *Circ. Res* 2002, 90:1147-1149; Ferri, N, *Am J Pathol,* 2004, 164:1575-1585). Aberrant activity of both receptors has been linked to human diseases such as lung, kidney and liver fibrosis, atherosclerosis, osteoarthritis, and rheumatoid arthritis. DDR1 and DDR2 have also been implicated in primary and metastatic cancer progression through regulation of metalloproteinase production, cell growth, and chemotactic invasion of normal tissue (Badiola I, *Oncol Rep,* 2011, 26:971-978).

Hepatic fibrosis in response to chronic injury is similar in all forms of liver disease and involves type I collagen accumulation in the subendothelial spaces between hepatocytes and endothelial cells. The newly generated fibrillar collagen replaces basement membrane like matrix containing type IV collagen. This conversion to fibrillar collagen is pivotal in mediating the loss of differentiated function that characterizes progressive liver disease. Liver stellate cells are the major source of fibrosis as they convert from quiescent cells to proliferative and fibrogenic myofibroblasts. In liver fibrosis mouse models, DDR2 is upregulated in stellate cells following increased collagen synthesis and is an inducer of MMP-2 mediated growth stimulation suggesting this collagen receptor may help perpetuate the fibrosis (Olaso E, *J Clin Invest*. 2001, 108:1369-1378). DDR2 has also been found at increased levels in the mesenchymal compartment as well as the biliary epithelial cells in cirrhotic livers (Mao T K, *Autoimmunity* 2002, 35(8):521.).

DDRs have also been shown to play a role in fibrosis of the kidney and lung. DDR1-null mice have also been found to have significantly reduced fibrotic and inflammatory responses in kidney hypertension models (Vogel W, *Cellular Signalling,* 2006, 18:1108-1116.). The DDR1b isoform was found to be selectively induced in idiopathic pulmonary fibrosis (IPF) patients during disease progression and high levels of DDR1 can be found in CD14 positive cells from bronchioalveolar lavage fluid from these patients compared to healthy volunteers or patients with other lung diseases (Matsuyama W, *FASEB J*, 2003, 17(10):1286).

The discoidin domain receptors are also associated with inflammation and arthritis. LPS and IL-1β induces monocyte and neutrophil expression of the DDR1a and DDR1b isoforms. Transfection of DDR1a into leukemia cell lines promotes adhesion while DDR1b enhances monocyte differentiation to macrophages and upregulates their MIP-1α and MCP-1 production during extravasation (Matsuyama W, *J. Immunol.* 2005 174(10):6490). DDR1 is upregulated in activated T cells and can act as a co-stimulator under suboptimal TCR/CD3 activating conditions (Dang N, *J Immunother.* 2009, 32(8):773-784). The receptor kinase also enhances primary human T cell migration through 3D collagen by a mechanism not dependent on adhesion (Hachehouche L N, *Mol. Immunol.* 2010, 47(9):1866-1869; Chetoui N, *J Cell Biochem.* 2011, 112(12)3666-3674).

DDR2 has been found to be integral in the maintenance and progression of osteoarthritis and rheumatoid arthritis. DDR2 mediated MMP-13 induction exacerbates the articular cartilage degeneration found in osteoarthritis patients. Reports both in mouse arthritis models and from human knee joints found a correlation between increased DDR2 and MMP-13 expression and the degree of type II collagen breakdown. These results suggest the perpetuation of DDR2 activation becomes a vicious circle where by DDR2 promotes tissue catabolism which leads to cartilage damage and further DDR2 upregulation and activation (Sunk I G, *Arthritis & Rheumatism*, 2007, 56(11):3685-3692.). Xu and his colleagues demonstrated that reducing DDR2 expression by using DDR2$^{-/+}$ heterozygous mutant mice led to decreased articular cartilage degeneration of the knee joints induced by injury or type XI collagen deficiency (Xu L, *Arthritis & Rheumatism* 2010, 62(9):2736-2744). These data suggest that regardless of the initiating event, osteoarthritis disease progression is perpetuated by the continued activation of DDR2 and therefore therapeutic agents that specifically inhibit this kinase may be successful agents in the prevention and treatment of osteoarthritis.

The preponderance of evidence from research on discoidin domain receptor function demonstrates that DDRs are molecular sensors that monitor extracellular matrix integrity. However, aberrant or uncontrolled DDR1 and DDR2 signaling has been associated with a variety of illnesses such as arthritis, fibrotic disorders and cancer highlighting the potential importance of these collagen receptors in human health and disease. These data suggest DDR1 and DDR2 may be good targets for therapeutic intervention in multiple indications.

Pain:

Tropomyosin-related Kinases (Trk's) are the high affinity receptor tyrosine kinases activated by a group of soluble growth factors called neurotrophins (NT). There are 3 Trk receptor family members: TrkA, TrkB and TrkC. Trk's are widely expressed in neuronal tissue and are important in the maintenance, signaling and survival of neuronal cells (Patapoutian A., *Current Opinion in Neurobiology*, (2001), 11, 272-280) Inhibitors of the Trk/neurotrophin pathway have been shown to be effective in many pre-clinical animal models of pain. For example, antagonistic NGF and TrkA antibodies have been shown to be efficacious in inflammatory and neuropathic pain models (Woolf C. J., *Neuroscience* (1994), 62:327-331.; Zahn P. K., *J. Pain* (2004), 5:157-163; Shelton D. L., *Pain* (2005), 116:8-16; Delafoy L., *Pain* (2003) 105: 489-497; Theodosiou M, *Pain* (1999) 81:245-255; Li L., *Mol. Cell. Neurosci.* (2003), 23, 232-250; Gwak Y. S., *Neurosci. Lett.* (2003), 336: 117-120). Furthermore, several groups have demonstrated that BDNF levels and TrkB signaling is increased in the dorsal root ganglion after inflammation (Cho H. J., *Brain Res* (1997) 764: 269-272.) and antibodies that decrease signaling through the BDNF/TrkB pathway inhibit neuronal hypersensitization and the associated pain (Li C-Q., *Molecular Pain*, (2008), 4(28), 1-11).

It has also been reported that NGF secreted by tumor cells and tumor invading macrophages directly stimulates TrkA located on peripheral pain fibers. Using various tumor models in both mice and rats, it was shown that neutralizing NGF antibodies inhibit cancer related pain to a degree equal to or better than the highest tolerated dose of morphine. In addition, activation of the BDNF/TrkB pathway has been implicated as a modulator of neuropathic, inflammatory and surgical pain (Matayoshi, *J. Physiol.* (2005), 569:685-95; Thompson S. W. N., *Proc. Natl. Acad. Sci. USA* (1999), 96:7714-18; Li C-Q., *Molecular Pain*, (2008), 4(28), 1-11). These bodies of data suggest inhibitors of TrkA and/or other Trk kinases may provide an effective treatment for chronic pain states.

Kinases in Cancer:

Although kinase mediated pro-inflammatory or wound healing signaling pathways play important support roles in cancers (Karin M., *Proc. Am. Thor. Soc.* (2005) 2: 368-390; Rakoff-Nahoum S., *Yale J. Biol. Med.* (2006), 79:123-130; Gust T. C., *Anti-Inflammatory & Anti-Allergy Agents in Medicinal Chemistry*, (2007), 6:19-27), these processes are usually not sufficient to initiate tumorigenesis. More often, the transformation process requires the aberrant activation of or activating mutation in kinases involved in other tumor specific key signaling pathways. The term 'oncogenic addiction' is often used when gene mutations provide a survival advantage for tumor cells over non-transformed cells and the expression of that gene product is required to avoid cell death. These oncogenes are commonly receptor tyrosine kinases (e.g. EGFR, PDGFRA, MET) or kinases in the PTEN/PI3K/AKT or Ras/Raf/MEK/ERK signaling pathways. For example, it has been estimated that 88% of all glioblastomas have altered signaling in one of these kinase pathways (Cancer Genome Atlas Research Network, Nature; (2008), 455: 1061-1068).

The Ras/Raf/MEK/ERK and PI3K/Akt Pathways:

The RAS/RAF/MEK/ERK and the RAS/PI3K/PTEN/mTOR kinase cascades are two key pathways that contribute to many cancers that are illustrative of the compensatory crosstalk and redundancies in signalling networks that can lead to development of innate or acquired resistance to their individually targeted therapies, FIG. 1 (Gibbony G. T. and Smalley K. S. M., *Cancer Discovery* (2013) 4(3): 260-263).

The Ras/Raf/MEK/ERK mitogen-activated protein kinase (MAPK) pathway mediates cellular responses to different growth signals and is frequently dysregulated in cancer. The RAF family proteins are serine/threonine specific kinases and are key players in the MAPK pathway. These proteins act immediately downstream of Ras to conduct extracellular signals from the cell membrane to the nucleus via a cascade of phosphorylation events. Thereby cell growth, proliferation, and differentiation can be regulated in response to growth factors, cytokines, and hormones (Christensen C., *Oncogene* (2005), 24(41):6292-6302.; Schnidar H., *Cancer Res.* (2009), 69(4):1284-1292.). The Ras/Raf/MEK/ERK pathway has been found to be upregulated in approximately 30% of all cancers with higher percentages seen in cutaneous melanomas as well as colon, lung, ovarian, and kidney tumors (Hoshino R. Oncogene, (1999) 18:813-822). Mutated RAS, especially KRAS, is seen in over 20% of all human cancers (Bamford S., *Br. J. Cancer* 91 (2): 355-358; Bos J. L., *A Review Cancer Res* (1989) 49(17):4682-4689). RAS mutations have also been shown to lead to the promotion of PI3K signaling and dysregulation of the downstream RAF/MEK/ERK signaling pathways. Although early attempts to target Ras have not yielded any viable drug candidates, many novel compounds inhibiting the activities of Raf and MEK have been developed and investigated in clinical trials in recent years. Although the first MEK inhibitor (CI-1040) lacked efficacy in clinical trials, its low toxicity has encouraged the search for novel compounds with enhanced target potency (Wong K-K, *Recent Patents on Anti-Cancer Drug Discovery*, (2009), 4:28-35).

The three Raf kinases are designated as A-Raf, B-Raf, and C-Raf. At this time only B-Raf (v-Raf murine sarcoma viral oncogene homologue B1) is frequently found mutated in various cancers (Palanisamy N., *Nature Medicine*(2010), 16(7):793-798.). The most common B-Raf mutation constitutes 90% of all mutations to this kinase. The substitution of a glutamic acid residue for a valine moiety at codon 600 (V600E) results in a constitutively activated kinase that is ~500-fold more active than the wild-type protein (Hoeflich K. P., *Methods in Enzymology* (2008), 439: 25-38). This mutation, which occurs with a frequency of 50-70% in cutaneous malignant melanoma, is also present in a wide range of other human cancers, particularly thyroid (30%), colorectal (10%), and ovarian (35%) cancers (Flaherty K T, et al., *NEJM*(2010) 363:809-819; El-Osta H, et al., PLoS ONE (2011) 6(10): e258060). Advanced malignant melanoma has a tendency to rapidly metastasize throughout the body and develop resistance to treatment. In addition, melanoma rates continue to rise and the average patient age continues to decrease. Observation that inhibition of B-Raf signaling blocks cancer cell proliferation and induces apoptosis and its dysregulation in multiple tumor types validates V600E B-Raf as an important therapeutic target with excellent opportunities for anticancer drug development. Increased phosphatidylinositol 3-kinase (PI3K) signaling is also prevalent in many types of cancer (Vivanco I., *Nat Rev Cancer* (2002),2(7):489-501; Serra V., *Oncogene* (2011) 2; 30(22):2547-57). Dysregulation of this pathway may be caused at a molecular level by activating mutations of PI3K itself, by loss of PTEN, a negative regulator of PI3K activity, mutations in regulatory proteins, or by a variety of factors both up and downstream of PI3K. PTEN is one of the most commonly mutated or deleted genes in human cancer, second only to p53 (Cantley L. C., *Proc Natl Acad Sci USA*. (1999) 96(8):4240-4245), and somatic mutations of the PI3K p110α chain are found in 30% of all epithelial cancers (Engelman J. A., *Clin Cancer Res* 2008; 14:2895-2899). In addition, P70S6K1, a kinase downstream of PI3K/AKT pathway that is principle to the expression of VEGF and survivin, has become a target of recent interest for cancer therapy (Skinner H. D., *J. Boil. Chem*. (2004) 279(44): 45643-45651; Zhao P., *Biochem. Biophys. Res. Commun*. (2010), 395(2): 219-224). Finally, activation of the PI3K/AKT pathway has been strongly implicated in escape mechanism that compromise the effectiveness of specific kinase targeted therapies (Wee S., *Cancer Res*. (2009) 69(10) 4286-4293; Hynes N. E, *Cancer Cell* (2009)15: 353-355; Villanueva J., *Cancer Cell* (2010) 15(6)):683-695; Paraiso K. H. T., *Cancer Res*. (2011) 71(7): 2750-60).

Stimulation of the Ras/PI3K/PTEN/AKT/mTOR pathway and hyper-activation of the Ras/Raf/Mek/Erk axis are dominant compensatory mechanism by which inhibition of B-Raf (V600E) is ultimately circumvented (Davies M A et al., *Cancer J*. (2012) 18(2):142-7, Steelman L S, et al. *J Cell Physiol*. (2011) 226(11):2762-81; Yajima J, et al., *Dermatology Research and Practice* 2012; Article ID 354191), FIG. 1. Mutations that result in loss of PTEN function, activation of Ras, and/or loss of the RAS suppressing effects of neurofibromin (via the NF1 gene) have been identified as major contributors to both the innate and acquired resistance to current front line B-Raf inhibitor therapies, FIG. 1 (Maertens O., *Cancer. Discovery*. (2013) 3(3); 338-49; Gibbony G T and Smalley K S M: 2013.

Other Important Receptor Kinases in Cancer:

Kinases upstream or outside of the Ras/Raf/Erk and PI3K/Akt pathway have also been implicated in cancer cell differentiation and proliferation including the receptor tyrosine kinases in the Axl/Mer/TYRO3 and the Trk neurotrophin receptors (TrkA, TrkB TrkC) families.

The Axl/Mer/Tyro3 kinase family members have been implicated in tumor cell proliferation, cell-cell interactions, and cell migration and invasion, suggesting multiple roles for this pathway in tumorigenesis.

Axl and Mer are expressed in various organs including the brain and testes during development (Nagata K, *J. Biol. Chem*. (1996) 271 (47): 30022-30027.). However in human adults their expression, which is normally very low, returns to high levels in a variety of tumors including glioblastoma, pancreatic, lung, thyroid, hepatocellular, colon, renal, gastric, and breast carcinomas (Funakoshi H., *J. Neurosci. Res*. (2002) 68:150-160; Li Y., *Oncogene* (2009), 28:3442-3455.; Chattier C., *Leukemia* (1996) 10:781-787; Craven R. J., *Int. J. Cancer* (1995) 60:791-797; Vajkoczy P., *Proc. Nat. Acad. Sci*. (2006):103(15): 5799-5804; Sheih Y—S., *Neoplasia*. (2005) 7(12): 1058-1064; Xianzhou S., *Cancer* (2011), 117(4):734-743). Tyro3 is also expressed in the brain and testes and has also been linked to NK cell differentiation. Recently Tyro3 has been identified as the upstream regulator of microphthalmia-associated transcription factor (MITE), the 'lineage addiction' oncogene in malignant melanoma. In animal models, blocking Tyro3 repressed cellular proliferation and colony formation in melanoma cells thereby inhibiting tumorigenesis in vivo (Zhu S., *Proc. Nat. Acad. Sci*. (2009) 106(4):17025-17030). Axl, Mer, and Tyro-3 mediate multiple oncogenic phenotypes and activation of these receptor tyrosine kinases has been shown to provide a mechanism of chemoresistance in a variety of solid tumors. The role of Axl and Gas6 in downstream signaling leading to drug resistance involves a cancer cell's transition from an epithelial phenotype to one with mesenchymal properties (epithelial-to-mesenchymal transition or EMT). The EMT process allows a cancer cell to acquire many of the hallmarks required for oncogenesis and drives the cell into a state that is more resistant to therapy. The literature suggests that selective inhibition of Axl signaling reverses EMT (Byer L A, et. al., *Clin Cancer Res*. (2013) 19(1):279-290) and shifts the cell back into a sensitive state which can then respond to targeted therapy. Targeted inhibition of these RTKs may be effective as anti-tumor and/or anti-metastatic therapy, particularly if combined with standard cytotoxic therapies (Linger R. M. A., *Targets*(2010) 14(10):1073-1090).

The Trk family of neurotrophin receptors are crucial for the normal development of the peripheral nervous system. These receptor tyrosine kinases signal through the PI3K, Ras/Raf/MEK and PLCγ1/PKC pathways and have been found to play a critical role in neuroblastomas, the most common and deadly solid tumor in children (Brodeur G. M., *Clin Cancer Res* (2009) 15(10): 3244-3250). The Trk isoform expressed by the neruoblastoma can be prognostic as TrkA and TrkC expressing tumors are more prone to spontaneous regression and a more favorable outcome whereas TrkB are more often very aggressive and frequently have concomitant MYCN amplification. TrkB has been shown to suppress anoikis, or cell death induced by cell detachment, and thereby allowing the metastatic spread of tumor cells (Geiger T. R., *Cancer Res* (2007) 67(13):6221-9). Trk family gene rearrangements or aberrant expression have also been identified in papillary thyroid carcinomas, breast cancers, non-small cell lung cancer, prostate cancer, pancreatic ductal adenocarcinoma, pediatric sarcomas, and leukemias (Tognon C., *Cancer Cell* (2002), 2:367-76; Liu Q., *EMBO J.* (2000); 19: 1827-38; Eguchi M., *Blood* (1999), 93:1355-63; Harada T., *Clin Cancer Res.* (2011), 17(9):2638-45.; Jones-Bolin S. E., *Proc Amer Assoc Cancer Res* (2005) 46: Abstract #3026).

Osteolytic metastases are common in many types of cancer and have been found in up to 70% of patients with advanced breast or prostate cancer and in approximately 15% to 30% of patients with lung, colon, stomach, bladder, uterus, rectum, thyroid, or kidney carcinomas. Bone metastases can cause severe pain, hypercalcemia, pathologic fractures, spinal cord compression, and other nerve-compression syndromes. Expression of TrkA and TrkC receptor kinases have been observed in the bone forming area in mouse fracture models and NGF expression was observed in almost all bone forming cells (Asaumi K., *Bone* (2000) 26(6): 625-633.). These data support exploring the use of pan Trk inhibitors for the treatment of bone remodeling diseases such as bone metastases in cancer patients as well as osteoporosis and rheumatoid arthritis.

Discoidin Domain Receptors 1 and 2 (DDR1 and DDR2) are collagen receptors with protein tyrosine kinase activity that control fundamental cell processes including cell proliferation, adhesion, migration, and extracellular matrix remodeling (Vogel W, *Cellular Signalling*, (2006) 18:1108-1116). These RTKs are important in embryonic development, skeletal growth, tissue repair and injury-induced remodeling of blood vessels and the liver (Olaso E, *J Clin Invest.* (2001) 108:1369-1378; Zhang X H, *Arch Med. Res.* 2010, 41(8):586-92; Ali B R, *Hum Mol Gen*, (2010) 19(11):2239-2250; Hou G, *Circ. Res* (2002) 90:1147-1149; Ferri, N, *Am J Pathol*, (2004) 164:1575-1585). Aberrant activity of both receptors has been linked to human diseases such as lung, kidney and liver fibrosis, atherosclerosis, osteoarthritis, and rheumatoid arthritis. DDR1 and DDR2 have also been implicated in primary and metastatic cancer progression through regulation of metalloproteinase production, cell growth, and chemotactic invasion of normal tissue (Badiola I, *Oncol Rep*, (2011) 26:971-978).

DDR1 and DDR2 have been linked to several human cancers. DDR1 has been found in breast, ovarian, brain, esophageal, lung and immune system cancers (Vogel W, *Cellular Signalling*, 2006, 18:1108-1116).). Barker et al demonstrated DDR1 was more highly expressed in cancerous breast epithelial cells than in adjacent normal breast tissue (Barker K T, gene, 1995 10:569). This collagen receptor has also been shown to be a direct transcriptional target for the p53 tumor suppressor gene. DDR1 inhibition in tumor cells with wild type p53 activity results in increased apoptosis (Ongusaha P P, *EMBO J*, (2003) 22(6):1289). DDR2 has been shown to play a role in breast, lung and immune system cancers as well. Recently a group reported that approximately 3% of 277 lung squamous cell carcinoma patients had DDR2 mutations (Kotz J, *SciBX* 2011, 4(20):1-2). Though DDR1 and DDR2 have not been shown to be oncogenes in carcinogenesis, they likely act through regulating tumor cell growth, adhesion and metastasis by controlling collagenous extracellular matrix remodeling and metalloproteinase expression.

Other Non-receptor Tyrosine Kinases in Cancer:

Several non-receptor tyrosine kinases such thirty-eight-negative kinase 1 (Tnk1), JAK kinases, breast tumor kinase (Brk or PTK6), ROS, and ARG have also been implicated in tumor progression, survival and metastasis. Though the tyrosine kinase Tnk1 has been identified as a tumor suppressor gene in some cellular contexts, recently a novel gene translocation has been identified that results in a fusion protein combining part of C17ORF61 with Tnk1 kinase (Gu T-L., *Leukemia*(2010), 24:861-865.). The TNK1-C17ORF61 fusion protein, which retains constitutive Tnk1 tyrosine kinase activity, was confirmed to drive the proliferation and survival of Hodgkin's lymphoma (HL) cell line, L-540. In addition, the application of functional genomics by using HT-RNAi screens has allowed researchers to identify TNK1 as a growth-associated kinase in pancreatic cancer cells (Henderson M. C., *Mol Cancer Res*. (2011) 9(6).).

Activating mutations in JAK family members are observed in leukemias and myeoloproliferative neoplasms (Verstovsek S., *Hematology* (2009) 636-642). Seveal lines of evidence support the conclusion that JAK/STAT signaling is exaggerated in hematological malignancies and likely contributes to disease pathogenesis. Activating mutations in Jak1 have been described in acute lymphoblastic liekemia (ALL) and the $Jak2^{V617F}$ mutation is particularly important in myeleoproliferative neoplasms (MPNs) and myelofibrosis.

Brk is a member of a novel family of soluble protein tyrosine kinases, considered to be distantly related to c-Src (Ostrander J. H., *Cancer Res* (2007); 67: 4199-4209). Brk has been shown to localize to the nucleus of some breast and prostate cancer cell lines and is coamplified and coexpressed with ErbB2 in human breast cancers. Brk has been shown to interact with EGFR and ErbB3 and the expression of Brk enhances EGF-induced ErbB3 phosphorylation and the recruitment of p85 phosphatidylinositol 3-kinase to ErbB3, which potentiates PI3K activity (Xiang B., *Proc. Nat. Acad. Sci.* (2008); 105(34): 12463-12468). Data from these recent studies place Brk in a novel signaling pathway downstream of ErbB receptors and upstream of Rac, p38 MAPK, and ERK5 and establish the ErbB-Brk-Rac-p38 MAPK pathway as a critical mediator of breast cancer cell migration. Furthermore, overexpression of Brk conferred resistance to the ability of Lapatinib, an ErbB2 kinase inhibitor, to inhibit ErbB2-induced proliferation.

ROS kinase is one of the last remaining orphan receptor tyrosine kinases with an as yet unidentified ligand and the normal function so this kinase in different body tissues have not been fully identifies. However, ectopic expression, as well as the production of variable mutant forms has been reported in a number of cancers, such as glioblastoma mutifore and non-small cell lung cancer, suggesting a rolefor ROS kinase in deriving such tumors. The recent discovery of new selective inhibitors for ROS, along with the development of new diagnostic tools for the detection of ROS fusion proteins, indicates that targeting of this kinase and its mutant forms may have clinical applications for the treatment of cancers (El-Deeb I. M. et al., *Medicinal Research Reviews*, (2011) 31(5) 794-818).

ARG is an ABL-related kinase very similar to c-ABL at the SH3, SH2, and kinase domains and is expresses widely in normal cells (Krushe G. D., *Science* (1986) 234:1545-1548; Perego R., *Oncogene* (1991) 6, 1899-1902). ARG is also implicated in leukemogenesis by the fusion between ARG and ETV6 (ETS translocation variant 6), also known as TEL (translocation ETS leukemia). The ARG:ETV6 fusion was identified in two independent cases of human leukemias with t(1;12)(q25;p13) translocation (Cazzaniga G., *Blood*, (1999).

94:4370-4373; Iijima Y. *Blood*, (2000) 95: 2126-2132) and in a T-lymphoblastic cell line derived from a patient with acute lymphoid leukemia carrying t(1;10;12)(q25;q23;p13) (Nishimura N., *Oncogene* (2003) 22: 4074-4082). Constitutive activation of ARG and Abl kinases has also been implicated in the promotion of breast cancer cell invasion (Srinivasan D., *Cancer Res* (2006) 66(11): 5648-55). It has been reported that ARG is a target of the small molecule, tyrosine kinase inhibitor STI571 (Okuda K., *Blood* (2001), 97:2440-2448) which may contribute to the ability of STI571 (Imatinib/Gleevec) to induce hematologic remission in most patients with chronic myeloid leukemia.

Roles of Escape Mechanisms in the Treatment of Cancer:

Targeted inhibitors against specific tyrosine kinases known to be critical in tumor cell growth, differentiation, and survival have generated a lot of excitement over the last decade. Although there have been some dramatic examples of clinical responses in tumors known to have genetic mutations in single genes, i.e. the BCR:Abl fusion protein in CML and the B-Raf (V600E) mutation, highly specific kinase inhibitors can be met ultimately with resistance and tumor escape due to pathway enabling mutations in the target or suppressor proteins and up-regulation of compensatory proteins or pathways. In spite of recent advances, improving the outcomes for patients afflicted with relapsed and refractory cancer still represents a significant challenge. Too often, newly approved, targeted agents produce a significant upfront response in cancer patients only to be followed by drug resistance and progressive disease. Significant efforts have been made to understand the mechanisms of drug resistance, particularly to targeted agents.

Tumor cells that harbor B-Raf(V600E) exhibit oncogenic addiction and targeted inhibitors, such as the Type-I inhibitor Vemurafenib, have demonstrated remarkable efficacy in advanced stage disease driven by this mutation (Ribas A, et al., *Clin Oncol* (2011) 29:Suppl:8509; Chapman P. B., et al. New Engl. J. Med. (2011) 364: 2507-25161. However, resistance to Raf inhibitors, such as Vemurafenib, develops quickly (within 6-7 months) and recent studies have suggested that drug addiction pays a role and that removal of drug may be required to halt this life threatening resistance (Das M. et al. 2013 e-print, doi:10.1038/nature11814). In addition, cell population heterogeneity, compensatory pathway activation, inactivation of suppressor proteins, and external stimulation by the micro-environment can conspire to promote resistant disease, FIG. 1 (Gibbony G. T. and Smalley K. S. M., *Cancer Discovery* (2013) 4(3): 260-263; Paraiso K H T, et al., *Clinical Cancer Research*, (2012) 18(9):2502-2514.).

Another limitation of Type-I, ATP competitive, B-Raf inhibitors have is due to their ability to transactivate wild-type B-Raf and Raf-1 in normal cells (Hatzivassiliou G, et al *Nature*, (2010) 464:431-435; Heidorn S J, et al. *Cell* (2010) 140:209-221; Poulikakos P I, et al. *Nature* 2010 464:427-430) and intermittent treatment has again been proposed as a means of improving patient outcomes (Thakur M D, et al., *Nature* (2013) 494: 251-255). Therefore, efforts continue to understand the limitations of current targeted therapies and escape mechanisms with improved inhibitors and adjunct therapies.

Recently, new insights into the mechanisms of resistance have been provided (Maertens O. et al., *Cancer Discovery* (2012) 3(3): 338-349; Whittaker S. R. et al., *Cancer Discovery* (2012) 3(3): 350-362; Gibney G. T. and Smalley K. S. M., *Cancer Discovery* (2013) 4(3): 260-263). Although B-Raf mutations play a well established role in melanogenesis, without additional genetic alteration, tumor development is often restricted to oncogene-induced senescence (OIS). Nf1 mutations suppress B-Raf induced senescence, promote melanocyte hyperproliferation, and enhance melanoma development. Nf1 mutations function by deregulating both PI3K and ERK pathways. As such, Nf1/B-Raf mutant tumors are resistant to B-Raf inhibitors but are sensitive to combined inhibition of MAPK/ERK and mTOR. If Nf1 is mutated or suppressed in human melanomas that harbor concurrent B-Raf mutations, the Nf1 ablation decreases the sensitivity of melanoma cell lines to B-Raf inhibitors. Importantly, loss of Nf1 activity is seen in patients following sustained treatment with B-Raf inhibitors and mechanisms of Nf1 inactivation have been associated with acquired or innate resistance to these targeted therapies in melanoma.

Constitutive activation of signaling upstream or further downstream from the inhibited target protein is a common resistance mechanism. For example, blockade of mTOR with rapamycin analogs results in an increase in AKT signaling that reduces their overall therapeutic effect (Zitzmann K., *Cancer Letters*(2010), 295(1): 100-109; O'Reilly K. E., *Cancer Res*. (2006), 66: 1500-1508). In such cases, targeting multiple kinases in the affected signaling pathway can maximize pathway inhibition. Consequently, mixed inhibitors of PI3K and mTOR have been developed (Brachmann S., *Curr. Opin. Cell Biol*. (2009) 21(2): 194-198; Venkatesan A. M., *Bioorg. Med. Chem. Lett*. (2010), 20(2): 653-656).

Another common cause of specific inhibitor resistance is through the activation of a redundant receptor or parallel pathway that can functionally substitute for the inhibited one. This type of resistance occurs with receptor tyrosine kinases when related family members can perform overlapping functions and inhibiting one receptor cannot completely block downstream signaling. It has been found that approximately 20% of tumor samples from patients that became resistant to EGFR inhibitors had MET gene amplification (Engleman J. A., *Clin Cancer Res* 2008; 14:2895-2899). The crosstalk between EGFR and MET, observed in breast cancer cells, explains the EGFR inhibitor resistance seen in such tumors (Tao Y., *Nat. Clin. Pract. Oncol*, (2007) 4(10): 591-602). Therefore an inhibitor that inhibits both EGFR and MET could be efficacious in treating such patients. Up-regulation of the PI3K/PTEN signaling through PIK3CA activating mutations or PTEN loss is another mechanism found in EGFR inhibitor resistance (Janmaat J. L., *Clin Cancer Res*, (2003), 9(6):2316-2326). Chemotherapy resistance has also been tied to PI3K/Akt activation through EGFR (Winograd-Katz S., *Oncogene* (2006), 25:7381-7390).

Of particular interest is the crosstalk between the PI3K/AKT/mTOR and RAS/Raf/MEK/ERK pathways often utilized by tumors as a compensatory mechanism when specific inhibitors of a single pathway are used (Faber A. C., *Cell Cycle* (2010) 9(5) 851-852). It has been shown that PI3K inhibition in HER2-overexpressing breast cancers can lead to the up-regulation of the compensatory ERK signaling pathway Inhibition of both PI3K and MEK simultaneously has been demonstrated to lead to decreased proliferation and superior anti-tumor activity in animal models and this combination therapy is currently being studied in the clinic (Worcester S., *Elsevier Global Medical News*. (2011) Apr. 11).

As described above, the issues surrounding the mono-specific TKIs has led to the revitalization of interest in development of 'dirtier' kinase inhibitors that hit multiple kinases at the same time. One early successful multikinase inhibitor is Sorafanib (Naxavar) which targets Raf, VEGFR, PDGFRβ, FLT3, p38 and c-Kit all with $IC_{50}$s in the nanomolar range. Other examples of approved multikinase inhibitors include Sunitinib (Sutent), Erlotinib (Tarceva) and Imatinib (Gleevac). However, these early versions of multikinases rarely hit both the Ras/Raf/ERK and PI3K/AKT/mTOR pathways at the same time.

It has been reported that tumors, such as AML acquire resistance to these multikinase Raf/Flt3/c-Kit inhibitors, due to the activation of compensatory PI3K/AKT pathways after several months of treatment. It is becoming increasingly apparent that inhibiting both the target oncogene and kinases involved in the commonly used escape mechanisms will be required to achieve durable responses with targeted cancer therapies. Single target TKIs currently in phase 1 or phase 2 clinical trials are providing significant amounts of data on which pathways are commonly dysregulated in the most prevalent tumor types and more importantly which compensatory pathways lead to tumor escape. This information will help determine which specific inhibitors would be most effective given in combination leading to more durable tumor growth inhibition in the patients.

Another reoccurring mechanism that appears to be an underlying cause to both upfront and acquired resistance to many receptor tyrosine kinase (RTK) inhibitors is the up-regulation of Axl. This has been demonstrated in multiple cancer types with numerous targeted agents, including imatinib resistance in gastrointestinal stromal tumors (GIST), erlotinib resistance in non-small cell lung cancer (NSCLC) (Byers, et. al., *Clin Cancer Res.* 2013; 19(1):279-290), PKC412 resistance in acute myeloid leukemia (AML), cetuximab resistance in squamous cell carcinoma of the head and neck (SCCHN) (Giles, et al., *Mol Cancer Res* (2013) 12(11): 2541-2558), and lapatinib resistance in breast cancer (Liu L, et al., *Cancer Res* (2009) 69(17):6871-6878.; Holland S, et. al. (*Cancer Res.* 2010) 70:1544-1554). Axl is also one of the most common RTKs detected in breast cancer (Meric F, et. al., *Clin Cancer Res.* (2002) 8:361-367) where expression promotes metastasis and is associated with a poor prognosis (Gjerdrum C, et. al., *Proc Natl Acad Sci USA.* (2010) 107: 1124-1129). Moreover, inhibition of Axl has been shown to restore sensitivity to targeted agents in a synergistic manner (Verma A, et. al., *Mol Cancer Ther*. (2011) 10(10); 1763-73). Axl is a member of the TAM receptor kinase family that includes Mer and Tyro3. The over expression of any of the three family members has been associated with tumor cell survival and growth, increased migration, and angiogenesis (Linger R M, *Adv Cancer Res*. (2008) 100:35-83 and Linger R M., *Expert Opin Ther Targets*. (2010) 14:1073-1090). AML cells are known to induce the expression and secretion of the TAM receptor ligand Gas6 (growth arrest-specific gene 6) by bone marrow-derived stroma cells, which in turn mediates proliferation, survival and chemo-resistance in AML cells. Mer receptor tyrosine kinase over expression has been shown to contribute to leukemogenesis (Lee-Sherick A B, *Oncogene*, (2013) 32(46):5359-68) and its inhibition increases chemo-sensitivity and decreases oncogenic potential in T-cell acute lymphoblastic leukemia (Brandao L N, *Blood Cancer Journal*, (2013) 3 (1): e101 DOI: 10.1038/bcj.2012.46). A good case has also been made that Axl, Mer and Tyro3 are potential targets in Melanoma and as an adjunct to immunotherapies (Sensi M, et al, *J. Invest. Derm.* (2011) 131:2343-57; Schlegel J, et. al., *J Clin Invest*. (2013) 123(5):2257-2267; Demarest S J, et. al., *Biochemistry*. (2013) 52(18):3102-18).

Deregulation of protein synthesis is also a common event in human cancers. A key regulator of translational control is eIF4E and reports indicate that eIF4E activity is a key determinant of both Ras/PI3K/Akt/mTOR and Ras/Raf/Mek/Erk mediated tumorigenic activity. Because activation of eIF4E involves phosphorylation of a key serine (Ser209) specifically by MAP kinase interacting ser/thr kinases (Mnk1 and Mnk2) (Hou J., *Oncotarget* (2012) 3:118-131), efforts to discover either selective or combined targeted inhibitors of these kinases are underway by several research groups (Kassoum N, et. al. -2013). Indeed, Mnk inhibition by the antifungal agent Cercosporamide suppresses primitive leukemic progenitors (CFU-L) from AML patients in a dose-dependent manner (Altman J K, *Blood* (2013) 121(18) 3675-3681). Resistance in chronic myeloid leukemia (CML) is also facilitated through eIF4E over expression by blast-crisis granulocyte macrophage progenitors (GMPs) which then act as leukemia stem cells (LSCS) (Smith C C, *Hematology Am Soc Hematol Educ Program*. (2011) 2011:121-7). Although eIF4E activation is necessary for oncogenic transformation, it seems dispensable for development of normal hematopoietic stem cells (HSCs).

Moreover, since Mnks act downstream of both MAPK and PI3K pathways, their inhibition may also have utility in Vemurafenib resistant cancers where Raf up-regulation and aberrant Ras/PI3K/Akt/mTOR axis activity conspire to promote resistant disease within 6-7 months (Davies M A, *Cancer J.* (2012)18(2):142-7). Simultaneous inhibition of both TAM and Mnk family members should be more effective as an adjunct to targeted therapies than either TAM or Mnk inhibition alone and data suggests that such an agent may not significantly increase the side effect burden of targeted therapies (Linger R M., *Expert Opin Ther Targets*. (2010) 14:1073-1090).

Applications of Imaging Agents:

Use of imaging agents for monitoring disease progression is well established (Smith-Jones K. M., *J. Nuclear Medicine* (1994), 35(2): 219-325; Solit D. B, *Cancer Res* (2007), 67(23):11463-11469). Interest has intensified regarding the application of such agents for the diagnosis, localization, and characterization of cancers (Hoffman J. M., *Radiology* (2007) 244(1): 39-47; Stehouwer J. S., *J. Med. Chem.* (2010), 53(15): 5549-5557) as well as both acute and chronic inflammatory and degenerative diseases. More recently, applications directed specifically at the monitoring of kinase activity have also been reported (Dumont R. A., *Cancer Res*. (2009), 69(7): 3173-3179; Samén E., *Eur. J. Nucl. Med. Mol. Imaging* (2009), 36:1283-1295; Pisaneschi F., *Bioorg. Med. Chem.* 2010, 18: 6634-6645; Koehler L., *European Journal of Medicinal Chemistry* (2010) 45: 727-737.). The promise of imaging technologies for improved benefit, reduced cost, and personalization of medicine is significant.

General Construction of Kinase Inhibitors:

The general construction strategies and key structural elements for kinase inhibitors have been analyzed and reviewed extensively (Liu Y., *Nature Chemical Biology* (2006) 2:358-364; Goshe A. K. *J. Med. Chem.* (2008), 51(17):5149-5171; Zhang J., *Nat. Rev. Cancer* (2009) 9(1): 28-39) and, based on their mechanism of inhibition, they can be classified as either of five types, (Cozza G., *Anti-Cancer Agents in Medicinal Chemistry*, 2009, 9:778-786).

Type-I inhibitors compete at the ATP binding site of a kinase and typically bind to three subsites: 1) the purine binding site or "Hinge Region", 2) the solvent exposed "Flap Region" at the entrance to the ATP site, and 3) a lipophilic site adjacent to the purine site that is often referred to as the "Gatekeeper Region". Taken together, these binding sites recognize "Hinge-Gatekeeper Motifs" (HGM) that can achieve useful selectivity and profiles of inhibition, FIG. 2A. One major disadvantage of Type-I, ATP competitive, inhibitors is the kinetic challenge resulting from the millimolar physiological concentrations of ATP. The second challenge is achieving selectivity for a particular kinase since the basic construction, functionality, and topography of ATP binding sites are necessarily similar.

In contrast, Type-II inhibitors bind to an alternate inactive conformation, exhibited by some kinases, in which a conserved Aspartyl-Phenylalanyl-Glycine (DFG) containing loop is reoriented such that the Phenylalanine side chain is removed from its lipophilic binding pocket, FIG. 2B. As a result of this conformational change, new binding sites just adjacent to the "Gatekeeper Region" become accessible. Therefore, compounds that bridge from the HGM to these new "Selectivity Sites" can build in new structural elements that take advantage of differences between kinases in this region. Because the DFG-out conformation represents a minor population, Type-II inhibitors display time dependent kinetics resulting from slow on rates and the energetics of conformational equilibration. Consequently, potent Type-II inhibitors must also exhibit slow rates of disassociation while further kinetic advantages of Type-II result from this conformations inability to bind ATP and be recognized by upstream regulatory kinases. (Goshe A. K. *J. Med. Chem.* (2008), 51(17):5149-5171).

Typically, Type-II inhibitors incorporate a carboxamide, urea, or similar H-bond bridging bioisoster linkage to span from the Selectivity Sites into the ATP binding region. Therefore, Type-II inhibitors can be viewed as a Hinge-Gatekeeper Motif (HGM) appropriately connected to a lipophilic template that penetrates into and is complimentary to the adjacent "Selectivity Sites". Using this construct, Type-I inhibitors have been converted to Type-II inhibitors (Liu Y., *Nature Chemical Biology* (2006) 2:358-364; Kufareva I., *J, Med. Chem.* (2008), 51(24):7921-32).

Type-III inhibitors are relatively uncommon as they occupy a region adjacent to but not overlapping with the ATP binding site that does not require significant conformational change of the DFG-loop. Because Type-III inhibitors coexist with ATP binding, they are non-competitive with ATP and unaffected by the high physiological ATP concentrations. Since Type-III inhibition is rarely observed, inhibitors of this type offer potential selectivity advantages over Type-I inhibitors. MEK1 and MEK2 are important kinases for which Type-III inhibitors have been reported (Tecle H., *Bioorg. Med. Chem. Lett.* (2009), (19)1: 226-229).

Type IV inhibitors compete with a protein kinase substrates and target regions outside the ATP binding site that may avoid some crucial problems associated with the more conventional ATP competitive kinase inhibitors, such as the development of drug resistance as a result of accumulating mutations in the ATP binding site of the kinase.

Type V inhibitors are defined as a family of allosteric inhibitors that recognizes a binding domain well outside the ATP-binding cleft and not necessarily close to the substrate pocket. Therefore, this type of inhibition can be very specific for a given kinase.

Use of 5-Membered Heterocyclic Scaffolds at the ATP Binding Site:

The tri-substituted imidazole template has been applied very successfully to the Type-I inhibition of kinase. (Takle H., *Bioorg. Med. Chem. Lett.* (2009), (19)1: 226-229.) and knowledge gained from binding at the ATP site (Bennett et. al., WO2007105058A2) has been extended by appending functionality to provide structurally related Type-II inhibitors. (Tang J., *Bioorg. Med. Chem. Letts.*, (2008), 18:4610-4614), FIG. 3 A & B. In fact, structural information gained from Type-I inhibitors has been translated to the design of a type-II inhibitor intentionally by the same group (Wolin R. L., *Bioorg Med Chem. Letts.* (2008), 18(9):2825-2829), FIG. 3 C & D. These examples illustrate how chemotypes that target the ATP binding site can be adapted to provide Type-II inhibitors through an appropriate urea, amide, or ether, FIG. 3E & F, linkage to an additional lipophilic aromatic ring that occupies the lower selectivity-site (Meyers M. J., *Bioorg Med. Chem. Letts.* (2010) 20:1543-1547). It is estimated that approximately 50 of the 518 kinases adopt the DFG-out conformation (Fabian M. A., *Nat Biotechnol* (2005) 23:329-336), thus limiting the targets for Type-II inhibitors. However, recent studies suggest that the DFG-out conformation may be more common than initially thought (Kufareva I, J, Med. Chem. (2008), 51(24):7921-32).

Use of Urea-Linked 5-Membered Heterocyclic Scaffolds in Type-II Inhibitors:

Urea linked aryl-substituted 5-membered heteroaryl scaffolds have been used previously to create favorable "Selectivity Site" interactions for the Type-II inhibition of kinases, FIG. 4 A-D, (Smith R. A., *Bioorg. Med. Chem. Letts.* (2001), 11: 2775-2778; Regan J., *J. Med. Chem.* (2002), 45: 2994-3008.; Regan J., *J. Med. Chem.* (2003), 46: 4676-4686; Michellotti E. L., et. al., WO/2006/062982; Raeppel .S, *Bioorg. Med. Chem. Letts.* (2009), 19:1323-1328). The urea function acts as a critical hydrogen bonding bridge between a conserved Glutamate side chain and the aspartyl NH from the DFG-loop. In addition to urea linages, carboxamide linages have also been widely employed to profide Type-II inhibitors, (Zhang J, *Nat. Rev. Cancer* (2009) 9(1): 28-39). The closest prior art to that described herein is the cyclic urea c-Met inhibitor illustrated in FIG. 4-D. To our knowledge, the only previous description of a Type-II kinase inhibitor containing an ortho-Aryl-substituted 5-membered heteroaryl carboxamide scaffold is from our previous work, (Dietrich J., *Bioorg. Med. Chem.* (2010), 18(1): 292-304), which is limited to the imidazole scaffold with a quinazolinone HGM, and is the only example of a carboxamide linked aryl-substituted 5-membered heteroaryl Type-II inhibitor. We have recently become aware of a recent patent (Son, J B, et. al., WO 2011093684) which claims the use of 5-arylmethyl-2-methyl-pyrazole-4-carboxamide kinase inhibitors, see Table 1, HGM#10. In this patent, the lack of direct aryl substitution on the pyrazole ring significantly changes the scaffold geometry that is necessary for the unique properties describe for the scaffolds herein.

Compared to the limited structural variations that have been utilized to interact at the "Selectivity Site" of the DFG-out conformation of kinases, the structural Hinge Gatekeeper-interacgting Motif (HGM) variations that bind to the ATP binding site has been well studies. A survey of the kinase inhibitor are reveals this diversity, see Tables 1-9. In these tables, the HGM amine is illustrated in the first column while the amine capping group is illustrated, where applicable, in the adjacent column. Variations on the imatinib HGM are depicted in Table 1, while a series of difluoroanaline HGMs normally capped by a sulfonyl group are depicted in Table 2. A series of biaryl HGM amines are summarized in Table 3 and a series of HGMs with Bicyclic Gatekeeper Interacting Ring Systems are illustrated in Table 4. Following Tables 5 and 6, which illustrate the wide variety of diaryl ether HGMs that have been explored, Table 7 displays related but atypical linker strategies between the Hinge and Gatekeeper-interacting groups. Table 8 illustrates how derivatives of heteroaryl linked ATP site inhibitors can be adapted to the design of Type-II inhibitors. Lastly, Table 9 illustrated non-amine HGMs that, although not directly applicable to the construction of Type-II inhibitors, could be adapted, as indicated, for construction of Type-II inhibitors.

TABLE 1

Hinge Gatekeeper-interacting Motifs (HGMs) with 4-methyl-1-3 Disubstituted-Phenyl Amine Gatekeeper-interacting Groups.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 1 | | | Imatinib | ABL, KDR, Kit, PDGFR, CSF-1R, FLT-3, DDR | Zimmerman 1996 Zimmermann, J. et al. Bioorg. Med. Chem. Lett. 1996, 6, 1221-1226. Order # A2308 sales@tciamerica.com | 1IEP.pdb Imatinib in ABL |
| 2 | | | | | Zhang 2010 WO2010-US41872 | |
| 3 | | | Masitinib (AB1010) | Kit PDGFR FGFR3 | A01.743.786 www.aurora-finechemicals.com | |
| 4 | | | Ponatinib | BCR-ABL, mutants, KDR, FGFR1, PDGRα, FLT3, LYN | Huang 2010 Huang, WS et al. Journal of Medical Chemistry 2010, 53 (12): 4701-19 | 3CS9.pdb Poltinib in ABL |
| 5 | | | GSK Cpd-14d | CSF-1R LCK, EGFR, ErbB4, KDR | Baldwin 2008 Baldwin I., et al. Bioorg. Med. Chem. Lett. 18 (2008) 5285-5289 | Best CSF-1R from libratry approach |

TABLE 1-continued

Hinge Gatekeeper-interacting Motifs (HGMs) with 4-methyl-1-3 Disubstituted-Phenyl Amine Gatekeeper-interacting Groups.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 6 | | | Bafetinib (INNO-406) | ABL LYN | Kamitsuji 2007 Kamitsuji Y, et al. Bioorg Med Chem Lett. (2007) 17: 12-17 | |
| 7 | | | AZ628 | B-RAF PDGFR-a/b KIT, CSF1R | Aquila 2007 Aquila, B., Lyne, P., Pontz, T.: WO2007113558 (2007) | |
| 8 | | | | TIE-2 | Hodous 2007 Hodous B. L., et. al. Bioorg. Med. Chem. Let. (2007) 17: 2886-1889 | |
| 9 | | | ZM 336372 | CRAF | Hall-Jackson 1999 Hall-Jackson C. A., et. al. Chem Biol (1999) 6(8): 559-68 | |
| 10 | | | 1318242-17-9P | | Son 2011 Son, J B, et. al., WO 2011093684 | |

TABLE 2

Representative 4-6-Difluoro-1-3-disubstituted Gatekeeper Containing Inhibitors.

| HGM # | ATP-Site Interating Group-Hinge-Gatekeeper Motif-HGM | Sulfonamide Cap | Inhibitor Name or ID # | Kinases Inhibited | Reference or Vendor Source | Comment or Crystal Structure |
|---|---|---|---|---|---|---|
| 11 | (structure) | (structure) | | B-RAF | Ignacuo 2011 Ignacio A., et. al. WO 2011025940 | Novel Type-I Inhibitor |
| 12 | (structure) | (structure) | vemurafenib (Zelboraf) PLX-4032 | B-RAF(V600E) 31 nm C-RAF (48 nM) SRMS (18 nM) MAP4K5 51 nM FGR (63 nM) B-RAF 100 nM | Bollag 2010 Bollag, G., et. al., Nature (2010) 467: 596-599 | 3OG7_B.pdb Raf (V600E) |
| 13 | (structure) | (structure) | PLX-4720 | B-RAF | Tsai 2008 Tsai, J., et. al., Proc. Natl. Acad. Sci. Usa (2008) 105: 3041-3046 | 3C4C-pdb B-RAF |
| 14 | (structure) | (structure) | PLX-3203 | B-RAF | Tsai 2008 Tsai, J., et. al., Proc. Natl. Acad. Sci. Usa (2008) 105: 3041-3046 | 3C4D.pdb BRAF |
| 15 | (structure) | (structure) | | B-RAF | Wenglowsky 2011 Wenglowsky, S., et. al. ACS Medicinal Chemistry Letters (2011) 2: 342-347 | 3TV4.pdb BRAF |

TABLE 2-continued

Representative 4-6-Difluoro-1-3-disubstituted Gatekeeper Containing Inhibitors.

| HGM # | ATP-Site Interating Group-Hinge-Gatekeeper Motif-HGM | Sulfonamide Cap | Inhibitor Name or ID # | Kinases Inhibited | Reference or Vendor Source | Comment or Crystal Structure |
|---|---|---|---|---|---|---|
| 16 | | | | B-RAF | Wenglowsky 2011 Wenglowsky S., et. al., Bioorg. Med. Chem. Lett. (2011) 21: 5533-5537 | 3TV6.pdb BRAF |
| 17 | | | | B-RAF | Joachim 2011 Joachim R., et. al., WO(2011) 025951 A1 | Novel Type-I Inhibitor |
| 18 | | | | | Wenglowsky 2011 Wenglowsky S., et. al., Bioorg. Med. Chem. Lett. (2012) 22: 912-915 | Novel Type-I Inhibitor |
| 19 | | | | B-RAF VEGFR-2 | Ren 2012 Ren, L., et. al. Bioorg. Med. Chem. Lett (2012).22: 3387-3391 | 4E4X.pdb B-Raf |

TABLE 3

Representative Biaryl-amine Hinge Gatekeeper-Interacting Motifs (HGMs).

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 20 | | | AC-220 | FLT-3 | WO/2005/048953; WO/2009/038757 | |

TABLE 3-continued

Representative Biaryl-amine Hinge Gatekeeper-Interacting Motifs (HGMs).

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 21 | | | | BRAF | Berger 2009 Berger, D. M., et. al. Bioorg. Med. Chem. Lett. (2009) 19: 6519-6523 US20070219186 | 3II5.pdb BRAF |
| 22 | | | PF-4594755 | PYK2 | Shena 2011 Shena C. J., et. al., Experimental Cell Research (2011) 317: 1860-1871 | |
| 23 | | | Linifanib (ABT-869) 375.4 | PDGFR-b CSF-1R KDR | Shankar 2007 D. B. Shankar, et al. BLOOD 109(8), 2007, 3400-3408 WO/2004/113304 | |
| 24 | | | | KDR, TIE-2 | Dai 2008 Dai Y., et. al., Bioorg. Med. Chem. Lett. (2008) 18: 386-390 | |
| 25 | | | | KDR | Dai 20085 Dai Y., et. al., J. Med. Chem. (2005) 48: 6066-6083 | |
| 26 | | | | KDR, TIE-2 | Miyazaki 2005 Miyazaki Y., et. al., Bioorg. Med. Chem. Lett. (2005) 15: 2203-2207. | |

TABLE 4

Representative HGMs with Bicyclic Gatekeeper Interacting Ring Systems.

| HGM # | ATP-Site Interating Group-Hinge-Gatekeeper Motif-HGM | Type-II-Selectivity-Site Interacting Group | Inhibitor Name or ID # | Kinases Inhibited | Reference or Vendor Source | Comment or Crystal Structure |
|---|---|---|---|---|---|---|
| 27 | 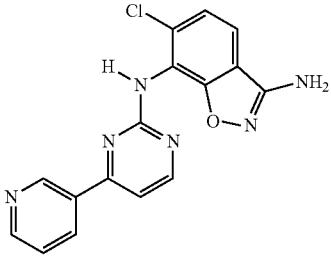 [SMILES: Nc1noc2c(Nc3nccc(-c4cccnc4)n3)c(Cl)ccc12] | 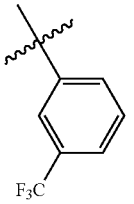 | | | Chen 2007 Chen, Ning; Hu, Essa WO 2007-US16383 | |
| 28 | 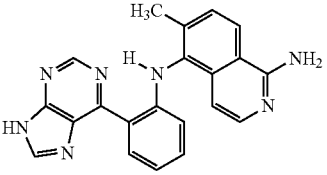 [SMILES: Cc1ccc2c(N)nccc2c1Nc1ccccc1-c1ncnc2[nH]cnc12] | 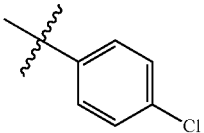 [SMILES: *c1ccc(Cl)cc1] | | BRAF | Smith 2009 Smith, A. L., et. al., J. Med. Chem. (2009) 52: 6189-6192 | 3IDP.pdb BRAF |
| 29 | 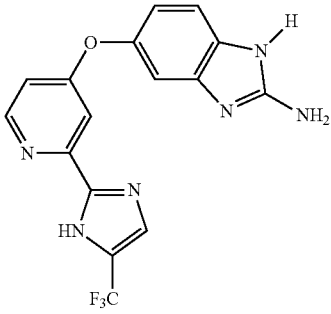 [SMILES: Nc1nc2cc(Oc3ccnc(-c4ncc(C(F)(F)F)[nH]4)c3)ccc2[nH]1] | 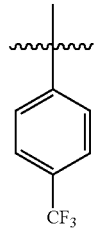 [SMILES: *c1ccc(C(F)(F)F)cc1] | Raf-265 (CHIR-265) | RAF VEGFR | Amiri P, et al. US20070299039 Mol Cancer Ther 2010; 9:358-368 | |
| 30 | 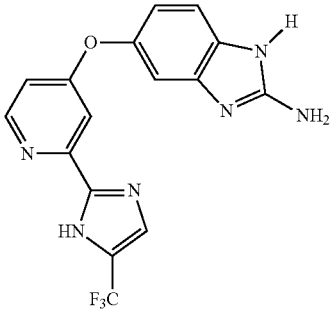 | 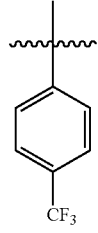 [SMILES: *c1ccc(C(F)(F)F)cc1] | Raf265 des-methyl derivative | RAF VEGFR | Amiri P, et al. US20070299039 | |
| 31 | 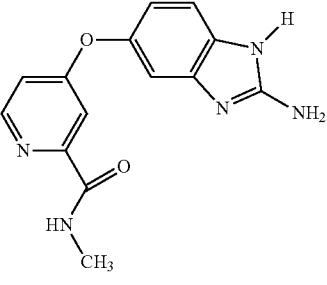 [SMILES: CNC(=O)c1cc(Oc2ccc3[nH]c(N)nc3c2)ccn1] | 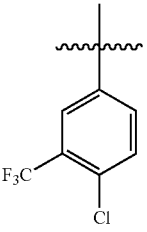 [SMILES: *c1ccc(Cl)c(C(F)(F)F)c1] | | RAF VEGFR | US 2003-675927 WO 2003-US10117 | |

TABLE 4-continued

Representative HGMs with Bicyclic Gatekeeper Interacting Ring Systems.

| HGM # | ATP-Site Interating Group-Hinge-Gatekeeper Motif-HGM | Type-II-Selectivity-Site Interacting Group | Inhibitor Name or ID # | Kinases Inhibited | Reference or Vendor Source | Comment or Crystal Structure |
|---|---|---|---|---|---|---|
| 32 | | | | KDR | Hasegawa 2007 Hasegawa, M., et. al., J. Med. Chem (2007) 50: 4453-4470 | |
| 33 | | | | | Bauer, D., et. al., Bioorg. Med. Chem. Lett. (2008) 18: 4844-4848 | |

TABLE 5

Representative Diaryl Ether Hinge Gatekeeper-Interacting Motifs HGMs.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 34 | | | BIRB 796 Doramapimod | p-38 | Regan 2003 Regan, J., et. al. J. Med. Chem. (2003) 23; 46(22): 4676-86. | IKV2.pdb Human p38 MAP Kinase in Complex with BIRB 796 |
| 35 | | | Sorafenib Nexavar | KDR, Kit, PDGFRs, CSF-1R, FLT-3, DDR, Raf, Tie2 | Wood 1998 Reidl B., et. al., WO-1998-53559 | |

TABLE 5-continued

Representative Diaryl Ether Hinge Gatekeeper-Interacting Motifs HGMs.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 36 | | | Regorafenib BAY 73-4506 | VEGFR-2/3, RET, KIT, PDGFR, and Rafs | Onyx-Sorafenib patent U.S. Pat. No. 7,351,834 (filed on 1999) | |
| 37 | | | | B-Raf | Niculescu-Duvaz 2009 Niculescu-Duvaz, D., et. al., J. Med. Chem. (2009) 52: 2255-2264 | |
| 38 | | | | B-Raf | Menard 2009 Menard, D., et. al., J. Med. Chem. (2009) 52: 3881-3891 | |
| 39 | | | | B-RAF VEGFR-2 | Okaniwa 2012 Okaniwa, M., et. al., J. Med. Chem (2012) 55: 3452-3478 | 4DBN.pdb BRAF |

TABLE 5-continued

Representative Diaryl Ether Hinge Gatekeeper-Interacting Motifs HGMs.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 40 | | | | KDR TIE-2 | Hasegawa 2007 Hasegawa, M., et. al., J. Med. Chem (2007) 50: 4453-4470 | |
| 41 | | | | B-RAF(V600E) BRAF, CRAF, SRC, LCK, PDGFR-a, p38-a, p38-g. | Whittaker 2010 Whittaker S., et. al. Cancer Res; (2010) 70(20) 8036-8044. | |

TABLE 6

Representative Diaryl Ether Hinge Gatekeeper-Interacting Motifs HGMs continued.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 42 | | | KI-20227 480.54 | CSF-1R> KDR> Kit, PDGFR-b | Ohno 2008 Ohno, H. et al. Eur. J. Immunol. (2008) 38: 283-291 | R and S isomers are slightly different |
| 43 | | | BMS 777607 | c-MET | Schroeder_2009 Schroeder GM, et. al. J. Med. Chem. (2009) 52(5): 1251-1254. | 3F82.pdb |

TABLE 6-continued

Representative Diaryl Ether Hinge Gatekeeper-Interacting Motifs HGMs continued.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 44 | | | | c-MET | Schroeder 2009<br>Schroeder G. M., et. al.<br>J. Med. Chem. 52(5), 2009,<br>1251-4 | 3CE3.pdb |
| 45 | | | | c-MET | Schroeder_2009<br>Schroeder<br>G M, et. al. J. Med. Chem.<br>(2009) 52(5): 1251-1254. | 3CTH.pdb |
| 46 | | | Foretinib<br>GSK-<br>1363089<br>XL880<br>EXEL-<br>2880 | c-MET<br>VEGFR-1,<br>VEGFR-2 | Qian 2009<br>Qian F., et. al., Cancer Res<br>(2009) 69: 8009-8016 | |
| 47 | | | MGCD265 | c-MET<br>VEGFR-1,<br>VEGFR-2,<br>VEGFR-3,<br>RON<br>and TIE2 | U.S. Pat. No. 7,772,247 | |
| 48 | | | Lenvatinib<br>(E7080) | VEGFR<br>2/3 | Matsui 2008<br>Matsui, J.; et. al., Clinical<br>Cancer Research (2008) 14<br>(17): 5459-65 | |

TABLE 6-continued

Representative Diaryl Ether Hinge Gatekeeper-Interacting Motifs HGMs continued.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 49 | [structure] | | PYP-4-0001 | | Scientific Laboratory Inc. sales@sphinxscientificlab.com | |

TABLE 7

Hinge Gatekeeper-Interacting Motifs (HGMs) with Atypical Linker Groups.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 50 | [structure] | [structure] | Astra Zeneca Cpd-27 | CSF-1R> EphA2, Hck, Fyn, cRaf, KDR, Src PDGFRs | D. A. Scott et al. Bioorg Med. Chem. 198 (2008) 4794-4797 WO/2007/071955 | |
| 51 | [structure] | [structure] | | KIT CSF1R | US20070032519 WO/2007/013896 | |
| 52 | [structure] | [structure] | | p38 | Millan 2011 Millan, D. S., et. al., J. Med. Chem. (2011) 54: 7797 | 2YIX.pdb p38 and trialopyridine inhibitor |
| 53 | [structure] | [structure] | PF-4618433 | PYK2 | Han 2009 Han, S., et. al., J. Biol. Chem. (2009) 284: 13193-13201 | 3FZT[.pdbPYK2 and PF-4618433 |

TABLE 7-continued

Hinge Gatekeeper-Interacting Motifs (HGMs) with Atypical Linker Groups.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 54 | | | Cytopia-Australia 441.48 | CSF-1R Kit, DDR1 PDGRs, VEGFR-1,2,3 FRK, RET | C. J. Burns et al. Bioorg. Med. Chem. Lett. 19 (2009) 1206-1209 | Stereo Chemistry Important |
| 55 | | | Telatinib (BAY 57-9352) | PDGFR-b VEGFR-2/3 KIT | Neeltje 2009 Neeltje Steeghs N., J Clin Oncol (2009) 27: 4169-4176 | |
| 56 | | | | RAF | Bartovitz D. J., et al., US20070060607 | |
| 57 | | | MK-2461 | c-Met Ron, Flt1-4, PDGFRβ, FGFR1-3 KDR, TrkA/B and Mer | Pan B-S., et. al., Cancer Res 2010; 70(4), 1524-1533 | |
| 58 | | | PYP-4-0025 | | Scientific Laboratory Inc. sales@sphinx-scientificlab.com | |

TABLE 8

Hinge Gatekeeper-Interacting Motifs (HGMs) with Azole Linking Ring Systems.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 59 | | | Dabrafenib GSK-2118436A | BRAF | Stellwagen J. C., et. al. Bioorg. Med. Chem. Lett. (2011) 21: 4436-4440 WO201104441 WO2011044414 WO2011047238 | |
| 60 | | | | BRAF | Tang 2008 Tang J., et. al., Bioorg. Med. Chem. Lett. (2008) 18: 4610-4614 | |
| 61 | | | | TIE-2 | Lee 2010 Lee J., et. al., Bioorg. Med. Chem. Lett. (2010) 20: 1573-1577 | |
| 62 | | | | TIE-2 | Adjabeng G., et al. WO 2009076140 A1 | |
| 63 | | | | B-RAF | Stellwagen J. C. et al., Bioorg. Med. Chem. Lett. (2011) 21: 4436-4440 WO2009032667 A1 | |

TABLE 8-continued

Hinge Gatekeeper-Interacting Motifs (HGMs) with Azole Linking Ring Systems.

| HGM # | ATP-Site Interating Group-Hinge-Gatekeeper Motif-HGM | Type-II-Selectivity Site Interacting Group | Inhibitor Name or ID # | Kinases Inhibited | Reference or Vendor Source | Comment or Crystal Structure |
|---|---|---|---|---|---|---|
| 64 | [structure] | | BKM120 NVP-BKM120 | Pan-PI3K | Burger 2011 Burger T. M., et. al., ACS Med. Chem. Lett. (2011) 2: 774-779 | |

The structures in Table 9 represent kinase inhibitors that contain interesting HGMs that, because they lack an appropriately positioned amine group, can not be directly used to construct Type-II inhibitors. As illustrated in FIG. 3, ATP binding site inhibitor motifs from Type-I inhibitors have been adapted to the construction of Type-II inhibitors (Wolin R. L., *Bioorg. Med. Chem.* (2010), 18(1): 292-304; Meyers M. J., *Bioorg Med. Chem. Letts.* (2010) 20:1543-1547).

TABLE 9

Type-I Inhibitors that could be adapted to Library HGM Amines as Indicated.

| HGM # | ATP-Site Interating Group - Hinge-Gatekeeper Motif - HGM | Type-II - Selectivity Site Interacting Group | Inhibitor Name or ID# | Kinases Inhibited | Reference or Vendor Source | Comment or Crystal Structure |
|---|---|---|---|---|---|---|
| 65 | [structure] Replace F with —NH$_2$ | | Crizotinib PF02341066 | ALK | | |
| 66 | [structure] Cl - Here in Dasatinib but no —NH$_2$ | None - Type-I | Dasatinib | ABL KDR, Kit, PDGFR, CSF-1R, FLT-3, DDR | Lombardo, L. J. et al. J. Med. Chem. 2004, 47, 6658-6661. | 2GQG.pdb Dasatinib in ABL |

TABLE 9-continued

Type-I Inhibitors that could be adapted to Library HGM Amines as Indicated.

| HGM # | ATP-Site Interating Group - Hinge-Gatekeeper Motif - HGM | Type-II - Selectivity Site Interacting Group | Inhibitor Name or ID# | Kinases Inhibited | Reference or Vendor Source | Comment or Crystal Structure |
|---|---|---|---|---|---|---|
| 67 | 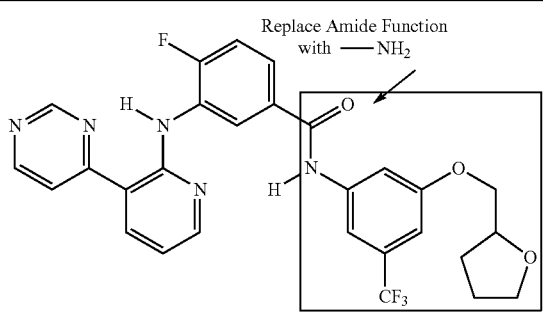 | Want Reverse Amide | | | Geuns-Meyer, S. D.; et.al., WO 2005113494 A2 | |
| 68 | 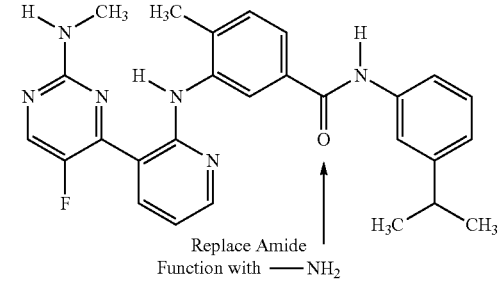 | Want Reverse Amide | | | PCT Int. Appl., 2005113494, 01 Dec. 2005 | |
| 69 | 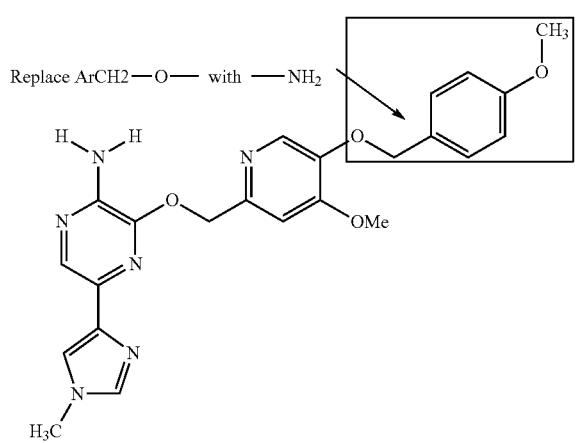 | Replace Benzyloxy Group with Amine Function | Pfizer - 12b 448.47 | CSF-1R | Meyers 2010 Meyers M. J., etal. Bioorg. Med. Chem. Lett. (2010) 20: 1543-1547 | 3LCO.pdb CSF1R |
| 70 | 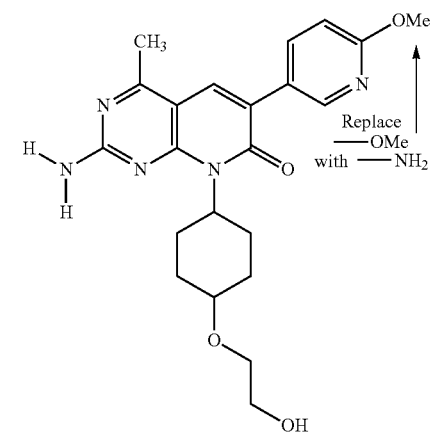 | Replace Methoxy Group with Amine Function | | PI3K/ mTOR | Liu 2010 Liu, K. K.-C., et.al., Bioorg. Med. Chem. Lett. 2010, 20 (20), 6096-6099. | 3ML9.pdb PI3K-gamma |

TABLE 9-continued

Type-I Inhibitors that could be adapted to Library HGM Amines as Indicated.

| HGM # | ATP-Site Interating Group - Hinge-Gatekeeper Motif - HGM | Type-II - Selectivity Site Interacting Group | Inhibitor Name or ID# | Kinases Inhibited | Reference or Vendor Source | Comment or Crystal Structure |
|---|---|---|---|---|---|---|
| 71 | 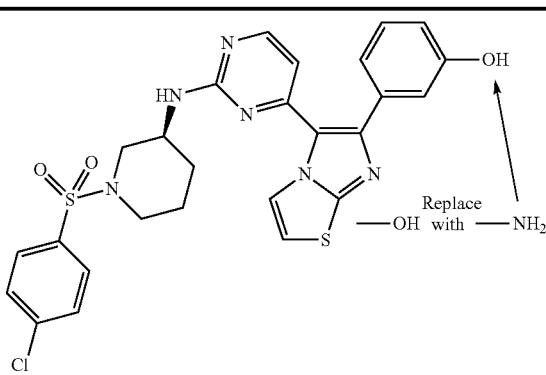 | Replace Hydroxy Group with Amine Function | | | WO 2007-123892 | |
| 72 | 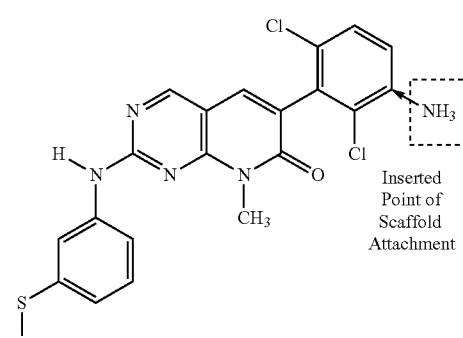 | None - Type-1 Add Amine Function as Indiacated | PD173955 | ABL KIT, SRC, HCK, LCK, | Klutchko 1998 Klutchko, S. R. et al. J. Med. Chem. 1998, 41, 3276-3292. | 1M52.pdb Abl |
| 73 | 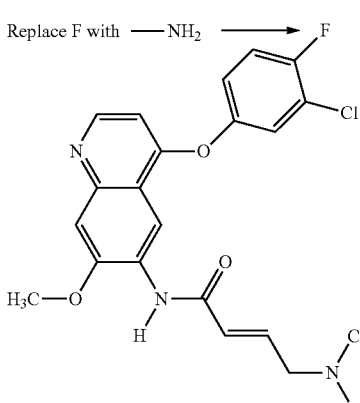 | | Pelitinib (EKB-569) | (EGFR) ErbB-1, -2 and -4 | J. Med. Chem. 2003; 46, 49-63 | Covalent Inhibitor |

An efficient synthesis of 2-trifluoromethyl-4-aryl-imidazole-5-carboxylic acids FIG. 5A, has been reported (Hagiwara K., et. al, WO/1995/004724). Quinazolinone containing amides, FIG. 5B, have been claimed to potently inhibit the oncongenic B-Raf (V600E) mutant kinase (Aquila B., et. al, WO2006/024834). Attachment of a 2-trifluoromethyl-4-aryl-imidazole-5-carboxylic acid, A, to this quinazolinone containing (HGM) resulted in a homologous series of hybrid compounds, FIG. 5C, some of which were reported to be highly potent B-Raf(V600E) inhibitors (Dietrich J., et al. *Bioorg. Med. Chem.* (2010), 18(1): 292-304).

This previous disclosure described computational experiments using 1UWJ.pdb, the co-crystal structure of B-Raf (V600E) with Sorafenib, in which no attractive low-energy pose were produced during docking studies. This poor fit, thought to result from a steric clash between the inhibitor and Glutamate 500 in 1UWJ.pdb, FIG. 6A, prompted exploration of alternate binding modes. Thus, this report proposed an alternative mode of binding based on docking experiments using the DFG-out monomer-B co-crystal structure of B-Raf (V600E) with PLX-4720 (Tsai J., PNAS USA. (2008) 105 (8):3041-6). By utilizing this co-crystal structure, 3C4C.pdb, the proposed negative steric interaction with glutamate 500 appeared to be removed, FIG. 6B.

FIG. 6 illustrates the binding mode of quinazolinone containing inhibitors with B-Raf.

This publication also described the structure activity relationship within a small series of structurally related compound which all shared the quinazolinone HGM and imidazole scaffold. The only structural variations reported were limited to the 2- and 5-positions of an imidazole scaffold with the three compounds depicted in FIG. 7 displaying the most potent activity against B-Raf(V600E). The apparent time dependence reported was consistent with Type-II inhibition.

The phosphor-protein gel assay used in this report revealed sub-nanomolar IC50 values for these three inhibitors when the inhibitor and enzyme were preincubated for 1 hour prior to addition of the MEK1 substrate. When evaluated against a panel of 96 kinases, Table-10, all three compounds displayed potent and selective inhibition of B-Raf(V600E), B-Raf(Wt), C-RAF(Raf-1), PDGFR-α, PDGFR-β, c-Kit, and p38-α.

TABLE 10

Summary of inhibition profiles for the imidazole quinazolinone inhibitors KIN-035, KIN-038, and KIN-057, (Dietrich, 2010).

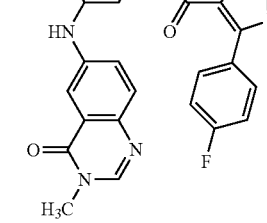

| Ambit Biosciences Gene Symbol | KIN-035 Mol. Wt.: 536.48 cLogP: 5.04 | KIN-038 Mol. Wt.: 550.51 cLogP: 5.53 | KIN-057 Mol. Wt.: 554.47 cLogP = 5.20 |
|---|---|---|---|
| ABL1 | | | |
| ABL1(E255K) | | | |
| ABL1(T315I) | | | |
| ACVR1B | | | |
| ADCK3 | | | |
| AKT1 | | | |
| AKT2 | | | |
| ALK | | | |
| AURKA | | | |
| AURKB | | | |
| AXL | | | |
| BMPR2 | | X | |
| BRAF | XXXX | XXX | XXX |
| BRAF(V600E) | XXXX | XXXX | XXX |
| BTK | | | X |
| CDK11 | XX | X | XX |
| CDK2 | | | |
| CDK3 | | X | |
| CDK7 | | | X |
| CDK9 | | | |
| CHEK1 | | | |
| CSF1R | XXX | | X |
| CSNK1D | | | |
| CSNK1G2 | | | |
| DCAMKL1 | X | X | X |
| DYRK1B | | | |
| EGFR | X | | |
| EGFR(L858R) | X | | |
| EPHA2 | XX | | |
| ERBB2 | X | X | |
| ERBB4 | X | | |
| ERK1 | | | |
| FAK | | | |
| FGFR2 | | | |
| FGFR3 | | X | |
| FLT3 | | | |
| GSK3B | | | |
| IGF1R | | | |
| IKK-alpha | | X | |
| IKK-beta | | | X |
| INSR | | | |
| JAK2(catalytic) | | | X |
| JAK3(catalytic) | | | |
| JNK1 | | | |
| JNK2 | | | |
| JNK3 | | | |

TABLE 10-continued

Summary of inhibition profiles for the imidazole quinazolinone inhibitors KIN-035, KIN-038, and KIN-057, (Dietrich, 2010).

| | Inhibitor Code | | |
|---|---|---|---|
| | KIN-035 | KIN-038 | KIN-057 |
| | 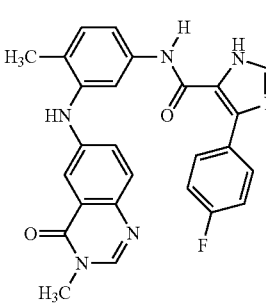 | 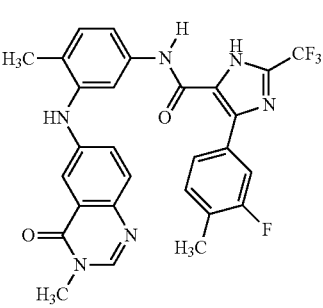 | 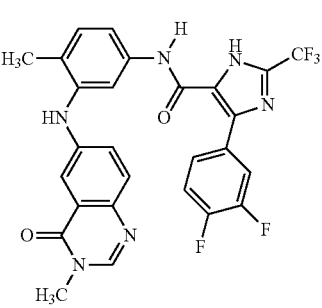 |
| Ambit Biosciences Gene Symbol | Mol. Wt.: 536.48<br>cLogP: 5.04 | Mol. Wt.: 550.51<br>cLogP: 5.53 | Mol. Wt.: 554.47<br>cLogP = 5.20 |
| KIT | XXXX | XXXX | XXX |
| KIT(D816V) | | X | |
| LKB1 | | | |
| MAP3K4 | | | |
| MAPKAPK2 | | | |
| MARK3 | | | |
| MEK1 | | | |
| MEK2 | | | |
| MET | | | |
| MKNK1 | XX | X | |
| MKNK2 | X | | |
| MLK1 | | | |
| p38-alpha | XXXX | XX | XXX |
| p38-beta | X | X | X |
| PAK1 | | | |
| PAK2 | | | |
| PAK4 | | | |
| PCTK1 | | X | |
| PDGFRA | XX | XX | X |
| PDGFRB | XXX | XX | XXX |
| PDPK1 | | | |
| PIK3C2B | | | |
| PIK3CA | X | X | |
| PIK3CG | | | |
| PIM1 | | | |
| PIM2 | | | |
| PIM3 | | | |
| PKAC-alpha | | | |
| PLK1 | | | |
| PLK3 | | | |
| PLK4 | X | X | X |
| PRKCE | X | X | X |
| RAF1 | XXXX | XXXX | XXXX |
| RET | | | |
| RIOK2 | X | X | |
| ROCK2 | | | |
| RPS6KA3(Kin.) | | | |
| SNARK | | | |
| SRC | | | |
| SRPK3 | | | |
| TGFBR1 | | | |
| TIE2 | | | |
| TRKA | | | |
| TSSK1B | | | |
| TYK2(catalytic) | X | X | |
| ULK2 | | X | X |
| VEGFR2 | X | | |
| YANK3 | | | |
| ZAP70 | | | |

Inhibition Scale
X >25% @ 1 μM
XX >50% @ 1 μM
XXX >75% @ 1 μM
XXXX >90% @ 1 μM

Compounds were assayed at 1 μM concentrations in duplicate without preincubation. An X—indicates better than 25% inhibition, XX—indicates better than 50% inhibition, XXX—represents better than 75% and XXXX represents better than 90% inhibition under the conditions of these assays. Note atypical Structure-Activity Relationship of KIN-035 for CSF1R compared to KIN-38 and KIN-57.

The present disclosure addresses and interconnects two important applications relating to the treatment of diseases. Because understanding of the disease specific roles, complex interactions, mechanisms of dysregulation, activating mutations, and compensatory back-up systems of kinase pathways, i.e. "Systems Biology", continues to evolve, multi-targeted kinase (MTK) inhibitors with unique properties and selectivity profiles will continue to be needed. The development of advanced tools for the non-invasive mechanism-based characterization and monitoring of disease in preclinical, clinical, and therapeutic settings is also perceived as a critical unmet need.

The present disclosure describes a novel scaffold geometry and its application to the design and preparation of selective or multi-targeted kinase (MTK) inhibitors as therapeutic agents and/or disease specific PET imaging agents. Enabling technologies for the early diagnosis, accurate characterization, patient specific treatment, and real time monitoring of therapies will be essential for the realization of personalized medicine. By combining therapeutic and imaging agents that share similar structural elements and/or activity profiles, significant synergies can be realized in clinical development and personalized medicine. Taken together, these concepts constitute a platform technology with unique applications and utilities. Although this disclosure focuses on representative examples for the purposes of illustration, the implications of and applications for this platform technology are quite broad and, using the information disclosed herein, one skilled in the construction of Type-I and/or Type-II kinase inhibitors and the mode of binding of Hinge-Gatekeeper interacting Motifs (HGM) should be able to easily employ this platform technology.

SUMMARY

The present disclosure describes compounds of Formula (I):

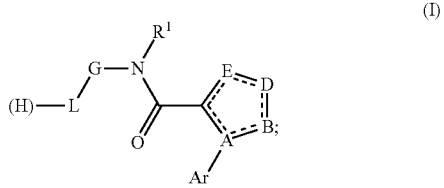

(I)

or a pharmaceutically acceptable salt thereof, wherein the values for Ar, A, B, D, E, $R^1$, G, L, and (H) are as defined herein.

Provided compounds and pharmaceutical compositions thereof are novel kinase inhibitors and are useful in treating a variety of diseases and conditions.

The present disclosure also provides the application of the combination of functionality and scaffold geometry defined by Formula (I), or a pharmaceutically acceptable salt thereof, to the design of novel kinase inhibitors as imaging agents. Appropriate selection of the substituted heterocyclic ring, $R^1$, Ar, (H)-L-G- and A/B/D/E can provide a variety of kinase inhibitors with diverse and often unique selectivity profiles. This specific scaffold geometry is uniquely complementary to the DFG-out conformation of many kinases yet tightly anchors the inhibitor so that interactions with a particular kinase, or profile of kinases, can be selectively enhanced.

The disclosure also provides a pharmaceutical composition comprising a disclosed kinase inhibitor, including a compound of Formula (I), and a pharmaceutically acceptable carrier or diluent, wherein the values for the variables are as described below for the compounds of Formula (I).

The disclosure further provides a method of inhibiting kinases, comprising administering to a mammal in need thereof an effective amount of a disclosed kinase inhibitor, including a compound of Formula (I), wherein the values for the variables are as described below.

The disclosure further provides a method of imaging tumors with the B-Raf(V600E) mutation, comprising administering to a mammal in need thereof an effective amount of a disclosed kinase inhibitor, including a compound of Formula (I), wherein the values for the variables are as described herein.

This disclosure further provides therapeutic agents and imaging agents with unique selectivity profiles useful for the treatment of various cancers resulting from the appropriate selection of the substituted 5-membered heterocyclic scaffold, (H)-L-G-, Ar-, and A/B/D/E.

Also included in the present disclosure is the use of a disclosed kinase inhibitor, including a compound of Formula (I), or a pharmaceutically acceptable salt thereof, for the manufacture of a medicament for inhibiting kinase activity in a mammal in need of such treatment.

Also included in the present disclosure is the use of a disclosed kinase inhibitor, including a compound of Formula (I), or a pharmaceutically acceptable salt thereof, for the manufacture of a medicament for treating a disease or disorder related to the activity or expression of kinases, or for diseases or disorders in which activating mutations in, over expression of, or aberrant activity of kinase targets contributes to progression of a disease or disorder.

Also included in the present invention is a pharmaceutical composition comprising a disclosed kinase inhibitor, including a compound of Formula (I), or a pharmaceutically acceptable salt thereof, and a pharmaceutically acceptable carrier or diluent.

BRIEF DESCRIPTION OF THE DRAWINGS

FIG. 3: Illustrates representative trisubstituted imidazoles A) and C) known to interact at the Hinge and Gatekeeper Sites that have been appended to provide type-II inhibitors B) and D) as well as the strategy use to convert Type-I inhibitor C) to Type-II inhibitor.

DETAILED DESCRIPTION

Figure 1:
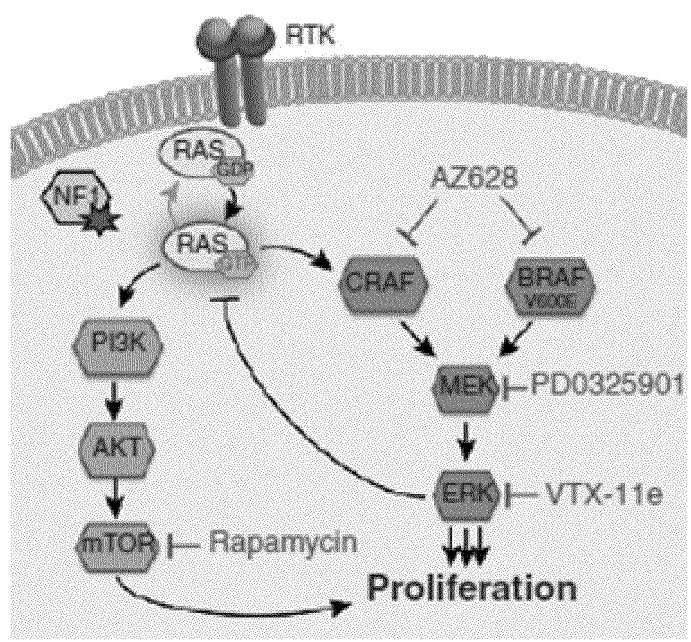
FIG. 1: Illustrates how proliferation can be stimulated through either the Ras/Raf/Mek/Erk or Ras/PI3K/Akt/mTOR pathways and how loss of the Ras negative regulatory protein Nf1 can enhance proliferation and contribute to resistance to targeted PI3K or MAPK inhibitor therapies.

In a first embodiment, the present disclosure provides kinase inhibitors of the Formula (I):

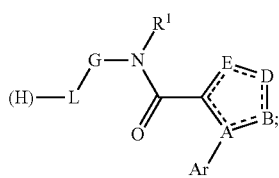

or a pharmaceutically acceptable salt thereof, wherein:
wherein
A is C or N;
B, D, and E are each independently selected from CR$_0$, N, O, and S;
R$_0$ is selected from H, —F, —Cl, —CH$_3$, —C$_2$-C$_4$ linear or branched alkyl, —C$_2$-C$_4$ alkenyl, —C$_2$-C$_4$ alkynyl, —CHR$^A$R$^B$, —(CH$_2$)$_n$—Y, —CO(CH$_2$)$_n$Y, —(CH$_2$)$_n$—NR$^A$R$^B$, [O—(CH$_2$)$_2$]$_n$Y, —(CH$_2$)$_n$SO$_2$NR$^A$R$^B$, —S(O)$_m$—(CH$_2$)$_m$—R$^1$, —S(O)$_m$R$^1$, —NR$^A$R$^B$, —OR$^2$, —CH$_2$—F, —CH$_2$[18]F, —CHF, —CHF[18]F, —CH[18]F$_2$, —CF$_3$, —CF$_2$[18]F, —CF[18]F$_2$, and —C[18]F$_3$;
provided that R$^0$ is not CF$_3$ when A, B, D, and E form a 1H-imidazole ring;
Ar is a 6-membered substituted aryl, a 6-membered optionally substituted heteroaryl, a 5 membered optionally substituted heteroaryl, or a 5,6-fused bicyclic optionally substituted heteroaryl ring system;
R$^1$ is independently H, CH$_3$, —CH$_2$CH$_3$, or cyclopropyl;
R$^2$ is independently H, —CH$_3$, —(CH$_2$)$_n$—CH$_3$, or —(CH$_2$)$_n$—NR$^A$R$^B$;
R$^A$ and R$^B$ are each independently H, CH$_3$, —CH$_2$CH$_3$, or cyclopropyl; R$^A$ and R$^B$ taken together form a 3-6 membered carbocyclic ring system or 5-7 membered saturated heterocyclic ring system;
Y is —CHR$^1$R$^2$, —CN, —COR$^1$, —CONR$^A$R$^B$, —OR$^1$, —NR$^A$R$^B$, —NR$^1$COR$^2$, —S(O)$_m$R$^1$, —SO$_2$NR$^A$R$^B$, —[O—(CH$_2$)$_2$]$_n$—CH$_2$F, —S(O)$_m$[11]CH$_3$, —[O—(CH$_2$)$_2$]$_n$—CH$_2$$^{18}$F, —CH$_2$—F; —CH$_2$[18]F, —CHF$_2$, —CHF[18]F, —CH[18]F$_2$, —CF$_3$, —CF$_2$[18]F, —CF[18]F$_2$, or —C[18]F$_3$;
m is 0, 1, or 2;
n is 1, 2, or 3;
G is an appropriate group that interacts with the Gatekeeper region in the ATP binding site of a specific kinase or profile of kinases of interest;
L is a linker group or ring system; and
(H) is an appropriate group that interacts with the Hinge-region in the ATP binding site of a specific kinase or profile of kinases of interest.

In a second embodiment, the present disclosure provides kinase inhibitors of the Formula (I), wherein R$_0$ is selected from H, —F, —Cl, —CH$_3$, —C$_2$-C$_4$ linear or branched alkyl, —C$_2$-C$_4$ alkenyl, —C$_2$-C$_4$ alkynyl, —CHR$^A$R$^B$, —Y, —CO (CH$_2$)$_n$Y, —(CH$_2$)$_n$—NR$^A$R$^B$, —[O—(CH$_2$)$_2$]$_n$Y, —(CH$_2$)$_n$SO$_2$NR$^A$R$^B$, —S(O)$_m$—(CH$_2$)$_m$—R$^1$, —S(O)$_m$R$^1$, —NR$^A$R$^B$, OR$^2$, C$_2$—F, —CHF$_2$, and —CF$_3$; provided that R$^0$ is not CF$_3$ when A, B, D, and E form a 1H-imidazole ring; and Y is —CHR$^1$R$^2$, —CN, —COR$^1$, CONR$^A$R$^B$, —OR$^1$, —NR$^A$R$^B$, —NR$^1$COR$^2$, —S(O)$_m$R$^1$, —SO$_2$NR$^A$R$^B$, —[O—(CH$_2$)$_2$]$_n$—CH$_2$F, —CH$_2$—F, —CHF$_2$, or —CF$_3$; and wherein the remaining variables are as described in the above embodiment.

In a third embodiment, the compounds of Formula (I) are represented by the following structural formulae:

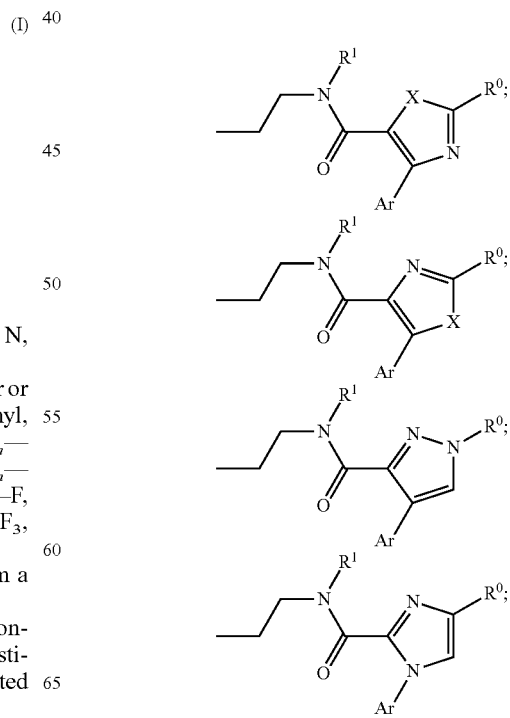

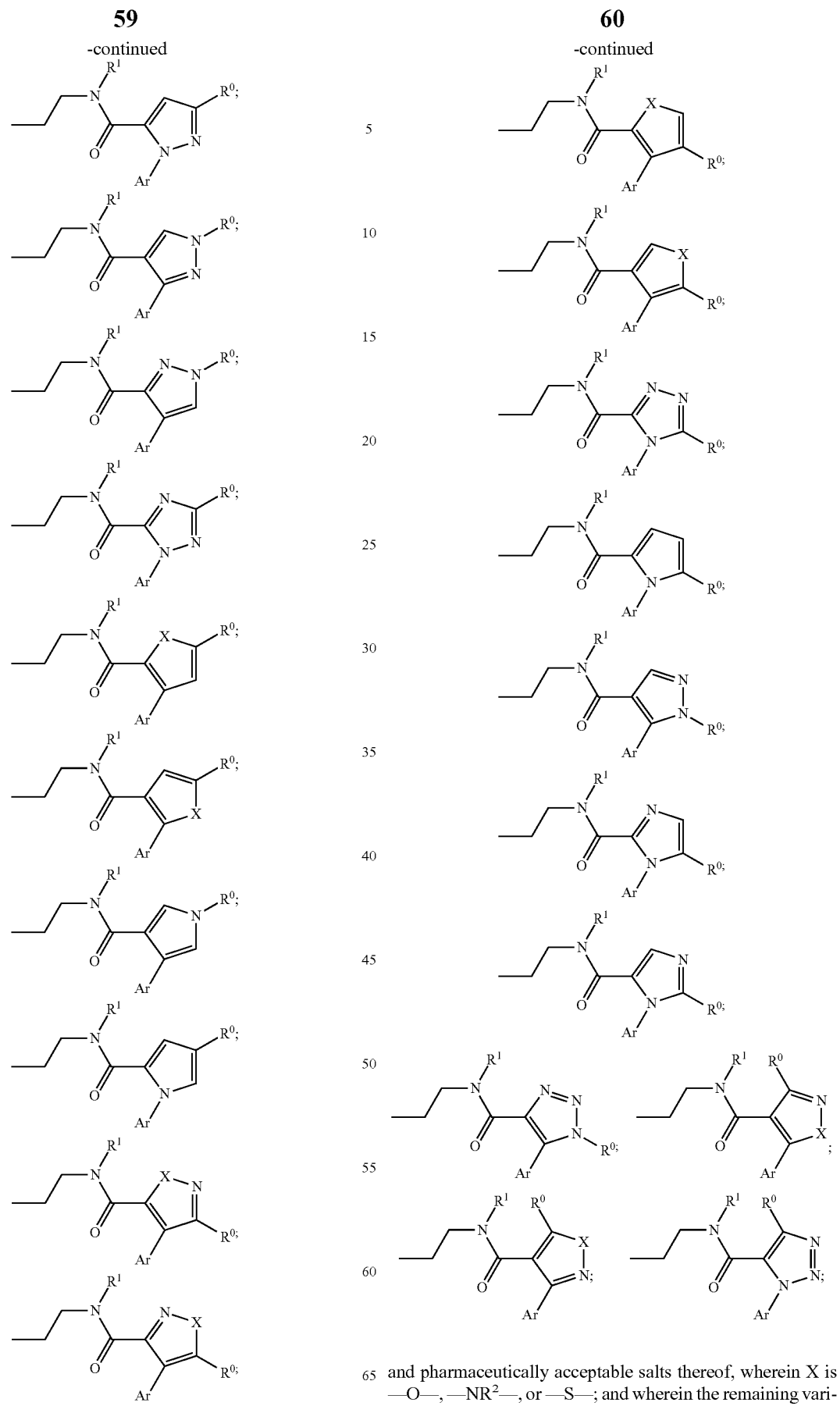
and pharmaceutically acceptable salts thereof, wherein X is —O—, —NR²—, or —S—; and wherein the remaining variables are as described in the above embodiments.

In a fourth embodiment, Ar is of the structural formulae:

In a fifth embodiment, G is of the structural formulae:

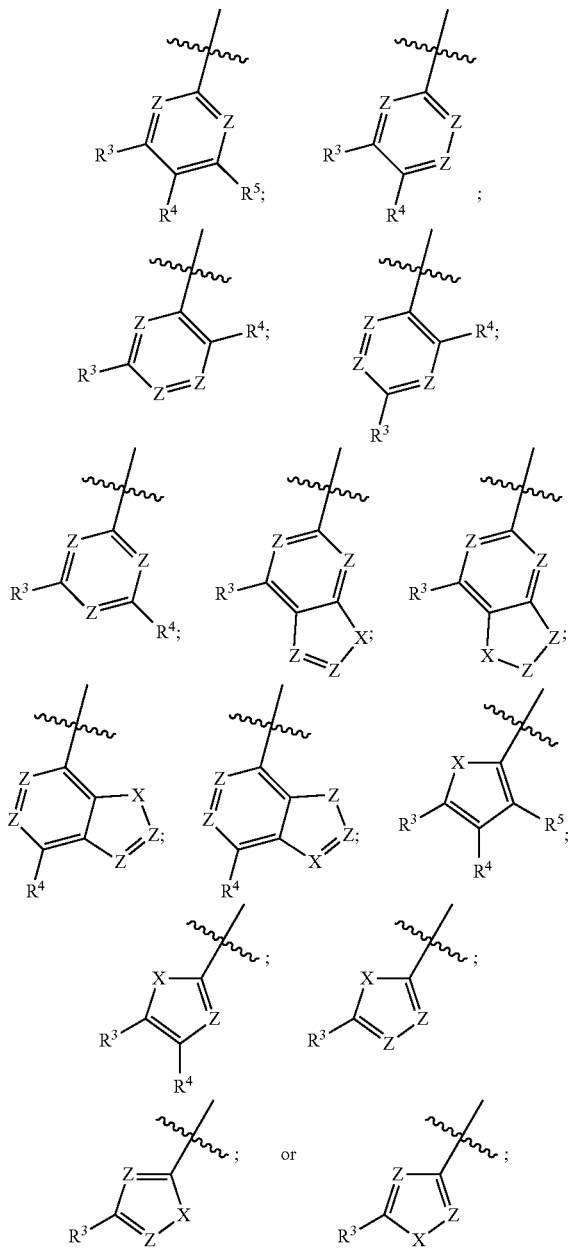

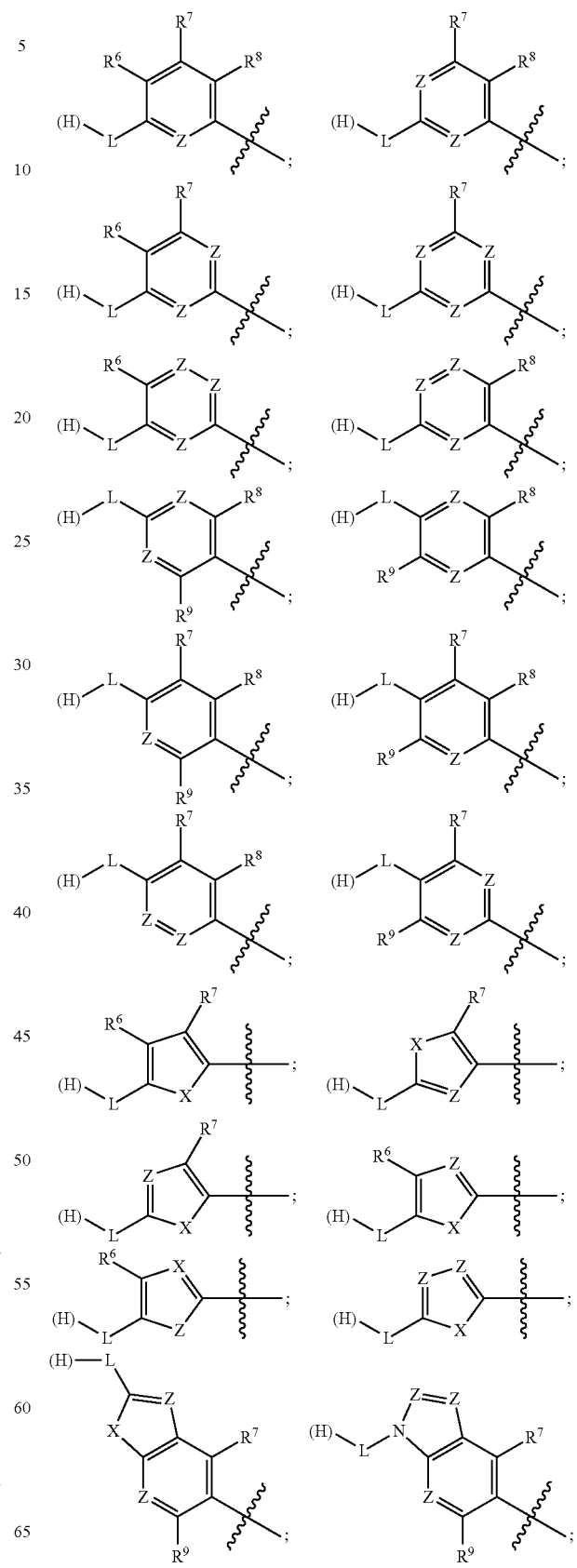

wherein:

Z is independently selected from —CH—, —CF—, or —N—;

X is selected from —O—, —S—, —NR$^2$—;

R$_3$, R$_4$, and R$_5$ are each independently selected from H, —CH$_3$, —CH$_2$CH$_3$, cyclopropyl, —F, —[18]F, —Cl, —Br, —CH$_2$F, —CH$_2$[18]F, —CHF$_2$, —CF$_3$, —HC=CHR$^1$, —CCR$^1$; —CN, —OCF$_3$, —NHR$^1$—OR$^1$, and —S(O)$_m$R$^1$; and wherein the remaining variables are as described in the above embodiments. Alternatively, R$_3$, R$_4$, and R$_5$ are each independently selected from H, —CH$_3$, —CH$_2$CH$_3$, cyclopropyl, —F, —Cl, —Br, —CH$_2$F, —CHF$_2$, —CF$_3$, —HC=CHR$^1$, —CCR$^1$; —CN, —OCF$_3$, —NHR$^1$—OR$^1$, and —S(O)$_m$R$^1$.

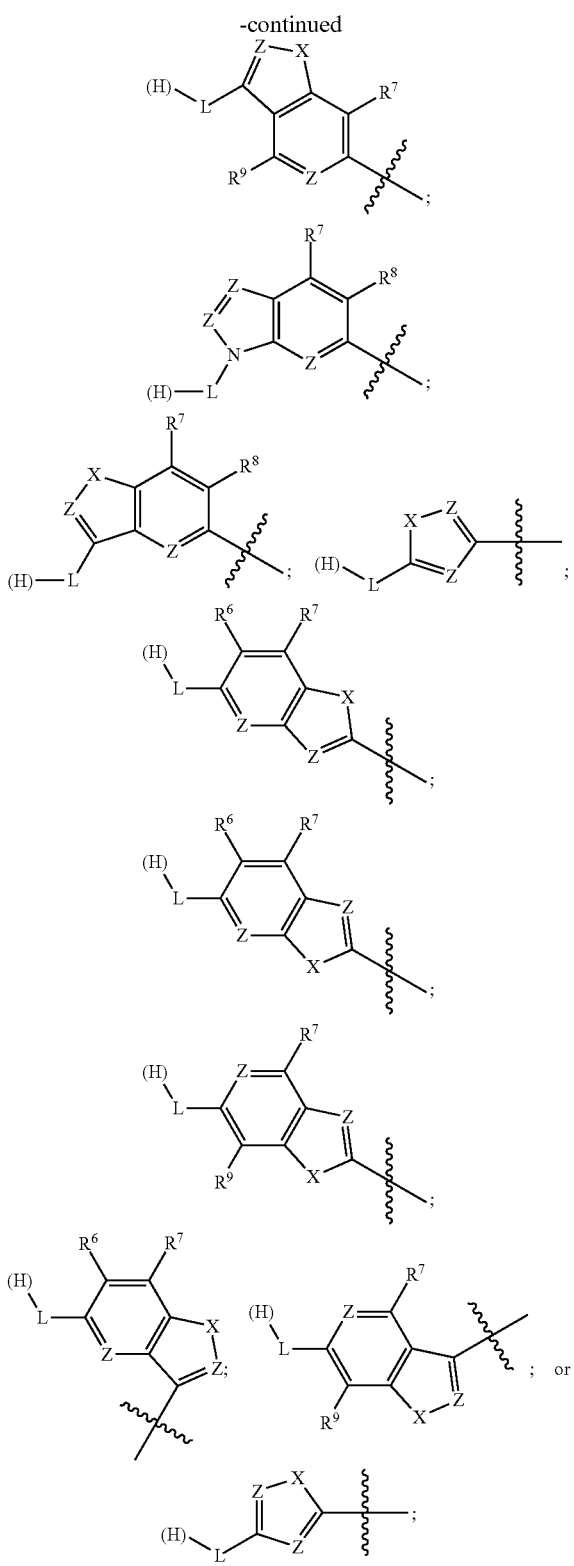

wherein:

R⁶, R⁷, and R⁸ are each independently selected from H, —CH₃, —CH₂CH₃, cyclopropyl, —CN; —OR¹, —(CH₂)ₙOR¹, —NR^A R^B, —(CH₂)ₙNR^A R^B, —S(O)ₘR¹, —(CH₂)ₙ—S(O)ₘR¹, —F, and —Cl; and wherein the remaining variables are as described in the above embodiments.

In a sixth embodiment, G is of structural formulae:

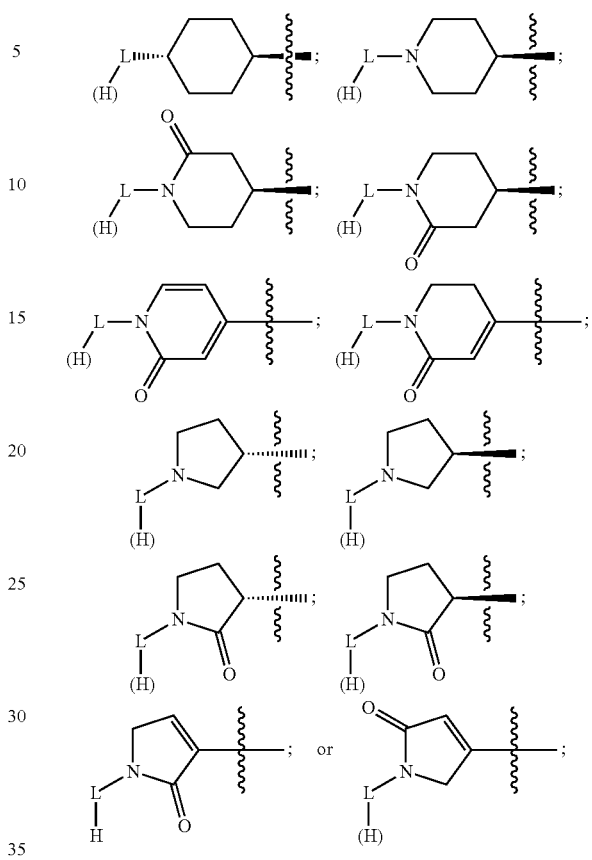

and wherein the remaining variables are as described in the above embodiments.

In a seventh embodiment, L is i. a bond, —(CH₂)ₙ—, —(CH₂)ₙ—O—, -(cis)CH═CH—, -(trans)CH═CH—, —CC—, —OCH₂—, —OCH(CH₃)—, —CH(CH₃)O—, —S(O)ₘ—, —(CH₂)ₙS(O)ₘ—, —S(O)ₘ(CH₂)ₙ—, —(CH₂)ₙNH—, —NH—(CH₂)ₙ—, —NHCH(CH₃)—, —CH(CH₃)NH—, —NR₁C(O)—, —C(O)NR₁—, —XC(O)NH—, —NHC(O)X—, —(CH₂)ₙ—CO—, or —CO—(CH₂)ₙ—; or ii. of the structural formulae

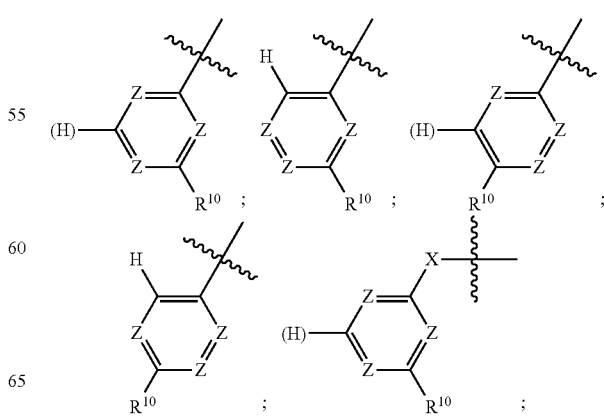

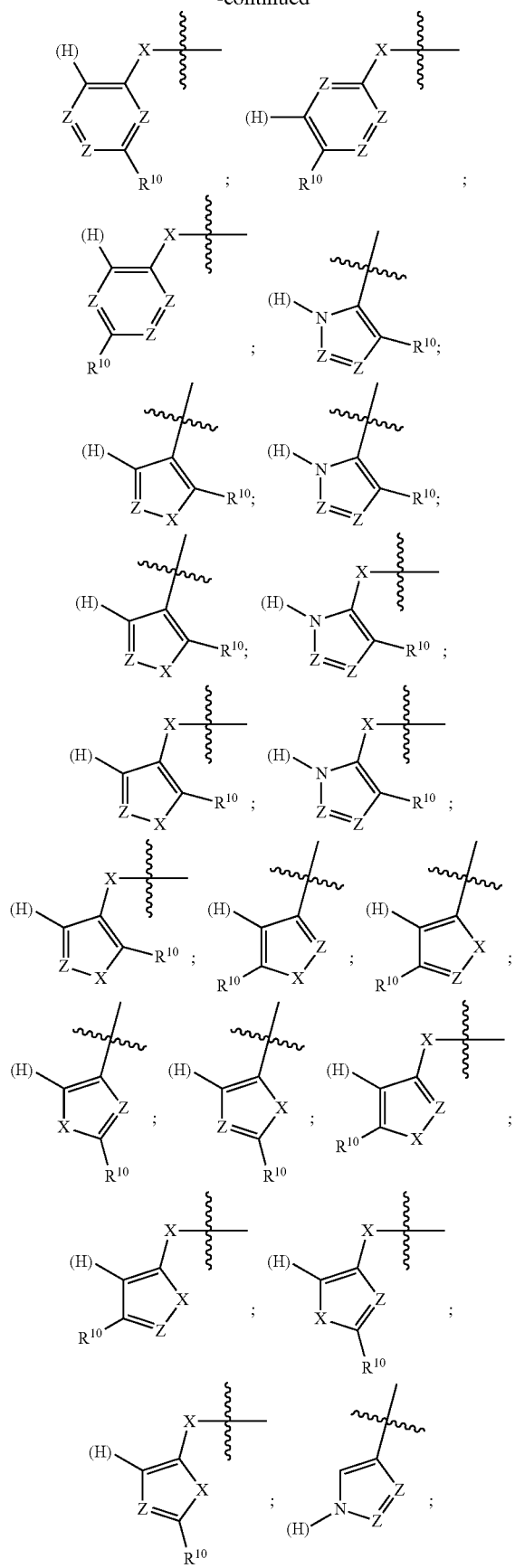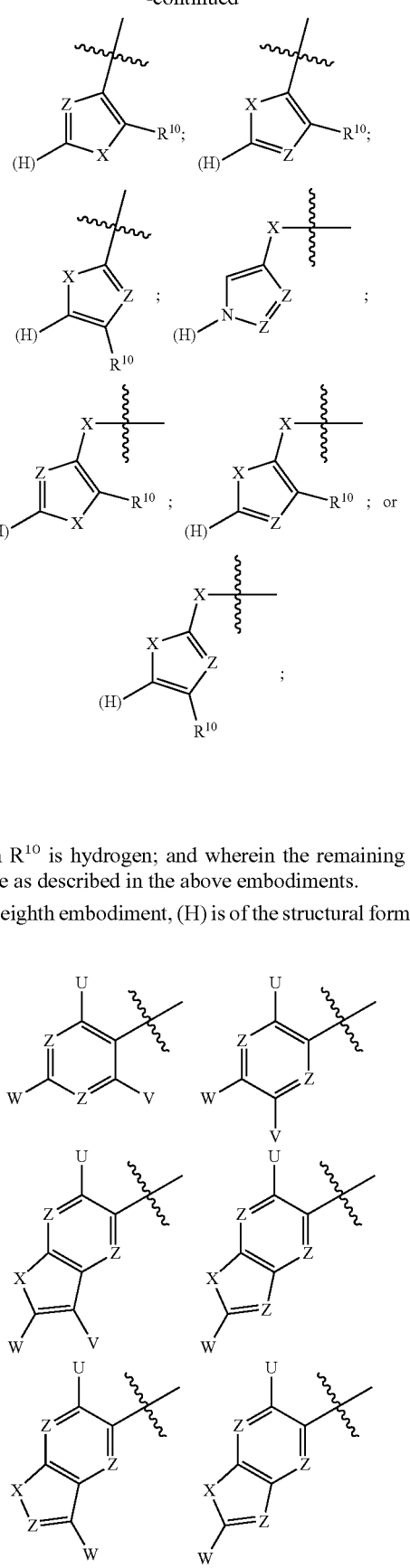
wherein $R^{10}$ is hydrogen; and wherein the remaining variables are as described in the above embodiments.
In an eighth embodiment, (H) is of the structural formulae:
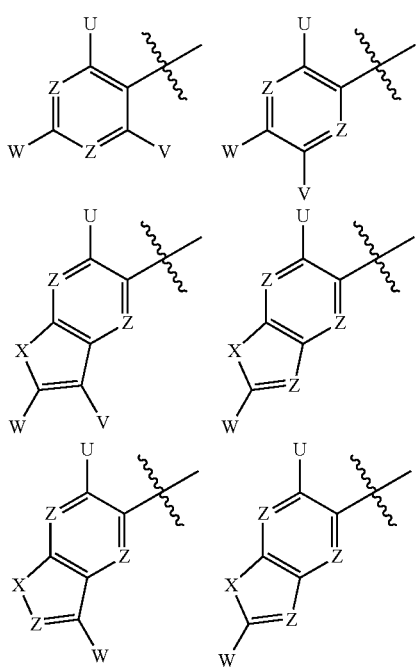

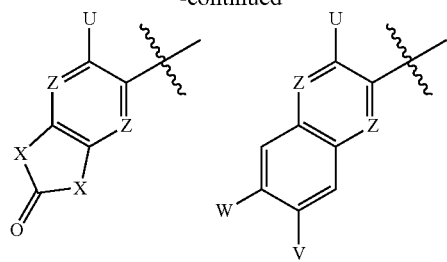
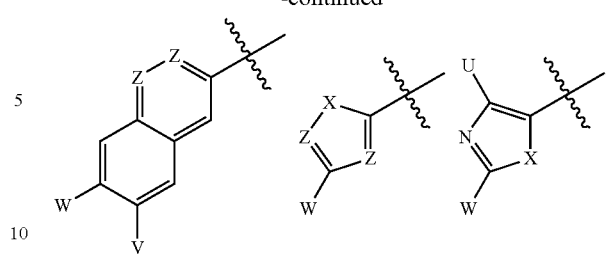
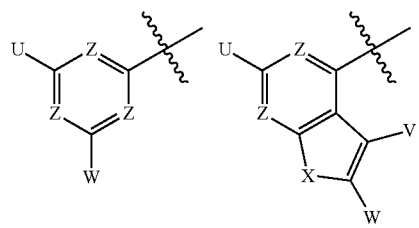
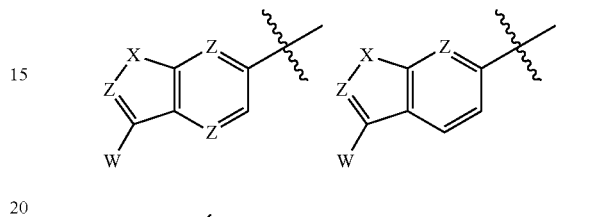
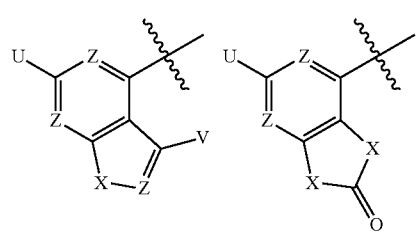
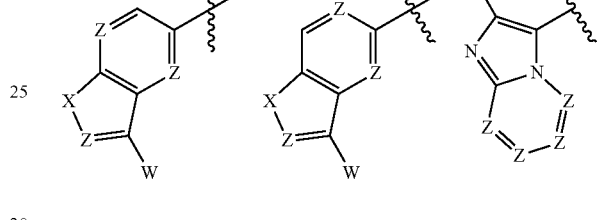
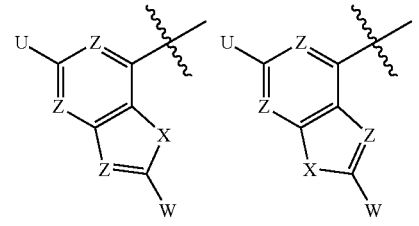
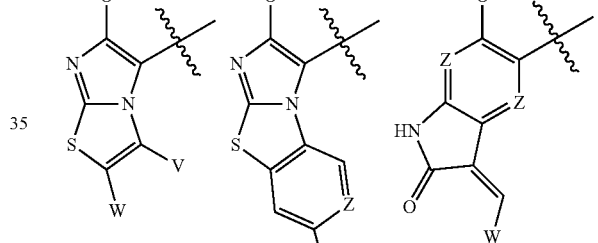
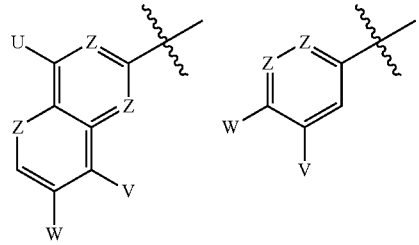
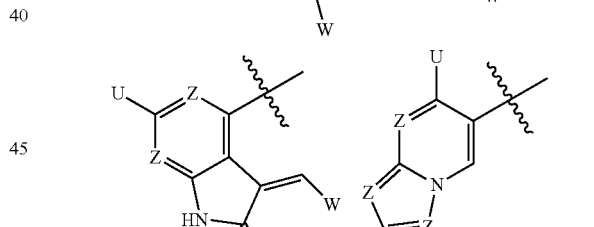
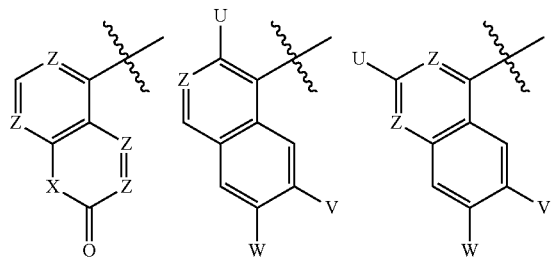
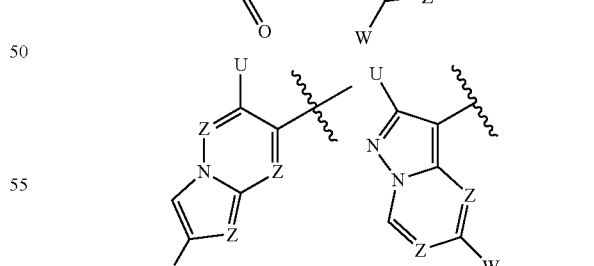
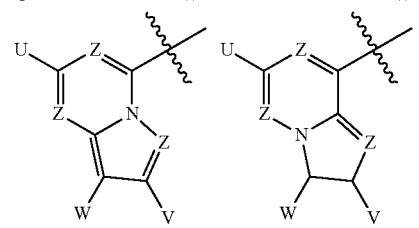
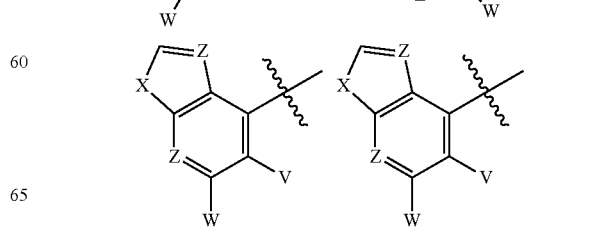

-continued

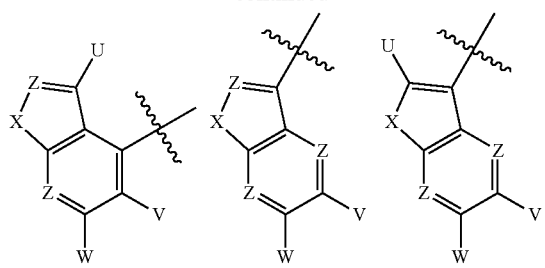

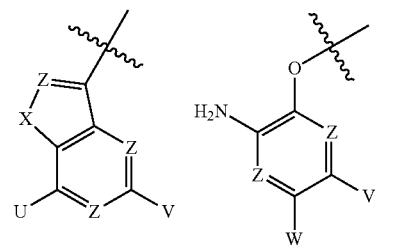

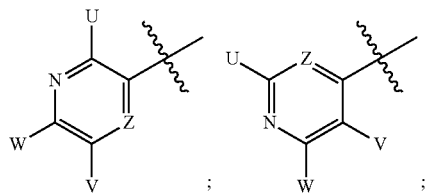

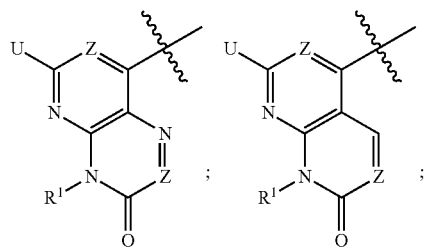

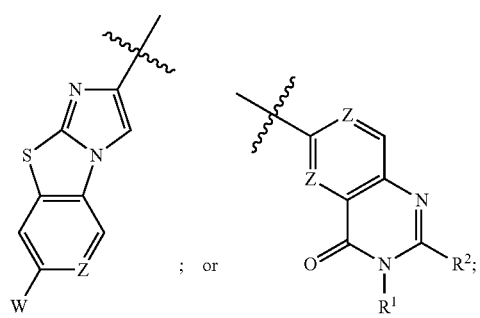

; or wherein:

U is —H, F, Cl, —OR$^1$, or —NHR$^1$;

V and W are each independently selected from —H, —F, —Cl, —CF$_3$, —CONHR$^2$, —X—R$^2$, —X—(CH$_2$)$_n$CN, —X—(CH$_2$)$_m$COR$^1$, X—(CH$_2$)$_m$CONR$^A$R$^B$, —X—CH$_2$—(CH$_2$)$_n$OR$^1$, —X—CH$_2$—(CH$_2$)$_n$NR$^A$R$^B$, —X—CH$_2$—(CH$_2$)$_n$S(O)$_m$R$^1$, —X—(CH$_2$)$_m$S(O)$_m$NR$^A$R$^B$, —O—(CH$_2$)$_2$NR$^A$R$^B$, —O—(CH$_2$)$_3$NR$^A$R$^B$, —O—(CH$_2$)$_n$CONR$^A$R$^B$, —C$_5$-C$_6$heteroaryl, —COCH=CH—(CH$_2$)$_n$NR$^A$R$^B$, and T; and T is:

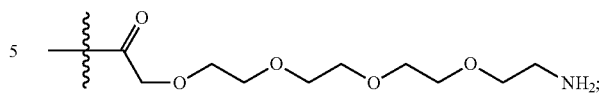

and wherein the remaining variables are as described in the above embodiments.

In an ninth embodiment, (H) is alternatively of the structural formulae:

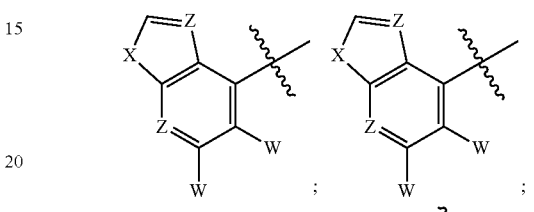

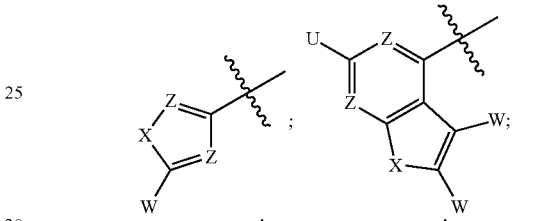


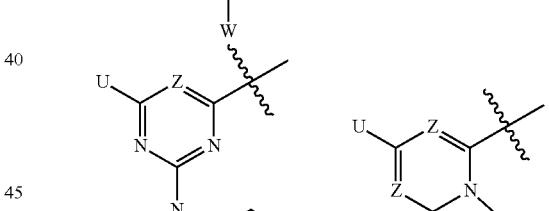


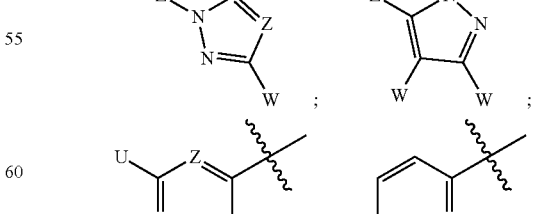

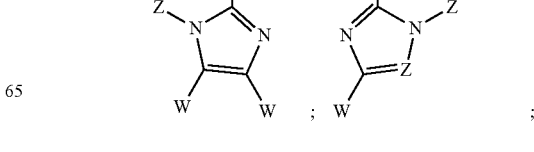

-continued

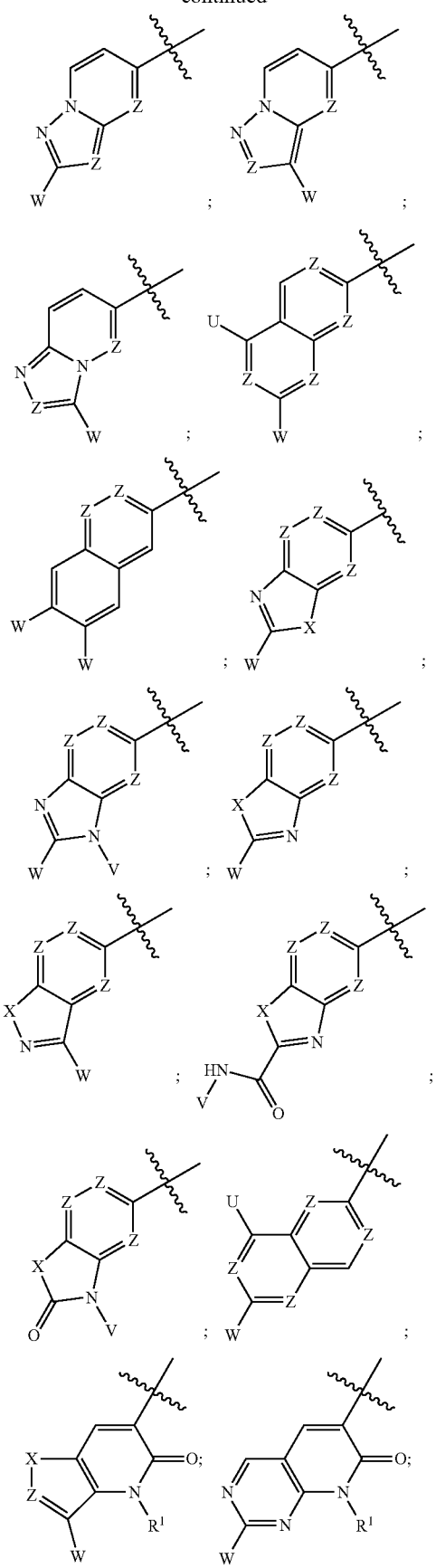

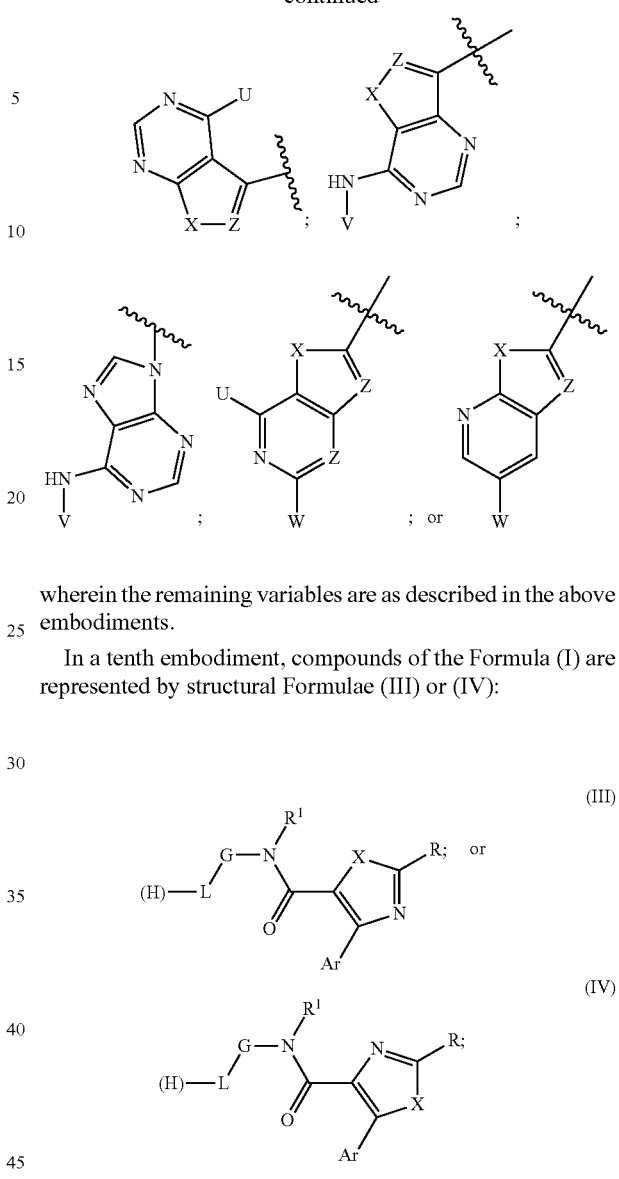

wherein the remaining variables are as described in the above embodiments.

In a tenth embodiment, compounds of the Formula (I) are represented by structural Formulae (III) or (IV):

$$(H)-L-G-N(R^1)-C(=O)-\underset{Ar}{\underset{|}{\overset{X}{\diagdown}}}\overset{R}{\diagup}_{N} \quad (III)$$

or $$(H)-L-G-N(R^1)-C(=O)-\underset{Ar}{\underset{|}{\overset{N}{\diagdown}}}\overset{R}{\diagup}_{X} \quad (IV)$$

or a pharmaceutically acceptable salt thereof, and wherein the remaining variables are as described in the above embodiments.

In an eleventh embodiment, compounds described herein are represented by structural Formulae (V) or (VI):

(V)

$$(H)-L-G-N(R^1)-C(=O)-\text{thiazole}-\text{aryl}(R^3,R^4)$$

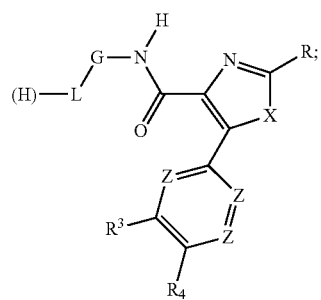
(VI)
and pharmaceutically acceptable salts thereof, and wherein the remaining variables are as described in the above embodiments.
In a twelfth embodiment, compounds described herein are represented by structural Formulae (VII) to (XIV):
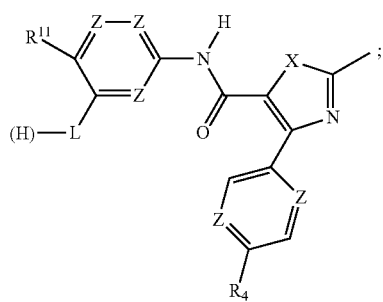
(VII)
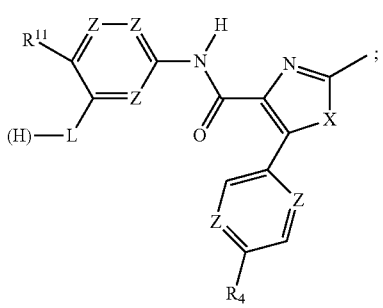
(VIII)
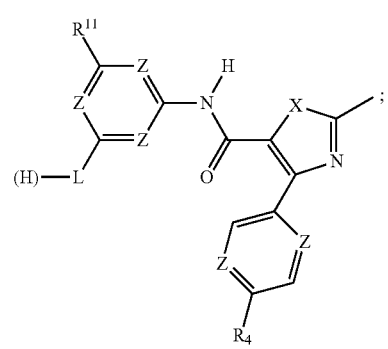
(IX)
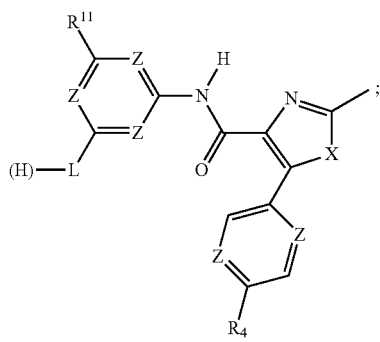
(X)
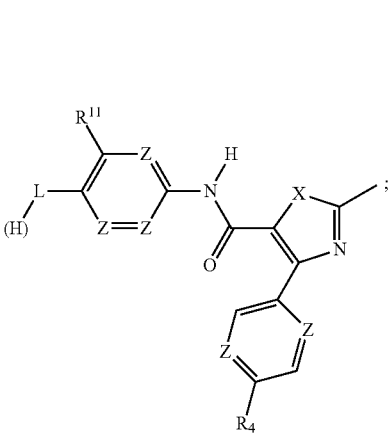
(XI)
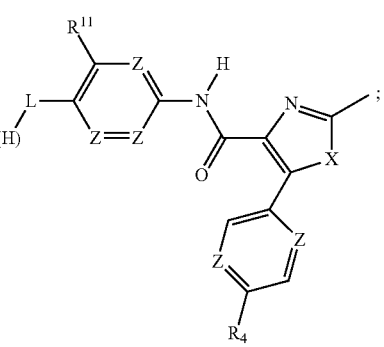
(XII)
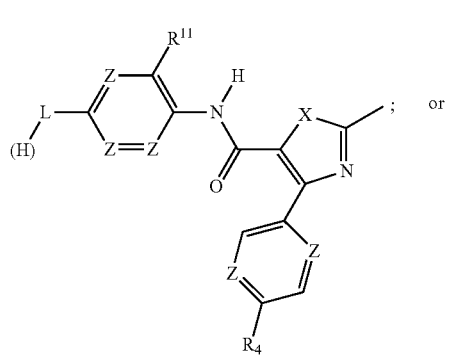
(XIII) or

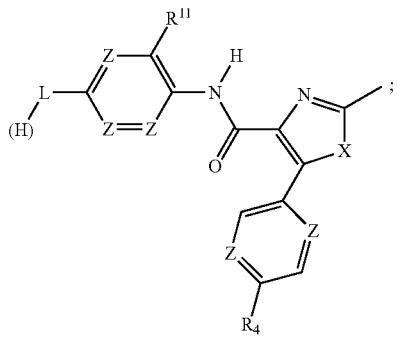

or a pharmaceutically acceptable salt, wherein $R^{11}$ is selected from H, —CH₃, —CH₂CH₃, cyclopropyl, —F, —Cl, —CN, —OCH₃, and —S—CH₃; and wherein the remaining variables are as described in the above embodiments.

In a thirteenth embodiment, L is a bond, —O—, =NH—, —S(O)$_m$—, —CC—, —O—CHR¹—, —NHCHR¹—, S(O)$_m$CHR¹—, —CHR¹⁰—, —CHR¹NH—, or —CHR¹S(O)$_m$—; and wherein the remaining variables are as described in the above embodiments.

In a fourteenth embodiment, L is of the structural formulae:

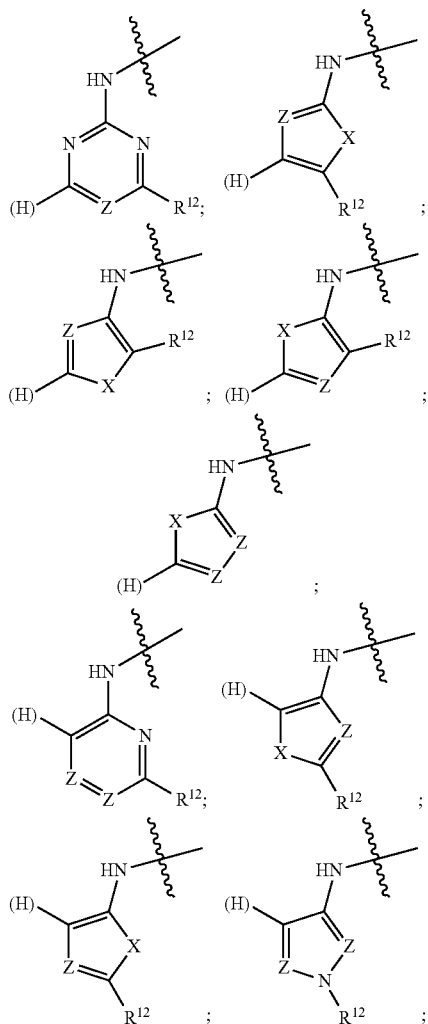

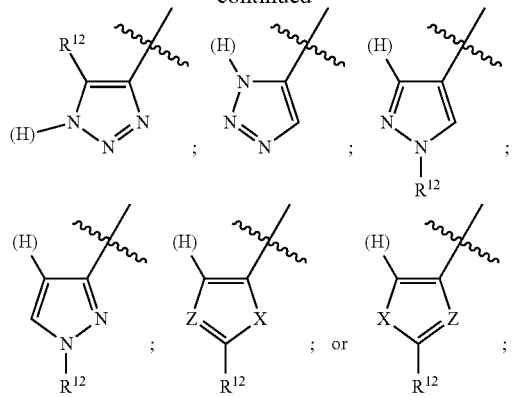

wherein $R^{12}$ is selected from H, —CH₃, —CH₂—CH₃, cyclopropyl, —S(O)$_m$R², —O—R², and NR$^A$R$^B$; and wherein the remaining variables are as described in the above embodiments.

In a fifteenth embodiment, (H) is of structural formulae:

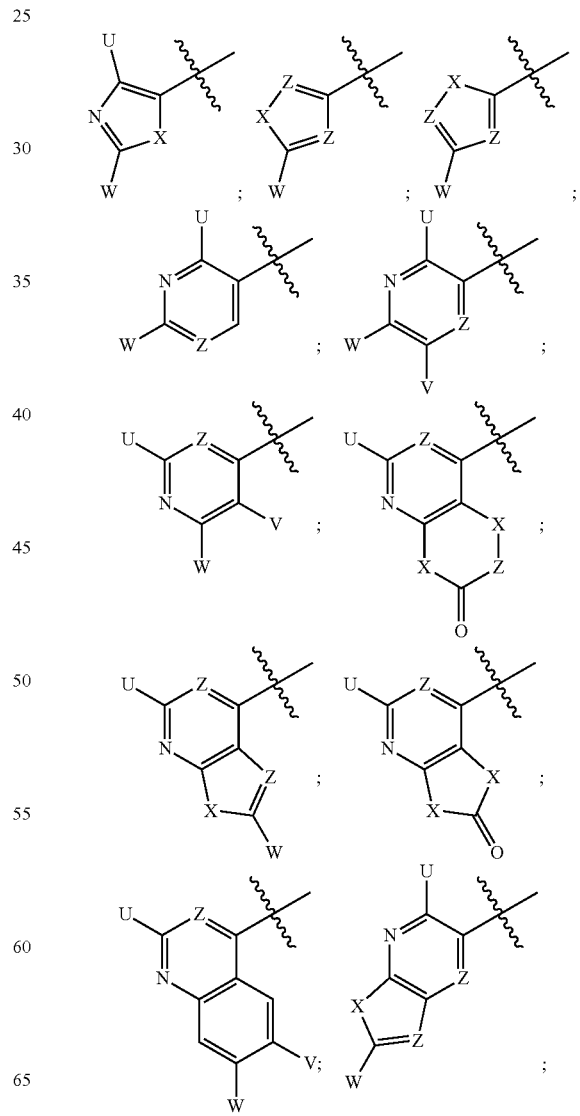

-continued
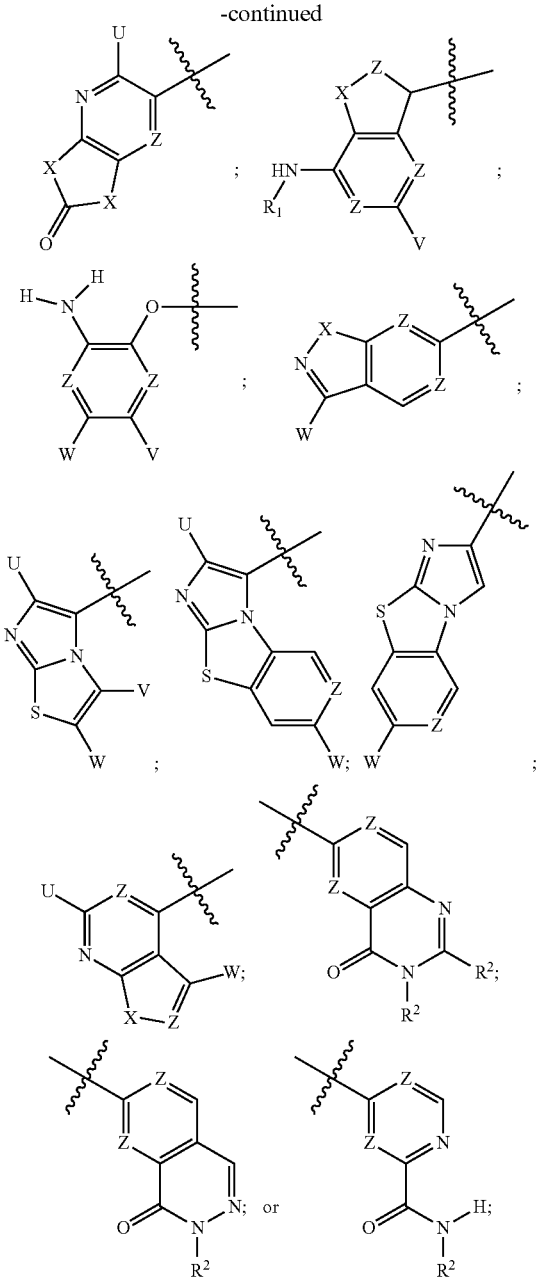
wherein C$_5$-C$_6$ heteroaryls selected from
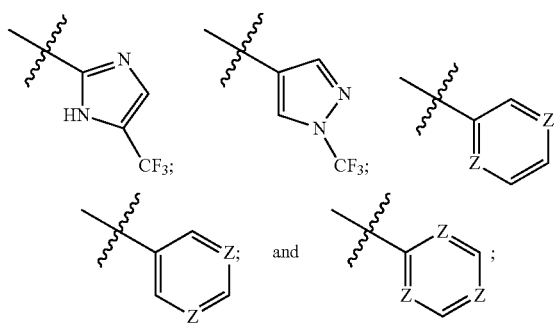
and wherein the remaining variables are as described in the above embodiments.
In a sixteenth embodiment, the compounds provided herein are of the formulae:
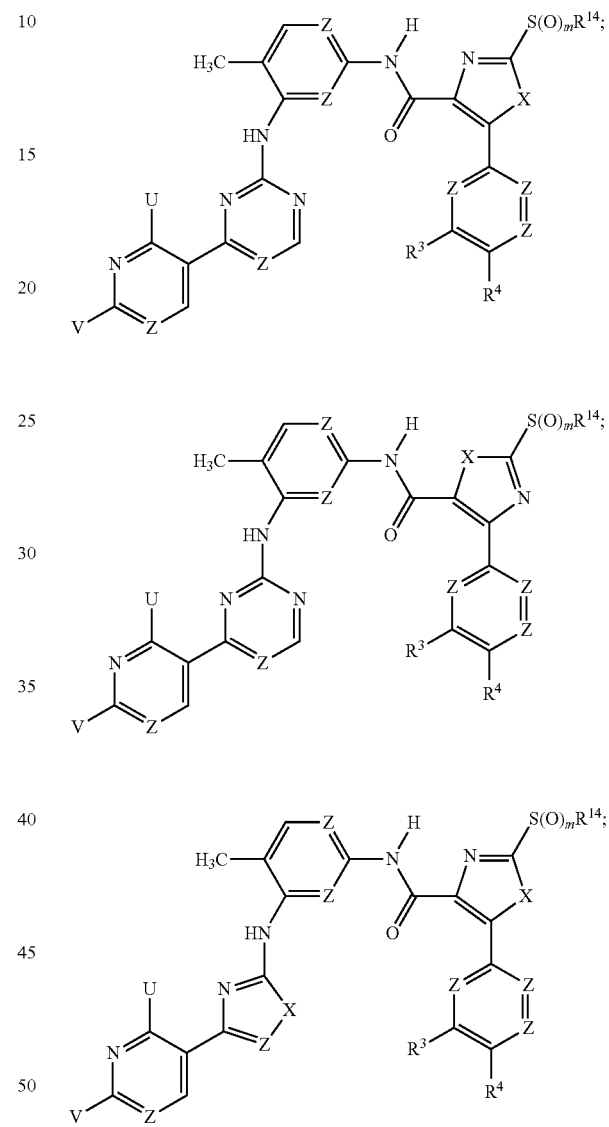
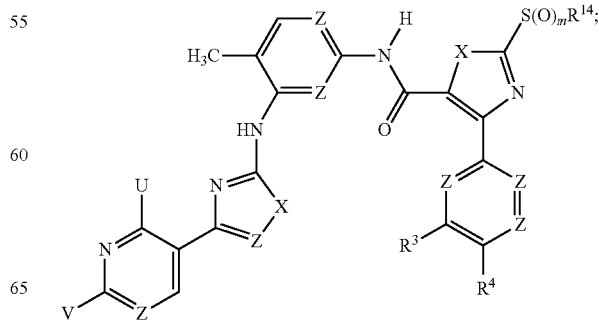

-continued
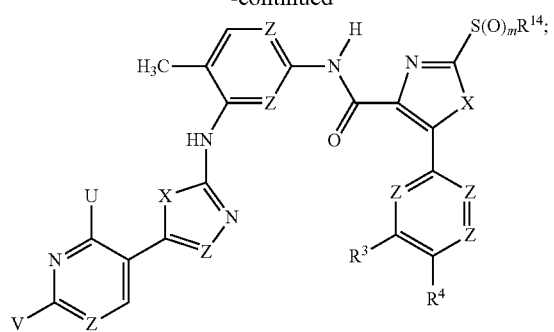
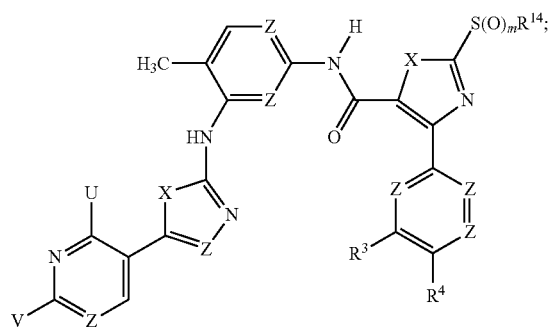
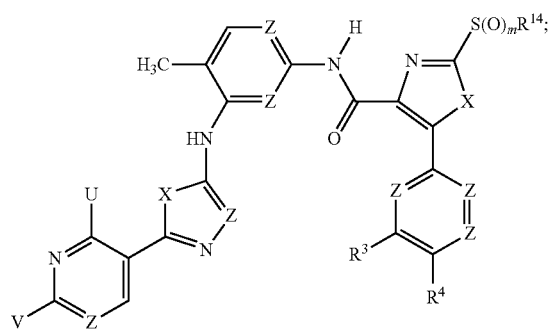
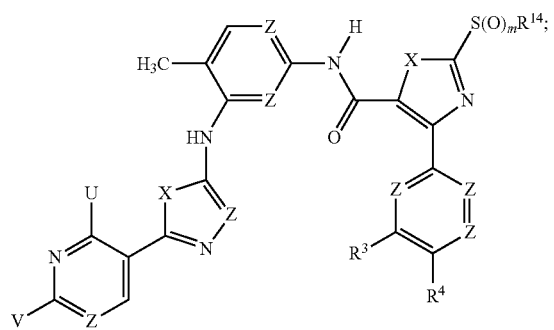
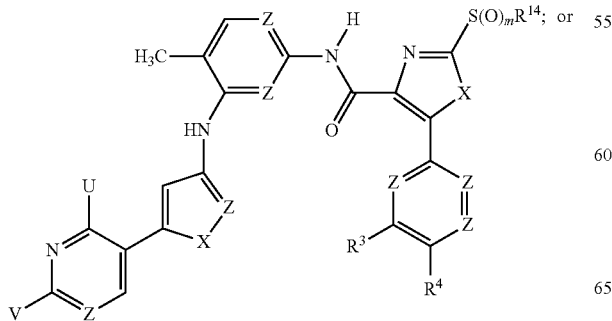
-continued
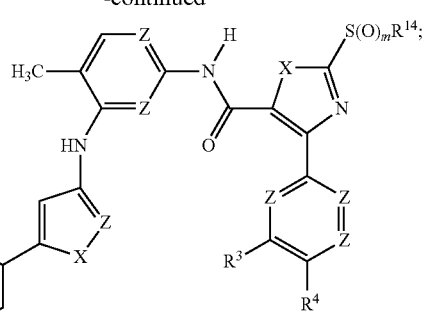
or a pharmaceutically acceptable salt thereof, wherein $R_{14}$ is —$(CH_2)_m$—$CH_3$, —$(CH_2)_nCH_2[18]F$—$[11]CH_3$ or —$(CH_2)_mNR^AR^B$; and wherein the remaining variables are as described in the above embodiments. Alternatively, $R_{14}$ is —$(CH_2)_m$—$CH_3$, or —$(CH_2)_mNR^AR^B$.
In a seventeenth embodiment, the compounds provided herein are of the formula:
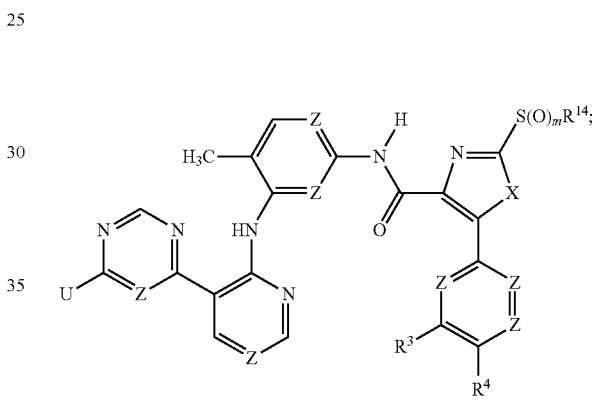
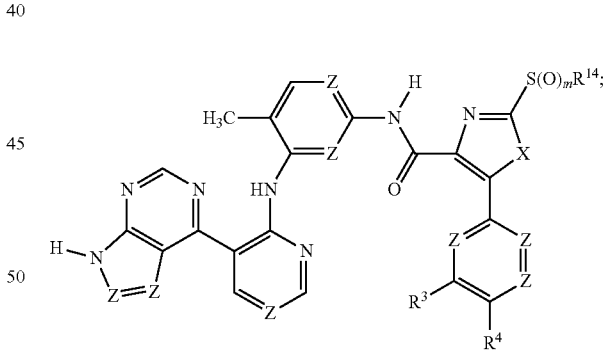
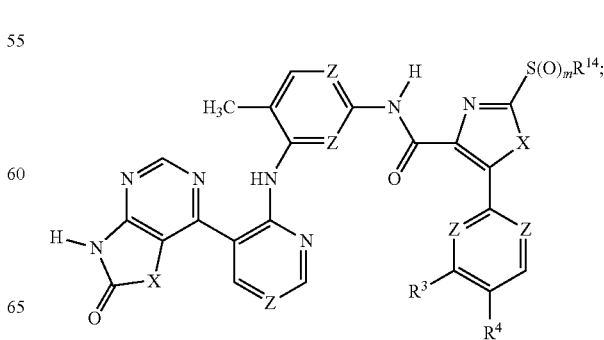

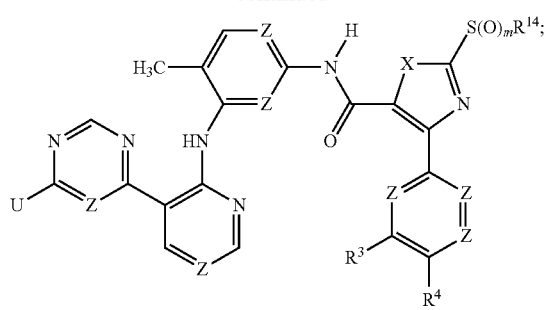
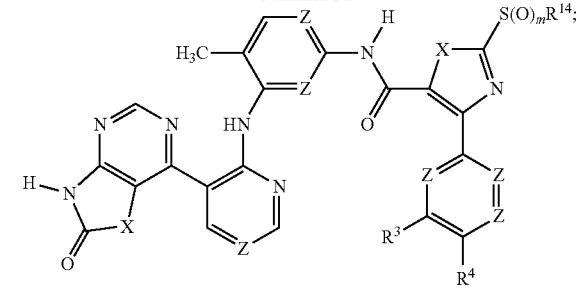
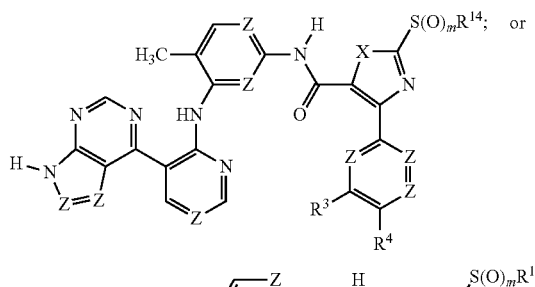
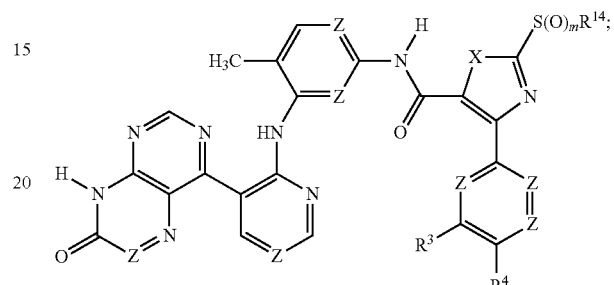
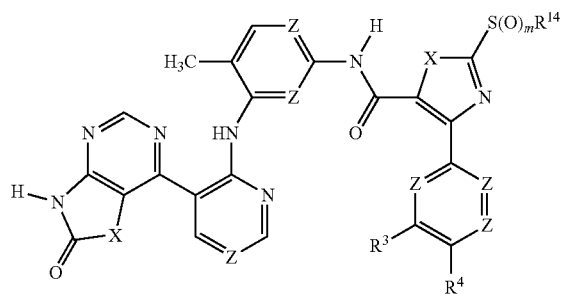
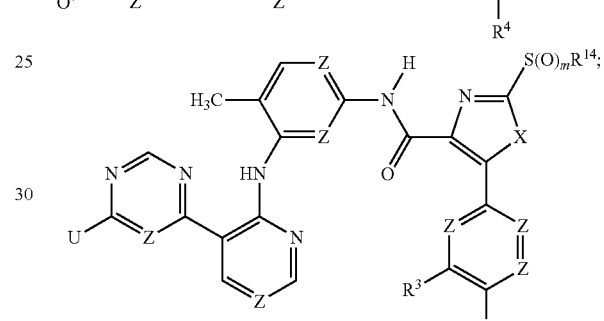
and pharmaceutically acceptable salts thereof, wherein $R_{14}$ is —$(CH_2)_m$—$CH_3$ or —$(CH_2)_m NR^A R^B$; and wherein the remaining variables are as described in the above embodiments.
In an eighteenth embodiment, the compounds provided herein are of the formula:
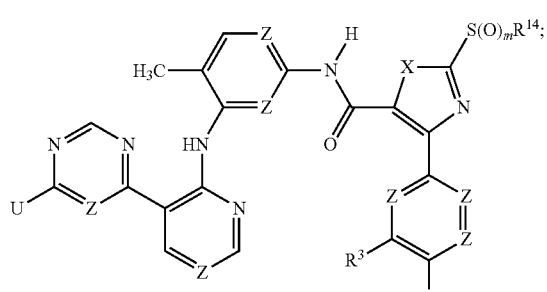
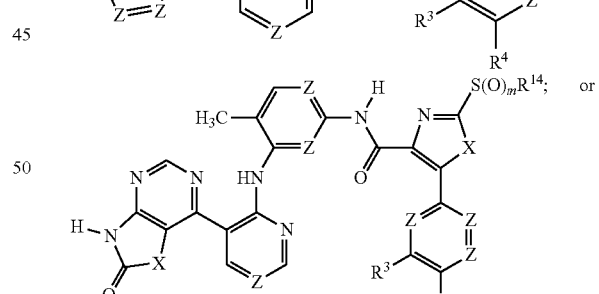
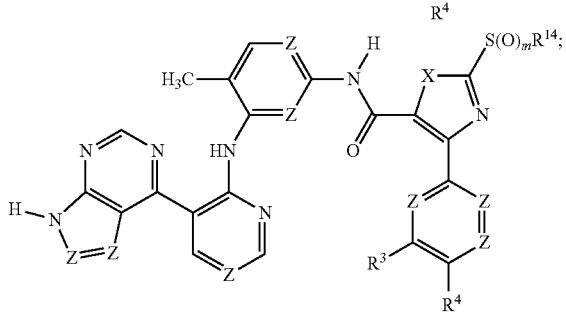
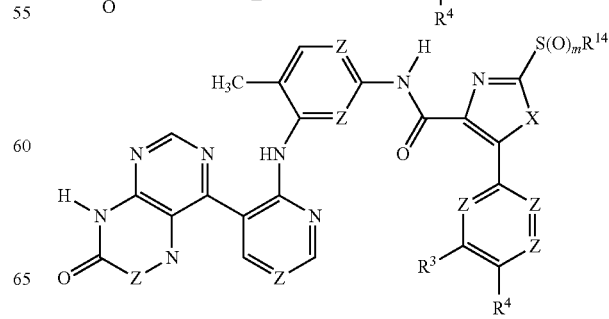

or a pharmaceutically acceptable salt thereof, wherein $R_{14}$ is —$(CH_2)_m$—$CH_3$, —$(CH_2)_nCH_2[18]F$—$[11]CH_3$ or —$(CH_2)_mNR^AR^B$; and wherein the remaining variables are as described in the above embodiments. Alternatively, $R_{14}$ is —$(CH_2)_m$—$CH_3$, or —$(CH_2)_mNR^AR^B$.

In a nineteenth embodiment, the compounds provided herein are of the formula:

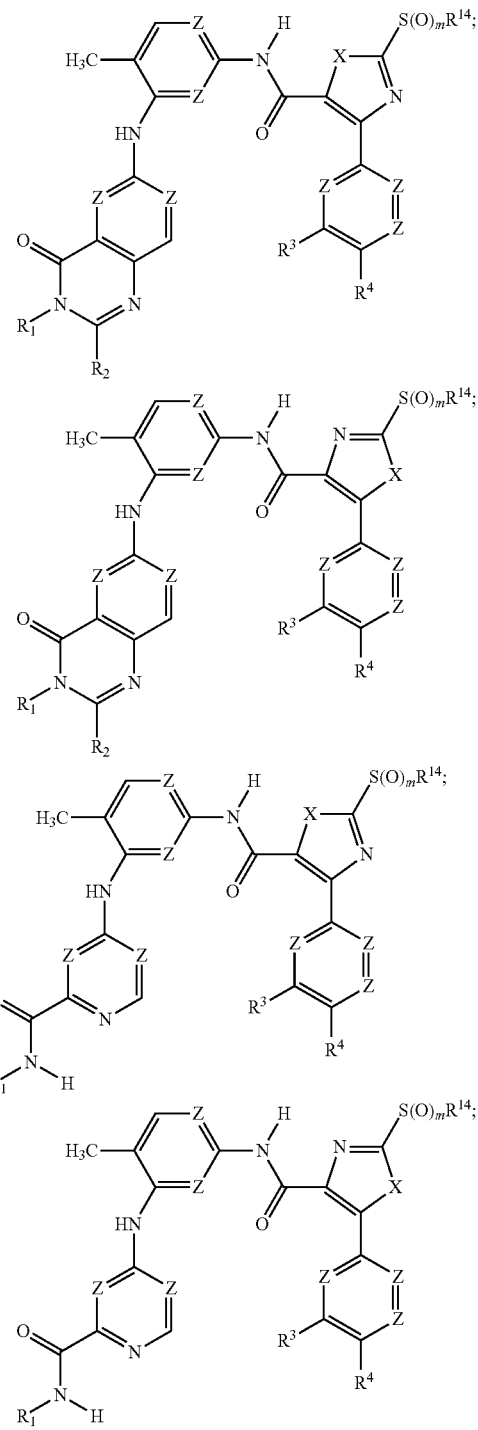

and pharmaceutically acceptable salts thereof, wherein $R_{14}$ is —$(CH_2)_m$—$CH_3$, —$(CH_2)_nCH_2[18]F$—$[11]CH_3$ or —$(CH_2)_mNR^AR^B$; and wherein the remaining variables are as described in the above embodiments. Alternatively, $R_{14}$ is —$(CH_2)_m$—$CH_3$, or —$(CH_2)_mNR^AR^B$.

In a twentieth embodiment, the compounds provided herein are of the formula:

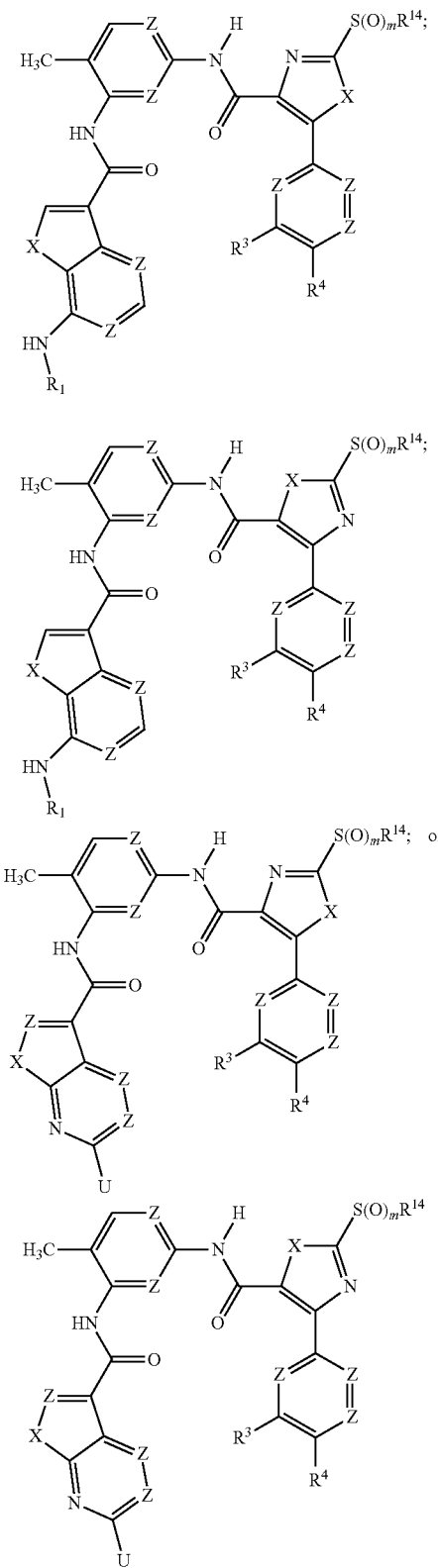

and pharmaceutically acceptable salts thereof, wherein $R_{14}$ is —$(CH_2)_m$—$CH_3$, —$(CH_2)_nCH_2[18]F$—$[11]CH_3$ or —$(CH_2)_mNR^AR^B$; and wherein the remaining variables are as described in the above embodiments. Alternatively, $R_{14}$ is —$(CH_2)_m$—$CH_3$, or —$(CH_2)_mNR^AR^B$.

In a twenty-first embodiment, the compounds provided herein are of the formula:

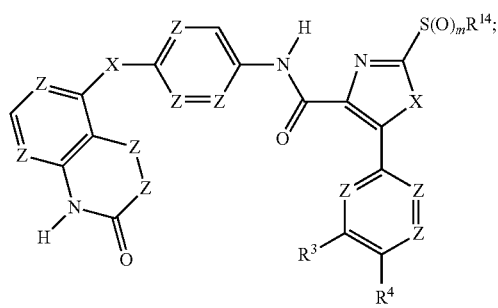

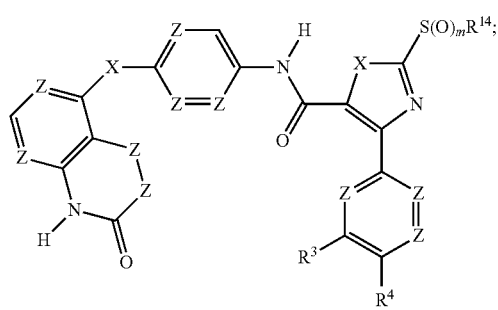

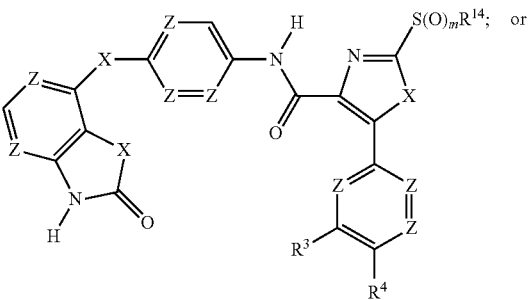

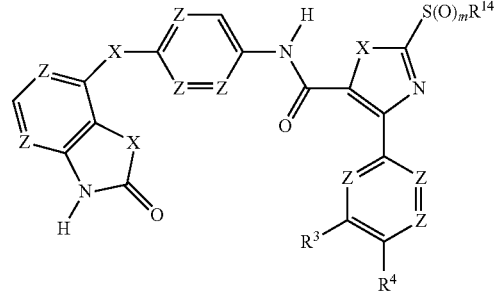

and pharmaceutically acceptable salts thereof, wherein $R_{14}$ is —$(CH_2)_m$—$CH_3$, —$(CH_2)_nCH_2[18]F$—$[11]CH_3$ or —$(CH_2)_mNR^AR^B$; and wherein the remaining variables are as described in the above embodiments. Alternatively, $R_{14}$ is —$(CH_2)_m$—$CH_3$, or —$(CH_2)_mNR^AR^B$.

In a twenty-second embodiment, the compounds provided herein are of the structural formulae (XX-XXV):

XX
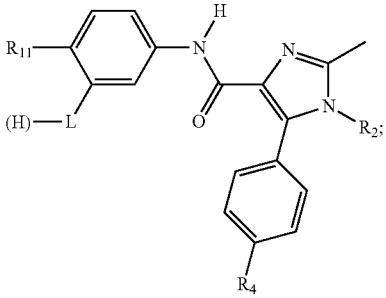

XXI
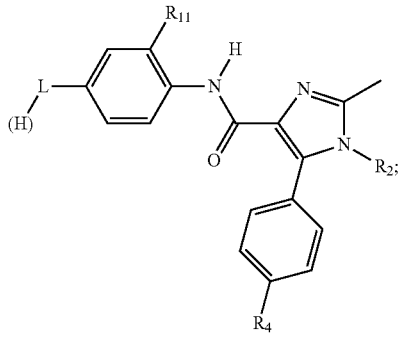

XXII
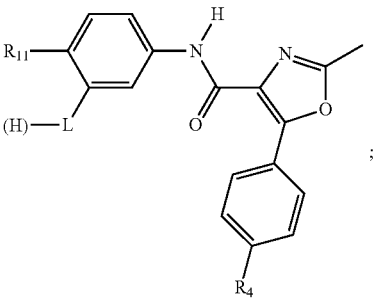

XXIII
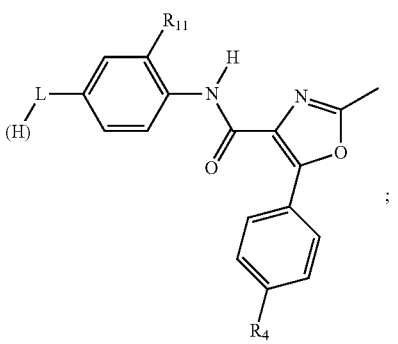

XXIV
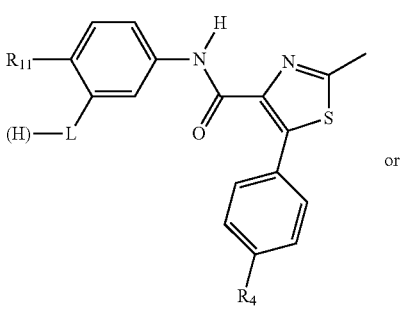

or

XXV

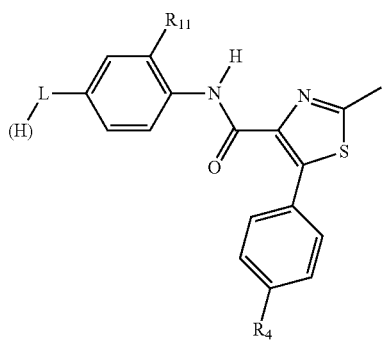

XXVIV

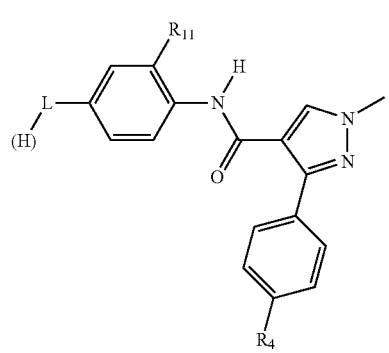

and pharmaceutically acceptable salts thereof; wherein the variables are as described in the above embodiments. Alternatively, the compounds provided herein are of the structural formulae (XXVI-XXVIV):

and pharmaceutically acceptable salts thereof; wherein the variables are as described in the above embodiments.

In a twenty-third embodiment, L is —O—, —S—, —NH— or —C(O)NR¹; and (H) is of the structural formulae:

XXVI

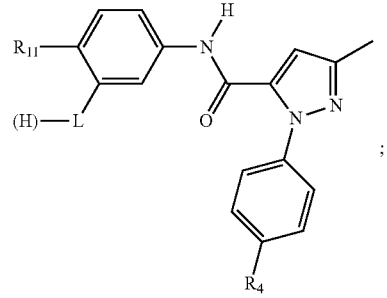

XXVII

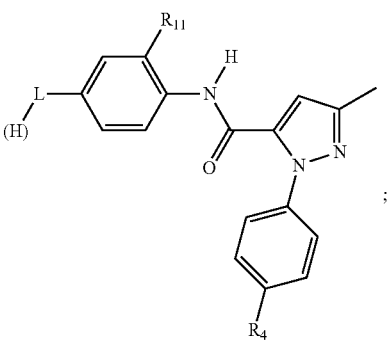

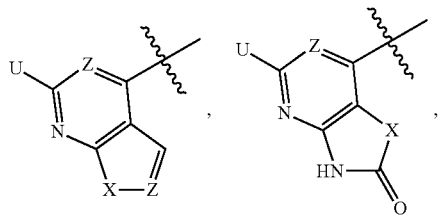

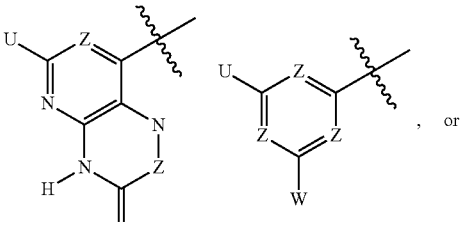

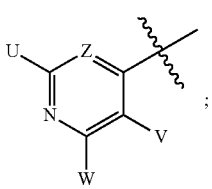

wherein the remaining variables are as described in the above embodiments.

In a twenty-fourth embodiment, L is —O— or —C(O)NR¹; and (H) is of the structural formulae:

XXVIII

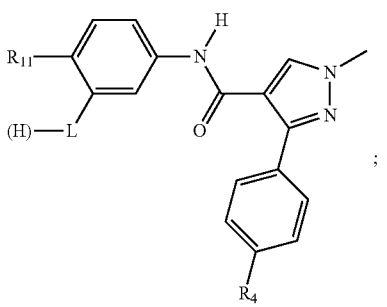

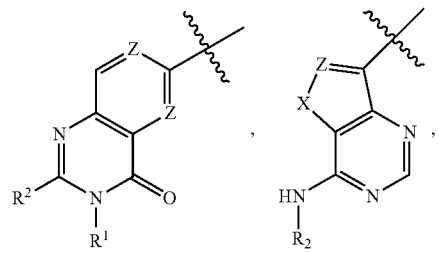

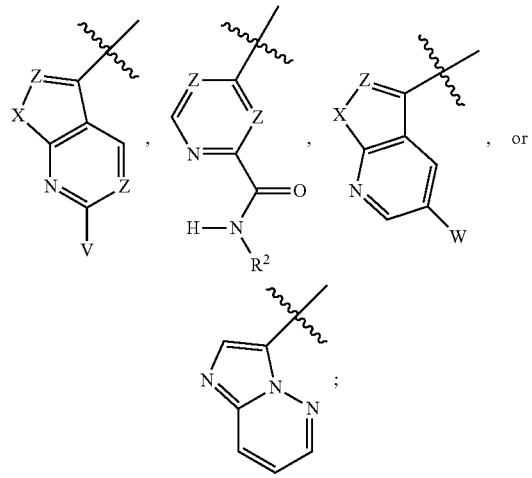
wherein the remaining variables are as described in the above embodiments.
In a twenty-fifth embodiment, (H) is of structural formulae:
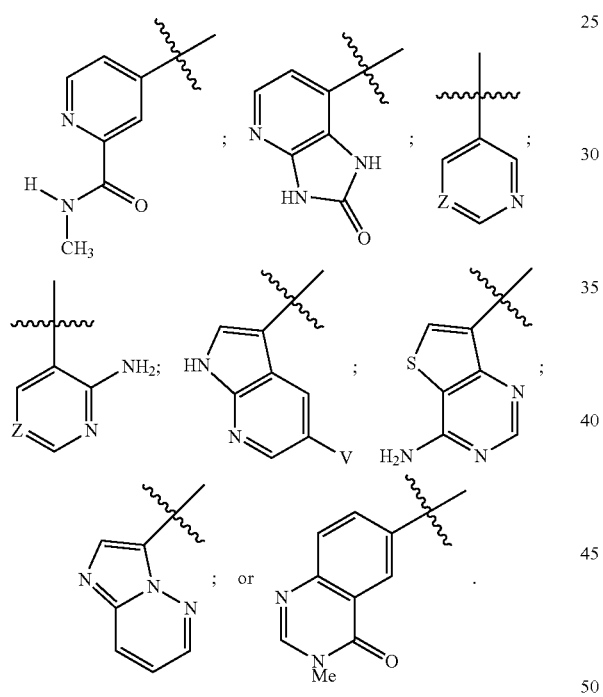
In a twenty-sixth embodiment, the compounds described herein are selected from:
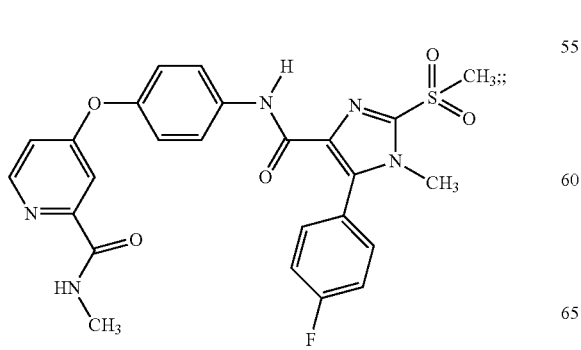
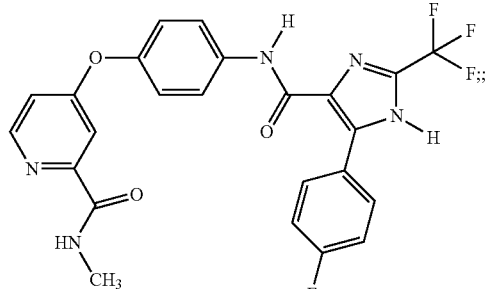
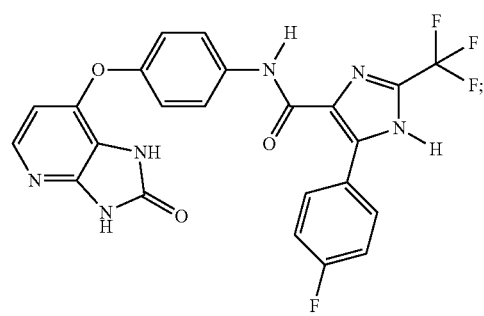
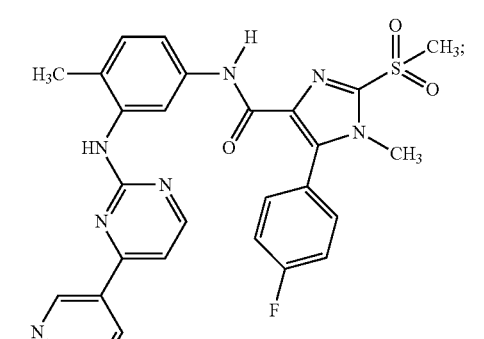
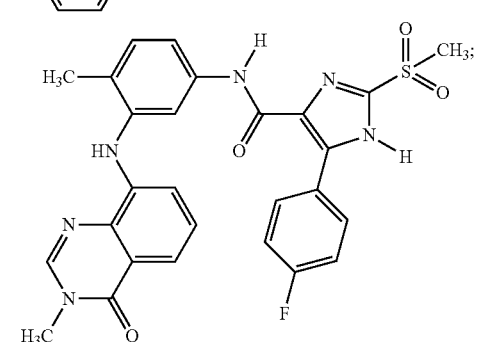
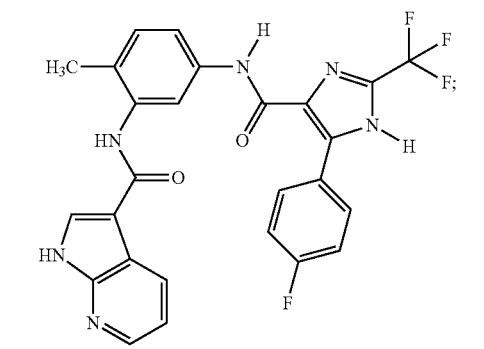

91
-continued
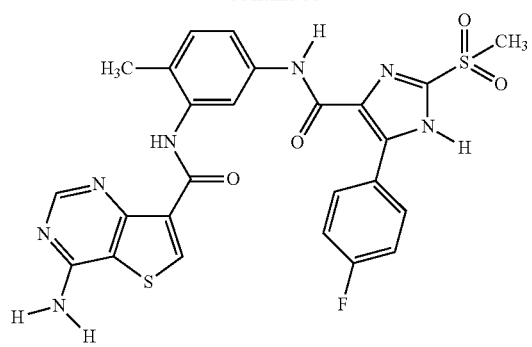
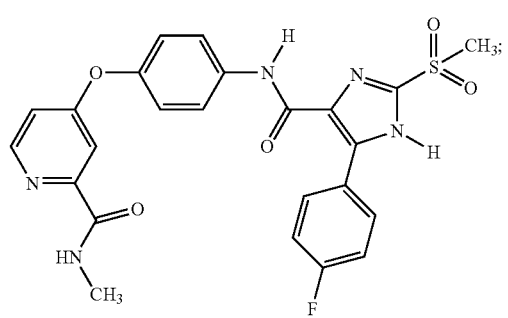
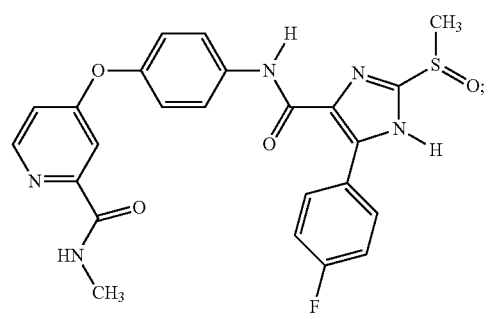
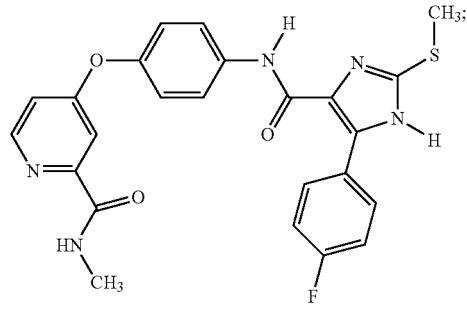
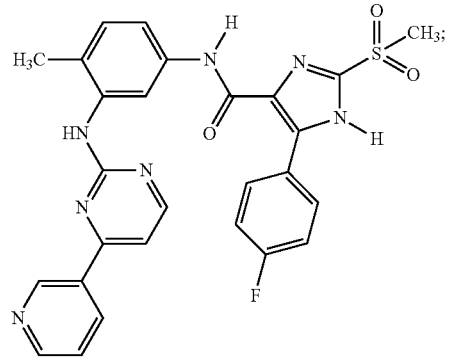
92
-continued
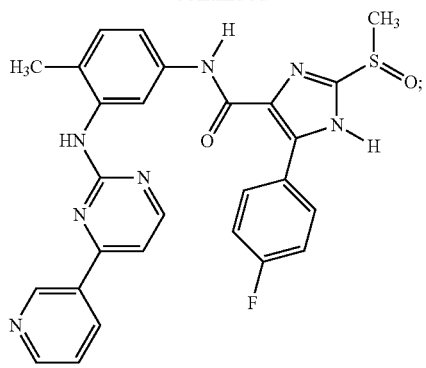
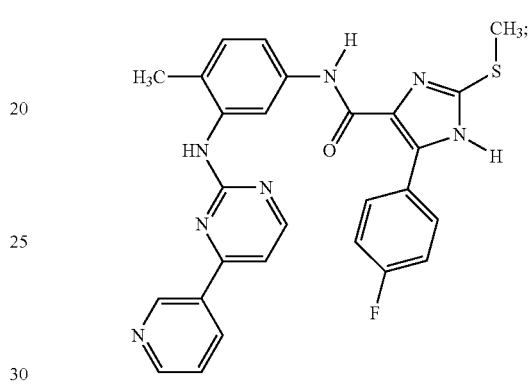
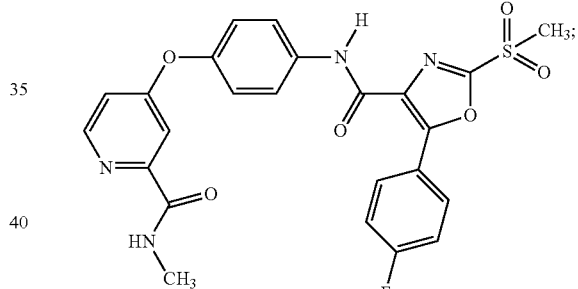
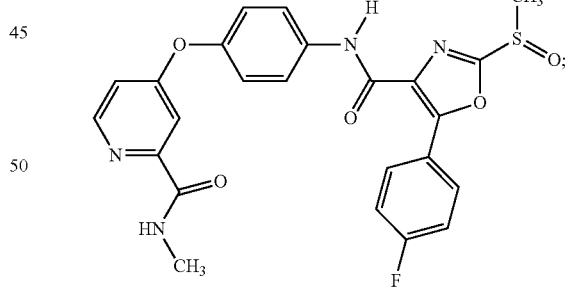
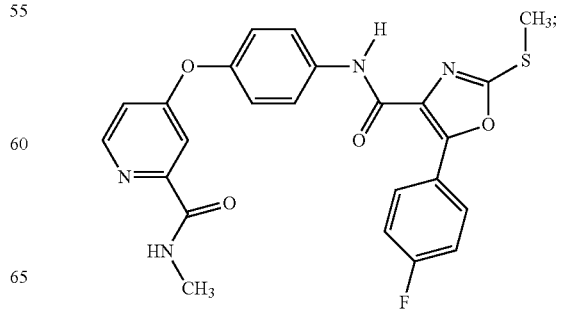

93
-continued
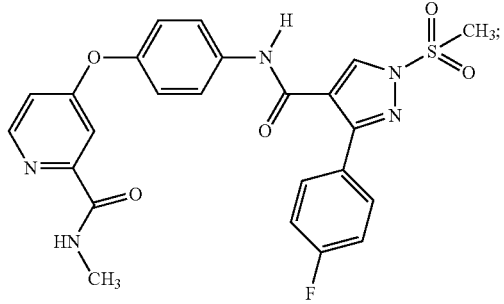
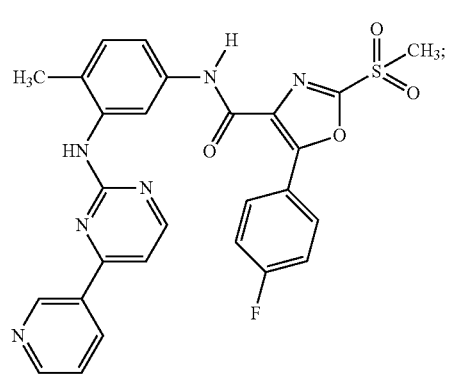
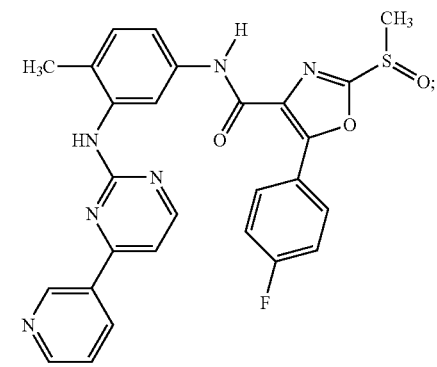
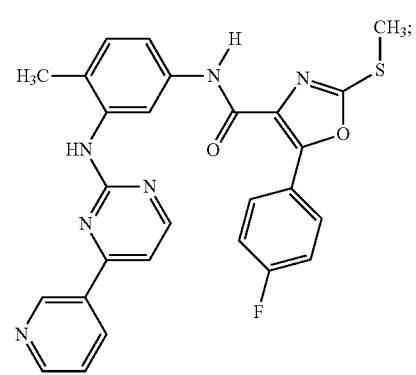
94
-continued
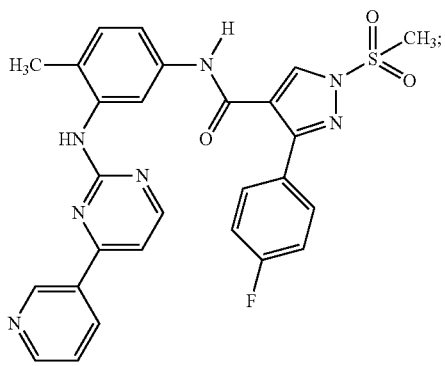
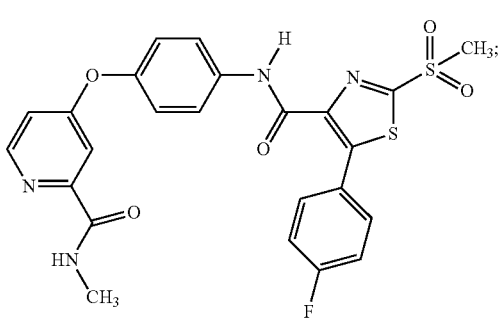
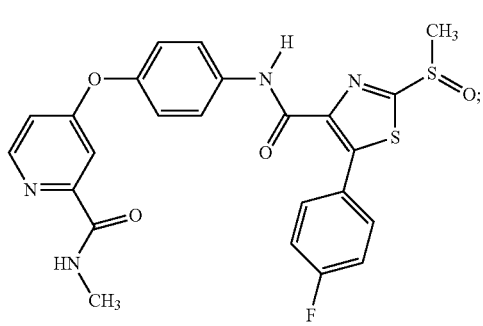
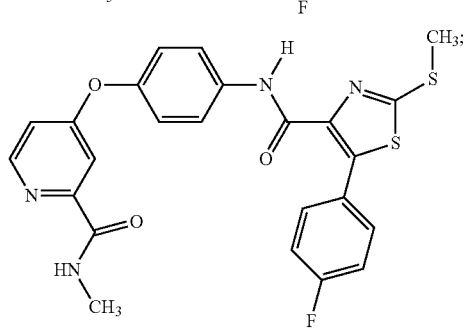
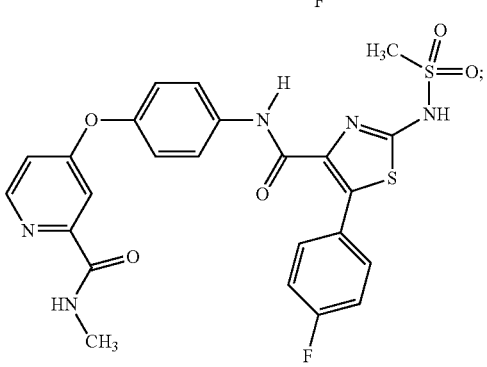

-continued
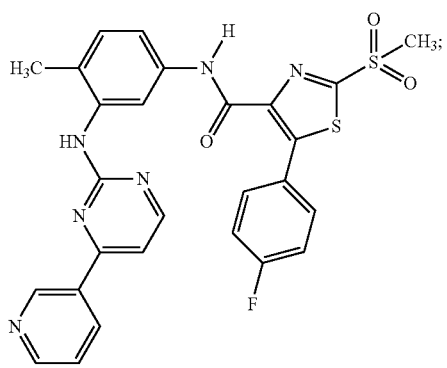
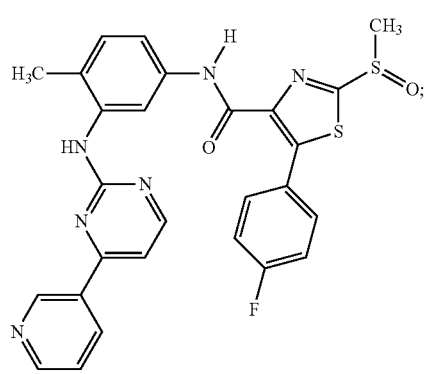
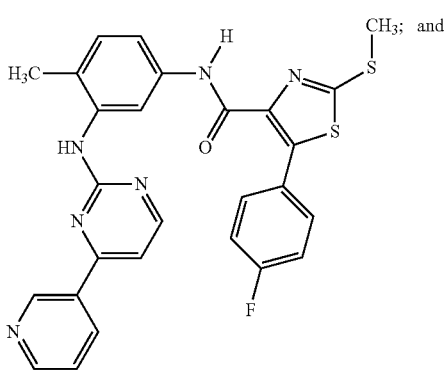
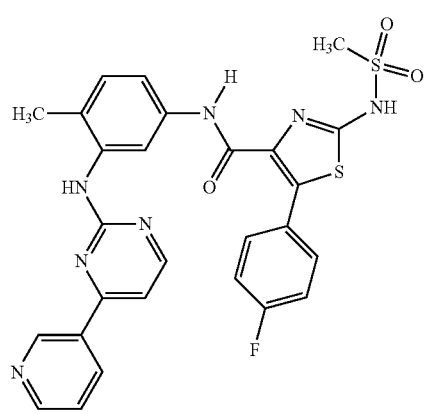
and pharmaceutically acceptable salts thereof.
In a twenty-seventh embodiment, the compounds described herein are selected from:
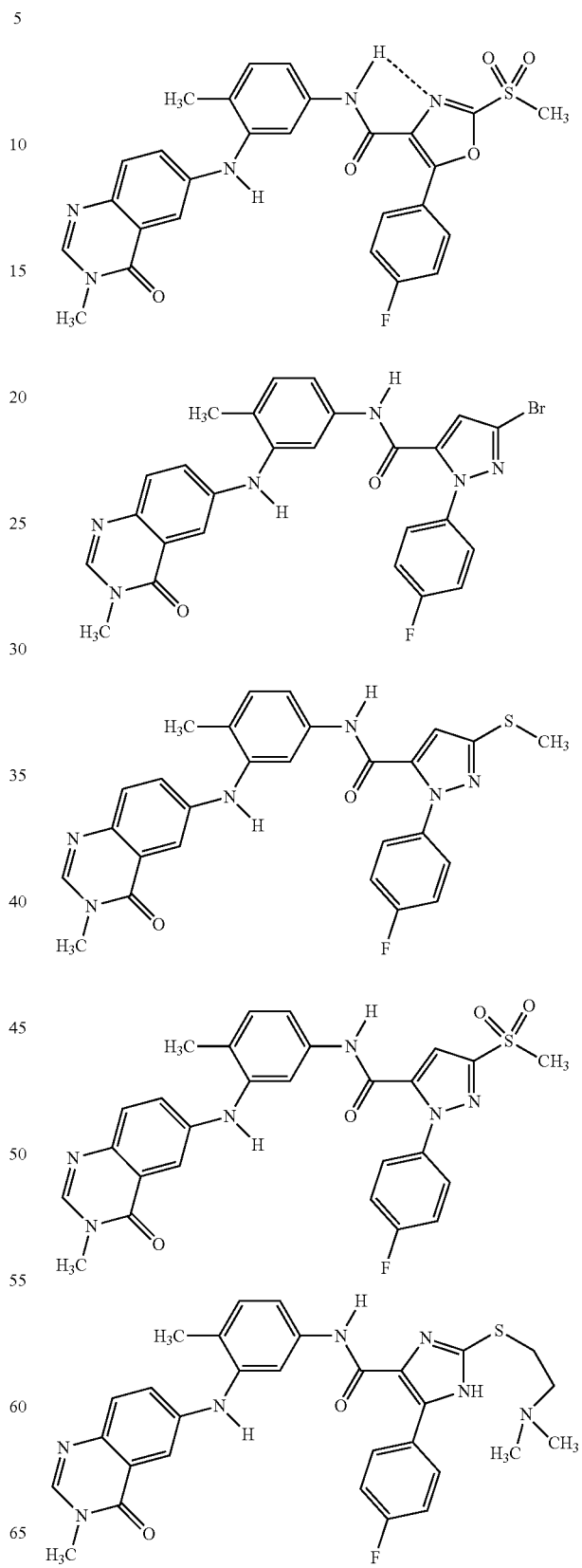

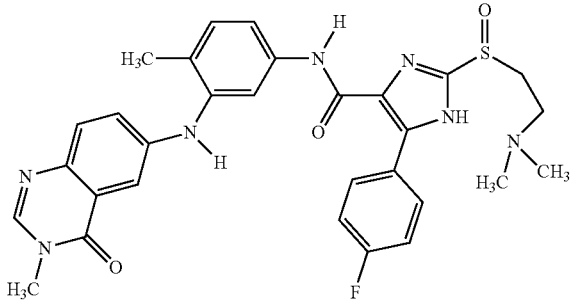

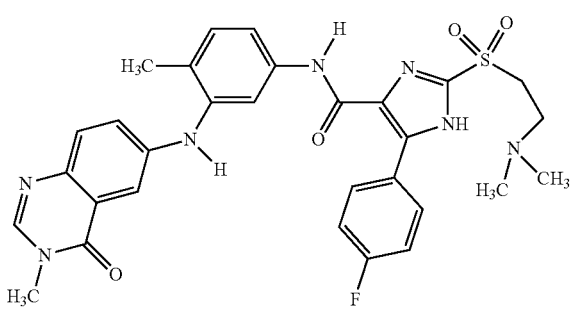

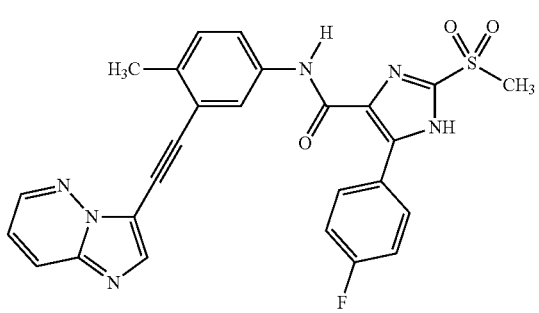

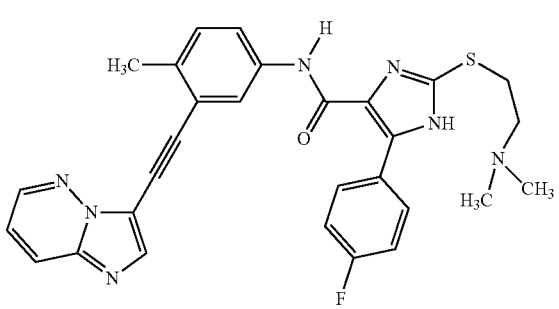

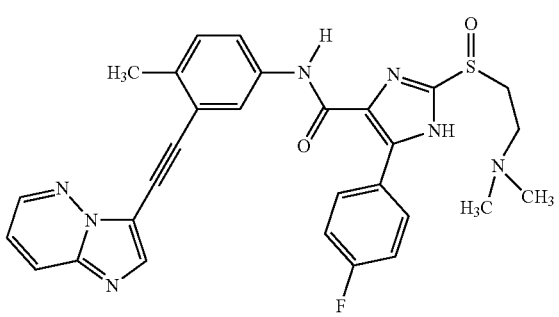

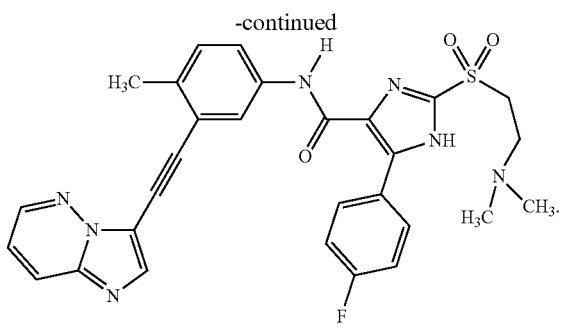

Specific kinase inhibitors and pharmaceutically acceptable salts thereof are provided in Examples below.

In an embodiment, the compounds described herein are useful for inhibiting kinases or a profile of kinases, such as, by administering to a subject an effective amount of one or more of the compounds described herein. The kinases may be selected from e.g., Raf, PI3K, and P38, or combinations thereof, and from type-III kinases members, including e.g., CSF1R(FMS), PDGFR-α, PDGFR-β, KIT, and DDR kinases and/or C-Raf. Such inhibition may be used for the treatment of inflammatory conditions and cancers. Additionally, the compounds described herein inhibit members of the TAM and/or MNK family of kinases and are useful in treating cancers, in particular resistant cancers, and for means of enhancing immunotherapies.

Diseases and conditions treatable by the compounds described herein include, but are not limited to, chronic inflammatory conditions, neurodegenerative disorders, cancers, cardiovascular diseases, restenosis after percutaneous coronary intervention, venous bypass graft disease, type-2 diabetes, infectious diseases, and neuropathic pain. The compounds described herein may also be used as positron emission tomography tracers.

Specific examples of compounds of disclosed Formulae may exist in various stereoisomeric or tautomeric forms. The invention encompasses all such forms, including active compounds in the form of essentially pure enantiomers, racemic mixtures, and tautomers, including forms those not depicted structurally.

When any variable (e.g., aryl, heterocyclyl, $R^1$, $R^2$, etc.) occurs more than once in a compound, its definition on each occurrence is independent of any other occurrence.

The term "alkyl", used alone or as part of a larger moiety such as "alkoxy", "hydroxyalkyl", "alkoxyalkyl", "alkylamine", "dialkyamine", "alkoxycarbonyl" or "alkylaminocarbonyl", means a saturated straight or branched hydrocarbon radical having (unless otherwise specified) 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a saturated hydrocarbon ring having 3-8 carbon atoms and includes, for example, cyclopropyl, cyclobutyl, cyclopentyl, cyclohexyl, cycloheptyl, cyclooctyl, and the like.

The term "aryl" means means a 6-10 membered carbocyclic aromatic monocyclic or polycyclic ring system, such as phenyl or naphthyl. The term "aryl" may be used interchangeably with the terms "aryl ring" "aromatic ring", "aryl group" and "aromatic group".

"Heteroaromatic group" or "heteroaryl" used alone or as part of a larger moiety as in "heteroaralkyl" or "heteroarylalkoxy", means a 5-10 membered monovalent monocyclic and polycylic aromatic group radical containing 1 to 4 heteroatoms independently selected from N, O, and S. Heteroaryl groups include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. The terms "heteroaryl", "heteroaromatic", "heteroaryl ring", "heteroaryl group" and "heteroaromatic group" are used interchangeably herein.

The term "heterocyclic group" or "heterocyclic ring" means a 4-, 5-, 6- and 7-membered saturated or partially unsaturated heterocyclic ring containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide. The terms "heterocyclyl", "heterocycle", "heterocyclic group" and "heterocyclic ring" are used interchangeably herein.

Suitable substituents for a aryl, heteroaryl and heterocyclic group are those which do not significantly reduce the ability of the compound to inhibit the activity of kinases. Unless otherwise specified, suitable substituents for an aryl, heteroaryl and heterocyclic group include halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, halo$(C_1-C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a $(C_1-C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$, wherein $R^{11-13}$ are each independently $C_1-C_6$alkyl; $C_1-C_6$haloalkyl, or $C_1-C_6$hydroxyalkyl. Preferred substituents an alkyl, aryl, heteroaryl and heterocyclyl include, unless otherwise specified, halogen, $(C_1-C_6)$alkyl, hydroxy, $(C_1-C_6)$alkoxy, $(C_1-C_6)$alkylamino, di$(C_1-C_6)$alkylamino, $NO_2$, CN, $CONH_2$, $(C_1-C_6)$haloakyl or $(C_1-C_6)$haloalkoxy.

An appropriate group that interacts with the Gatekeeper region in the ATP binding side includes either an optionally substituted planar monocyclic or bicyclic aromatic groups or rarely cyclic aliphatic groups. These lipophilic groups interact with the lipophilic pocket adjacent to the ATP purine binding site of a kinase. Many small-molecule kinase inhibitors have exploited a conserved threonine residue within the ATP binding site for binding specificity. This threonine controls access of the inhibitors to a hydrophobic pocket deep in the active site that is not contacted by ATP, hence leading to its designation as a 'gatekeeper' residue. Substitution of the gatekeeper threonine residue with bulky side chains is a common mechanism of resistance to pharmacological ATP-competitive kinase inhibitors. Representative gatekeeper interacting groups have been defined earlier.

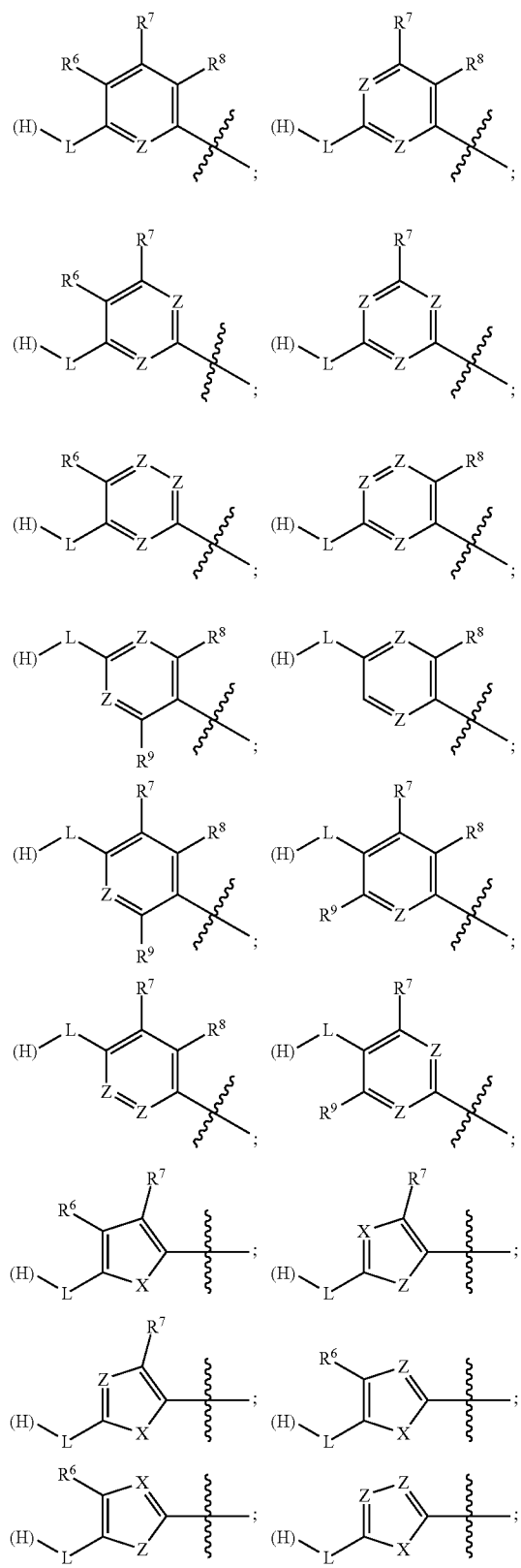

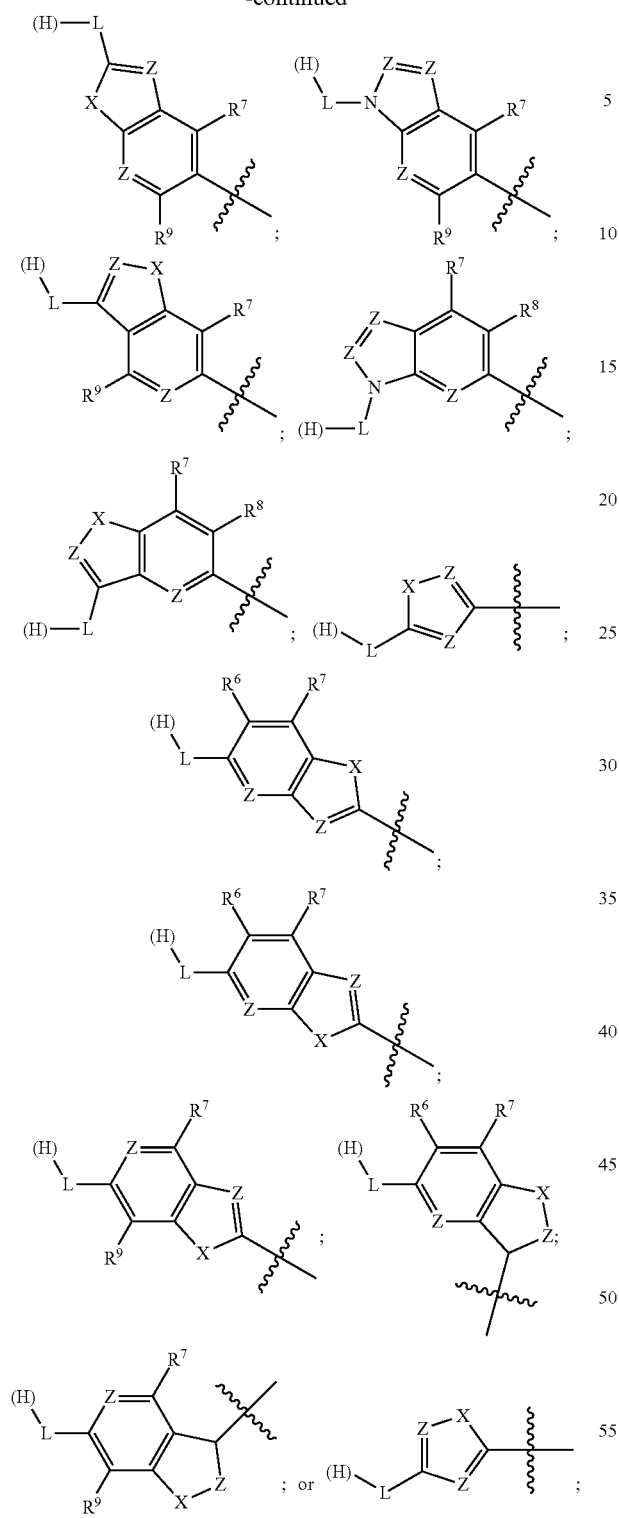
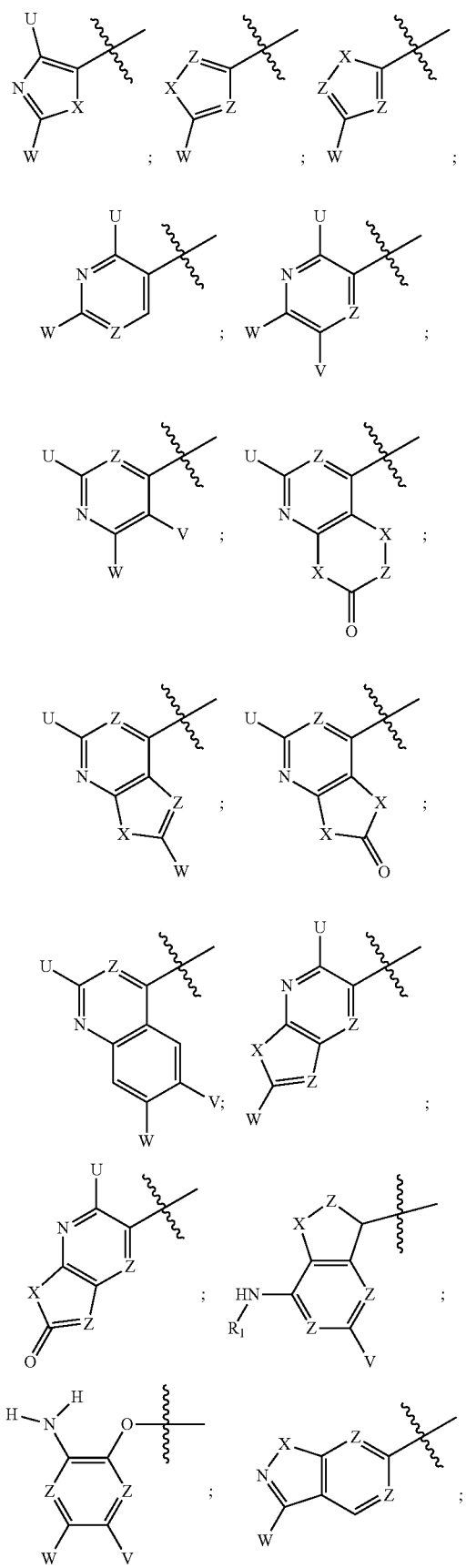

An appropriate group that interacts with the Hinge-region in the ATP binding site includes optionally substituted planar monocyclic or polycyclic aromatic ring systems with a network of hydrogen-bond acceptors and donors that are complimentary to the conserved hinge region that interact with the purine ring of ATP. Representative Hinge-region interacting groups are illustrated below.

-continued
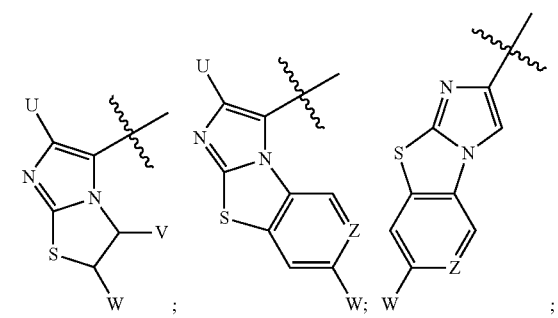
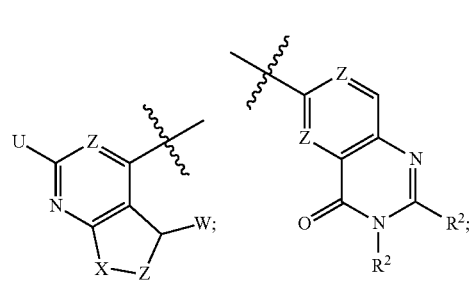
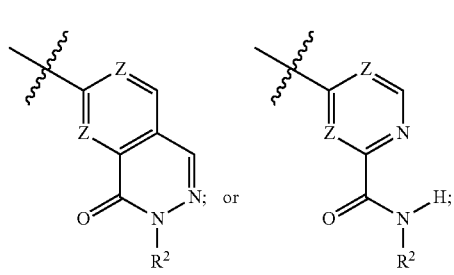
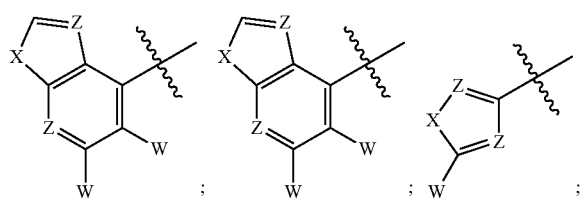
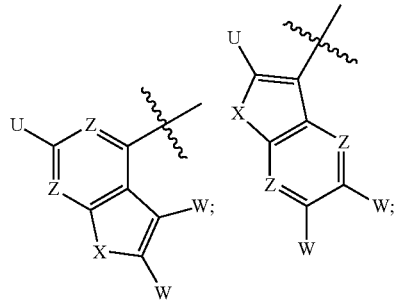
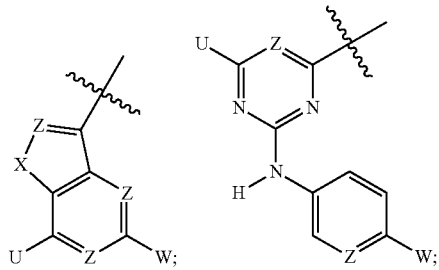
-continued
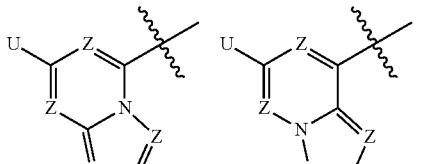
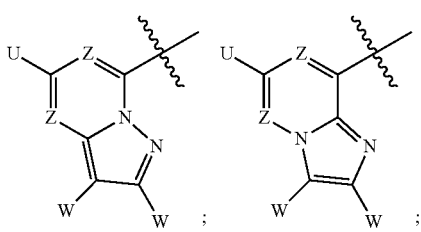
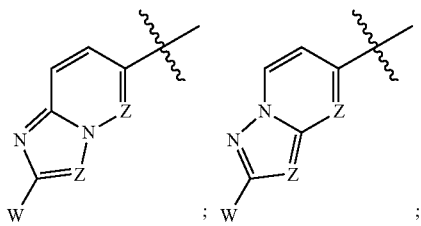
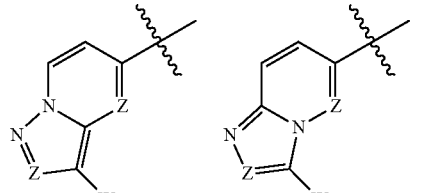
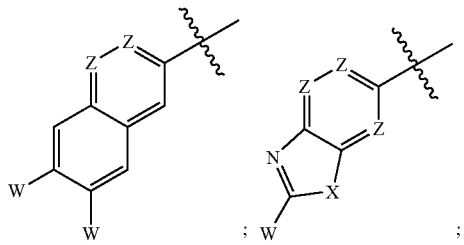
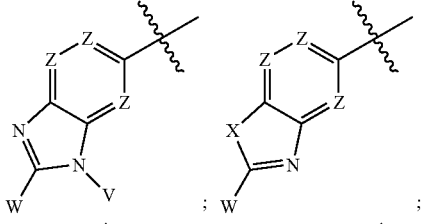
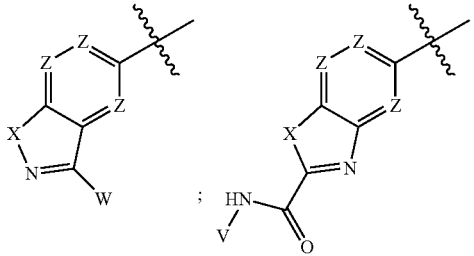

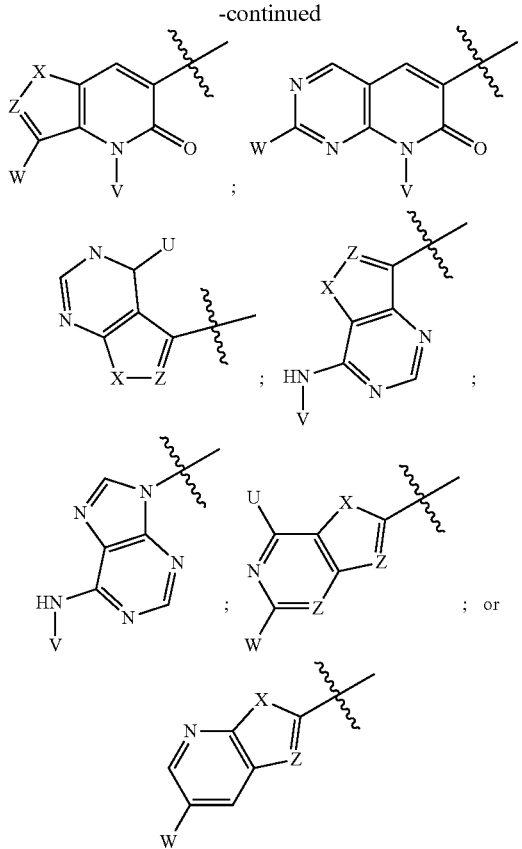

The compounds described herein may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The compounds described herein may also include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

Salts of the disclosed kinase inhibitors containing an acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl) amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

When a disclosed compound or its pharmaceutically acceptable salt is named or depicted by structure, it is to be understood that solvates or hydrates of the compound or its pharmaceutically acceptable salts are included as well as anhydrous forms of the compound and forms without solvent. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include stoichiometric hydrates as well as compositions containing variable amounts of water.

When a disclosed compound or its pharmaceutically acceptable salt is named or depicted by structure, it is to be understood that the compound, including solvates thereof, may exist in crystalline forms, non-crystalline forms or a mixture thereof. The compound or its pharmaceutically acceptable salts or solvates may also exhibit polymorphism (i.e. the capacity to occur in different crystalline forms). These different crystalline forms are typically known as "polymorphs." It is to be understood that when named or depicted by structure, the disclosed compound and its pharmaceutically acceptable salts, solvates or hydrates also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

The present disclosure also includes various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Certain disclosed kinase inhibitors may exist in various stereoisomeric forms. Stereoisomers are compounds that differ only in their spatial arrangement. Enantiomers are pairs of stereoisomers whose minor images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When a disclosed compound is named or depicted by structure without indicating the stereochemistry, and the compound has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When the stereochemistry of a disclosed compound is named or depicted by structure, the named or depicted stereoisomer is at least 60%, 70%, 80%, 90%, 95%, 98%, 99% or 99.9% by weight pure relative to the other stereoisomers. When a single enantiomer is named or depicted by structure, the depicted or named enantiomer is at least 60%, 70%, 80%, 90%, 95%, 98%, 99% or 99.9% by weight optically pure. Percent optical purity by weight is the ratio of the weight of the enantiomer over the weight of the enantiomer plus the weight of its optical isomer. When a single geometric isomer, e.g., a geometric isomer with a double bond, is depicted by name or structure and the stereochemistry about the double is indicated, the compound is considered to be at least 60%, 70%, 80%, 90%, 95%, 98%, 99% or 99.9% steroechemically pure by weight. Percent stereochemically purity by weight is the ratio of the weight of the geometric isomer over the weight of the both geometric isomers. For example, 99% stereochemically pure means that at least 99% by weight of the compound is the indicated stereoisomer.

A pharmaceutical composition of the compounds disclosed herein may, alternatively or in addition to a compound of the above formulae, comprise a pharmaceutically acceptable salt of a compound of the above formulae, or a prodrug or pharmaceutically active metabolite of such a compound or salt and one or more pharmaceutically acceptable carriers therefor.

"Effective amount" means that amount of active compound agent that elicits the desired biological response in a subject. Such response includes alleviation of the symptoms of the disease or disorder being treated.

"Inhibiting kinase activity" means to decrease the production of an phosphor-peptide by a particular kinase tha can be separated by analytical techniques. For example, a comprehensive platform of kinase, protease, phosphatase and epigenetic assays that utilizes cutting-edge microfluidics and informatics tools to provide accurate and rapid results. Profiling data in this application were determined using these techniques at Nanosyn Inc. IC50 data were provided by Reaction Biology Inc using a P33 radiolabeled kinase assay.

"Pharmaceutically acceptable carrier" means compounds and compositions that are of sufficient purity and quality for use in the formulation of a composition of the present disclosure and that, when appropriately administered to an animal or human, do not produce an adverse reaction.

"Treatment" or "treating", as used herein, includes therapeutic treatment. "Therapeutic treatment" includes partially or totally inhibiting, delaying, or reducing the severity of the disease or disorder related to kinases. "Prophylactic treatment" encompasses administration of a compound of the invention to a subject susceptible to a disease or disorder related to the activity or expression of kinases in an effort to reduce the likelihood of a subject developing the disease or disorder, or slowing or preventing progression of the disease. Prophylactic treatment includes suppression (partially or completely) of the disease or disorder, and further includes reducing the severity of the disease or disorder, if onset occurs. Prophylactic treatment is particularly advantageous for administration to mammals at risk for developing a disease or disorder related to kinase activity.

The compounds disclosed herein can be prepared and administered in a wide variety of oral and parenteral dosage forms. Thus, the compounds of the present disclosure can be administered by injection, that is, intravenously, intramuscularly, intracutaneously, subcutaneously, intraduodenally, or intraperitoneally. Additionally, the compounds of the present disclosure can be administered intranasally or transdermally.

For preparing pharmaceutical compositions from the compounds of the present disclosure, pharmaceutically acceptable carriers can either be solid or liquid. Solid form preparations include powders, tablets, pills, capsules, cachets, suppositories, and dispersable granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium carboxymethylcelluose, a low melting wax, cocoa butter, and the like. Tablets, powders, cachets, lozenges, fast-melt strips, capsules and pills can be used as solid dosage forms containing the active ingredient suitable for oral administration.

For preparing suppositories, a low melting wax, such as a mixture of fatty acid glycerides or cocoa butter, is first melted and the active ingredient is dispersed homogeneously therein, as by stiffing. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethyl cellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

The compounds provided herein are useful for ameliorating or treating disorders or diseases in which inhibition of a kinase or profile of kinases has utility for the treatment of certain cancers for which activating mutations in, over expression of, or aberrant activity of these kinase targets contribute to the progression of the disorder or disease.

The compounds provided herein are also useful as multi-targeted kinase inhibitors of the Protein Tyrosine Kinases (PTK), Receptor Tyrosine Kinases, (RTK), Serine/Theonine Kinases. And alipid kinases such as the PI3K kinase family. As such, these inhibitors will have utility for the treatment of cancers and/or inflammatory conditions sensitive to kinase inhibitors. In particular, the ability to inhibit MAP-kinases such as p38 and Raf kinases in combination with PI3K kinases is novel and offers advantages for unique therapies not previously available.

Compounds described herein, that inhibit a kinase or profile of relevant kinases will have utility for the treatment of chronic inflammatory conditions such as rheumatoid arthritis; neurodegenerative disorders such as Alzheimer's disease; cardiovascular diseases such as atherosclerosis, restenosis after percutaneous coronary intervention, and venous bypass graft disease; type-2 diabetes; certain infectious diseases such as parasitic infections; and neuropathic pain, for which over expression or aberrant activity of specific kinase targets contribute to progression of the disease.

Figure 12:
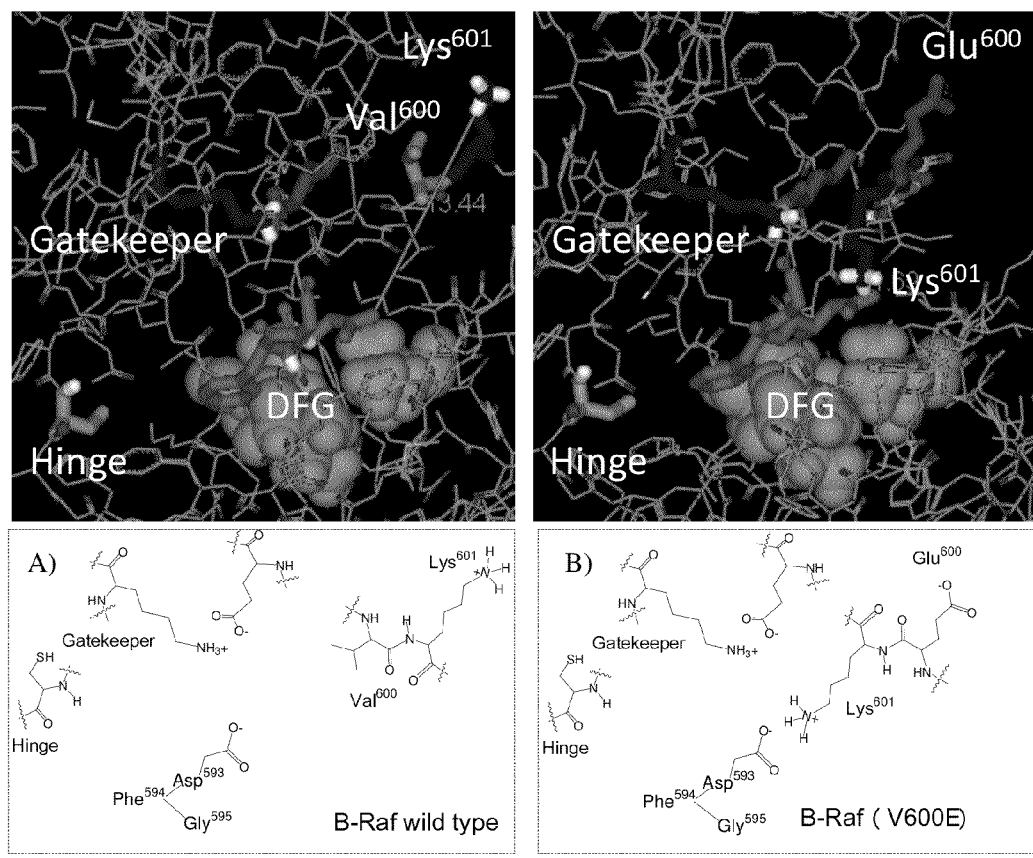
FIG. 12: Summary of SAR studies for imidazole quinazolinone inhibitors.
Figure 13:
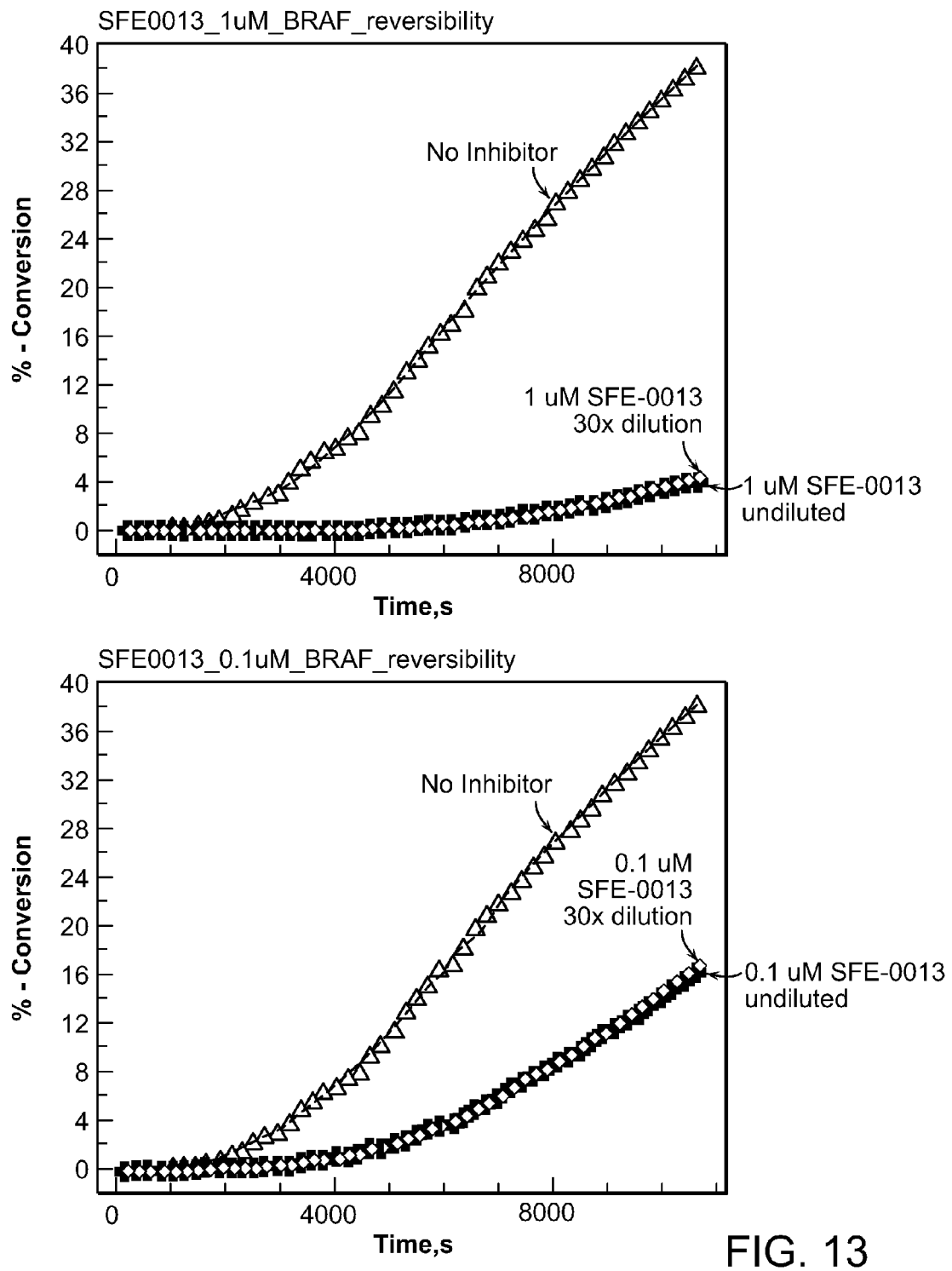
FIG. 13: Represents inhibitors modeled into the crystal structures of B-RAf, p38-α, CSF1R, KDR, FLT-3, and c-Met.

Compounds described herein, also have utility as positron emission tomography tracers, such as those in FIG. 12 and FIG. 13. These agents will enable diagnostic PET imaging studies that will have utilities for the identification, characterization, and monitoring of diseases in which the mutation or aberrant activity of diagnostically relevant kinase targets as well as selection of appropriate patient populations for clinical studies.

Figure 11:
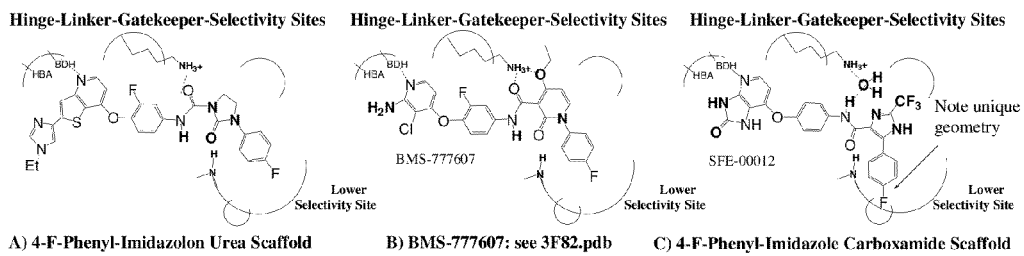
FIG. 11: Panel A) SFE-in B-Raf(V600E) with Lys601 moved slightly to better interact with or displace the 2-MeSO$_2$-imidazole substituent. Panel B) Putative covalent adduct from reaction with Lys601 (yellow) vs original Lys601 position

Compounds described herein which have utility, when attached to an appropriate vehicle through the free amine group, as affinity probes for the identification of kinases that can adopt the DFG-out conformation, such as those illustrated in FIG. 11. These agents will enable the identification and kinetic study of new kinases for which Type-II inhibitors have thus far not been reported.

Compounds, methods, and utilities described herein may be used as a platform technology for the patient specific study of kinase inhibitors and their efficacy in the clinic. In particular, this disclosure describes how the chemistry methods for preparation of multi-targeted kinase inhibitors can be easily adapted to the preparation of radiolabeled tracers for PET imaging. The integrated use of PET imaging probes with very similar properties and inhibition profiles as the therapeutic agent of interest will offer significant and unique advantages for selection of most appropriate patient populations for clinical studies. Targeted monitoring of kinases using PET imaging represents a significant step toward the realization of personalized medicine The term "mammal" is preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The following abbreviations have the indicated meanings:

| Abbreviation | Meaning |
| --- | --- |
| Boc | tert-butoxy carbonyl or t-butoxy carbonyl |
| $(Boc)_2O$ | di-tert-butyl dicarbonate |
| BOP | (Benzotriazole-1-yl-oxy-tris-(dimethylamino)-phosphonium hexafluorophosphate) |
| Cbz | Benzyloxycarbonyl |
| CbzCl | Benzyl chloroformate |
| $CS_2$ | Carbon disulfide |
| DAST | diethylaminosulfur trifluoride |
| DBU | 1,8-diazabicyclo[5.4.0]undec-7-ene |
| DCC | N,N'-dicyclohexylcarbodiimide |
| DCM | dichloromethane |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC, EDC•HCl, EDCI | 1-[3-(dimethylamino)propyl]-3-ethylcarbodiimide hydrochloride |
| Equiv | Equivalents |
| Fmoc | 1-[[(9H-fluoren-9-ylmethoxy)carbonyl]oxy]- |
| Fmoc—OSu | 1-[[(9H-fluoren-9-ylmethoxy)carbonyl]oxy]-2,5-pyrrolidinedione |
| h, hr | hour(s) |
| HOAc | acetic acid |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| $I_2$ | iodine |
| KHMDS | potassium hexamethyldisilazane |
| LAH or $LiAlH_4$ | lithium aluminum hydride |
| LC-MS | liquid chromatography-mass spectroscopy |
| LHMDS | lithium hexamethyldisilazane |
| Lawesson's Reagent | 2,4-bis(4-methoxyphenyl)-1,3,2,4-dithiadiphosphetane-2,4-disulfide |
| MCPBA: | Meta-chloroperoxybenzoic acid |
| Me | Methyl |
| MsCl | methanesulfonyl chloride |
| Min | Minute |
| MS | mass spectrum |
| NaH | sodium hydride |
| $NaHCO_3$ | sodium bicarbonate |
| $NaN_3$ | sodium azide |
| NaOH | sodium hydroxide |
| $NaNO_2$ | sodium nitrite |
| $Na_2SO_4$ | sodium sulfate |
| $NH_3$ | ammonia |
| NMM | N-methylmorpholine |
| NMP | N-methylpyrrolidinone |
| Oxone | potassium monopersulfate |
| $Pd_2(dba)_3$ | tris(dibenzylideneacetone)dipalladium(0) |

-continued

| Abbreviation | Meaning |
| --- | --- |
| PE | petroleum ether |
| PhI + (OCOCF$_3$)$_2$ | bis(trifluoroacetoxy)iodo]benzene |
| PPh$_3$ | triphenyl phosphene |
| Quant | quantitative yield |
| Satd | Saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc—OSu | 1-[2-(trimethylsilyl)ethoxycarbonyloxy]pyrrolidin-2,5-dione |
| TFA | trifluoroacetic acid |
| TFAA | trifluoroacetic anhydride |
| Tlc, TLC | thin layer chromatography |
| THF | tetrahydrofuran |
| TMS | Trimethylsilyl |
| TMSCl | chlorotrimethylsilane or trimethylsilyl chloride |
| t$_R$ | retention time |
| TsOH | p-toluenesulfonic acid |

EXEMPLIFICATION

General Description of Synthetic Methods

Compounds disclosed herein can be prepared by several processes. In the discussion below, the variables have the meanings indicated above unless otherwise noted. In cases where the synthetic intermediates and final products described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Preparation of Ortho-Aryl-5-Membered-Heteroaryl Carboxylic Acid Scaffolds

The following paragraphs outline similar and alternative scaffolds and their preparation in order to define the scope of this invention.

Figure 14:
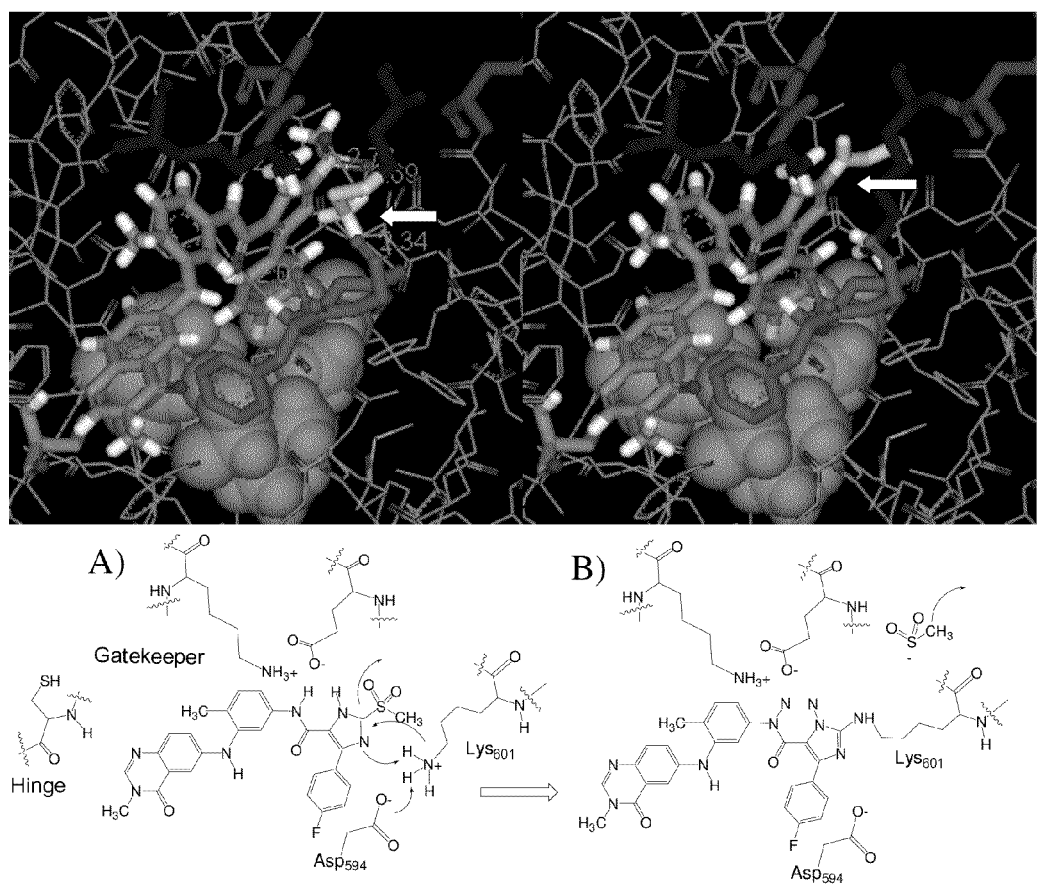
FIG. 14: Illustrates Hinge-Gatekeeper-Selectivity Site interactions for c-Met inhibitors.

Kinase inhibitors and imaging agent precursors described herein may be prepared by coupling of an appropriate substituted ortho-aryl-5-membered heterocyclic carboxylic acid scaffold with an appropriate amine containing intact Hinge-Linker-Gatekeeper motif (HGM), FIG. 14. Standard coupling conditions such as EDC/HOAT/DIEA or HATU/DIEA can be used to affect this transformation (Route-1). Other methods of construction may involve coupling with a partially elaborated HGM which can then be further modified to give the final product. For example, in Route-2 an appropriately protected gatekeeper amine may be coupled to the scaffold acid. If needed, deprotection of the resulting amide intermediate and coupling of a optionally protected Hinge-Linker group would give the assembled product. Alternatively, the scaffold acid could be coupled to an appropriately protected Linker-Gatekeeper amine which, after deprotection if needed, would be coupled to an appropriately protected Hinge interacting group P—(H). Depending on the protection state of these assembled product, a final deprotection step may be required.

General methods for the preparation of a variety of scaffolds are illustrated in Schemes 1-12.

Scheme 1:
Assembly methods for kinase inhibitors and imaging agent precursors.

Route-1

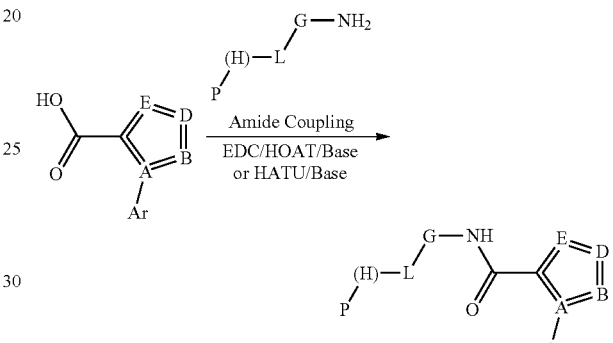

Route-2

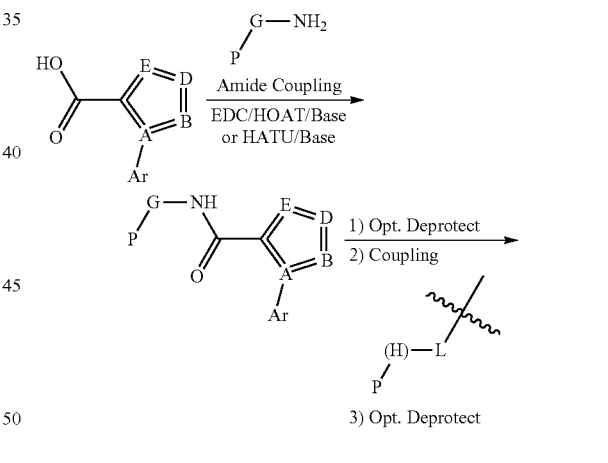

Route-3

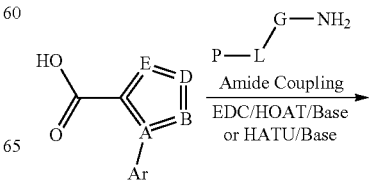

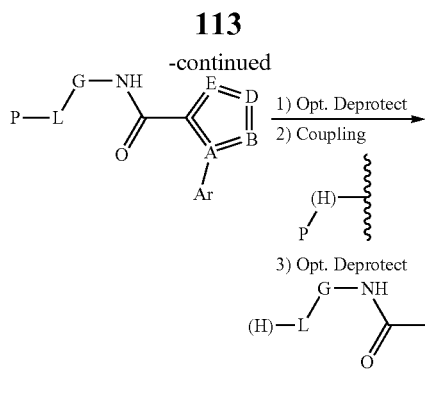

2-Substituted 5-aryl-imidazole-4-carboxylic acid scaffolds can be prepared as illustrated in Scheme 2. In Route-1, a racemic phenyl glycine 1 is first converted to a variety of amides, ureas, or carbamates derivatives 2. Cyclo-dehydration with trifluoro acetic anhydride (TFAA) provides oxazolidinone 3 which can be isolated and purified or utilized directly in the same flask after removal of volatiles in vacuo. Reaction of 3 with benzyl cyanoformate and tributyl phosphine in toluene in the same flask smoothly provides 2-substituted imidazoles 4 via [3+2]cycloaddition reaction accompanied by decarboxylative aromatization (Hagiwara, K. et. al., WO1995004724).

Route-2 represents a special case of this process in which a phenylglycine derivative 1 is first treated with excess of trifluoroacetic anhydride. Formation of the intermediate trifluoroacetamide 6 is accompanied by in situ cyclo-dehydration to provide oxazolidinone 7 which can be isolated or utilized directly in the same flask after removal of volatiles in vacuo. Reaction of 7 as described in Route-1 provides 2-trifluoromethyl imidazole 8 in a three-step one-pot procedure. Hydrogenolysis or hydrolysis of the benzyl esters then results in the desired imidazole carboxylic acid scaffold 5 and 9 respectively. Some of the previously reported 2-trifluoromethyl imidazoles scaffolds S-1 to S-8 prepared by this method are listed in Table 11 (Deitrich J., *Bioorg. Med. Chem.* (2010), 18(1): 292-304.).

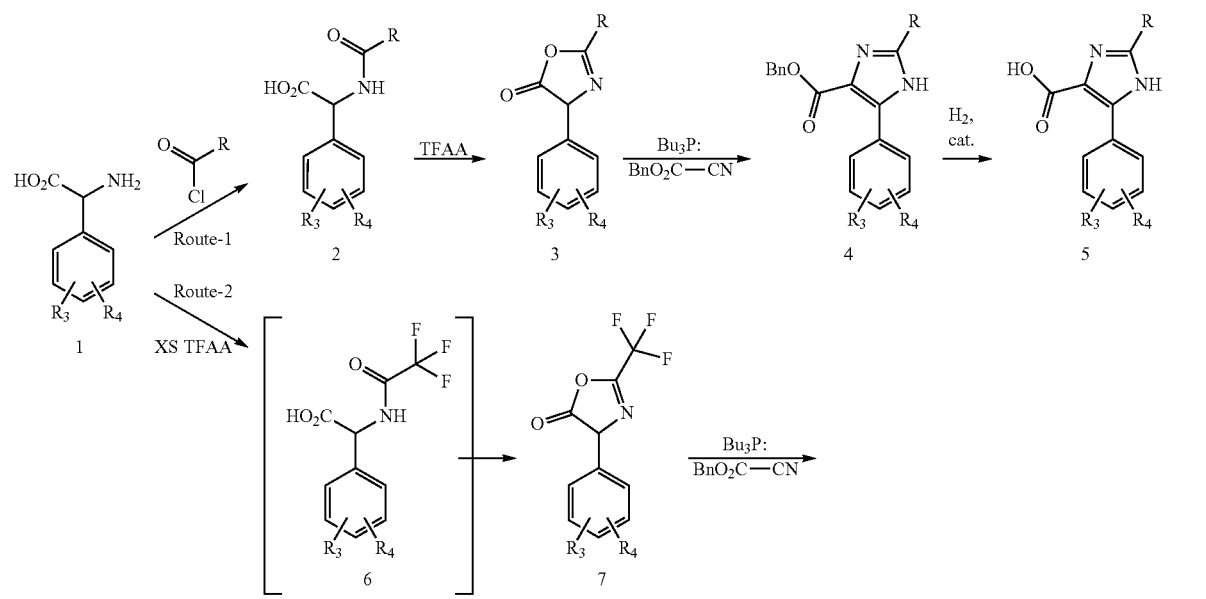

Scheme 2: [3 + 2] Cycloaddition routes to trisubstituted imidazoles.

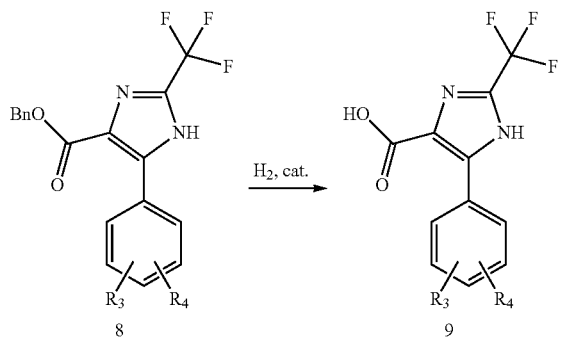

TABLE 11

Previously Prepared 2-CF₃-Imidazole Scaffolds. (Dietrich 2010)

| Scaffold Structure | Scaffold ID # | Comment | Source or Reference. | Order # | Available Precursor | ID # |
|---|---|---|---|---|---|---|
| | S-1 | | Dietrich, J.; Gokhale, V.; Wang. X.; Hurley, L. H. and Flynn, G. A. Bioorg, Med. Chem., 2010, 18, 292-304. | | | |
| | S-2 | | Dietrich, J.; Gokhale, V.; Wang. X.; Hurley, L. H. and Flynn, G. A. Bioorg, Med. Chem., 2010, 18, 292-304. | | | |
| | S-3 | | Dietrich, J.; Gokhale, V.; Wang. X.; Hurley, L. H. and Flynn, G. A. Bioorg, Med. Chem., 2010, 18, 292-304. | | | |
| | S-4 | | Dietrich, J.; Gokhale, V.; Wang. X.; Hurley, L. H. and Flynn, G. A. Bioorg, Med. Chem., 2010, 18, 292-304. | | | |
| | S-5 | | Dietrich, J.; Gokhale, V.; Wang. X.; Hurley, L. H. and Flynn, G. A. Bioorg, Med. Chem., 2010, 18, 292-304. | | | |
| | S-6 | | Dietrich, J.; Gokhale, V.; Wang. X.; Hurley, L. H. and Flynn, G. A. Bioorg, Med. Chem., 2010, 18, 292-304. | | | |

TABLE 11-continued

Previously Prepared 2-CF₃-Imidazole Scaffolds. (Dietrich 2010)

| Scaffold Structure | Scaffold ID # | Comment | Source or Reference. | Order # | Available Precursor | ID # |
|---|---|---|---|---|---|---|
| | S-7 | | Dietrich, J.; Gokhale, V.; Wang. X.; Hurley, L. H. and Flynn, G. A. Bioorg, Med. Chem., 2010, 18, 292-304. | | | |
| | S-8 | | Dietrich, J.; Gokhale, V.; Wang. X.; Hurley, L. H. and Flynn, G. A. Bioorg, Med. Chem., 2010, 18, 292-304. | | | |

Alternatively, a more traditional general approach to 2,4,5-trisubstituted imidazoles can be employed, Scheme 3. In Route-1, an aroylacetic ester 10 is halogenated (Lee L. F., *J. Hetrocyclic Chem.* (1985), 22(6):1621-1630) followed by reaction of the 2-halo intermediate 11 with an amidine derivative to provide a variety of imidazole esters of general structure 12 that can then be hydrolyzed to provide 2-substituted imidazole carboxylic acid scaffolds 13. Alternatively, the aroylacetic ester 10 can be treated with sodium nitrite in acetic acid to provide an intermediate oxime 14 that can be reduced to 2-amino keto ester 15. Reaction of 15 with an imidate salt 16 provides an efficient complimentary entrance to imidazole esters 12.

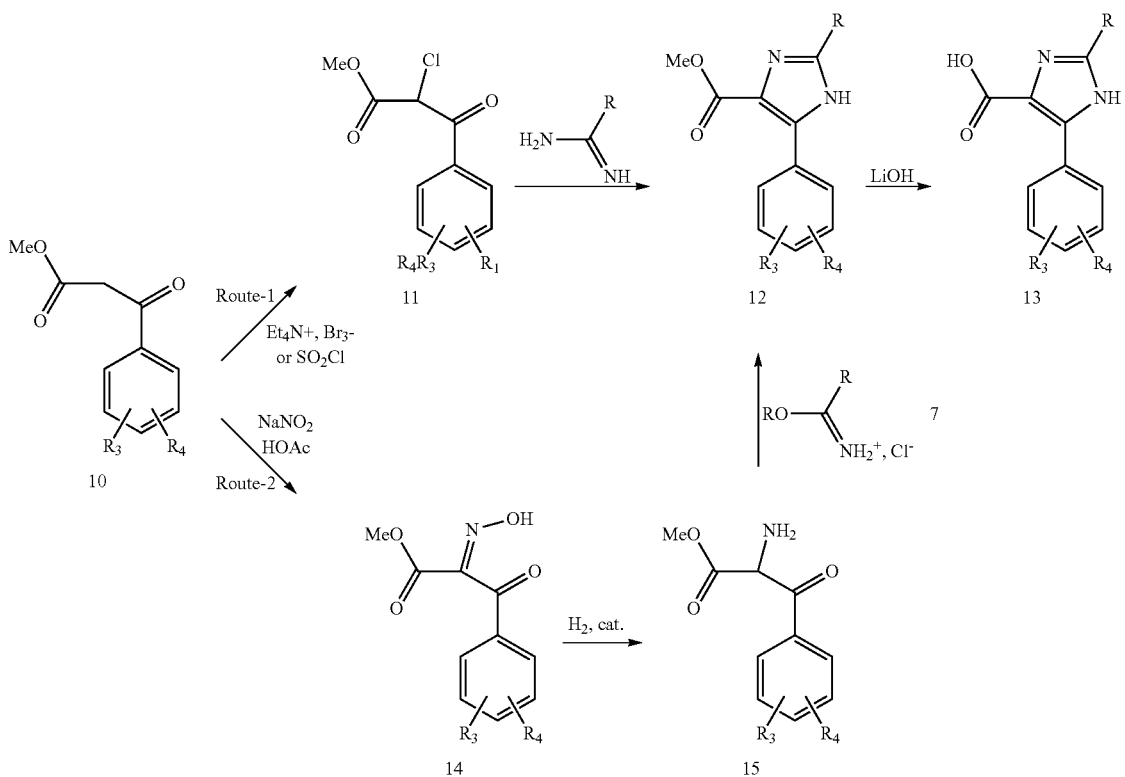

Scheme 3: Traditional approaches to trisubstituted imidazoles.

A variety of imidazolidin-2-one acid scaffolds are commercially available, Table 12, or can be easily accessed synthetically, Scheme 4. For example, reaction of chloro-ketoester 11 with urea (Route-1), provides a facile entrance to imidazolidin-2-oness 16 and reaction of amine 15 with an isocyanate affords the N-substituted derivative. 18 (Route-2).

Scheme 4:
Preparation of imidazolidin-2-one and 2-amino-thiazole derivatives.

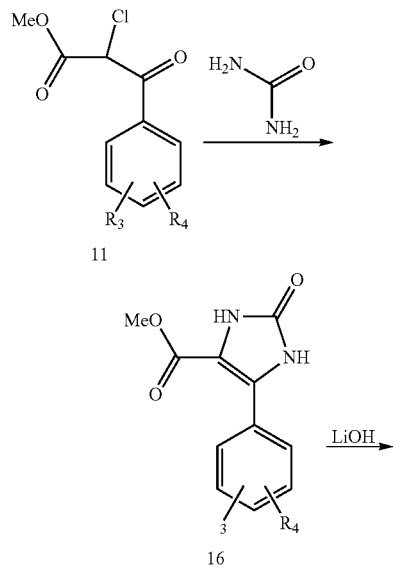

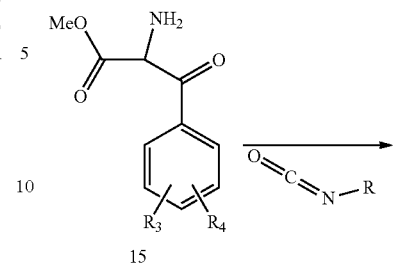

TABLE 12

Commercially available imidazole-2-one scaffolds of interest.

| Scaffold Structure | Scaffold ID # | Comment | Source or Reference | Order # | Available Precursor | ID # |
|---|---|---|---|---|---|---|
|  | S-9 |  | Best PharmaTech, Inc.<br>P O Box 59394<br>Schaumburg, IL, 60159 USA<br>http://www.bestpharmatech.com | BP21116 |  |  |
|  | S-10 |  | Best PharmaTech, Inc.<br>P O Box 59394<br>Schaumburg, IL, 60159 USA<br>http://www.bestpharmatech.com | BP21165 |  |  |

TABLE 12-continued

Commercially available imidazole-2-one scaffolds of interest.

| Scaffold Structure | Scaffold ID # | Comment | Source or Reference. | Order # | Available Precursor | ID # |
|---|---|---|---|---|---|---|
| (structure with CN and COOH) | S-11 | | Best PharmaTech, Inc. P O Box 59394 Schaumburg, IL, 60159 USA http://www.bestpharmatech.com | BP21194 | | |
| (structure with OCH₃ and COOH) | S-12 | | Best PharmaTech, Inc. P O Box 59394 Schaumburg, IL, 60159 USA http://www.bestpharmatech.com | BP19184 | | |
| (structure with F and COOH) | S-13 | Prepared from Precursor P-13 by LiOH ester hydrolysis | | | (structure with F and COOCH₃) | P-13 |

Scheme 5: Alternate Preparation of Imidazolidine-2-one and Imidazolidine-3-thione derivatives.

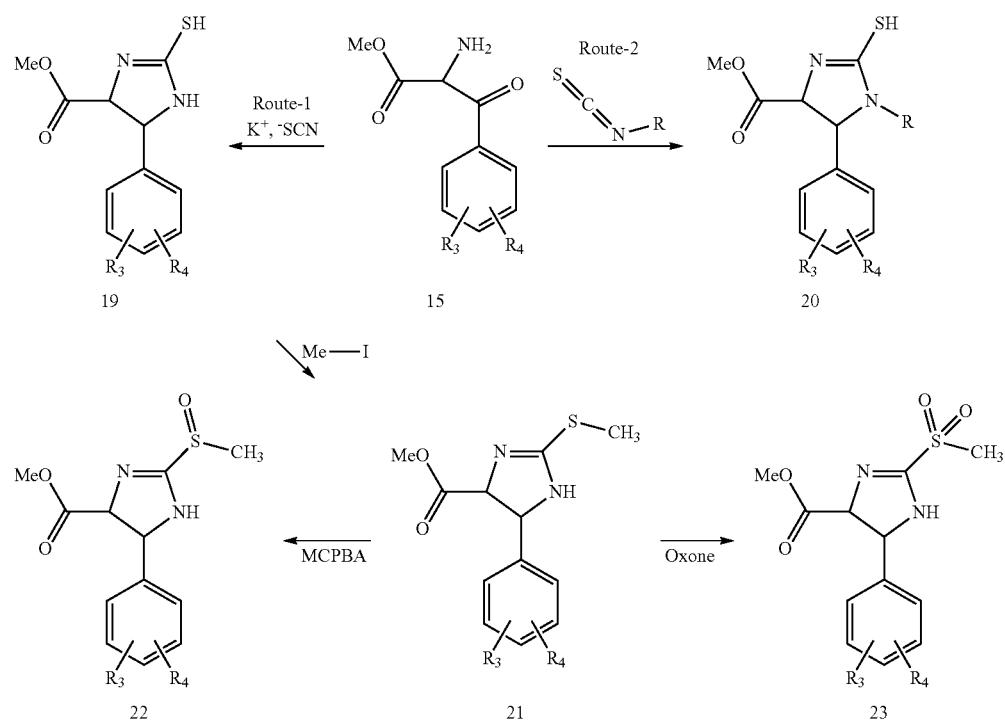

Alternative chemistry for the preparation and further conversion of mercapto-imidazoles is outlined in Scheme 5. Reaction of 2-amino-ketoester 15 with potassium isocyanate is known to be a very general synthetic approach to 2-mercapto-imidazoles 19, Route-1. (Maeda, 1984). Alternatively, reaction of 15 with and isothiocyanate yields the N-substituted derivative 20. Alkylation of 2-mercaptoimidaozles 19 and subsequent partial or complete oxidation proceeds smoothly to yield the 2-alkylthio-, 2-alkylsulfinyl-, and 2-alkylsulfonyl-imidazole esters 21, 22, and 23 as intermediates to their corresponding acid scaffolds., 3-arylpyruvate ester 25 with an appropriate thioamide or thiourea (PCT Int. Appl., 2009 016560. 05 Feb., 2009) to provide the 2-substituted thiazoles 26, or 2-amino-thiazole if R is $NH_2$. Route-1 in Scheme 6. Alternatively, reaction of a 3-chloro-3-arylpyruvate ester 2 with the condensation product between carbon disulfide and ammonia is reported to provide the corresponding thione intermediate 27, Route-2. Alkylation of thione ester 27 provides 2-alkylthio-5-aryl-thiazole-4-carboxylic esters 28 that can be optionally oxidized to provide thiazole scaffolds with either the sulfoxide and sulfone oxidation state 29. In an alternate approach to

TABLE 13

2-Mercapto-imidazole scaffolds prepared in this application.

| Scaffold Structure | Scaffold ID # | Comment | Source or Reference. | Order # | Available Precursor | ID # |
|---|---|---|---|---|---|---|
| (structure) | S-14 | | Maeda S. et.al. Synthesis of 2-mercapto-4-substituted imidazole derivatives with antiinflammatory activities. Chem. Pharm. Bull., 1984 32(7), 2536-43 | | (structure) | P-14 |
| (structure) | S-15 | Prepared from P-14 by alkylation with MeI then LiOH hydrolysis. | See experimental for S-15 | | | |
| (structure) | S-16 | Prepared from S-15 by treatment with MCPBA. | See experimental for S-16 | | | |
| (structure) | S-17 | Prepared from S-15 by treatment with Oxone. | See experimental for S-17 | | | |

The 2-mercapto-imidazole scaffolds in Table 13 have been prepared, see experimental section. Reaction of 2-mercaptoimidazole P-14 with methyl iodide followed by ester hydrolysis provides the 2-methylmercapto scaffold S-15. Whereas partial oxidation of S-15 with MCPBA provides the enantiomeric sulfoxides S-16, oxidation P-15 with oxone and subsequent ester hydrolysis provides the corresponding sulfone S-17.

A variety of 2-Substituted 5-aryl-thiazole-4-carboxylic acid scaffolds 30-33 can be prepared by reacting a 3-chloro-thione 27, a 2-amino-aroylacetic ester 15 is condensed with carbon disulfide and cyclo-dehydrated under acidic conditions to give 27, Route-3. Because a diverse set of intermediate 3-chloro-3-arylpyruvate esters 25 can easily be prepared from readily available aryl aldehydes 24 via a modified Knoevenagel condensation, this general approach to 2-substituted-5-aryl-4-thiazole carboxylic acid scaffolds is quite general.

Scheme 6: Synthetic routes to 2-substituted-5-aryl-4-thiazole carboxylic acid scaffolds

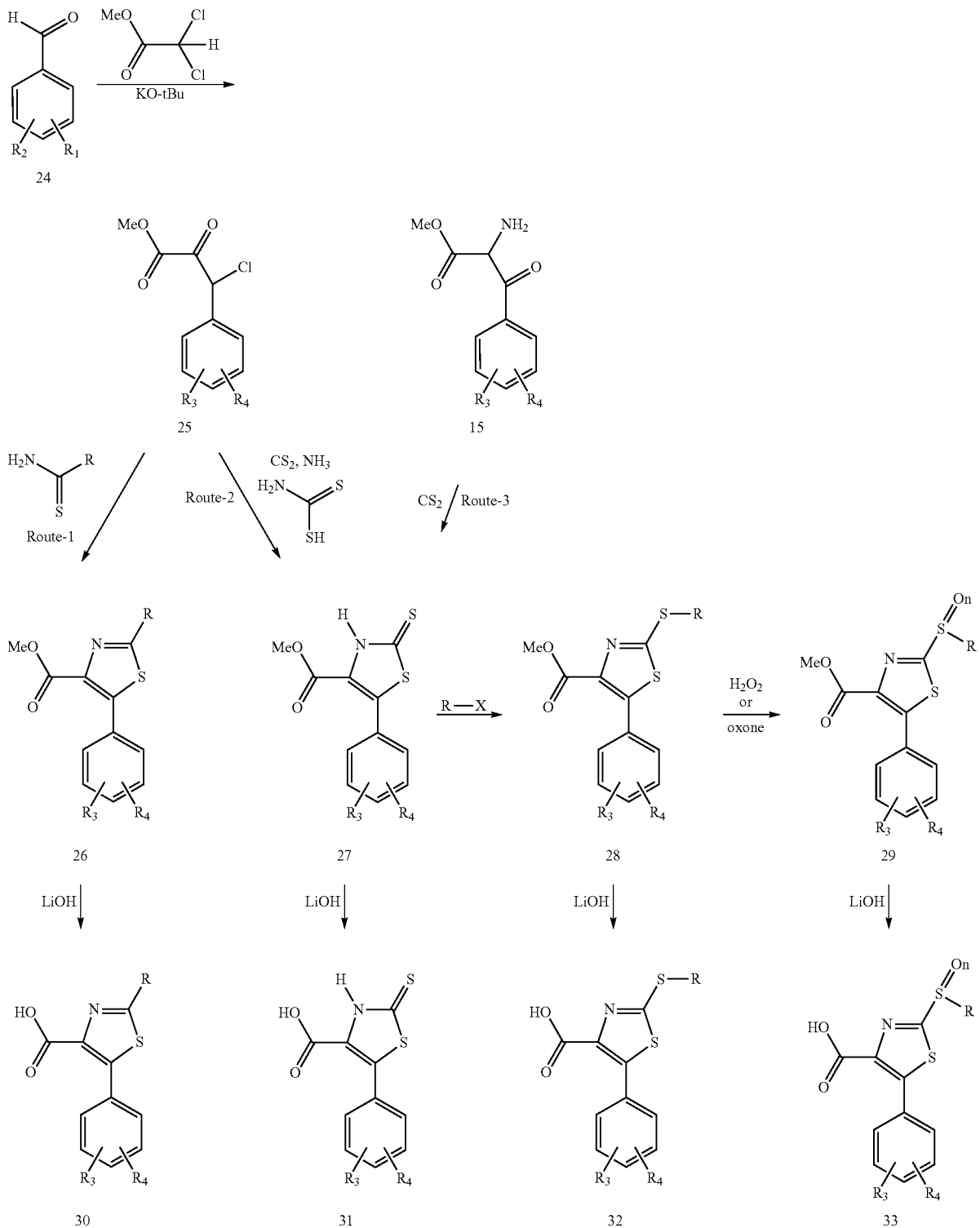

A variety of 2-mercapto-thiazole acid scaffolds S-18 to S-24 and esters P-21 and P-25 are commercially available, Table 14. Alkylation of P-25 with methyl iodide and ester hydrolysis provides scaffold S-25. Oxidation of S-25 with 1 or 2 equivalents of m-chlorobenzoic acid provides the respective sulfoxide and sulfone scaffolds S-26 and S-27, albeit in impure form, for S-25, S-26, and S-27.

TABLE 14

Available 2-substituted thiazole scaffolds S-18 to S-27.

| Scaffold Structure | Scaffold ID # | Comment | Source or Reference. | Order # | Available Precursor | ID # |
|---|---|---|---|---|---|---|
| 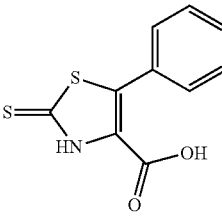 | S-18 | | ZereneX Molecular Limited<br>12 Manningham Road<br>Greater Manchester, BL3 5QS<br>United Kingdom<br>www.zerenex-molecular.com | ZXA008039 | | |
| 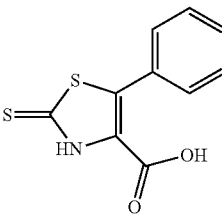 | S-19 | | ZereneX Molecular Limited<br>12 Manningham Road<br>Greater Manchester, BL3 5QS<br>United Kingdom<br>www.zerenex-molecular.com | ZXA008069 | | |
| 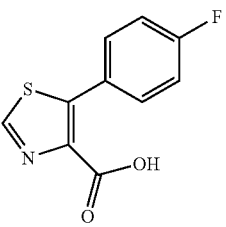 [SMILES: O=C(O)c1ncoc1-c1ccc(F)cc1] | S-20 | | Ryan Scientific, Inc.<br>P O Box 703<br>Mt. Pleasant, SC, 29465 USA<br>Email: sales@ryansci.com<br>Web: http://www.ryansci.com | CA00660 | | |
| 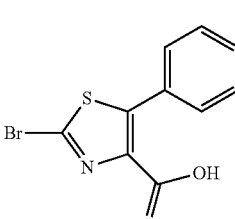 | S-21 | | Preparation of ester precursor P-26: see PCT Int. Appl., 2009104155, 27 Aug. 2009 | | 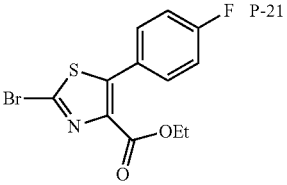 | P-21 |
| 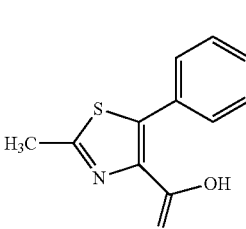 | S-22 | | Otava Building Blocks Otava<br>55 Ellerslie Avenue, Suite 524<br>Toronto, ON, M2N 1X9<br>Canada<br>http://www.otavachemicals.com | 1805700 | | |
| 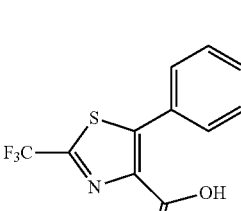 | S-23 | | See experimental for S-23 | | | |

TABLE 14-continued

Available 2-substituted thiazole scaffolds S-18 to S-27.

| Scaffold Structure | Scaffold ID # | Comment | Source or Reference. | Order # | Available Precursor | ID # |
|---|---|---|---|---|---|---|
| 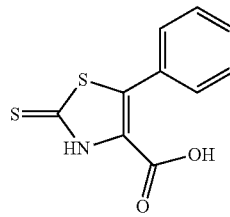 | S-24 | | ZereneX Molecular Limited 12 Manningham Road Greater Manchester, BL3 5QS United Kingdom www.zerenex-molecular.com | ZXA008054 | | |
| 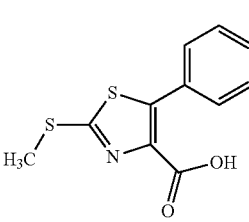 | S-25 | Prepared from Precursor P-25 with MeI and LiOH ester hydrolysis | Kingsh Chemicals Ltd. 27-201 Jinwan Garden, Zhongbao St. Nanjing, 210036 People's Republic of China http://www.kingshchem.com | 42487 | 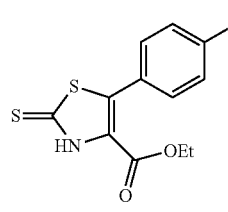 | P-25 |
| 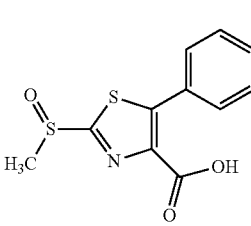 | S-26 | Prepared from S-25 by treatment with 1 eq. MCPBA | See experimental for S-26 | | | |
| 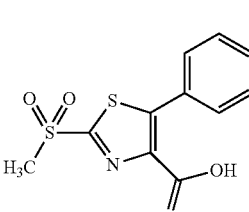 | S-27 | Prepared from S-25 by treatment with 2 eq. MCPBA | See experimental for S-27 | | | |

Analogous chemistry, using a 2-halo-aroylacetic ester 11 as the common starting material, can be applied to prepare 2-Substituted 4-aryl-thiazole-5-carboxylic acid scaffolds (Zawadzka, *Acta Poloniae Pharmaceutica* (1984), 41(6), 633-640), Scheme 7. Reaction of 11 with a thiourea, Route-1 (Narender M, Synthesis, (2007) 3469-3472); a thioamide, Route-2; or the adduct of carbon disulfide with ammonia, Route-3; affords the appropriate 2-substitute thiazole esters 34, 35, and 36, respectively. The 2-amino group of thiazole ester 3 can be further functionalized on nitrogen or converted to 2-halo derivative 37 through diazatization the action with the appropriate copper halide salt. A variety of 2-substituted thiazoles 38 can then be prepared by nucleophilic aromatic substitution or transition metal mediated coupling reactions. (Lee 1986). Thiazolidinethione 36 can be alkylated and optionally oxidized to provide 2-alkylmercapto-, 2-alkylsulfinyl-, or 2-alkylsulfonyl-thiazole 5-carboxylic esters 39. Route-3. Using these methods, a variety of 2-substituted 4-aryl-thiazole-5-carboxylic acid scaffolds 40-45 can be prepared. This approach has been expanded to allow the preparation of alternative 2-substituted thiazoles. Thiazole 2-carboxylic acid derivatives such as 46 may be prepared in an analogous manner, Route-4 (Lilienkampf A., *J. Med. Chem.* (2009) 52: 2109-2118).

A variety of functionalized 2-aminothiazole scaffolds can be prepared from commercially available 2-aminothiazole intermediates such as P-29, Table 15.

TABLE 15

Sources for 2-aminothiazole scaffolds.

| Scaffold Structure | Scaffold ID # | Comment | Source or Reference. | Order # | Available Precursor | ID # |
|---|---|---|---|---|---|---|
| 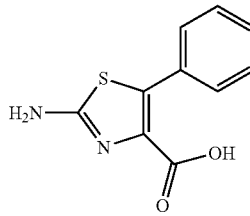 | S-28 | | Atlantic Research Chemicals Ltd. Unit A, Stratton View Business Park Stratton Bude, Cornwall EX23 9NR United Kingdom www.atlantic-chemicals.com | CA00659 | see Narender etal. Ref. Synthesis, (2007) 3469-3472 | |
| 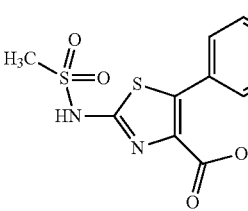 | S-29 | Prepared from P-29 with MsCl and base followed by LiOH | Combi-Blocks, LLC 7949 Silverton Ave. Suite 915 San Diego, CA 92126 USA www.combi-blocks.com | SS-5210 | 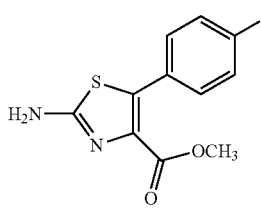 | P-29 |
| 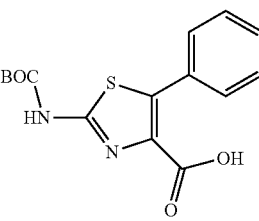 | S-30 | Prepared from P-29 with BOC anhydride and base followed by LiOH | | | | |
| 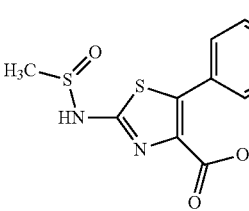 | S-31 | Prepared from P-29 with AcCl and base followed by LiOH | | | | |
| 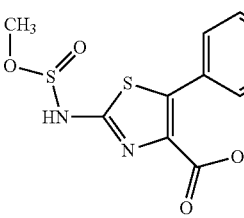 | S-32 | Prepared from P-29 with MeOCOCl and base followed by LiOH | | | | |

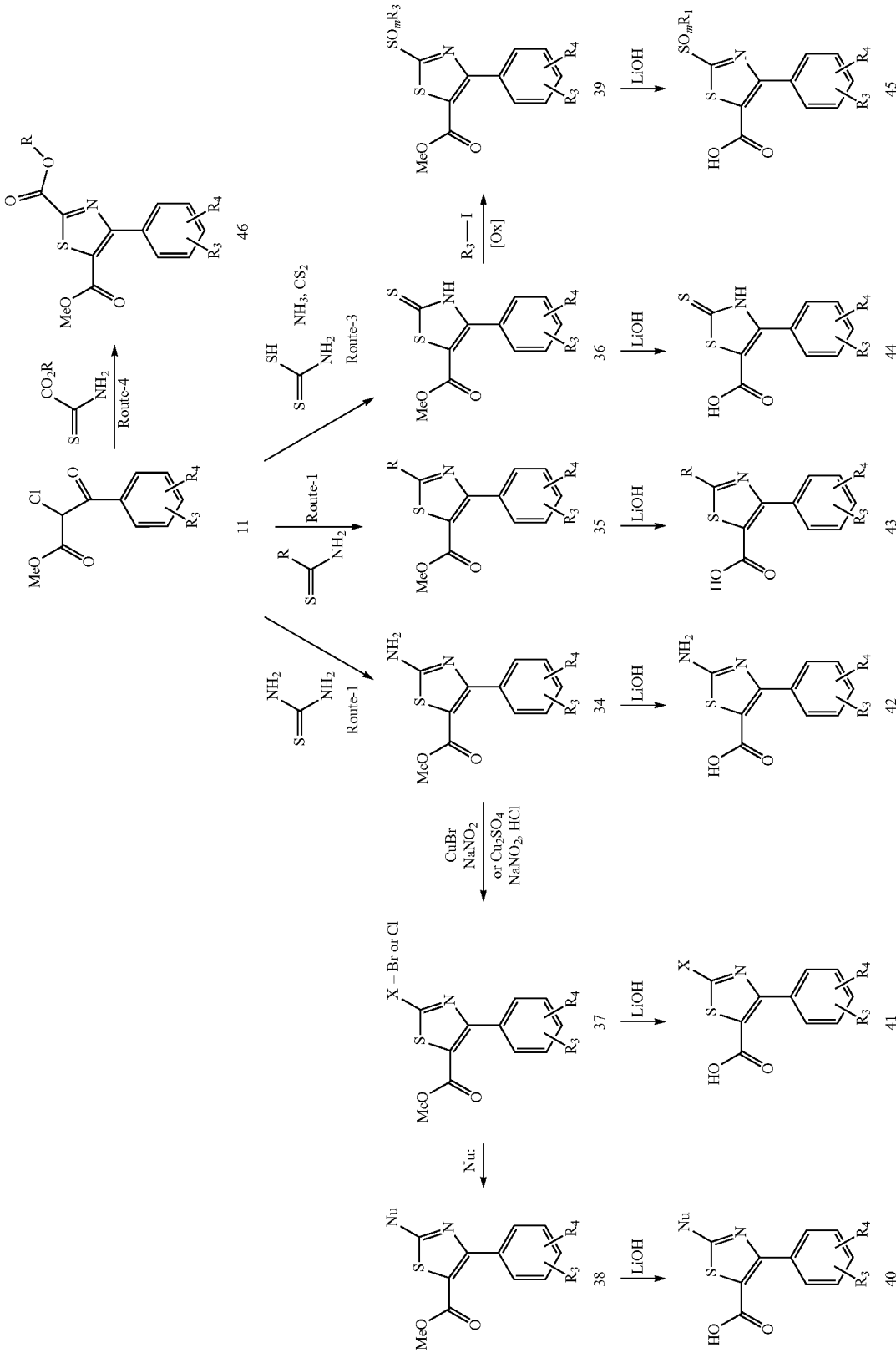
Scheme 7: Synthetic routes to 2-substituted-4-aryl-5-thiazole carboxylic acid scaffolds.

TABLE 16

Commercially Available Isomeric Thiazole acid Scaffolds and Ester Precursors.

| Scaffold Structure | Scaffold ID # | Comment | Source or Reference. | Order # | Available Precursor | ID # |
|---|---|---|---|---|---|---|
| | S-33 | | Aurora Fine Chemicals LLC<br>7929 Silverton Ave. Suite 609<br>San Diego, CA, 92126 USA<br>www.aurorafinechemicals.com | A02.445.497 | | |
| | S-34 | | Kingsh Chemicals Ltd. 27-201<br>Jinwan Garden, Zhongbao St.<br>Nanjing, 210036<br>People's Republic of China<br>http://www.kingshchem.com | 42198 | | |
| | S-35 | | Kingsh Chemicals Ltd. 27-201<br>Jinwan Garden, Zhongbao St.<br>Nanjing, 210036<br>People's Republic of China<br>http://www.kingshchem.com | 42196 | | |
| | S-36 | | ZereneX Molecular Limited<br>12 Manningham Road<br>Greater Manchester, BL3 5QS<br>United Kingdom<br>www.zerenex-molecular.com | ZXA008039 | | |
| | S-37 | | Kingsh Chemicals Ltd. 27-201<br>Jinwan Garden, Zhongbao St.<br>Nanjing, 210036<br>People's Republic of China<br>http://www.kingshchem.com | 43103 | | |
| | S-38 | Prepared from P-38 by ester hydrolysis with LiOH | Matrix Scientific<br>P O Box 25067<br>Columbia, SC, 29224-5067<br>USA<br>http://www.matrixscientific.com | 39519 | | P-38 |

TABLE 16-continued

Commercially Available Isomeric Thiazole acid Scaffolds and Ester Precursors.

| Scaffold Structure | Scaffold ID # | Comment | Source or Reference. | Order # | Available Precursor | ID # |
|---|---|---|---|---|---|---|
| 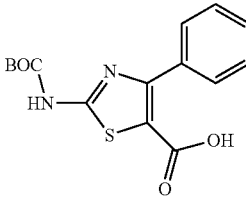 | S-39 | Prepared from P-39 with BOC anhydride and base then LiOH | Kingsh Chemicals Ltd. 27-201 Jinwan Garden, Zhongbao St. Nanjing, 210036 People's Republic of China http://www.kingshchem.com | 42007 | 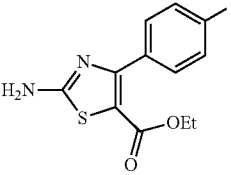 | P-39 |
| 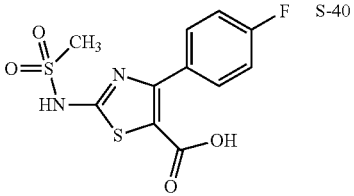 | S-40 | Prepared from P-39 with MsCl and base then LiOH | | | | |

A variety of additional ortho Aryl-5-membered heteroaryl carboxylic acid ring systems that share the imidazole scaffold geometry have been reported or are commercially available, Table 16. For example, Oxazole scaffolds 47 can be derived from 2-amino-ketoester 2 by simple acylation and acid catalyzed cyclization, Route-1, Scheme 8, (PCT Int. Appl. 2008 0704905, 21 Feb. 2008). The disubstituted triazole scaffold 49 can be prepared via the [3+2] cycloaddition of an aroyl actetic ester 10 with p-methoxybenzyl azide followed by deprotection, Route-2, (PCT Int. Appl. 2005 073192, 11 Aug. 2005). Reaction of hydrazone 50 with methyl acrylate followed by oxidation has be used to prepare the trisubstituted pyrazole 51, Route-3, (PCT Int. Appl. 2005 080380, 1 Sep. 2005). Another [3+2] cycloaddition reaction involving an aryl azide 52 and methyl propynate provides a simple entrance to N-aryl triazole 53, Route-4. All the scaffold acides 54-57 share a similar geometry between the carboxylic acid function and the substitute aryl ring that is defined by the 5-membered scaffold.

Scheme 8: Synthetic routes to miscellaneous azole scaffolds with similar geometries.

Route-1

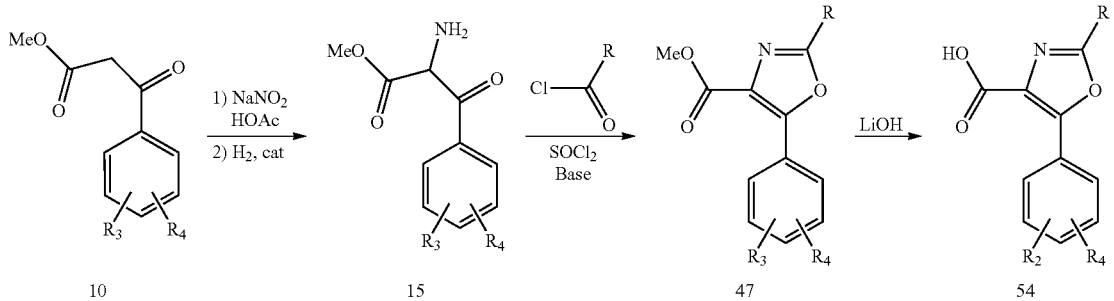

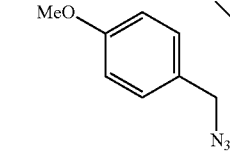

Route-2

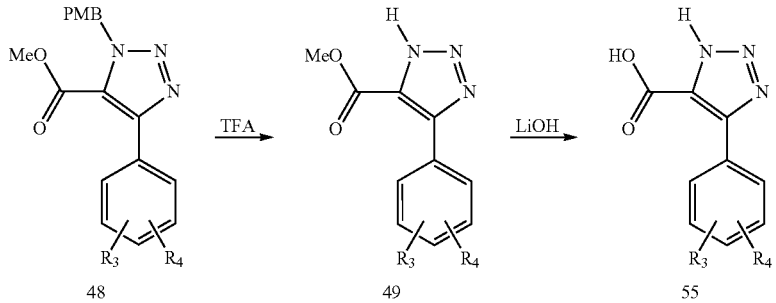

Route-3

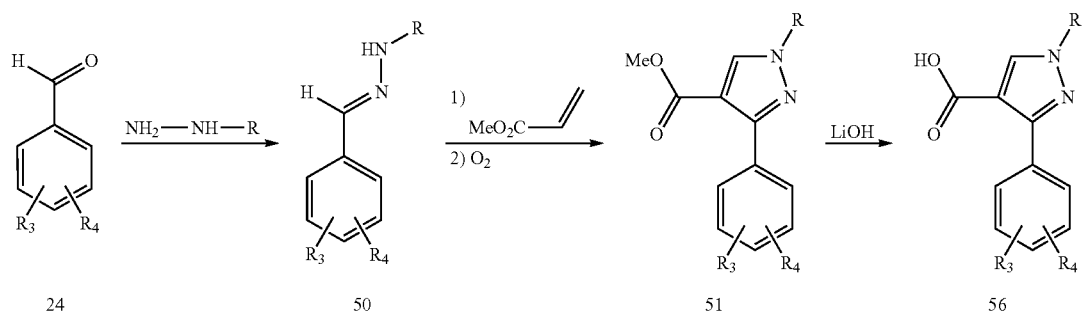

Route-4

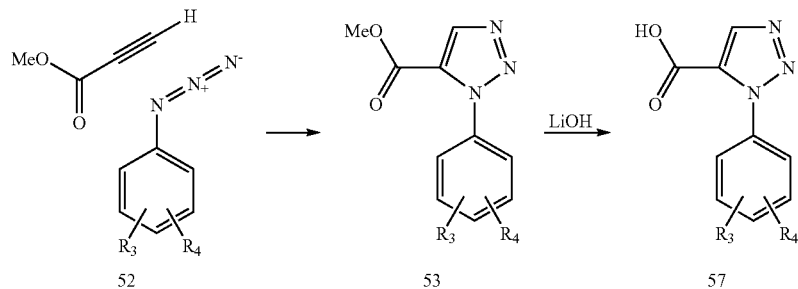

Commercially available oxazole acid scaffolds S-43 to S-49 and ester precursors P-49 and P-49 are listed in Table 17. Complimentary 2-mercaptooxazole derived scaffolds S-49, S-50 to S-53 and ester precursor P-49 are listed in Table 18.

The miscellaneous azoles acid scaffolds S-54 to S-64 summarized in Scheme 10 and bicyclic azole acid scaffolds S-65 to S-67 listed in Table 19 or their ester precursors are either commercially available or readily prepared as indicated.

TABLE 17

Commercially Available Oxazole Acid Scaffolds and Ester Precursors.

| Scaffold Structure | Scaffold ID # | Comment | Source or Reference. | Order # | Available Precursor | ID # |
|---|---|---|---|---|---|---|
| | S-41 | | See S-41 Experimental Section Feifei Zhao F., et.al., J. Org. Chem. (2011) 76 (24), pp 10338-10344 | | | |
| | S-42 | | Otava Building Blocks Otava 55 Ellerslie Avenue, Suite 524 Toronto, ON, M2N 1X9 Canada http://www.otavachemicals.com | 1788860 | | |
| | S-43 | | Best PharmaTech, Inc. P O Box 59394 Schaumburg, IL, 60159 USA http://www.bestpharmatech.com | BP21319 | | |

TABLE 17-continued

Commercially Available Oxazole Acid Scaffolds and Ester Precursors.

| Scaffold Structure | Scaffold ID # | Comment | Source or Reference. | Order # | Available Precursor | ID # |
|---|---|---|---|---|---|---|
| (5-(4-chlorophenyl)oxazole-4-carboxylic acid) | S-44 | | Combi-Blocks, LLC 7949 Silverton Avenue, Suite 915 San Diego, CA, 92126 USA www.combi-blocks.com | HI-1354 | | |
| (5-(4-nitrophenyl)oxazole-4-carboxylic acid) | S-45 | | OChem Incorporation 9044 Buckingham Park Drive Des Plaines, IL, 60016 USA www.ocheminc.com | 220N307 | | |
| (5-(4-fluorophenyl)isoxazole-4-carboxylic acid) | S-46 | | HDH Pharma, Inc. 7030 Kit Creek Road, Ste 250 Research Triangle Park, NC, 27709 USA www.hdhpharma.com | 14091 | | |
| (4-(4-fluorophenyl)-2-methyloxazole-5-carboxylic acid) | S-47 | Prepared from P-47 with LiOH | APAC Pharmaceutical, LLC 6851 Oak Hall Lane Suite 101 Columbia, MD, 21045 USA Email: sales@apacpharma.com www.apacparma.com | 650892 | (methyl 4-(4-fluorophenyl)-2-methyloxazole-5-carboxylate) | P-47 |
| (4-(4-fluorophenyl)oxazole-5-carboxylic acid) | S-48 | Prepared from P-48 with LiOH | Otava Building Blocks Otava 55 Ellerslie Avenue, Suite 524 Toronto, ON, M2N 1X9 Canada http://www.otavachemicals.com | 1788860 | (ethyl 4-(4-fluorophenyl)oxazole-5-carboxylate) | P-48 |

TABLE 18

2-mercapto-Oxazole Derived Scaffolds.

| Scaffold Structure | Scaffold ID # | Comment | Source or Reference. | Order # | Available Precursor | ID # |
|---|---|---|---|---|---|---|
| | S-49 | Prepared from P-49 by ester hydrolysis with LiOH | Nanosyn Inc. 3100 Central Expressway Santa Clara, CA www.nanosyn.com | NSN21446 | | P-49 |
| | S-50 | Prepared from Precursor P-49 by alkylation with MeI follow by LiOH | See S-50 experimental section | | | |
| | S-51 | Prepared from S-50 by treatmet with 1-eq. of MCPBA | See S-51 experimental section | | | |
| | S-52 | Prepared from S-50 by treatmet with 2-eq. of MCPBA | See S-52 experimental section | | | |

A variety of commercially available azole scaffolds are listed in Table 19 and Table-20.

TABLE 19

Sources for representative Miscellaneous Azole Scaffolds.

| Scaffold Structure | Scaffold ID # | Comment | Source or Reference. | Order # | Available Precursor | ID # |
|---|---|---|---|---|---|---|
| | S-53 | | ChemBridge Corporation 16981 Via Tazon, Suite G San Diego, CA, 92127 USA www.chembridae.com | 4042713 | | |

TABLE 19-continued

Sources for representative Miscellaneous Azole Scaffolds.

| Scaffold Structure | Scaffold ID # | Comment | Source or Reference. | Order # | Available Precursor | ID # |
|---|---|---|---|---|---|---|
| 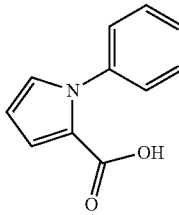 | S-54 | | ACB Blocks Ltd P O Box 10 Moscow, 121609 Russia Phone: +7(495)761-4365 | 2PA-0059 | | |
| 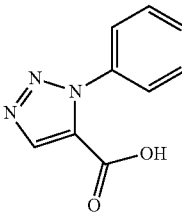 | S-55 | | Aurora Fine Chemicals LLC 7929 Silverton Ave. Suite 609 San Diego, CA, 92126 USA www.aurorafinechemicals.com | A00.603.652 | | |
| 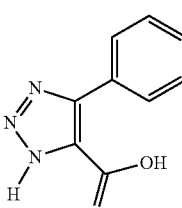 | S-56 | Prepared from P-56 by ester hydrolysis with LiOH | Biolecule 160 New Boston Street Woburn, MA, 01801 USA www.biolecule.com | Bi536 | 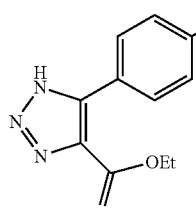 | P-56 |
| 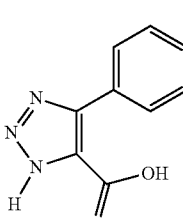 | S-57 | Prepared from P-57 by ester hydrolysis with LiOH | Biolecule 160 New Boston Street Woburn, MA, 01801 USA www.biolecule.com | Bi548 | 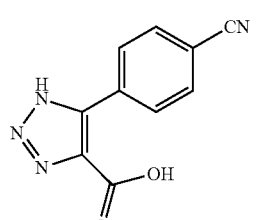 | P-57 |
| 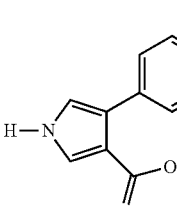 | S-58 | | Best PharmaTech, Inc. P O Box 59394 Schaumburg, IL, 60159 USA http://www.bestpharmatech.com | BP42828 | | |
| 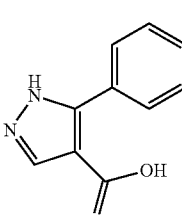 | S-59 | | Matrix Scientific P O Box 25067 Columbia, SC, 29224 USA http://www.matrixscientific.com | 38658 | | |
| 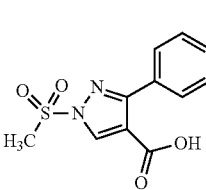 | S-60 | | Prepared by multistep sequence See S-60 experimental section | | | |

TABLE 19-continued

Sources for representative Miscellaneous Azole Scaffolds.

| Scaffold Structure | Scaffold ID # | Comment | Source or Reference. | Order # | Available Precursor | ID # |
|---|---|---|---|---|---|---|
| 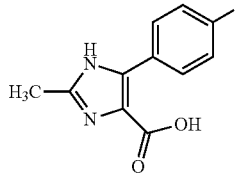 | S-61 | Prepared from P-61 by ester hydrolysis with LiOH | Lanzhou Chon Chemical Co. Ltd. D6, Guchengping Industrial Park Donggang Town Lanzhou City People's Republic of China Web: http://www.chonchem.com | P20978 | 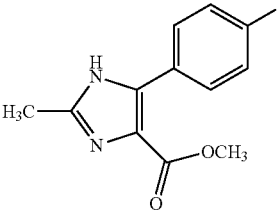 | P-61 |
| 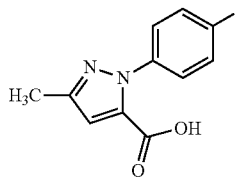 | S-62 | | May be repared from Ethyl 3-Acyl-pyruvate and an appropriate aryl hydrazine followed purification and LiOH hydrolysis. | | 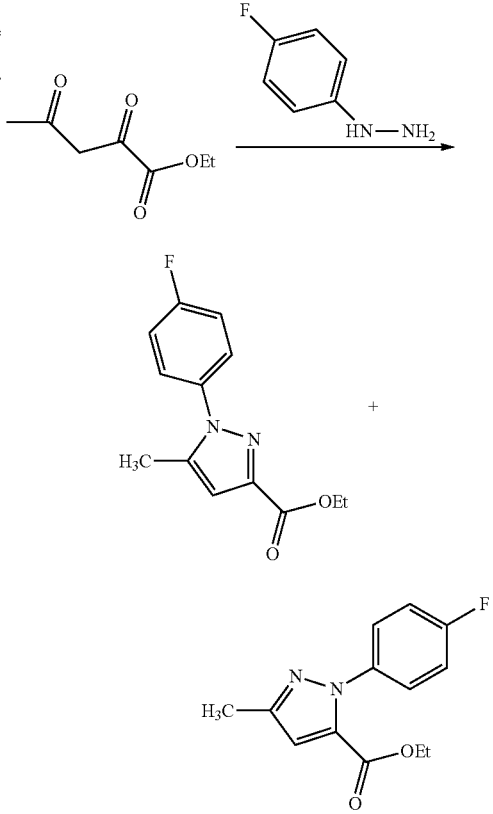 | |
| 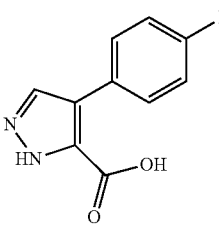 | S-63 | | PCT Int. Appl., 200305187226 | | | |
| 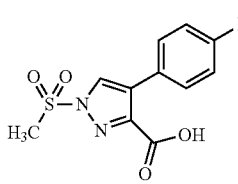 | S-64 | Prepared form S-64 by reaction with MsCl and base | PCT Int. Appl., 200305187226 | | | |

TABLE 20

Commercially Available Bicyclic Scaffolds.

| Scaffold Structure | Scaffold ID # | Comment | Source or Reference. | Order # | Available Precursor | ID # |
|---|---|---|---|---|---|---|
| | S-65 | | Kingsh Chemicals Ltd. 27-201 Jinwan Garden, Zhongbao St. Nanjing, 210036 People's Republic of China http://www.kingshchem.com | 44507 | | |
| | S-66 | | Otava Building Blocks Otava 55 Ellerslie Avenue, Suite 524 Toronto, ON, M2N 1X9 Canada http://www.otavachemicals.com | 1515836 | | |
| | S-67 | Prepared from P-65 by ester hydrolysis with LiOH | Kingsh Chemicals Ltd. 27-201 Jinwan Garden, Zhongbao St. Nanjing, 210036 People's Republic of China http://www.kingshchem.com | 44245 | | P-65 |

Efficient and general routes to oxazoles have been reported and may be utilized to prepare a wide variety of oxazole acid scaffolds, Scheme 9. As indicated, 2-amino-Aroylproionic esters 1 can be accessed by several procedures. Reaction of 1 with trifluoroacetic anhydride and cyclodehydration provides an efficient approach to 2-substituted-oxazoles, Route 1, and thiazoles, Route-3 (Sanz-Cervera, 2009). Using these procedures, the oxazole scaffolds S-68 to S-80 may be readily prepared Scheme 11.

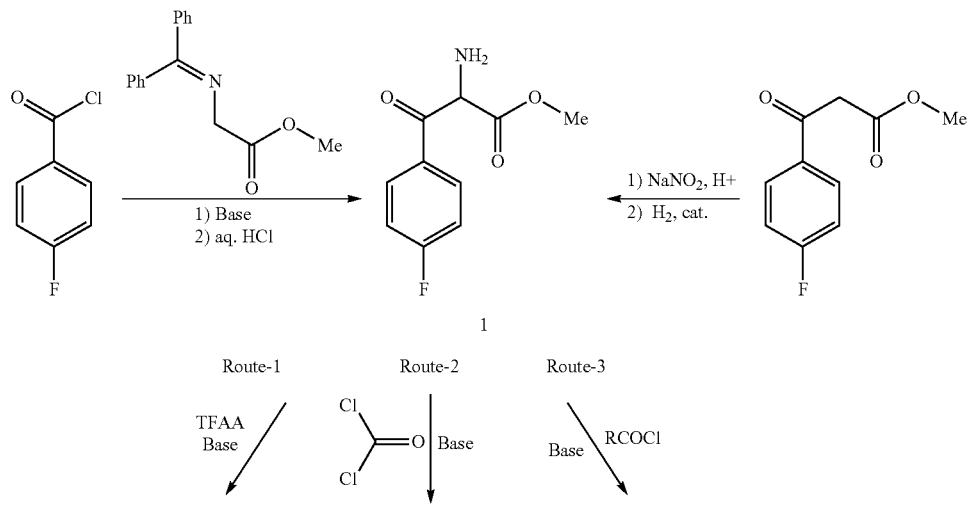

Scheme 9: General Synthetic Approaches to Oxazoles

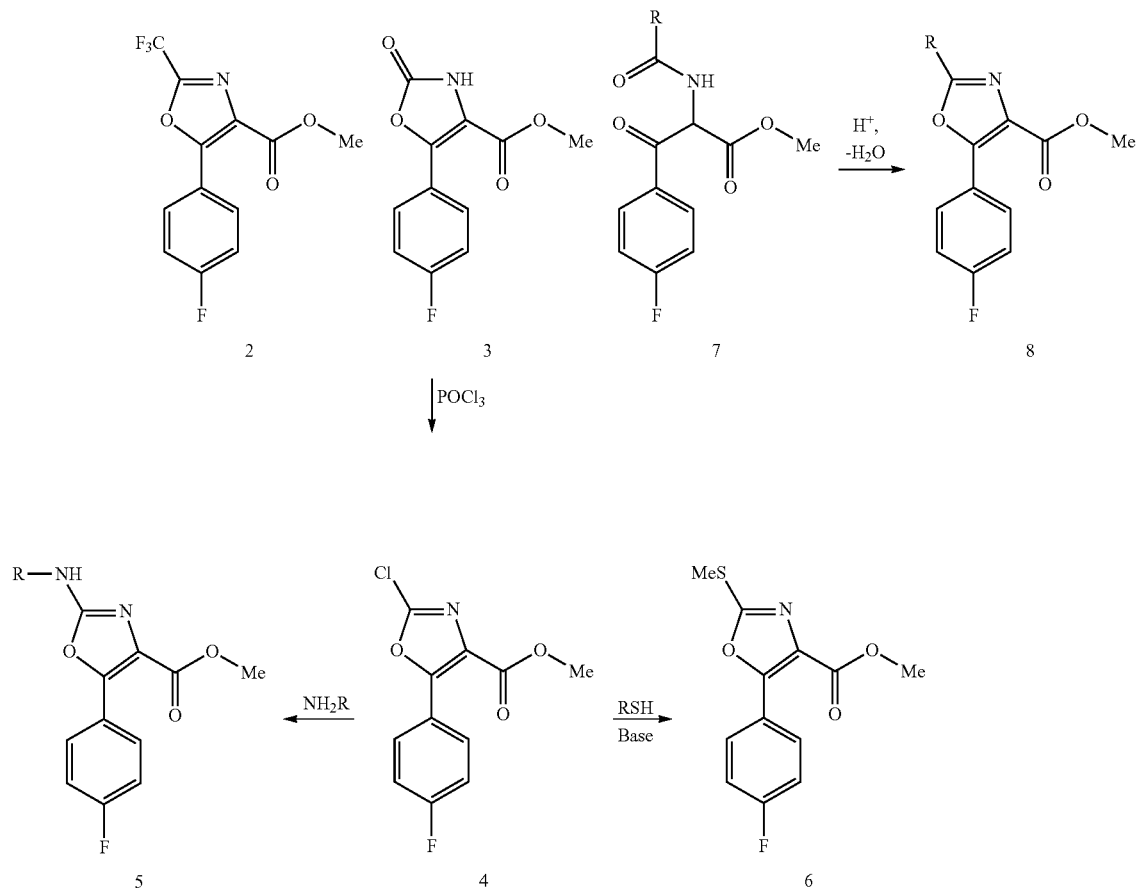
Using these procedures, the oxazole and thiazole acid scaffolds S-23 and S-68 to S-80 depicted in FIG. 11 may be prepared.
Scheme 10: Representative Readily Prepared Oxazole and Thiazole Acid Scaffolds (P is a protecting Group).
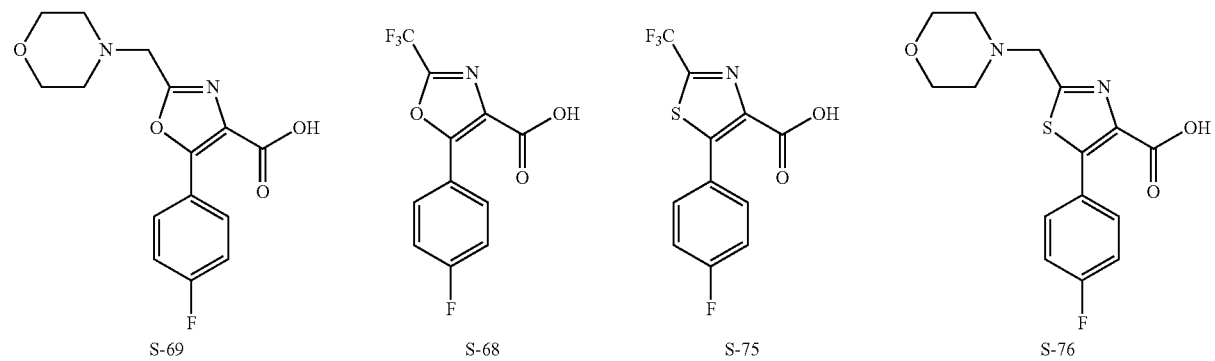

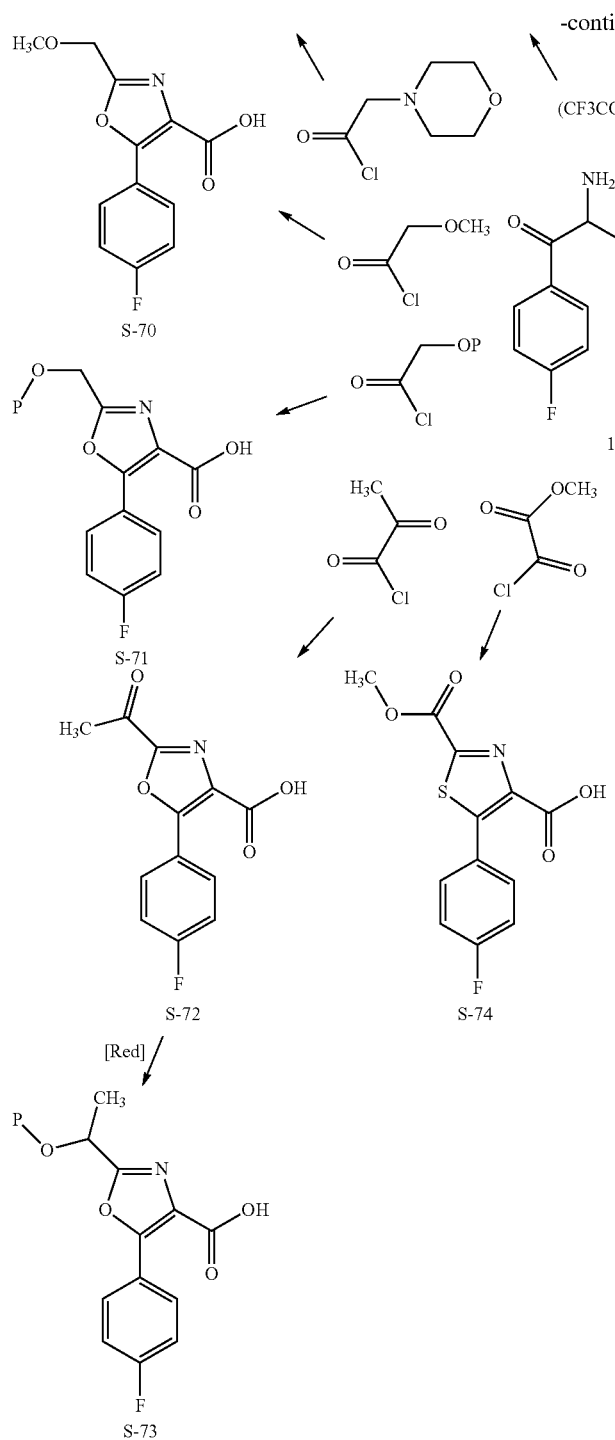
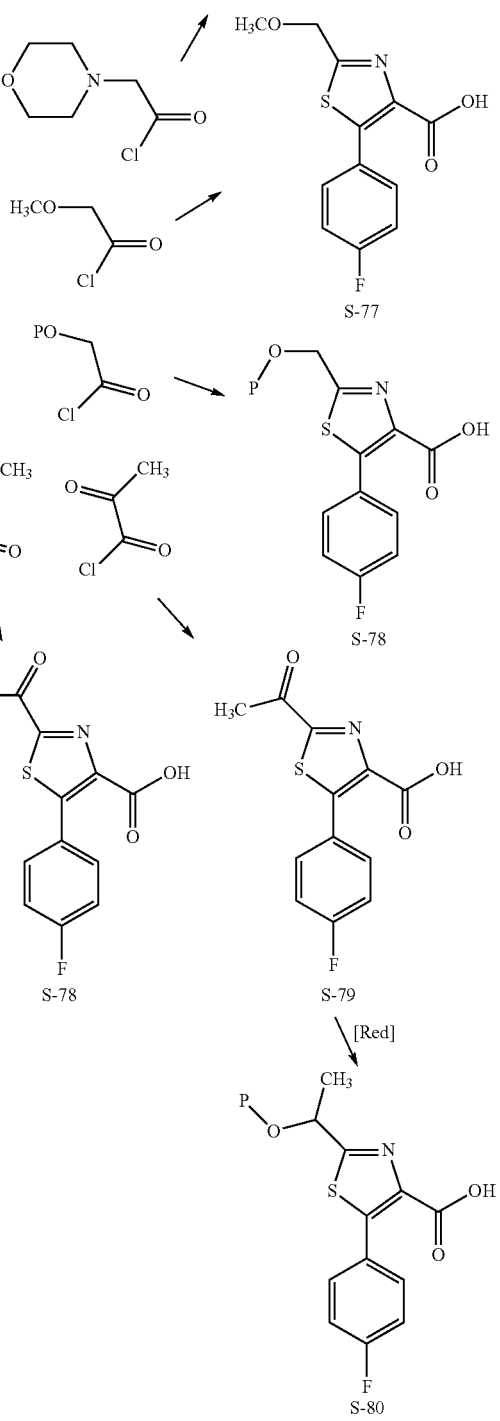

Using the construction method outlined in Scheme 1, one skilled in the art could reasonably construct a two dimensional combinatorial library comprised of HGM-1 to HGM-73 described in Tables 1-9 and scaffold acids S-1 to S-80 described in Tables 11 to 20 and Scheme 10. A constructed library of the 5,840 compounds derived from these building blocks would be expected to display interesting and new kinase inhibition profiles and attractive physical properties as lead compounds, useful tools for discovering new activities, and potential therapeutic agents.

In order to demonstrate the feasibility and usefulness of preparing such a library, the 2×10 library of new inhibitors described in was prepared by coupling of amines HGM-1 and HGM-35 with the indicated scaffolds, Table 21 (p 129 or 130). These compounds were profiled against a panel of 230 kinases (Nanosyn Inc.). The kinases inhibited by ≥50% at 5 uM concentration by these 20 new inhibitors is compared to the previously observed activity profiles for Inhibitors I-14 and I-15, Table 14. These data validate the utility of the scaffold geometry described herein for the discovery of novel kinase inhibition profiles.

Methods for Preparation of Kinase Targeted PET Imaging Probes:

Our hypothesis that this unique scaffold geometry is broadly applicable to the Type-II inhibition of kinases suggests that coupling of an established Hinge-Gatekeeper Motif (HGM) with this scaffold could convey a similar activity profile. An example of this is SFE-0006, where the HGM of Sorafenib is incorporated. Therefore it may be assumed that modification of the HGM from known or experimental inhibitors could convey a similar activity profile. Therefore, chemistries have been designed to allow adaptation of this scaffold geometry for the construction of PET imaging agents, Scheme 11.

Scheme 11: Synthetic schemes for intoduction of 18F or 11C radiolabel from inhibitor intermediates, where (H)—L—G— is an appropriate Hinge-Gatekeeper Motif (HGM) and X is either O, $NR^2$, or S.

Route-1

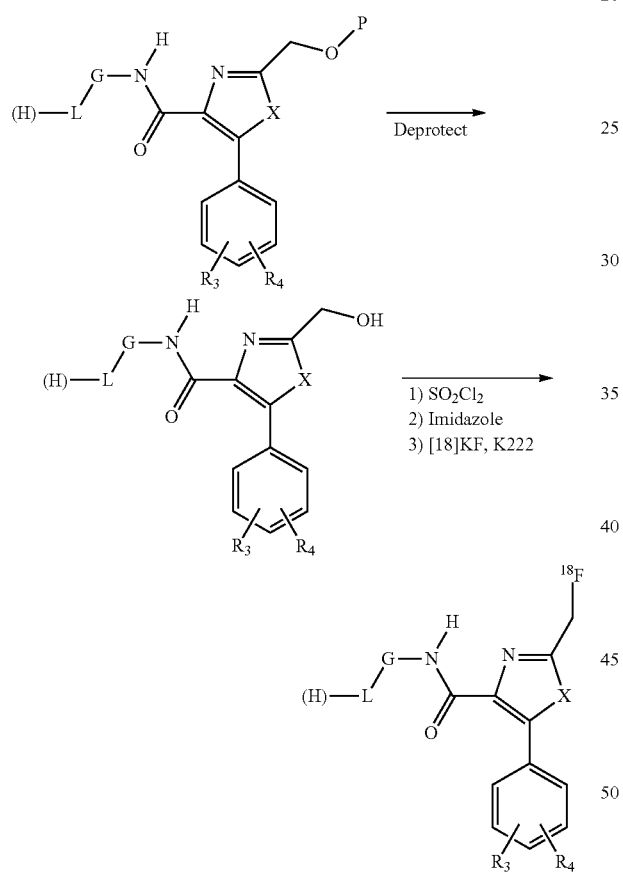

Route-2

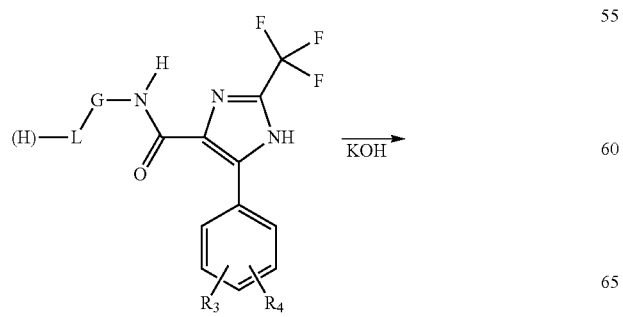

Route-3

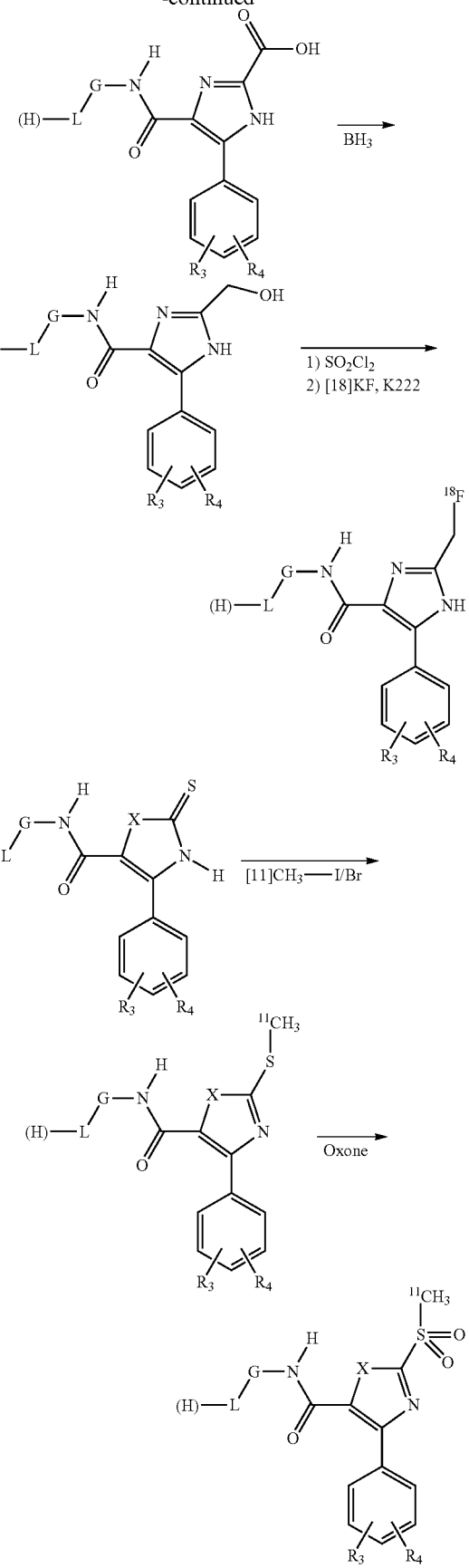

Route-4

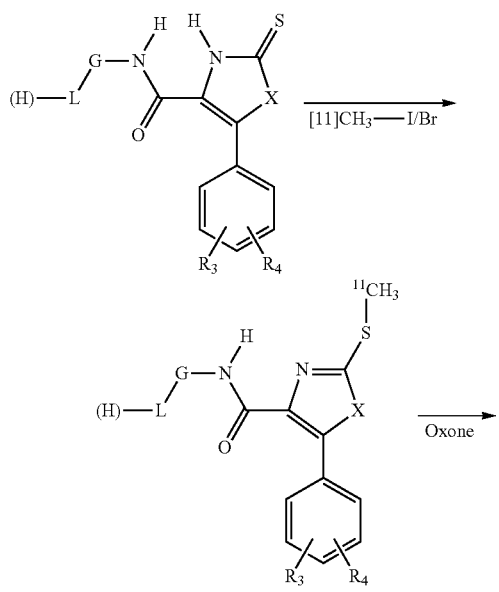

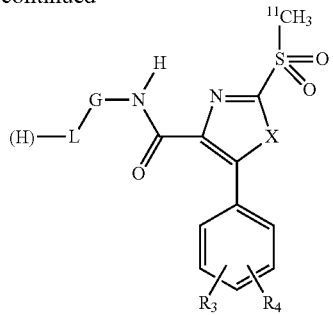

Preparation of Scaffolds

Although a wide variety of ortho-aryl-5-membered-heteroaryl carboxylic acid scaffolds can be made, the preparation of specific inhibitors described below use the scaffolds illustrated in Schemes 1 to 4. These scaffolds vary primarily in their 2-substituent which vary in their size, polarity, and ability to establish hydrogen-bonds. For example the 2-trifluoromethyl-imidazole scaffold S-1 and 2-methylthio-imidazole S-15 are more lipophilic while the 2-methylsulfinyl, 2-methyl sulfonyl-imidazole scaffolds S-16 and S-17 are significantly more polar, Scheme 12.

Scheme-12: Preparation scaffolds S-1, S-15, S-16, and S-17.

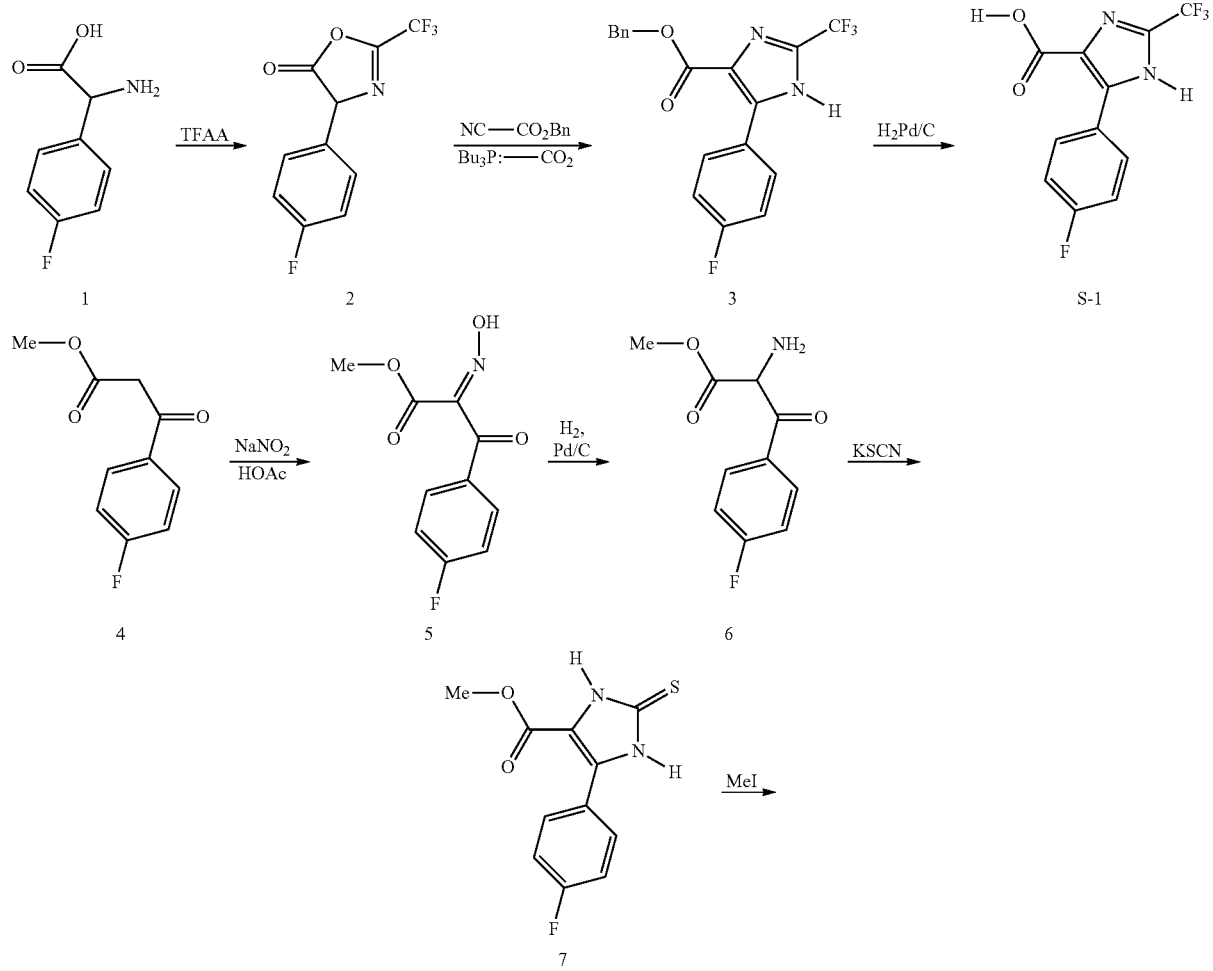

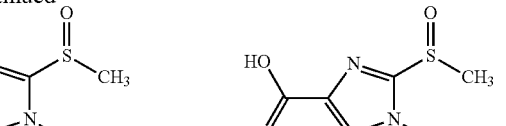
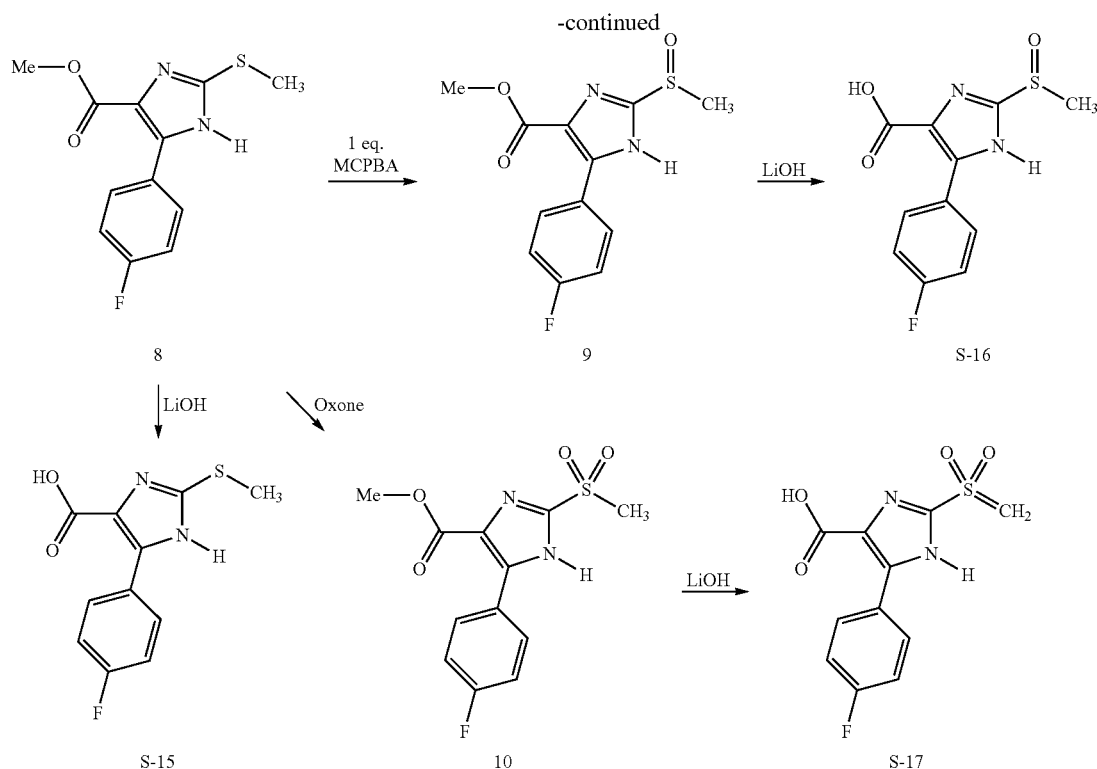

5-(4-Fluoro-phenyl)-2-trifluoromethyl-3,1-imidazole-4-carbonylic Acid (S-1)

4-Fluoro-phenyl glycine 1 (10 g, 66 mmol) was added to a 250 mL round bottomed flask that contained trifluoroacetic anhydride (30 mL) and stirred for 2 h at room temperature. Upon formation of oxazolinone 2, the excess TFAA and TFA were removed in vacuo as an azeotrope with toluene. The remaining yellow solid was dissolved in 750 mL dry toluene and benzylcyanoformate (11 mL, 1.1 equiv, 72 mmol) was added via syringe followed by the dropwise addition of tributylphosphine (17 mL, 1 equiv, 66 mmol). $CO_2$ emission from the reaction was observed with an oil bubbler. The reaction was allowed to stir at room temperature for 12 h and then was concentrated to dryness under reduced pressure, dissolved in EtOAc, and washed with sodium bicarbonate, 1M HCl, and brine. The crude mixture was purified by silica gel chromatography and eluted with a gradient of 0-60% EtOAc/Hex to give 7 g of the desired imidazole benzyl ester 3 (7.0 g, 19.2 mmol) as an off-white solid.

Benzyl 5-(4-Fluoro-phenyl)-2-trifluoromethyl-3H-imidazole-4-carbonylate 3 (7.0 g, 19.2 mmol) was dissolved in ethanol (200 mL) and Pd-c (5%, 200 mg) was added and the mixture was stirred under $H_2(g)$ at 50 PSI on a Parr shaker overnight. The mixture was filtered through celite and the solvent was evaporated to give the desired product S-1 (5.25 g, 10 mmol).

5-(4-Fluoro-phenyl)-2-methylthio-1H-imidazole-4-carboxylic acid (S-15)

3-(4-Fluoro-phenyl)-2-hydroxyimino-3-oxo-propionic acid methyl ester (5)

To a stirred solution of methyl 4-fluorobenzoyl acetate (15.7 g, 80.0 mmol) in HOAc (50 mL) was added a solution of $NaNO_2$ (8.28 g, 120 mmol) in water (80 mL) at 10° C. The resulting mixture was stirred at 10° C. for 1 h, then 16 h at rt. The precipitate formed in the reaction mixture was collected by filtration, washed with water and dried over vacuum to afford product 5 (18.0 g, 100%) as a white solid. ESI MS m/z 240.2 $(M+H)^+$.

2-Amino-3-(4-fluoro-phenyl)-3-oxo-propionic acid methyl ester hydrochloride (6)

A solution of oxime 5 (18.0 g, 80.0 mmol) in MeOH (220 mL) was mixed with 1.25 M HCl solution in MeOH (130 mL) at rt. The solution was flushed with $N_2$ and then charged with 5% Pd—C (3.1 g). A hydrogen balloon was attached to the flask and the resulting mixture was stirred at rt for 2.5 h. More 5% Pd-C (~1.8 g every 2 h) was added as the reaction was carefully monitored by LCMS. Eventually, the reaction was completed in 8 h with totally 9.4 g of 5% Pd—C added. After Pd catalyst was removed by filtering through a Celite pad, the clear solution was concentrated under reduced pressure to afford hydrochloride salt of pure product 6 (20.0 g, 100%) as a white solid. ESI MS m/z 212.2 $(M+H)^+$.

5-(4-Fluoro-phenyl)-2-thioxo-2,3-dihydro-1H-imidazole-4-carboxylic acid methyl ester (7)

To a stirred solution of aminoketone ester 6 hydrochloride (20.0 g, 80.0 mmol) in DMF (100 mL) was added KSCN (15.6 g, 160 mmol) at rt. The resulting mixture was stirred at 95° C. for 3 h and then allowed to cool to rt. After the reaction mixture was poured into brine (200 mL), a white precipitate formed. Water (200 mL) was added to ensure the entire product 7 precipitated out from the resulting mixture. The precipitate was collected by filtration, washed with water and dried on vacuum to afford product 7 (18.0 g, 89%) as a white solid. ESI MS m/z 253.2 $(M+H)^+$.

5-(4-Fluoro-phenyl)-2-methylsulfanyl-1H-imidazole-4-carboxylic acid methyl ester (8)

To a stirred solution of compound 7 (18 g, 71.0 mmol) in MeOH (200 mL) was added $K_2CO_3$ (12.0 g, 85.0 mmol), followed by the dropwise addition of a solution of MeI (8.9 mL, 143 mmol) in MeOH (200 mL) at rt. The resulting mixture was stirred at rt for 2 h and then concentrated under reduced pressure. The residue was treated with water (200 mL) and extracted with ethyl acetate (150 mL×3). The combined extracts were washed with brine (50 mL×2), dried over anhydrous $MgSO_4$, filtered, and evaporated to afford product 8 (19.0 g, 100%) as a white solid. ESI MS m/z 267.2 $(M+H)^+$.

5-(4-Fluoro-phenyl)-2-methylthio-1H-imidazole-4-carboxylic acid (S-15)

To a solution of 2-methylthioimidazole ester 8 (1 g, 3.6 mmol) in dioxane (10 mL) was added 2M lithium hydroxide (18 mL, 36 mmol). Oxygen was evacuated under vacuum and flask was flushed with nitrogen three times. Reaction mixture was stirred over night at 60° C. under nitrogen, brought to room temperature and gradually acidified with 1N HCl. The resulting mixture was diluted with water and extracted with ethyl acetate. Organic layer was washed with brine, dried with anhydrous sodium sulfate, filtered and concentrated in vacuo to give 0.9 g (quantitative yield) of the desired product S-15.

5-(4-Fluoro-phenyl)-2-methylsulfinyl-1H-imidazole-4-carboxylic acid (S-16)

A solution of m-chloroperoxybenzoic acid (MCPBA) (579 mg, 3.35 mmol) in 5 mL of dichloromethane was added drop wise to a stirred solution of 8 (940 mg, 3.35 mmol) in 5 mL of dichloromethane at room temperature. The reaction mixture was stirred for 4 h, and then transferred to a seperatory funnel and washed with saturated aq. $NaHCO_3$ solution, water and brine. The organic layer was dried with anhydrous $MgSO_4$, filtered and concentrated in vacuo to give 1 g of the desired sulfoxide 9. This crud sulfoxide intermediate was dissolved in 10 mL of dioxane and to it was added 2M lithium hydroxide (18 mL, 36 mmol). Oxygen was evacuated under vacuum and flask was flushed with nitrogen three times. Reaction mixture was then stirred over night at 60° C. under nitrogen. The reaction mixture was then gradually acidified with 1N HCl, diluted with water and extracted with ethyl acetate. Organic layer was washed with brine, dried with anhydrous sodium sulfate, filtered and concentrated in vacuo to give 0.75 g (79% over two steps) of the product 5-(4-Fluoro-phenyl)-2-methylsulfinyl-1H-imidazole-4-carboxylic acid S-16.

5-(4-Fluoro-phenyl)-2-methanesulfonyl-1H-imidazole-4-carboxylic acid (S-17)

5-(4-Fluoro-phenyl)-2-methanesulfonyl-1H-imidazole-4-carboxylic acid methyl ester (10)

To a stirred solution of compound 8 (19.3 g, 72.5 mmol) in MeOH (500 mL) was added a solution of OXONE (133 g) in water (500 mL) dropwise at rt in 1 h. The resulting mixture was stirred at rt for 4 h and then concentrated under reduced pressure. The slurry aqueous mixture was extracted with DCM (200 mL×4). The combined extracts were washed with brine (100 mL×2), dried over anhydrous $MgSO_4$, filtered, and evaporated to afford sulfone 10 (19.8 g, 92%) as a white solid. ESI MS m/z 299.2 $(M+H)^+$.

5-(4-Fluoro-phenyl)-2-methanesulfonyl-1H-imidazole-4-carboxylic acid

The sulfone 10 (19.8 g, 66.4 mmol) was treated with a mixture of LiOH (4.8 g, 200 mmol) in THF (240 mL) and water (80 mL) at 85° C. for 3 h. The resulting mixture was cooled to rt and then concentrated under reduced pressure. The aqueous solution was diluted with water (150 mL) and extracted with ethyl acetate (50 mL×2, discarded). The aqueous solution was acidified with 1N HCl aq. to pH 1 and then extracted with ethyl acetate (150 mL×3). The combined extracts were washed with brine (50 mL×2), dried over anhydrous $MgSO_4$, filtered, and evaporated to afford crude product 7 (18.0 g) as a white solid. ESI MS m/z 285.2 $(M+H)^+$. The crude product was suspended in a mixture of MTBE (50 mL) and dichloroethane (200 mL) and stirred at rt for 72 h. The remaining solid was collected by filtration, dried over vacuum to afford pure 5-(4-Fluoro-phenyl)-2-methanesulfonyl-1H-imidazole-4-carboxylic acid (S-17) as a white solid (14 g, 74%) with 96% purity by UV254 nm and 100% purity by ELS.

Scheme 13: Preparation of Thiazole Scaffolds S-25, S-26, S-27, and S-29

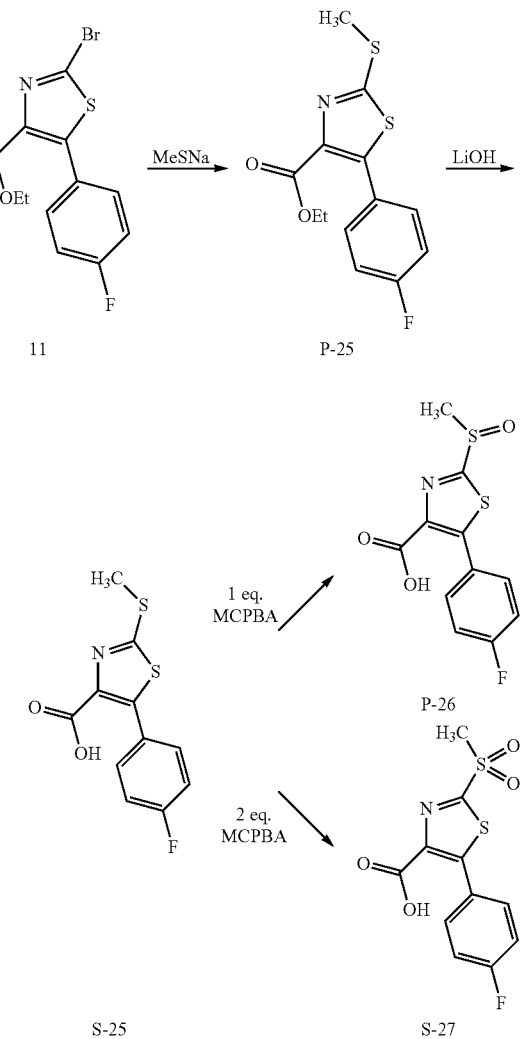

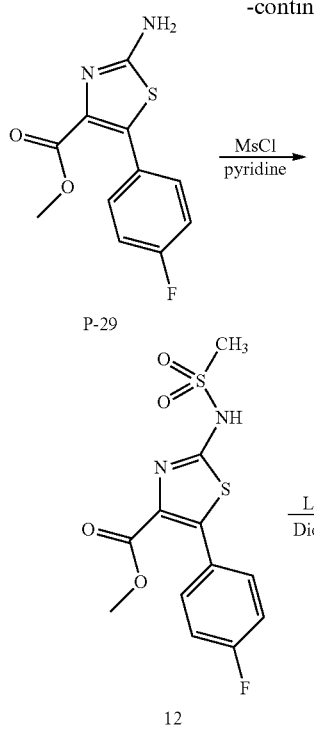

5-(4-fluorophenyl)-2-(methylthio)thiazole-4-carboxylic acid (S-25)

Ethyl 5-(4-fluorophenyl)-2-(methylthio)thiazole-4-carboxylate (P-25)

Sodium thiomethoxide (2.13 g, 30.4 mmol) was added in three portions over a period of 4 h to a solution of 2-Bromothiazole ester 11 (4 g, 12.6 mmol) in dimethoxyethane (50 mL). Reaction mixture was then stirred overnight at room temperature. Solvent was removed under reduced pressure and the residue was suspended in water, filtered, washed with small amount of ethyl acetate and dried under high vacuum to afford 2.6 g (72%) of 2-methylthio-thiazole ester P-25.

5-(4-fluorophenyl)-2-(methylthio)thiazole-4-carboxylic acid (S-25)

To a solution of ethyl 5-(4-fluorophenyl)-2-(methylthio)thiazole-4-carboxylate 2 (2.6 g, 9.1 mmol) in dioxane (20 mL) was added lithium hydroxide (0.32 g, 13.7 mmol) and the resulting mixture was stirred at 50° C. for two hours. Reaction mixture was then gradually acidified with 1N HCl. The precipitates were filtered, washed with water and dried under high vacuum to give 2.4 g of product S-25 (95%). $^1$H-NMR (CD$_3$OD, 250 MHz) δ 2.75 (s, 3H), 7.12 (t, 2H, J=8.75), 7.50 (dd, 2H, J=5.25, 8.75).

5-(4-fluorophenyl)-2-(methylsulfinyl)thiazole-4-carboxylic acid (S-26)

To a solution of S-25 (827 mg, 3 mmol) in dichloromethane (5 mL) was added m-CPBA (327 mg, 1.9 mmol) and the reaction mixture was stirred at room temperature for 10 h. Reaction mixture was then evaporated to dryness. To this residue diethylether was added to dissolve remaining m-CPBA and m-CBA. The suspended product was collected by filtration, washed with diethylether and dried under high vacuum to give 0.3 g (34%) of S-26. $^1$HNMR (CD$_3$OD, 250 MHz) δ 3.12 (s, 3H), 7.17 (t, 2H, J=8.75), 7.59 (dd, 2H, J=5.25, 8.75).

5-(4-fluorophenyl)-2-(methylsulfonyl)thiazole-4-carboxylic acid (S-27)

m-CPBA (516 mg, 3.3 mmol) was added to a stirred suspension of S-25 (300 mg, 1.1 mmol) in dichloromethane (6 mL) and stirred overnight. LCMS analysis showed some presence of sulfoxide. 86 mg (0.55 mmol) of m-CPBA was added and the reaction mixture was further stirred for 2 hours. Reaction mixture was then evaporated to dryness and partitioned between ethyl acetate and water. Organic layer was washed with brine, dried with anhydrous sodium sulfate, filtered and evaporated to dryness in rotary evaporator to afford S-27 as crude product which is used directly in the next step. $^1$H NMR (CD$_3$OD, 250 MHz) δ 3.45 (s, 3H), 7.19 (t, 2H, J=9), 7.62 (dd, 2H, J=5.25, 9).

5-(4-fluorophenyl)-2-(methylsulfonylamino)thiazole-4-carboxylic acid (S-29)

To a solution of P-29 (1 g, 3.96 mmol) in pyridine (10 mL) was added methanesulfonyl chloride (0.62 mL, 7.92 mmol) and the resulting mixture was stirred at 60° C. over night. Reaction mixture was then brought to room temperature and pyridine was evaporated under reduced pressure. The residue was dissolved in ethyl acetate and washed with saturated aq. sodium bicarbonate, water and brine. Organic layer was dried with anhydrous sodium sulfate, filtered and concentrated. The residue was purified by flash chromatography (hexanes/ethyl acetate) to afford 1 g (77%) of product 12.

To a stirred suspension of intermediate 2 (1 g, 3 mmol) was added 2M LiOH in dioxane (7.5 mL, 3 mmol) and the solution was stirred for 2 h at 40° C. The reaction mixture was then gradually acidified with 1N HCl. Diluted with water and extracted with ethyl acetate. Organic layer was washed with brine and dried with anhydrous sodium sulfate. Filtration and evaporation of organic layer afforded 0.9 g (94%) of the product S-29.

Scheme 14: Preparation of Scaffold S-41.

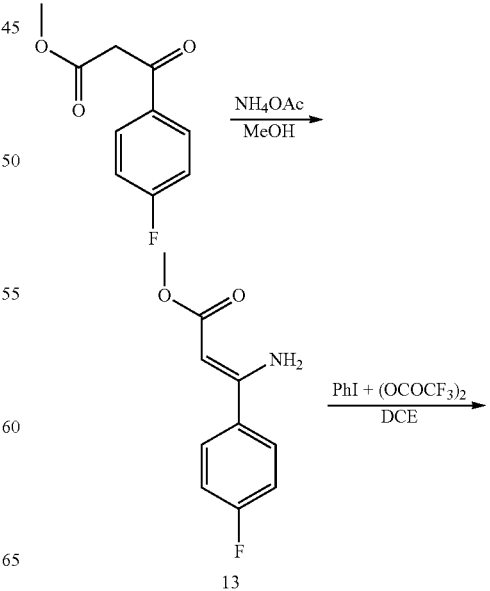

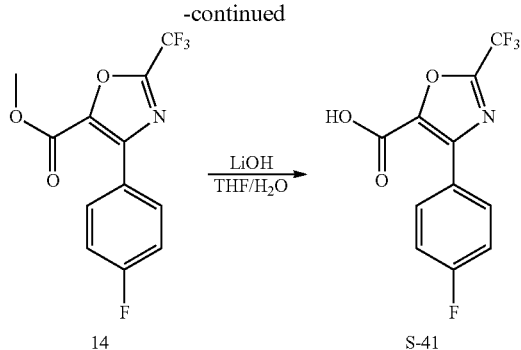

4-(4-Fluorophenyl)-2-(trifluoromethyl)oxazole-5-carboxylic acid. (S-41)

(Z)-methyl 3-amino-3-(4-fluorophenyl)acrylate (13)

A MeOH (10 mL) solution of methyl 3-(4-fluorophenyl)-3-oxopropanoate (200 mg, 1.02 mmol) and $NH_4OAc$ (393 mg, 5.10 mmol) was heated at reflux for 18 hrs. Solvent was removed in vacuo and the product isolated by $SiO_2$ chromatography (70% hexanes/30% DCM to 100% DCM) product elutes in 40% DCM (140 mg, colorless oil). 1HNMR (400 MHz, $CDCl_3$): d 7.46 (m, 2H), 7.03 (m, 2H), 4.85 (s, 1H), 3.64 (s, 3H). 19FNMR (400 MHz, $CDCl_3$): d −115.3

Methyl 4-(4-fluorophenyl)-2-(trifluoromethyl)oxazole-5-carboxylate (14)

To a solution of crude (Z)-methyl 3-amino-3-(4-fluorophenyl)acrylate (100 mg, 0.51 mmol) in dry DCE (5.1 mL) was added $PhI(OCOCF_3)_2$ (264 mg, 0.61 mmol) in one portion at 45° C. The reaction mixture was heated at 45° C. for 3 hours as the reaction was monitored by TLC. The solvent was evaporated and the crude material was separated by $SiO_2$ chromatography (Hexanes/DCM gradient from 80% hexanes/20% DCM to 100% DCM, desired product elutes in 70% hexanes/30% DCM) to yield a white solid (49 mg, 33% yield). $^1$HNMR (400 MHz, $CDCl_3$): d 8.15 (bs, 2H), 7.15 (m, 2H), 3.97 (s, 3H). 19FNMR (400 MHz, $CDCl_3$): d −66.53, −109.59. MS (ESI): m/z 290.0 [M+H]+

4-(4-Fluorophenyl)-2-(trifluoromethyl)oxazole-5-carboxylic acid (S-41)

To a solution of Methyl 4-(4-fluorophenyl)-2-(trifluoromethyl)oxazole-5-carboxylate (49 mg, 0.17 mmol) in THF (1.5 mL) was added LiOH (21 mg, 0.51 mmol) in water (0.4 mL). After 2 hours, the THF was evaporated, and the aqueous layer was acidified with 1N HCl and then extracted in EtOAc (3×15 mL). The organic fractions were dried over $Na_2SO_4$ and concentrated. $^1$HNMR (400 MHz, MeOD/$CDCl_3$): d 7.99 (m, 2H), 7.03 (t, 2H, J=8.4 Hz). MS (ESI): m/z 274.0 [M−H]− (S-41)

Scheme 15: Preparation of Scaffolds S-50, S-51, and S-52.

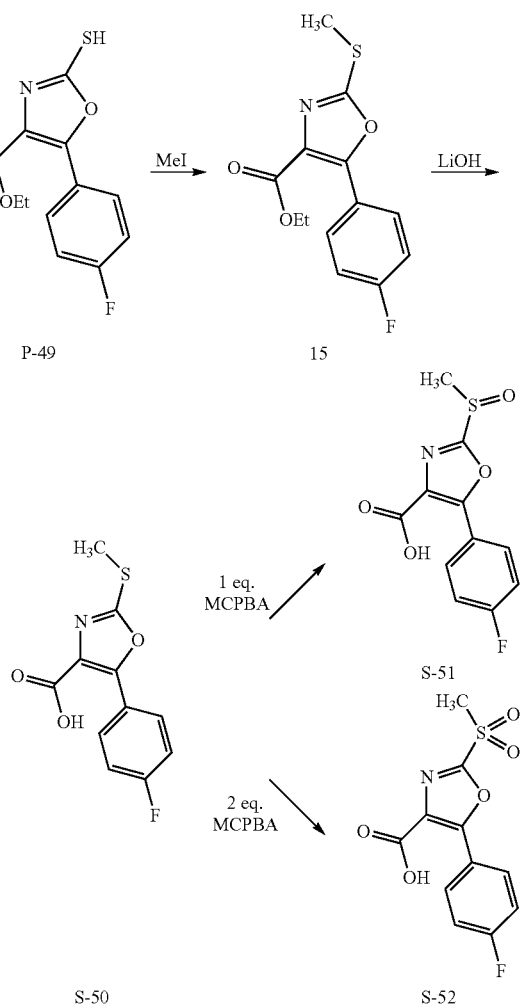

5-(4-fluorophenyl)-2-(methylthio)oxazole-4-carboxylic acid (S-50)

To a solution of P-49 (4 g, 15 mmol) in acetonitrile (30 mL) was added methyl iodide (1.4 mL, 22.5 mmol) and potassium carbonate (2 g, 15 mmol) and the resulting mixture was stirred at room temperature for 3 h. Reaction mixture was then diluted with water and extracted with ethyl acetate. Organic layer was washed with brine, dried with anhydrous sodium sulfate, filtered and concentrated in vacuo to give 4 g (95%) of the product 15.

To a solution of 1 (200 mg, 0.71 mmol) in dioxane (1 mL) was added 2M lithium hydroxide (5 mL, 10 mmol). Oxygen was evacuated under vacuum and flask was flushed with nitrogen three times. Reaction mixture was then stirred over night at 50° C. under nitrogen. The reaction mixture was then gradually acidified with 1N HCl, diluted with water and extracted with ethyl acetate. Organic layer was washed with brine, dried with anhydrous sodium sulfate, filtered and concentrated in vacuo to give 0.14 g (72%) of 5-(4-fluorophenyl)-2-(methylthio)oxazole-4-carboxylic acid S-50.

5-(4-fluorophenyl)-2-(methylsulfinyl)ozazole-4-carboxylic acid (S-51)

A solution of MCPBA (1.36 g, 7.9 mmol) in 10 mL of dichloromethane was added drop wise to a solution of S-50 (2 g, 7.9 mmol) in 10 mL of dichloromethane. Reaction mixture was stirred for 4 h. Solvent was then evaporated under reduced pressure and the product was purified by flash chromatography (MeOH/DCM) to give 1.57 g (73%) of sulfoxide S-51.

5-(4-fluorophenyl)-2-(methylsulfonyl)ozazole-4-carboxylic acid (S-52)

A solution of MCPBA (2.66 g, 15.4 mmol) solution in 10 mL of dichloromethane was added drop wise to a solution of S-50 (1.95 g, 7.7 mmol) in 10 mL of dichloromethane. Reaction mixture was stirred overnight at room temperature. Solvent was then evaporated under reduced pressure and the product was purified by flash chromatography (MeOH/DCM) to give 1.08 g (49%) of sulfone S-52.

Scheme 16: Preparation of 2-methylsulfonylpyrazole Scaffold S-60.

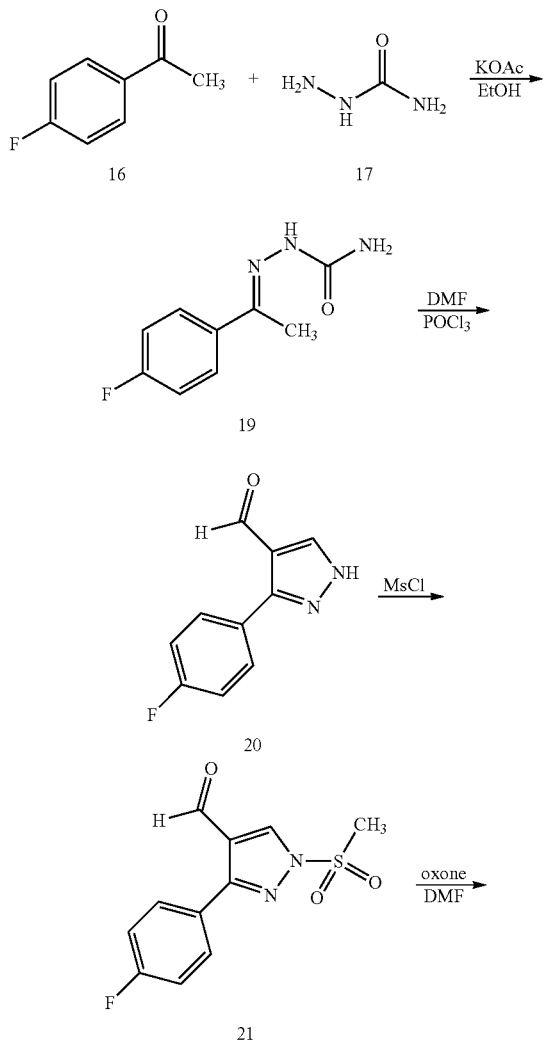

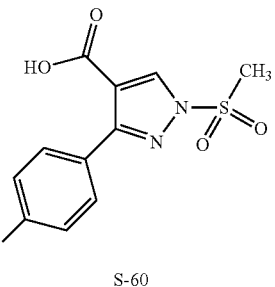

S-60

5-(4-fluorophenyl)-2-(methylsulfonyl)-1,2-pyrazole-4-carboxylic acid (S-60)

Semicarbazide hydrochloride 17 (16.8 g, 151 mmol) and potassium acetate (16.8 g, 171 mmol) were suspended in ethanol (170 mL) and refluxed for 1 h. The suspension was then filtered hot and 4-fluoroacetophenone 16 (20 g, 144.7 mmol) was added to the mother liquor under reflux. Reaction mixture was stirred under reflux for another hour then cooled to room temperature and stirred overnight. Formed precipitates were filtered off, washed with small amount of ethanol and vacuum dried to afford 24 g (87%) of product 18.

Phosphoryl chloride (2.1 mL, 23 mmol) was added drop wise to DMF (4.4 mL, 57 mmol) at 0° C. The resulting mixture was kept on stirring for 30 min at 0° C. and then 30 min at room temperature. Reaction mixture was cooled in ice/water bath and 18 (1.96 g, 10 mmol) was added slowly (not to exceed the temperature above 50° C.) then heated to 80° C. and stirred for 2 h at this temperature. Reaction mixture was then poured into ice (15 g), basified with 5N NaOH till pH 10 and stirred for 2 h then acidified with concentrated HCl and continued to stir for additional 4 h. Formed precipitates were filtered off, washed with small amount of water and dried under high vacuum to afford 1.5 g (79%) of aldehyde 19.

Methanesulfonyl chloride (5.4 mL, 70 mmol) was added to a solution of 17 (4 g, 21 mmol) in pyridine (50 mL) and stirred at 60° C. for 10 h. Additional 3 equivalents of MsCl (5.4 mL, 70 mmol) were added and the reaction was continued to stir at 60° C. for further 12 h. Reaction mixture was then brought to room temperature and pyridine was removed under reduced pressure. Residue was dissolved in ethyl acetate and washed carefully with saturated aq. sodium bicarbonate, water and brine. Organic layer was dried with anhydrous sodium sulfate, filtered and concentrated to give 3 g (54%) of product 20.

To a solution of 18 (1.75 g, 6.5 mmol) in DMF (50 mL) was added oxone (4.8 g, 7.8 mmol) and the resulting mixture was stirred overnight at room temperature. DMF was removed under reduced pressure and the residue was partitioned between ethyl acetate and water. Organic layer separated, washed with brine, dried with anhydrous sodium sulfate and concentrated in vacuo to afford 1.5 g (81%) of pyrazole acid S-60.

Scheme 17: Preparation of Oxazole Scaffold S-68 and Thiazole Scaffold S-75.

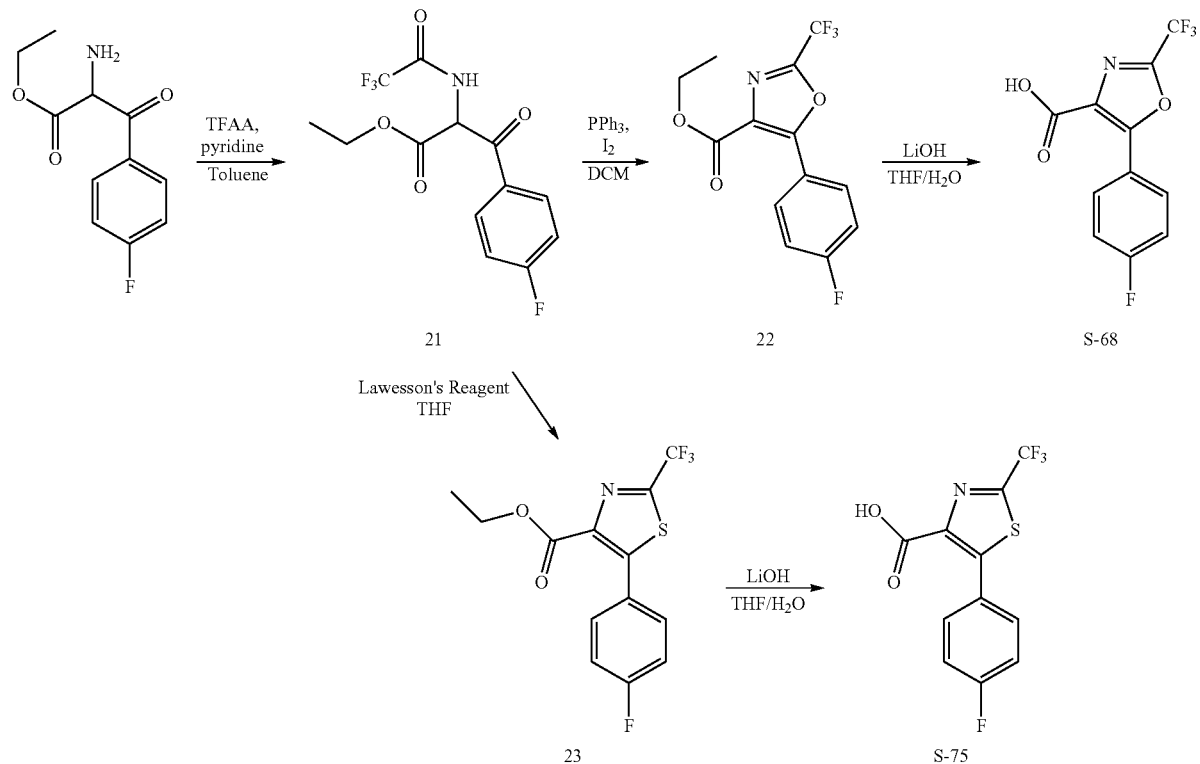

Ethyl 5-(4-fluorophenyl)-2-(trifluoromethyl)oxazole-4-carboxylate (S-68)

Ethyl 3-(4-F-phenyl)-3-oxo-2-(2,2,2-trifluoroacetamido)propanoate (21)

To a solution of ethyl 2-amino-3-(4-fluorophenyl)-3-oxopropanoate (50 mg, 0.22 mmol) and pyridine (105 uL, 1.34 mmol) in toluene (2.5 mL) and DCM (0.5 mL) on ice was added trifluoroacetic anhydride (78 mL, 0.56 mmol). The reaction was warmed to room temperature and allowed to stir overnight. The major product was isolated by SiO2 chromatography (isocratic DCM) to afford a colorless oil (37 mg, 51% yield). $^1$HNMR (400 MHz, CDCl$_3$): d 8.12 (m, 2H), 7.68 (bs, 1H), 7.15 (t, 2H, J=8.4 Hz), 6.03 (d, 1H, J=6.8 Hz), 4.14 (m, 2H), 1.10 (t, 3H, J=6.8 Hz). 19FNMR (400 MHz, CDCl$_3$): d −76.10, −101.37. MS (ESI): m/z 321.9 [M+H]+

Ethyl 5-(4-fluorophenyl)-2-(trifluoromethyl)oxazole-4-carboxylate (22)

Triethylamine (64 mL, 0.46 mmol)) was added to a solution of triphenylphosphine (60 mg, 0.23 mmol) and iodine (58 mg, 0.23 mmol) in dry DCM (0.5 mL) and stirred for 5 min. Then a solution of ethyl 3-(4-fluorophenyl)-3-oxo-2-(2,2,2-trifluoroacetamido)propanoate (37 mg, 12 mmol) in dry DCM (0.7 mL) was added and the reaction mixture was stirred for 1 hr. The solvent was removed under reduced pressure, and the residue was purified by SiO2 chromatography on silica gel (isocratic DCM) to yield a white solid (31 mg, 88% yield). 1HNMR (400 MHz, CDCl3): d 8.12 (m, 2H), 7.18 (t, 2H, J=8.8 Hz), 4.43 (q, 2H, J=7.2 Hz), 1.39 (t, 3H, J=7.2 Hz). 19FNMR (400 MHz, CDCl$_3$): d −66.10, −107.21. MS (ESI): m/z MS (ESI): m/z 303.9 [M+H]+

5-(4-fluorophenyl)-2-(trifluoromethyl)oxazole-4-carboxylic acid (23)

Compound ethyl 5-(4-fluorophenyl)-2-(trifluoromethyl)oxazole-4-carboxylate (150 mg, 0.49 mmol) was dissolved in THF (4.6 mL) and cooled on ice. To this solution is added LiOH (13 mg, 0.31 mmol) in water (1.5 mL) and the mixture was stirred for 1 hr then warmed to room temperature and stirred overnight. The THF was evaporated, and H2O (10 mL) was added and the solution then acidified with 1 N HCl and extracted in EtOAc (3×15 mL). The organic fractions were dried over Na$_2$SO$_4$ and concentrated. The crude material was fractionated by SiO2 chromatography (DCM to 90% DCM/10% MeOH gradient, the desired product elutes in 7% MeOH) to afford a white solid (17 mg, 11% yield). 1HNMR (400 MHz, MeOD, CDCl$_3$): d 8.17 (m, 2H), 7.14 (t, 2H, J=8 Hz).

Ethyl 5-(4-fluorophenyl)-2-(trifluoromethyl)thiazole-4-carboxylate (S-75)

To a solution of ethyl 3-(4-fluorophenyl)-3-oxo-2-(2,2,2-trifluoroacetamido)propanoate (271 mg, 0.84 mmol) in anhydrous THF (10 mL) was added Lawesson's reagent (682 mg, 1.69 mmol) in one portion and the resulting solution was refluxed for 22 hrs under nitrogen until no starting material is detected by TLC. The solvent was removed under reduced pressure and the crude material was purified by SiO$_2$ chromatography (80% hexanes/20% DCM to 100% DCM in a linear gradient, product elutes in 50% hexanes/50% DCM)

(175 mg, 64% yield). $^1$HNMR (400 MHz, CDCl$_3$): d 7.50 (m, 2H), 7.15 (t, 2H, J=8.8 Hz), 4.31 (q, 2H, J=6.8 Hz), 1.26 (t, 3H, 7.2 Hz).
Schem 18: Preparation of Scaffold Acids S-81 to S-84.
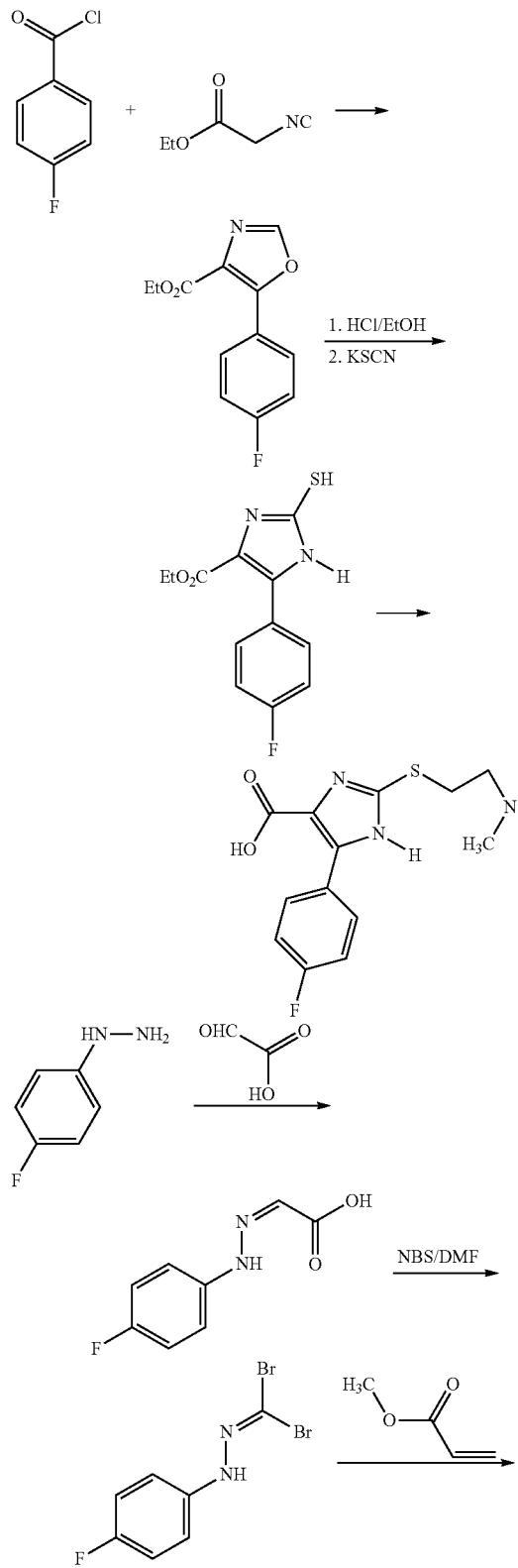
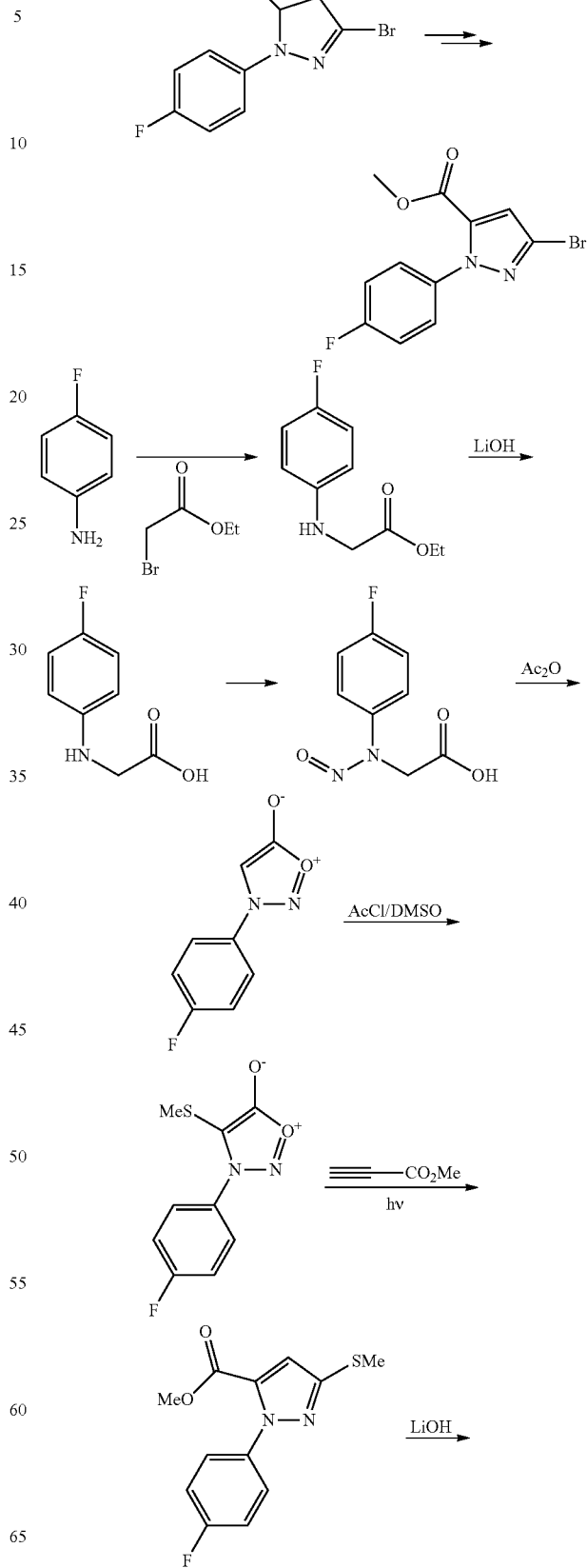
-continued -continued

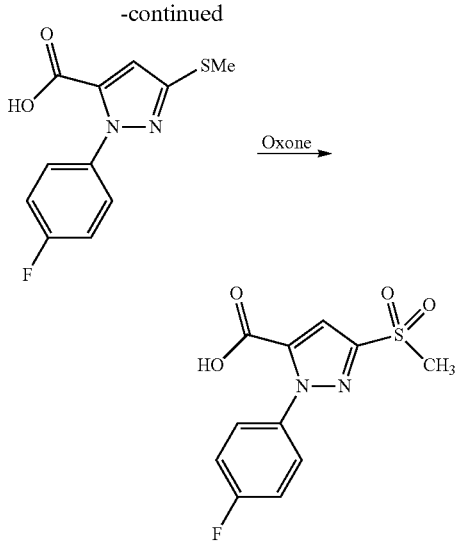

2-(2-(dimethylamino)ethyl)thio)-5-(4-fluorophenyl)-1H-imidazole-4-carboxylic acid, (S-81)

Step-1: ethyl 5-(4-fluorophenyl)oxazole-4-carboxylate

Using the procedure described in Russian Journal of Organic Chemistry 42 (7), 1031-1035 (2006), ethyl 5-(4-fluorophenyl)oxazole-4-carboxylate was prepared as follows: Sodium hydride (42 mg, 1.04 mmol, 60% in oil) was suspended in benzene (1 mL) and to this suspension was added ethyl isocyanoacetate (102 mg, 0.90 mmol) in benzene (0.5 mL) and the mixture was stirred until no more gas evolution was evident (1-2 h). To this mixture was added p-fluorobenzoyl chloride (165 mg, 1.04 mmole) in benzene (0.5 mL). The resulting reaction mixture was stirred overnight at room temperature. The crude product was obtained by partitioning between ethyl acetate and water and evaporation to dryness. Purification by flash chromatography afforded the title compound. LC/MS 236 M+H$^+$ Step-2: ethyl 5-(4-fluorophenyl)-2-mercaptoimidazole-4-carboxylate Using the procedure described in Chemical and Pharmaceutical Bulletin 32 (7), 2536-45 (1984), ethyl 5-(4-fluorophenyl)-2-mercaptoimidazole-4-carboxylate was prepared as follows:
Ethyl 5-(4-fluorophenyl)oxazole-4-carboxylate (0.235 g, 1 mmol) was dissolved in a mixture of concentrated HCl and ethanol (1:3) and the mixture was heated at 50° C. for 4 h. The solvents were removed under reduced pressure and the crude product thoroughly dried. The crude hydrochloride was dissolved in water and treated with excess potassium thiocyanate. The solution was heated at 80-90° C. for 4 h and then cooled in ice. The solution was filtered and the precipitate recrystallized from ethanol to afford the title compound.

Step-3: 2-(2-(dimethylamino)ethyl)thio)-5-(4-fluorophenyl)-1H-imidazole-4-carboxylic acid 5-(4-Fluoro-phenyl)-2-mercapto-1H-imidazole-4-carboxylic acid ethyl ester (3 g, 11.28 mmol) was dissolved in EtOH (30 mL) at RT. K$_2$CO3 (6.23 g, 45 mmol) and (2-chloro-ethyl)-dimethyl-amine HCl salt (1.54 g, 10.72 mmol) were added. The mixture was stirred at 50° C. for 48 h. It was then concentrated and the residue was dissolved in THF/water (20 mL each) at RT. NaOH (2 g, 50 mmol) was added. The mixture was stirred at RT for 12 h. It was then concentrated to remove most THF and the pH of the solution was adjusted to ~5 using 3 N HCl. The mixture was concentrated and residue was purified by prep HPLC. Lyophilization of pure fractions afforded 1.1 g pure 2-(2-dimethylamino-ethylthio)-5-(4-fluorophenyl)-1H-imidazole-4-carboxylic acid, S-81. LC-MS [M+H] 310.2.

1-(4-fluorophenyl)-3-(methylthio)-1H-pyrazole-5-carboxylic acid, (S-81)

5-(4-Fluoro-phenyl)-2-mercapto-1H-imidazole-4-carboxylic acid ethyl ester (3 g, 11.28 mmol) was dissolved in EtOH (30 mL) at RT. K$_2$CO3 (6.23 g, 45 mmol) and (2-chloro-ethyl)-dimethyl-amine HCl salt (1.54 g, 10.72 mmol) were added. The mixture was stirred at 50° C. for 48 h. It was then concentrated and the residue was dissolved in THF/water (20 mL each) at RT. NaOH (2 g, 50 mmol) was added. The mixture was stirred at RT for 12 h. It was then concentrated to remove most THF and the pH of the solution was adjusted to ~5 using 3 N HCl. The mixture was concentrated and residue was purified by prep HPLC. Lyophilization of pure fractions afforded 1.1 g pure 2-(2-dimethylamino-ethylthio)-5-(4-fluorophenyl)-1H-imidazole-4-carboxylic acid. LC-MS [M+H] 310.2.

Preparation of 3-bromo-1-(4-fluorophenyl)-1H-pyrazole-5-carboxylic acid, (S-82)

5-Bromo-2-(4-fluoro-phenyl)-2H-pyrazole-3-carboxylic acid was prepared following procedures from WO 2006055922, using 4-fluorophenylhydrazine instead of 2-chlorophenylhydrazine.

Step-1: (E)-2-(2-(4-fluorophenyl)hydrazono)acetic acid

To a solution of 4-fluorophenyl hydrazine 1.32 g (0.011 mol) in water (30 mL) at room temperature was added HCl (1.32 g, 0.014 mol) followed by the drop-wise addition of glyoxylic acid (50%, 1.71 g, 0.012 mol) over 20 minutes. The thick suspension was stirred for 30 m. The product was isolated by filtration, washed with water and then dissolved in ethyl acetate (40 mL), dried over magnesium sulfate, filtered and the product isolated as a solid.

Step-2: (4-fluorophenyl)carbonohydrazonic dibromide

To the crude product of the previous step 1.88 g (0.010 mol) dissolved in DMF (20 mL) at 0° C. was added N-bromosuccinimide (3.57 g, 0.021 mol) in portions over 30 m. The resulting mixture was stirred overnight at room temperature. The mixture was partitioned between ether and water (20:15) and extracted twice more with ether (20 mL). The combined organic extracts were evaporated and purified by flash chromatography to afford the title compound.

Step-3: methyl 3-bromo-1-(4-fluorophenyl)-4,5-dihydro-1H-pyrazole-5-carboxylate

To the crude product obtained in step 2, 1.14 g (3.85 mmol) in DMF (12 mL) was added methyl acrylate (1.39 mL, 15.4 mmol) all at once. Diisopropylethylamine (0.74 mL, 4.23 mmol) was added dropwise over 15 m. The mixture was stirred at room temperature for 1 h and then diluted with water and extracted twice with ether. Concentration of the solvent after drying over magnesium sulfate afforded the title compound.

Step-4: methyl 3-bromo-1-(4-fluorophenyl)-1H-pyrazole-5-carboxylate

The product obtained in step 3 1.15 g (3.84 mmol) was dissolved in acetone (40 mL) and treated with potassium permanganate (2.42 g, 15.4 mmol) in portions of 100 mg at 10 minute intervals taking care to keep the reaction temperature below 40° C. The mixture was stirred overnight at room temperature. Filtration through Celite removed the insoluble matter and the filter cake was washed with ether. Solvent was removed and the product purified by flash chromatography to afford the title product. (0.58 g).

Step-5: 3-bromo-1-(4-fluorophenyl)-1H-pyrazole-5-carboxylic acid

The crude ester 0.58 g (1.84 mmol) obtained in the previous step was hydrolyzed in methanol (5 mL) with aqueous sodium hydroxide (0.88 g in 7.5 mL, 3.05 mmol). After stirring at room temperature for 2 h, the mixture was diluted with water and extracted with ether. The aqueous layer was acidified with HCl to pH 2 and the product extracted with twice with ethyl acetate. The solution was dried and evaporated to dryness to afford the pure acid, S-82 (0.54 g).

1-(4-fluorophenyl)-3-(methylthio)-1H-pyrazole-5-carboxylic acid, (S-83)

2-(4-Fluoro-phenyl)-5-methylthio-2H-pyrazole-3-carboxylic acid was prepared following the procedure described in the literature (European Journal of Medicinal Chemistry, 43(8), p1715, 2008 and Chemische Berichte, 112(4), p1206, 1979).

Step 1: Preparation of Ethyl N-(4-fluorophenyl)glycine

Using the procedure described in WO 9857937 A2, to a solution of 13.56 g (122 mmole) p-fluoroaniline in DMF (100 mL) under nitrogen was added 23.5 g (141 mmol) of ethyl bromoacetate and 14.95 g (141 mmol) anhydrous sodium carbonate. The mixture was heated to 70° C. for 16 h and then cooled to room temperature. Water was added (500 mL) and the mixture stirred vigorously until a precipitate formed. The solid was filtered, washed with 100 mL water and dried to afford ethyl N-(4-fluorophenyl)glycine.

Step-2: Preparation of N-(4-fluorophenyl)glycine

To a solution of 21.3 g (108 mmole) of ethyl N-(4-fluorophenyl)glycine in THF (100 mL) under nitrogen was added LiOH (5.44 g (130 mmol) monohydrate in 25 mL water. After 15 h the mixture was concentrated to half the volume and acidified to pH 3 with HCl. The precipitated solid was collected and washed with water (100 mL) to afford the title compound.

Step-3: Preparation of N-(4-fluorophenyl)-N-nitrosoglycine

Sodium nitrite (3.97 g), 57.5 mmol) in 10 mL water was added to a suspension of N-(4-fluorophenyl)glycine 9.25 g (54.7 mmol) in water (50 mL) under nitrogen. The reaction mixture was stirred until clear, ca. 6 hours. Acidification to pH 3 with HCl precipitated the product which was filtered and washed with water (50 mL) and dried to afford the title product.

Step-4: Preparation of 3-(4-fluorophenyl)-3H-1,2,3-oxadiazol-1-ium-5-olate

N-(4-fluorophenyl)-N-nitrosoglycine (11.5 g, 54.7 mmol) was dissolved in acetic anhydride (100 mL) and heated to 70° C. for 14 h. The reaction mixture was cooled and then poured into ice water (300 mL) After for stirring for 30 m, the reaction mixture was filtered to provide 10.50 g (100%) of the title product.

Step 5—Preparation of 3-(4-fluorophenyl)-4-(methylthio)-3H-1,2,3-oxadiazol-1-ium-5-olate Using the procedure of Masada and Okutani (Tetrahedron 30, 409-414 (1974)) the crude 3-(4-fluorophenyl)-3H-1,2,3-oxadiazol-1-ium-5-olate (1.95 g, 10.82 mmol) was dissolved in anhydrous DMSO (27 mL) and cooled in ice. Acetyl chloride (2.0 g, 25.5 mmol) was added dropwise. The reaction mixture was allowed to come to room temperature. After stiffing overnight, the mixture was partitioned between ether and saturated NaHCO$_3$ solution. The organic layer was washed several times with water, dried and evaporated to dryness to afford 3-(4-fluorophenyl)-4-(methylthio)-3H-1,2,3-oxadiazol-1-ium-5-olate.

Step 6—Preparation of 1-(4-fluorophenyl)-3-methylthio-pyrazole-5-carboxylate 1-(4-fluorophenyl)-3-methylthio-pyrazole-5-carboxylate was prepared by the cycloaddition—rearrangement reaction described in Chemische Berichte, 112(4), 1206 (1979). Thus crude 3-(4-fluorophenyl)-4-(methylthio)-3H-1,2,3-oxadiazol-1-ium-5-olate, (1.73 g, 7.68 mmole) and methyl propiolate (6.45 g, 76.8 mmole) were dissolved in CH$_2$Cl$_2$ (10 mL) and the quartz reaction vessel purged with nitrogen. The reaction mixture was irradiated in a Rayonet RPR-100 photochemical reactor for 14 h. The crude product was concentrated in vacuo and then purified by flash chromatography to afford methyl 1-(4-fluorophenyl)-3-methylthio-pyrazole-5-carboxylate, 374 mg after flash chromatography.

Step 7—Preparation of 1-(4-fluorophenyl)-3-(methylthio)-1H-pyrazole-5-carboxylic acid The crude ester 0.374 g (1.40 mmol) obtained in the previous step was hydrolyzed in methanol (5 mL) with aqueous sodium hydroxide (0.67 g in 7.5 mL, 2.32 mmol). After stirring at room temperature for 2 h, the mixture was diluted with water and extracted with ether. The aqueous layer was acidified with HCl to pH 2 and the product extracted with twice with ethyl acetate. The solution was dried and evaporated to dryness to afford the pure acid S-83.

1-(4-fluorophenyl)-3-(methylsulfonyl)-1H-pyrazole-5-carboxylic acid, (S-84)

1-(4-fluorophenyl)-3-(methylthio)-1H-pyrazole-5-carboxylic acid (120 mg, 0.48 mmol) was dissolved in acetonitrile (5 mL) at RT. Oxone™ (440 mg, 1.4 mmol) was added. The mixture was stirred at RT for 30 min and then heated at 50° C. for 3 h. The mixture was cooled to RT and most volatiles were removed under vacuum. The residue was partitioned between DCM/brine. The DCM layer was dried over Na₂SO₄ and filtered. Concentration of the filtrate afforded the crude 1-(4-fluorophenyl)-3-(methylsulfonyl)-1H-pyrazole-5-carboxylic acid (~140 mg), which was used without further purification. LC-MS [M+H] 285.1.
Preparation of Inhibitors
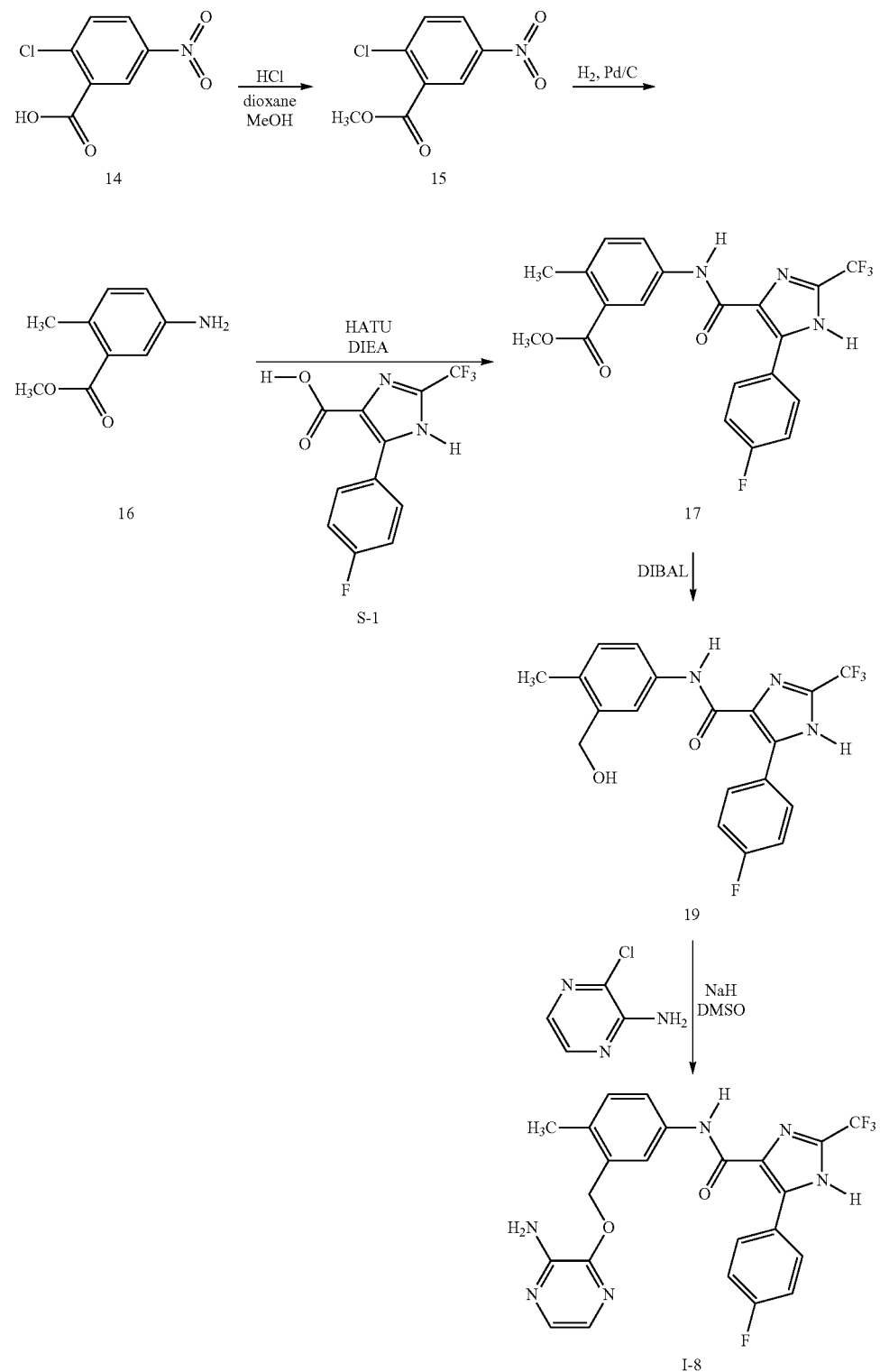

-continued

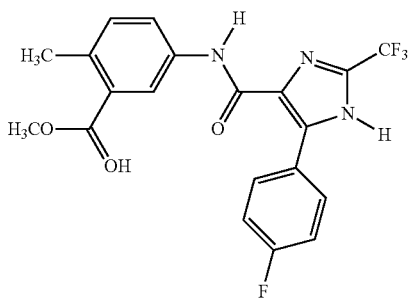

17

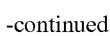

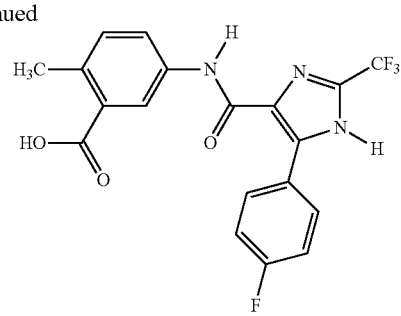

18

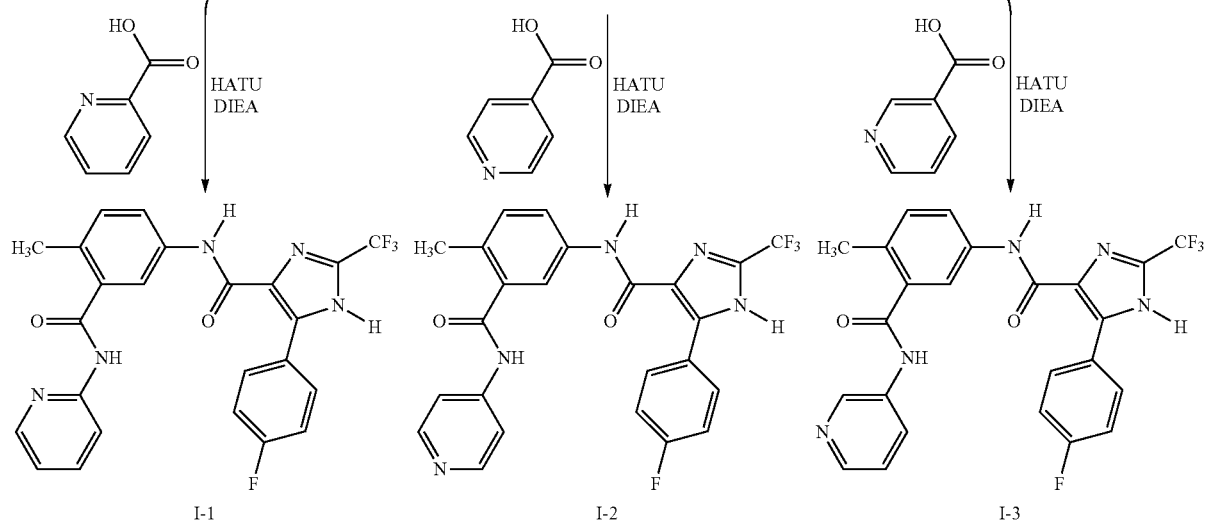

2-Chloro-5-nitro-benzoic acid methyl ester (15)

2-chloro-5-nitrobenzoic acid 14 (5.0 g, 24.8 mmol) was dissolved in methanol (10 mL) and 4 N HCl in dioxane (12 mL) was added. The mixture was stirred for 3 hr after which the solvents were evaporated and the residue was neutralized and extracted with EtOAc, washed with NaHCO$_3$, brine, dried over MgSO$_4$ and filtered. The solvent was evaporated to give the desired product 15 (3.9 g, 75%).

5-Amino-2-chloro-benzoic acid methyl ester (16)

2-Chloro-5-nitro-benzoic acid methyl ester 15 (4.3 g, 20.2 mmol), SnCl$_2$-2H$_2$O (45.5 g, 201.8 mmol) and ethanol (100 mL) were combined into a sealed pressure vial and was sonicated for 2 hr. The solvent was concentrated and the residue was dissolved in EtOAc, washed with NaHCO$_3$, brine, dried over MgSO$_4$ and filtered. The solvent was evaporated to give the desired product 16 (2.8 g, 73%).

Methyl 2-Chloro-5-{[5-(4-fluoro-phenyl)-2-trifluoromethyl-3,1-imidazole-4-carbonyl]-amino}-benzoate (17)

5-(4-Fluoro-phenyl)-2-trifluoromethyl-3H-imidazole-4-carbonylic acid 16 (2.0 g, 7.3 mmol) was dissolved in DCM (25 mL). To the mixture was added HATU (3.0 g, 7.95 mmol) and DIEA (3.5 mL, 19.9 mmol) after 15 min of stirring, 5-Amino-2-chloro-benzoic acid methyl ester (1.2 g, 6.6 mmol) was added. The reaction was refluxed for 48 hr. The solvent was evaporated and the residue was purified by silica gel chromatography (EtOAc/Hx, 0-40%) to yield 0.93 g (33%) of the desired product 17.

2-Chloro-5-{[5-(4-fluoro-phenyl)-2-trifluoromethyl-3,1-imidazole-4-carbonyl]-amino}-benzoic acid (18)

Methyl 2-Chloro-5-{[5-(4-fluoro-phenyl)-2-trifluoromethyl-3H-imidazole-4-carbonyl]-amino}-benzoate-17 (0.93 g) was dissolved in water (4.2 mL) and LiOH (177.2 mg, 4.2 mmol) was added and the mixture was stirred for 2 hr. Acetic acid (gl., 0.24 mL) was added. The resulting precipitated was filtered and washed with water. The solid was dissolved in EtOAc, dried over MgSO$_4$, filtered and the solvent was evaporated to give 1.0 g of the crude product 18 which was used without further purification.

5-(4-Fluoro-phenyl)-2-trifluoromethyl-3,1-imidazole-4-carboxylic acid [4-chloro-3-(pyridin-2-ylcarbamoyl)-phenyl]-amide—(I-1)

2-Chloro-5-{[5-(4-fluoro-phenyl)-2-trifluoromethyl-3H-imidazole-4-carbonyl]-amino}-benzoic acid 18 (0.2 g, 0.42 mmol) was dissolved in DCM (2 mL) and HATU (0.32 g, 0.84 mmol) and DIEA (0.16 mL, 0.94 mmol) after 15 min of stirring, 2-Aminopyridine (0.053 g, (1.2 g, 0.56 mmol) was added and the mixture was stirred overnight. The mixture was washed with NaHCO$_3$, water, brine. The organic layer was dried over MgSO$_4$, filtered and evaporated. The residue was purified by HPLC to give only 1.7 mg of the desired product (I-1).

5-(4-Fluoro-phenyl)-2-trifluoromethyl-3,1-imidazole-4-carboxylic acid [4-chloro-3-(pyridin-4-ylcarbamoyl)-phenyl]-amide—(I-2)

2-Chloro-5-{[5-(4-fluoro-phenyl)-2-trifluoromethyl-3H-imidazole-4-carbonyl]-amino}-benzoic acid 18 (0.2 g, 0.42 mmol) was dissolved in DCM (2 mL) and HATU (0.32 g, 0.84 mmol) and DIEA (0.16 mL, 0.94 mmol) after 15 min of stirring, 4-Aminopyridine (0.053 g, (1.2 g, 0.56 mmol) was added and the mixture was stirred overnight. The mixture was washed with NaHCO$_3$, water, brine. The organic layer was dried over MgSO$_4$, filtered and evaporated. The residue was purified by HPLC to give 17.5 mg of the desired product (I-2).

5-(4-Fluoro-phenyl)-2-trifluoromethyl-3,1-imidazole-4-carboxylic acid [4-chloro-3-(pyridin-3-ylcarbamoyl)-phenyl]-amide—(I-3)

2-Chloro-5-{[5-(4-fluoro-phenyl)-2-trifluoromethyl-3H-imidazole-4-carbonyl]-amino}-benzoic acid 18 (0.2 g, 0.42 mmol) was dissolved in DCM (2 mL) and HATU (0.32 g, 0.84 mmol) and DIEA (0.16 mL, 0.94 mmol) after 15 min of stirring, 3-Aminopyridine (0.053 g, (1.2 g, 0.56 mmol) was added and the mixture was stirred overnight. The mixture was washed with NaHCO$_3$, water, brine. The organic layer was dried over MgSO$_4$, filtered and evaporated. The residue was purified by HPLC to give 95.7 mg of the desired product (I-3).

5-(4-Fluoro-phenyl)-2-trifluoromethyl-3,1-imidazole-4-carboxylic acid [3-(3-amino-pyrazin-2-yloxymethyl)-4-chloro-phenyl]-amide—(I-8)

2-Chloro-5-{[5-(4-fluoro-phenyl)-2-trifluoromethyl-3H-imidazole-4-carbonyl]-amino}-benzoic acid methyl ester 17 (0.165 g, 0.38 mmol) was dissolved in DCM (0.75 mL) and cooled to −78° C. To the mixture was added DiBAL-H (1M, 1.2 mL, 1.12 mmol) and the reaction was allowed to stir for 1 hr. The reaction was quenched with methanol and treated with ammonium chloride (sat.). The DCM layer was washed with water and dried over MgSO$_4$. The solvent was filtered and evaporated to provide the intermediate alcohol 19 (71 mg) which was used without further purification. (71 mg, 0.17 mmol) was dissolved in DMSO and NaH (60%, 0.024 g, 0.51 mmol) was added under N$_2$(g). To the mixture was added 2-amino-3-chloropyrazine (0.023 g, 0.17 mmol) and reaction was allowed to stir overnight. Water was added and the sample was extracted with DCM and dried over MgSO$_4$. After evaporation, the residue was dissolved in DMSO and purified by HPLC to give 11.6 mg of the desired product (I-8).

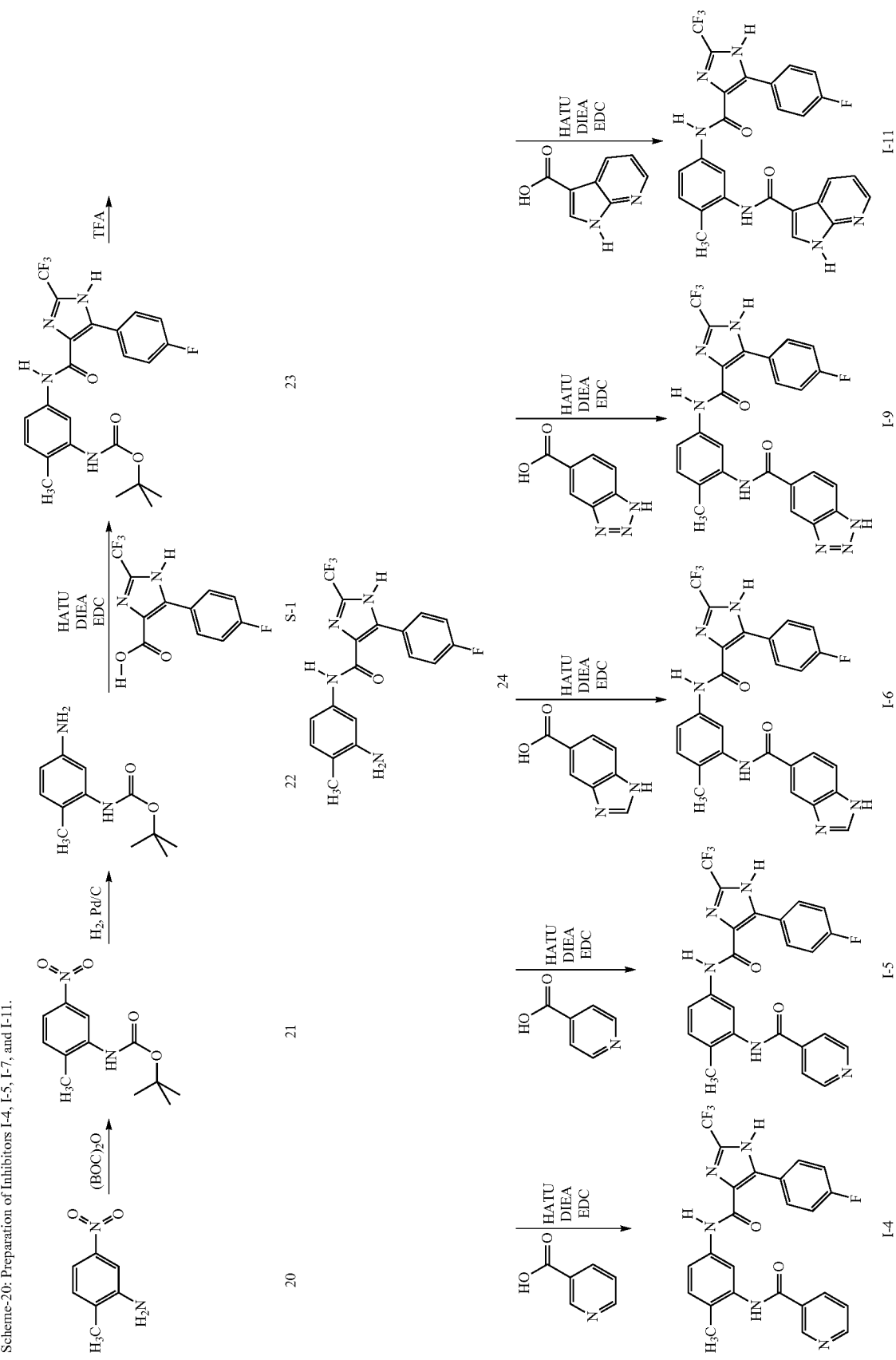
Scheme-20: Preparation of Inhibitors I-4, I-5, I-7, and I-11.

(2-Methyl-5-nitro-phenyl)-carbamic acid tert-butyl ester (21)

2-methyl-5-nitroaniline 20 (5.0 g, 32.86 mmol) and BOC anhydride (8.6 g, 39.44 mmol) were dissolved in dichloromethane (110 mL). Pyridine (5.4 mL, 65.72 mmol) was added to the mixture and the reaction was stirred for 16 hrs. The solvents were evaporated and the residue was purified by silica gel chromatography (EtOAc/Hx, 0-50%) to yield 4.5 g (54%) of the desired product 21.

(5-Amino-2-methyl-phenyl)-carbamic acid tert-butyl ester (22)

(2-Methyl-5-nitro-phenyl)-carbamic acid tert-butyl ester 21 (4.5 g, 17.8 mmol) was dissolved in ethanol (100 mL) and Pd-c (5%, 100 mg) was added and the mixture was stirred under $H_2(g)$ at 50 PSI on a Parr shaker overnight. The mixture was filtered through celite and the solvent was evaporated to give the desired product 22 (4.5 g, quantitative yield).

(5-{[5-(4-Fluoro-phenyl)-2-trifluoromethyl-3H-imidazole-4-carbonyl]-amino}-2-methyl-phenyl)-carbamic acid tert-butyl ester (23)

(5-Amino-2-methyl-phenyl)-carbamic acid tert-butyl ester 22 (2.0 g, 7.3 mmol) was dissolved in DCM (25 mL) and DIEA (3.8 mL, 21.8 mmol) was added. To the mixture was added HATU (3.3 g, 8.7 mmol), after 15 min of stirring, 5-(4-Fluoro-phenyl)-2-trifluoromethyl-3H-imidazole-4-carbonylic acid S-1 (2.0 g, 7.3 mmol) was added. The reaction was refluxed for 48 hr. The solvent was evaporated and the residue was purified by silica gel chromatography (EtOAc/Hx, 0-40%) to yield 2.5 g (72%) of the desired product 23.

(5-{[5-(4-Fluoro-phenyl)-2-trifluoromethyl-3,1-imidazole-4-carbonyl]-amino}-2-methyl-phenyl)-amine (24)

(5-{[5-(4-Fluoro-phenyl)-2-trifluoromethyl-3H-imidazole-4-carbonyl]-amino}-2-methyl-phenyl)-carbamic acid tert-butyl ester 23 (2.5 g, 5.2 mmol) was dissolved in a mixture of DCM/TFA (50%) and stirred overnight. The solvents were evaporated and the residue was neutralized and extracted with EtOAc, washed with brine, dried over $MgSO_4$, filtered and evaporated. The residue was purified by silica gel chromatography (EtOAc/Hx, 0-75%) to yield 2.5 g (72%) of the desired product 24 (1.6 g, 82%).

N-(5-{[5-(4-Fluoro-phenyl)-2-trifluoromethyl-3,1-imidazole-4-carbonyl]-amino}-2-methyl-phenyl)-nicotinamide—(I-4)

5-(4-Fluoro-phenyl)-2-trifluoromethyl-3H-imidazole-4-carboxylic acid and (3-amino-4-methyl-phenyl)-amide 6 (0.2 g, 0.53 mmol) was dissolved in DCM (2 mL) and DIEA was added to the solution (0.277 mL, 1.59 mmol). Nicotinyl chloride HCl (0.095 g, 0.53 mmol) was added and the mixture was stirred overnight. The mixture was washed with $NaHCO_3$, water, brine. The organic layer was dried over $MgSO_4$, filtered and evaporated. The residue was purified by HPLC to give 160 mg of the desired product (I-4).

N-(5-{[5-(4-Fluoro-phenyl)-2-trifluoromethyl-3,1-imidazole-4-carbonyl]-amino}-2-methyl-phenyl)-isonicotinamide—(I-5)

5-(4-Fluoro-phenyl)-2-trifluoromethyl-3H-imidazole-4-carboxylic acid and (3-amino-4-methyl-phenyl)-amide 6 (0.2 g, 0.53 mmol) was dissolved in DCM (2 mL) and DIEA was added to the solution (0.277 mL, 1.59 mmol). Pyridine-4-carboxylic acid chloride HCl (0.095 g, 0.53 mmol) was added and the mixture was stirred overnight. The mixture was washed with $NaHCO_3$, water, brine. The organic layer was dried over $MgSO_4$, filtered and evaporated. The residue was purified by HPLC to give 160 mg of the desired product (I-5).

1H-Benzoimidazole-5-carboxylic acid (5-{[5-(4-fluoro-phenyl)-2-trifluoromethyl-3,1-imidazole-4-carbonyl]-amino}-2-methyl-phenyl)-amide—(I-9)

5-(4-Fluoro-phenyl)-2-trifluoromethyl-3H-imidazole-4-carboxylic acid and (3-amino-4-methyl-phenyl)-amide 6 (0.20 g, 0.53 mmol) was dissolved in toluene (1.0 mL). To the reaction was added methyl-1H-benzimidazole-5-carboxylate (0.11 g, 0.63 mmol) and 2.0M tetramethyl aluminum (0.50 mL, 1.03 mmol). The mixture was heated under microwave conditions for 20 min at 160° C. The solvent was evaporated; DMSO was added to the residue and filtered. The filtrate was purified by HPLC to give 2.2 mg of the desired product (I-9).

1H-Benzotriazole-5-carboxylic acid (5-{[5-(4-fluoro-phenyl)-2-trifluoromethyl-3H-imidazole-4-carbonyl]-amino}-2-methyl-phenyl)-amide—(I-10)

1-H-Benzotriazole-5-carboxylic acid (0.19 g, 0.56 mmol) was dissolved in a mixture of DCM (2 mL) and DMF (1 mL). To the mixture was added HATU (0.21 g, 0.56 mmol) and DIEA (0.122 mL, 0.74 mmol) after 15 min of stirring, 5-(4-Fluoro-phenyl)-2-trifluoromethyl-3H-imidazole-4-carboxylic acid (3-amino-4-methyl-phenyl)-amide 6 (0.07 g g, 0.19 mmol) was added. The reaction was stirred at rt for 48 hr. The solvent was concentrated to dryness under reduced pressure, dissolved in EtOAc, and washed with sodium bicarbonate, 1M HCl, and brine. The solvent was evaporated and the residue was purified by HPLC to yield 28.4 mg of the desired product (I-10).

1H-7-Azaindole-3-carboxylic acid (5-{[5-(4-fluoro-phenyl)-2-trifluoromethyl-3,1-imidazole-4-carbonyl]-amino}-2-methyl-phenyl)-amide—I-11

7-azaindole-3-carboxylic acid (0.19 g, 0.56 mmol) was dissolved in a mixture of DCM (2 mL) and DMF (1 mL). To the mixture was added HATU (0.21 g, 0.56 mmol) and DIEA (0.122 mL, 0.74 mmol) after 15 min of stirring, 5-(4-Fluoro-phenyl)-2-trifluoromethyl-3H-imidazole-4-carboxylic acid (3-amino-4-methyl-phenyl)-amide 6 (0.07 g g, 0.19 mmol) was added. The reaction was stirred at rt for 48 hr. The solvent was concentrated to dryness under reduced pressure, dissolved in EtOAc, and washed with sodium bicarbonate, 1M HCl, and brine. The solvent was evaporated and the residue was purified by HPLC to yield 23.5 mg of the desired product (I-11).

The quinazolinone Hing-Gatekeeper anchor intermediate was prepared as outlined in WO 2007 GB 1389; WO2008120004, Scheme-4

Scheme 21: Preparation of 6-(5-Amino-2-methylphenylamino)-3-methylquinazolin-4(3H)-one (30; HGM-7)

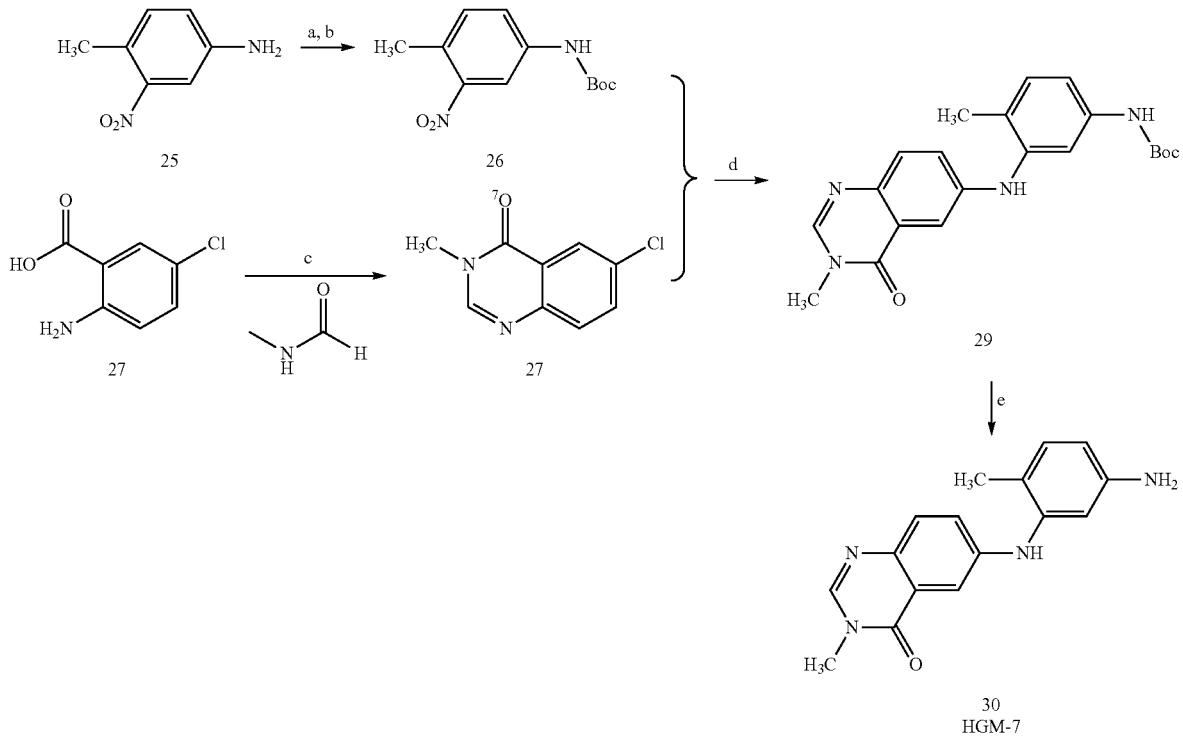

<sup>a</sup>Reagents and Conditions: (a) Boc₂O, THF, 65° C., overnight, 83% yield; (b) 40 psi H₂, 10% Pd/C, EtOH, 15 h, 92% yield; (c) 160° C., 8 h, 65% yield; (d) 1.4 Eq. t-BuONa, 3% Pd₂(dba)₃, 5% dbbp, 8 h, 82% yield; (e) 10% TFA/DCM, 1 h, 94% yield

6-(5-Amino-2-methylphenylamino)-3-methylquinazolin-4(3H)-one-30: Tert-butyl-4-methyl-3-nitrophenylcarbamate A solution of 4-methyl-3-nitroaniline 25 (15.0 g, 99 mmol) was dissolved in 50 mL THF at 65° C. 25.8 g Boc anhydride was dissolved in 30 mL THF and added dropwise over the course of 20 minutes. The reaction was refluxed overnight, cooled to room temperature, and then concentrated in vacuo to yield a brown oil. The oil was dissolved in 150 mL 20% EtOAc/Hex and 50 g of silica gel was added. The solution was stirred for 15 min on a rotovap and the silica was removed by filtration and washed with 300 mL 20% EtOAc/Hex. The organics were dried over magnesium sulfate and then concentrated by vacuum filtration to yield 20.7 g product in 83% yield. $^1$H NMR (300 MHz, D$_6$ DMSO): δ 9.75 (br s, 1H), 8.22 (d, 1H, J=2.1 Hz), 7.58 (dd, 1H, J=2.1 Hz, J=8.3 Hz), 7.37 (d, 1H, J=8.3 Hz), 2.43 (s, 3H), 1.48 (s, 9H). $^{13}$C NMR (75 MHz, D$_6$ DMSO): δ 153.50, 148.48, 139.45, 133.79, 126.65, 123.52, 113.81, 80.60, 28.84, 19.92. ESMS: m/z 270.0 [M+H20].

Tert-butyl 3-amino-4-methylphenylcarbamate—26

Tert-butyl 4-methyl-3-nitrophenylcarbamate (20.7 g, 82.0 mmol) was dissolved in 200 mL EtOH and 1.0 g of 5% Pd/C was added. The mixture was hydrogenated on a parr system at 50 PSI hydrogen for 15 hours. Completion of reaction was shown by TLC in 30% EtOAc/Hex, then filtered, concentrated, and dried in a vacuum oven to yield the product 26 (16.78 g, 75.0 mmol, 92% yield). $^1$H NMR (300 MHz, D$_6$ DMSO): δ 8.93 (br s, 1H), 6.85 (s, 1H), 6.75 (d, 1H, J=8.0 Hz), 6.5 (d, 1H, J=8.0 Hz), 4.75 (s, 2H), 1.97 (s, 3H), 1.46 (s, 9H). $^{13}$C NMR (75 MHz, D$_6$ DMSO): δ 153.58, 147.37, 138.777, 130.51, 115.87, 107.53, 105.07, 79.20, 29.05, 17.71. ESMS: m/z 223.2 [MH]$^+$

6-Chloro-3-methylquinazolin-4(3H)-one 28

2-amino-5-chlorobenzoic acid 27 (12.5 g, 73 mmol) was placed in a 250 mL beaker containing n-methylformamide (125 mL). A condenser was utilized and the reaction was heated overnight at 180° C. The reaction was complete the next morning and allowed to cool to room temperature for 1 hr and then poured into 500 mL of water and extracted three times with 250 mL of ethyl acetate. The organic phase was then washed with an additional 1 liter of water and concentrated under vacuum to yield 6-chloro-3-methylquinazolin-4 (3H)-one (9.2 g, 47.3 mmol, 65% yield) $^1$H NMR (300 MHz, D$_6$ DMSO): δ 8.39 (s, 1H), 8.04 (d, 1H, J=3.6 Hz), 7.82 (dd, 1H, J=2.4 Hz, J=8.7 Hz), 7.67 (1H, d, J=8.7 Hz), 3.49 (s, 3H). $^{13}$C NMR (75 MHz, D$_6$ DMSO): δ 160.49, 149.75, 147.65, 135.06, 131.99, 130.26, 125.61, 123.45, 34.53. ESMS: m/z 195.2 [MH]$^+$

Tert-butyl 4-methyl-3-(3-methyl-4-oxo-3,4-dihydroquinazolin-6-ylamino)phenylcarbamate 29

To refluxing toluene (50 mL) in a 150 mL round bottom flask was added 2-methyl-5-t-butylcarbamate aniline 23 (3 g, 13.50 mmol, 1.2 eq), -chloro-3-methyl-4-oxoquinazoline 28 (2.19 g, 11.25 mmol, 1 eq), NaOMe (1.51 g, 15.75 mmol, 1.4 eq), and 2-diphenylbistbutylphosphine (168 mg, 5 mol %, 0.561 mmol), and Pd2(dba)3 (309 mg, 3 mol %, 0.336 mmol). This mixture was refluxed for 8 hours when it was observed there was complete amination of quinazolinone starting material. The reaction mixture was cooled to room temperature and poured into 250 mL EtOAc and then washed with sodium bicarbonate (2×100 mL), water (2×100 mL), and then brine (2×100 mL). The light brown solid was then purified by flash chromatography on silica (70% EtOAc/Hex) to yield desired product 29 as a light yellow solid (3.6 g, 9.33 mmol, 83% yield). $^1$H NMR (300 MHz, D$_6$ DMSO): δ 7.91 (s, 1H), 7.64 (d, 1H, J=2.7 Hz), 7.61 (s, 1H, J=8.8 Hz), 7.34 (dd, 1H, J=2.7 Hz, J=8.8 Hz), 7.29 (s, 1H), 7.16 (d, 1H, J=8.2 Hz), 7.09 (d, 1H, J=8.2 Hz), 6.47 (s, 1H), 5.70 (s, 1H), 3.59 (s, 3H), 1.64 (s, 3H), 1.51 (s, 9H). $^{13}$C NMR (75 MHz, D$_6$ DMSO): δ 161.34, 153.57, 145.59, 145.58, 141.04, 139.09, 131.84, 129.01, 125.35, 123.96, 123.24, 114.31, 112.49, 108.33, 79.70, 34.26, 28.97, 18.14. ESMS: m/z 381.2 [MH]$^+$ 6-(5-Amino-2-methylphenylamino)-3-methylquinazolin-4(3H)-one 30

Tert-butyl 4-methyl-3-(3-methyl-4-oxo-3,4-dihydroquinazolin-6-ylamino)phenylcarbamate 26 (3.0 g, 7.89 mmol) was added to 50 mL of 10% TFA in DCM. After 1 hr, the reaction mixture was neutralized with 75 mL saturated Na$_2$CO3, extracted into EtOAc (3×100 mL), dried over MgSO$_4$ and concentrated in vacuo to yield the desired product (2.078 g, 7.41 mmol, 94% yield). $^1$H NMR (300 MHz, D$_6$ DMSO): δ 7.91 (s, 1H), 7.71 (d, 1H, J=2.7 Hz), 7.61 (s, 1H, J=8.8 Hz), 7.37 (dd, 1H, J=2.7 Hz, J=8.8 Hz), 7.31 (s, 1H), 7.03 (d, 1H, J=8.0 Hz), 6.67 (d, 1H, J=2.3 Hz), 6.40 (dd, 1H, J=2.4 Hz, J=8.0 Hz), 5.80 (br s, 1H), 3.63 (s, 3H), 2.16 (s, 3H), 1.64 (s, 3H), 1.51 (s, 9H). $^{13}$C NMR (75 MHz, D$_6$ DMSO): δ 160.73, 146.90, 144.88, 142.13, 138.84, 132.85, 131.08, 130.76, 126.96, 125.08, 122.78, 118.25, 115.49, 110.06, 34.87, 18.51. ESMS: m/z 281.2 [MH]$^+$ Scheme-22: Preparation of I-6, I-12, I-13, I-14. and I-15.

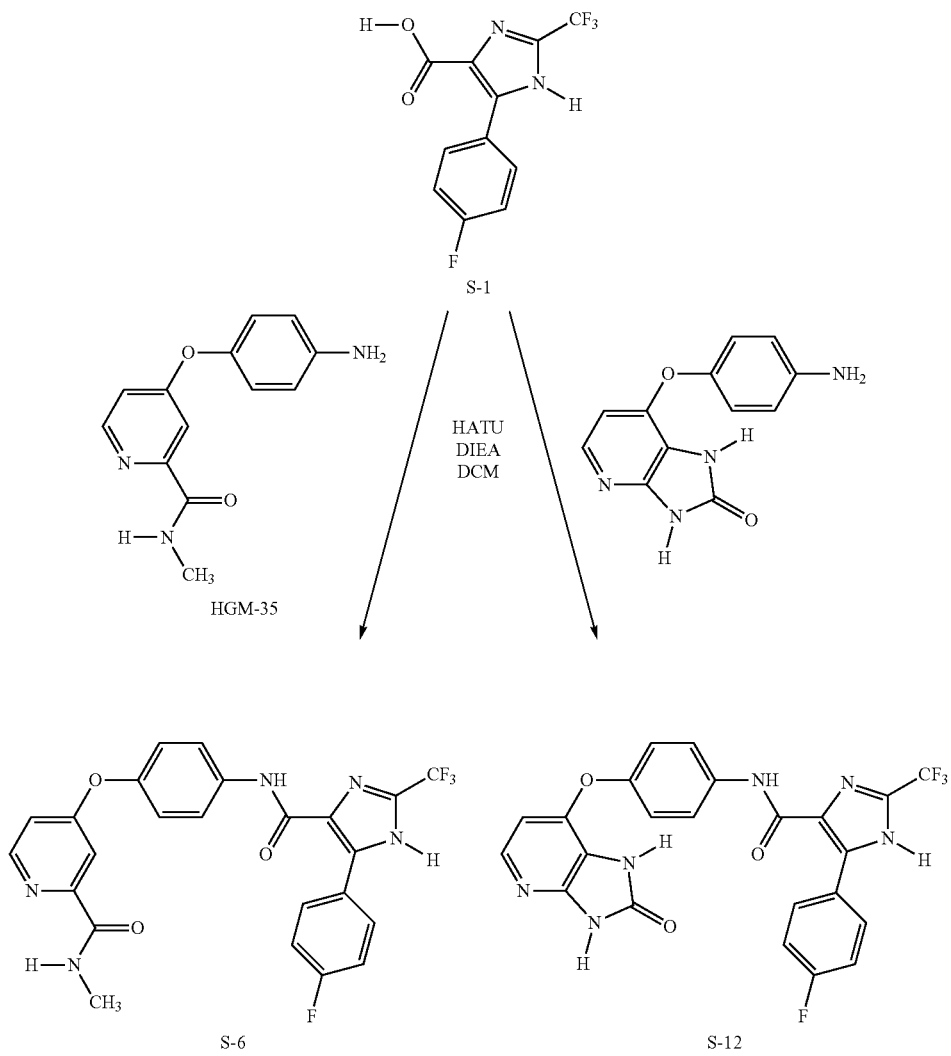

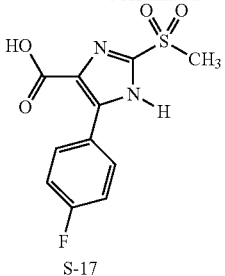
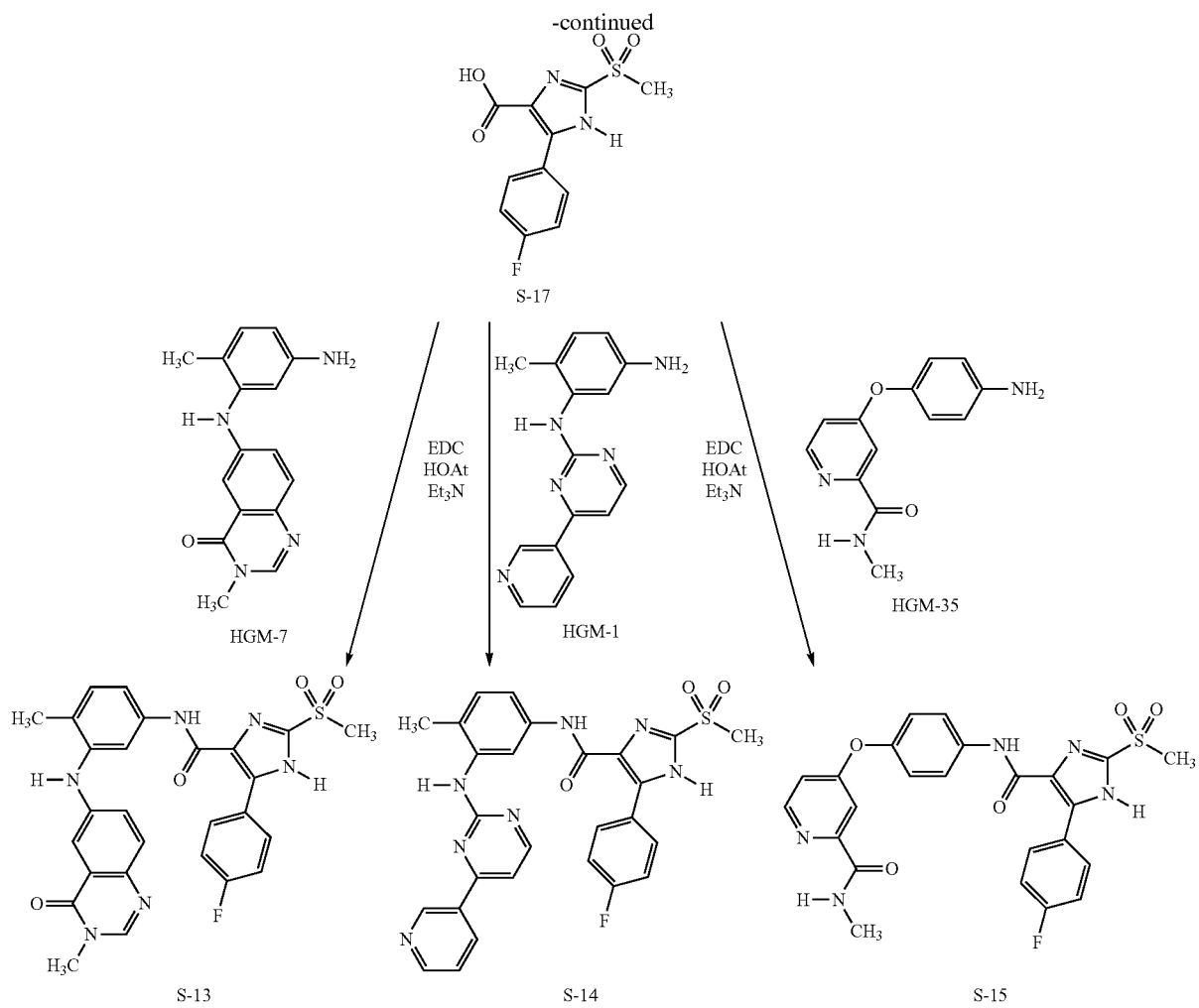

4-(4-{[5-(4-Fluoro-phenyl)-2-trifluoromethyl-3,1-imidazole-4-carbonyl]-amino}-phenoxy)-pyridine-2-carboxylic acid methylamide—(I-6)

5-(4-Fluoro-phenyl)-2-trifluoromethyl-3H-imidazole-4-carbonylic acid S-1 (0.20 g, 0.73 mmol) was dissolved in DCM (2 mL). To the mixture was added HATU (0.41 g, 1.1 mmol) and DIEA (0.38 mL, 2.19 mmol). After 15 min of stiffing, 4-(4-Amino-phenoxy)-pyridine-2-carboxylic acid methylamide (LeadGen Labs, LLC; BB-123) (0.18 g, 7.3 mmol) was added. The reaction was stirred overnight at rt. The solvent was evaporated and the residue was purified by silica gel chromatography (EtOAc/Hx, 0-40%) to yield 57 mg of the desired product, I-6.

4-(4-{[5-(4-Fluoro-phenyl)-2-trifluoromethyl-3,1-imidazole-4-carbonyl]-amino}-phenoxy)-pyridine-2, 3-benzimidazolone carboxylic acid methylamide—(I-12)

5-(4-Fluoro-phenyl)-2-trifluoromethyl-3H-imidazole-4-carbonylic acid S-1 (0.05 g, 0.18 mmol) was dissolved in DCM (2.0 mL) and SOCl$_2$ (2.0 mL). The mixture was refluxed for 2 hr and the solvents were evaporated to dryness. The residue was dissolved in DCM and 7-(4-aminophenoxy)-1,3-dihydroimidazole[4,5-b]pyridine-2-one (0.08 g, 0.33 mmol) and DIEA (0.12 mL, 0.72 mmol) was added. The mixture was heated for overnight and the solvents were evaporated. The residue was dissolved in DMSO and the product was purified by HPLC to give 8.7 mg of the target compound, I-12.

3-(3-methyl-4-oxo-3,4-dihydroquinazolin-6-ylamino)-4-methyl-analine, 5-(4-Fluorophenyl)-2-(methylsulfonyl)-1H-imidazole-4-carboxamide—(I-13)

In a 20 mL vial equipped with a magnetic stirrer and DCM (3 mL) at 0° C. was added the corresponding imidazole acid S-17 (71 mg, 0.250 mmol, 1 eq), EDCI (58.5 mg, 1.5 eq, 0.375 mmol), HOAt (44.25 mg, 1.3 eq, 0.33 mmol), DIPEA (175 uL, ~4 eq, 1.0 mmol). This solution was allowed to react for 1 hour at 0° C. and then amine (70 mg, 1 Eq, 0.25 mmol) was added. The reaction was allowed to react for 24 hours at which time it was added to 50 mL saturated sodium bicarbonate and extracted into 2×20 mL EtOAc. The organic layer was washed with water (20 mL 0.1M HCl) which extracted some of the color and left a neutral EtOAc extract-1. The aqueous acidic extract was neutralized with 20 mL saturated NaHCO$_3$ and back-extracted with 2×10 mL EtOAc to give a second organic extract-2. Both organic extracts were washed with Brine (30 mL), dried over magnesium sulfate and concentrated to give: Extract-1 totaled 113 mg and extract-2 totaled 30 mg of a dark amber film. Final compound was purified on a biotage sp1 system utilizing a 25 g silica column and a gradient of 2-8% MeOH/CHCl$_3$ to yield the desired productm SFE-0013 (97 mg, 0,177 mmol) in 71% yield.

3-(4-(pyridin-3-yl)-pyrimidinyl-2-yl)amino-4-methyl-analine, 5-(4-Fluorophenyl)-2-(methylsulfonyl)-1H-imidazole-4-carboxamide—(I-14)

In a 20 mL vial equipped with a magnetic stirrer and DCM (3 mL) at 0° C. was added 5-(4-fluoro-phenyl)-2-methanesulfonyl-1H-imidazole-4-carboxylic acid S-17 (71 mg, 0.250 mmol, 1 eq), EDCI (58.5 mg, 1.5 eq, 0.375 mmol), HOAt (44.25 mg, 1.3 eq, 0.33 mmol), DIPEA (175 uL, ~4 eq, 1.0 mmol). This solution was allowed to react for 1 hour at 0° C. and then N-(2-methyl-5-aminophenyl)-4-(pyridin-3-yl)-pyrimidazole acid S-17 (71 mg, 0.250 mmol, 1 eq), EDCI (58.5 mg, 1.5 eq, 0.375 mmol), HOAt (44.25 mg, 1.3 eq, 0.33 mmol), DIPEA (175 uL, ~4 eq, 1.0 mmol). This solution was allowed to react for 1 hour at 0° C. and then amine (61 mg, 1 Eq, 0.25 mmol) was added. The reaction was allowed to react for 24 hours at which time it was added to 50 mL saturated sodium bicarbonate and extracted into and extracted into 2×20 mL EtOAc. The organic layer was washed with water (20 mL 0.1M HCl) which extracted some of the color and left a neutral EtOAc extract-1. The aqueous acidic extract was neutralized with 20 mL saturated NaHCO$_3$ and back-extracted with 2×10 mL EtOAc to give a second organic extract-2. Both organic extracts were washed with Brine (30 mL), dried over magnesium sulfate and concentrated to give an amber semi-solid. The final compound was purified on a biotage sp1 system utilizing a 25 g silica column and a gradient of 2-8% MeOH/CHCl3 to yield the desired product I-15 (89 mg, 0.175 mg) 70% yield.

Scheme-23: Preparation of I-16 to I 35 as defined in Table 13.

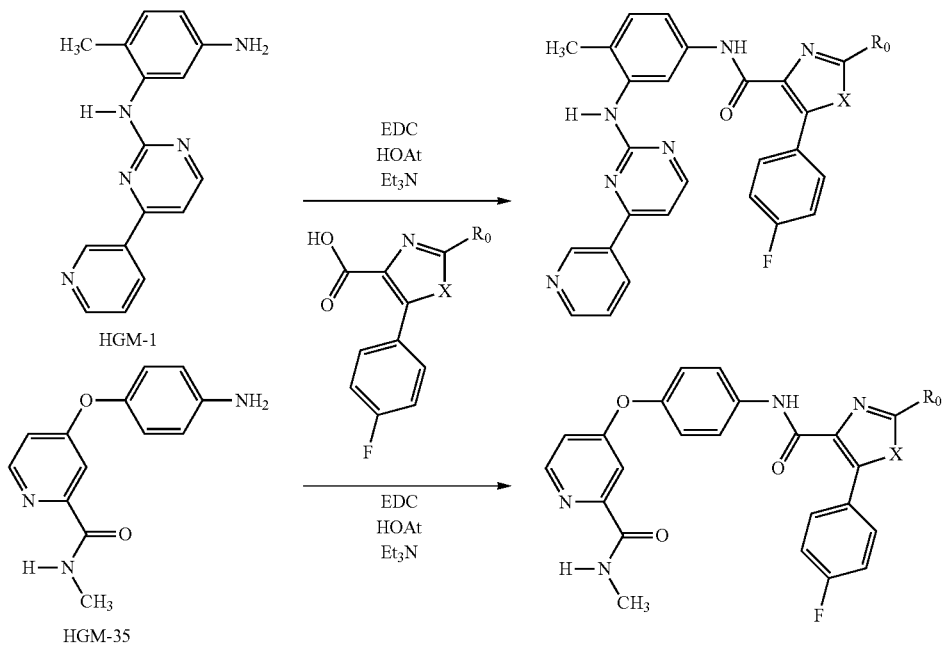

rimidine-2-amine (Alfa Pyridines, AP1C4100) (69 mg, 1 Eq, 0.25 mmol) was added. The reaction was allowed to react for 24 hours at which time it was added to 50 mL saturated sodium bicarbonate and extracted and extracted into 2×20 mL EtOAc. The organic layer was washed with water (20 mL 0.1M HCl) which extracted some of the color and left a neutral EtOAc extract-1. The aqueous acidic extract was neutralized with 20 mL saturated NaHCO$_3$ and back-extracted with 2×10 mL EtOAc to give a second organic extract-2. Both organic extracts were washed with Brine (30 mL), dried over magnesium sulfate and concentrated to give: Final compound was purified on a biotage sp1 system utilizing a 25 g silica column and a gradient of 2-8% MeOH/CHCl3 to yield the desired product, I-14 (108 mg, 0.199 mmol) in 79% yield.

4-(4-{[5-(4-Fluoro-phenyl)-2-methylsulfonyl-3,1-imidazole-4-carbonyl]-amino}-phenoxy)-pyridine-2-carboxylic acid methylamide—(I-15)

Procedure: In a 20 mL vial equipped with a magnetic stirrer and DCM (3 mL) at 0° C. was added the corresponding

3-(4-(pyridin-3-yl)-pyrimidinyl-2-yl)amino-4-methyl-analine, 5-(4-Fluorophenyl)-2-(methylthio)-1H-imidazole-4-carboxamide—(I-16)

Triethylamine (0.041 mL, 0.29 mmol) was added to a solution of S-15 (60 mg, 0.24 mmol), 2-(5-amino-2-methylanilino)-4-(3-pyridyl)pyrimidine (66 mg, 0.24 mmol) and HATU (115 mg, 0.29 mmol) in 3 mL DMF. The resulting mixture was stirred at room temperature overnight. Reaction mixture was then directly purified on HPLC which afforded 92 mg (76%) of the final product I-16. LC-MS: Rt 1.76 min, 99.8% pure by area.

3-(4-(pyridin-3-yl)-pyrimidinyl-2-yl)amino-4-methyl-analine, 5-(4-Fluorophenyl)-2-(methylsulfinyl)-1H-imidazole-4-carboxamide—(I-17)

I-17 was prepared from S-16 (50 mg, 0.186 mmol) following procedure described for the synthesis of I-16. After HPLC purification 78 mg (79%) of I-17 was obtained. LC-MS: Rt 1.51 min, 99% pure by area.

3-(4-(pyridin-3-yl)-pyrimidinyl-2-yl)amino-4-methyl-analine, 5-(4-Fluorophenyl)-2-(methylthio)-1H-thiazole-4-carboxamide—(I-18)

Diisopropylethylamine (0.484 mL, 2.7 mmol) was added to a solution of S-25 (150 mg, 0.55 mmol), 2-(5-amino-2-methylanilino)-4-(3-pyridyl)pyrimidine (154 mg, 0.55 mmol) and HATU (383 mg, 1.11 mmol) in 6 mL DMF. The resulting mixture was stirred at room temperature overnight. Reaction mixture was directly subjected to HPLC purification, which afforded 121 mg (41%) of the final product I-18. LC-MS: Rt 2.21 min, 98% pure by area.

3-(4-(pyridin-3-yl)-pyrimidinyl-2-yl)amino-4-methyl-analine, 5-(4-Fluorophenyl)-2-(methylsulfinyl)-thiazole-4-carboxamide—(I-19)

Compound I-19 was prepared from S-26 (90 mg, 0.3 mmol) following procedure described for the synthesis of I-18. After HPLC purification 29 mg (17%) of I-19 was obtained. LC-MS: Rt 1.7 min, 100% pure by area.

3-(4-(pyridin-3-yl)-pyrimidinyl-2-yl)amino-4-methyl-analine, 5-(4-Fluorophenyl)-2-(methylsulfonyl)-thiazole-4-carboxamide—(I-20)

Compound I-20 was prepared from S-27 (660 mg, 2.2 mmol) following procedure described for the synthesis of I-18. Half of the reaction mixture was purified by HPLC to give 52 mg (4%) of I-20. LC-MS: Rt 1.85 min, 97.9% pure by area.

3-(4-(pyridin-3-yl)-pyrimidinyl-2-yl)amino-4-methyl-analine, 5-(4-Fluorophenyl)-2-(methylsulfonylamino)-thiazole-4-carboxamide—(I-21)

Compound I-18 was prepared from S-29 (20 mg, 0.063 mmol) following procedure described for the synthesis of I-20. HPLC purification yielded 29 mg (80%) of the product I-21. LC-MS: Rt 1.72 min, 99.7% pure by area.

3-(4-(pyridin-3-yl)-pyrimidinyl-2-yl)amino-4-methyl-analine, 5-(4-Fluorophenyl)-2-(methylthio)-oxazole-4-carboxamide—(I-22)

Compound I-22 was prepared from S-50 (100 mg, 0.4 mmol) following procedure described for the synthesis of I-18. After HPLC purification 124 mg (61%) of I-22 was obtained. LC-MS: Rt 2.23 min, 98.9% pure by area.

3-(4-(pyridin-3-yl)-pyrimidinyl-2-yl)amino-4-methyl-analine, 5-(4-Fluorophenyl)-2-(methylsulfinyl)-oxazole-4-carboxamide—(I-23)

Compound I-23 was prepared from S-51 (60 mg, 0.21 mmol) following procedure described for the synthesis of I-18. After HPLC purification 53 mg (45%) of I-23 was obtained. LC-MS: Rt 1.71 min, 99.8% pure by area.

3-(4-(pyridin-3-yl)-pyrimidinyl-2-yl)amino-4-methyl-analine, 5-(4-Fluorophenyl)-2-(methylsulfonyl)-oxazole-4-carboxamide—(I-24)

Compound I-24 was prepared from S-52 (60 mg, 0.21 mmol) following procedure described for the synthesis of I-18. After HPLC purification 57 mg (50%) of I-24 was obtained. LC-MS: Rt 1.9 min, 97.3% pure by area.

3-(4-(pyridin-3-yl)-pyrimidinyl-2-yl)amino-4-methyl-analine, 5-(4-Fluorophenyl)-2-(methylsulfonyl)-1,2-pyrazole-4-carboxamide—(I-25)

Compound I-25 was prepared from S-60 (156 mg, 0.55 mmol) following procedure described for the synthesis of I-18. A portion of the reaction mixture was purified by HPLC to give 17.3 mg (6%) of I-25. LC-MS: Rt 1.75 min, 90.1% pure by area.

4-(4-{[5-(4-Fluoro-phenyl)-2-methylthio-1(H)-imidazole-4-carbonyl]-amino}-phenoxy)-pyridine-2-carboxylic acid methylamide—(I-26)

Triethylamine (0.041 mL, 0.29 mmol) was added to a solution of S-15 (60 mg, 0.24 mmol), 4-(4-aminophenoxy) pyridine-2-carboxilic acid methyamide (58 mg, 0.24 mmol) and HATU (115 mg, 0.29 mmol) in 3 mL DMF. The resulting mixture was stirred at room temperature overnight. Reaction mixture was then directly purified on HPLC which afforded 66.6 mg (59%) of the final product S-26. LC-MS: Rt 1.94 min, 99.8% pure by area.

4-(4-{[5-(4-Fluoro-phenyl)-2-methylsulfinyl-1(H)-imidazole-4-carbonyl]-amino}-phenoxy)-pyridine-2-carboxylic acid methylamide—(I-27)

Compound I-27 was prepared from S-16 (50 mg, 0.186 mmol) following procedure described for the synthesis of I-26. After HPLC purification 68 mg (74%) of I-27 was obtained. LC-MS: Rt 1.67 min, 99.9% pure by area.

4-(4-{[5-(4-Fluoro-phenyl)-2-methylthio-thiazole-4-carbonyl]-amino}-phenoxy)-pyridine-2-carboxylic acid methylamide—(I-28)

Diisopropylethylamine (0.484 mL, 2.7 mmol) was added to a solution of S-25 (150 mg, 0.55 mmol), 4-(4-aminophenoxy)pyridine-2-carboxilic acid methyamide (135 mg, 0.55 mmol) and HATU (383 mg, 1.11 mmol) in 6 mL DMF. The resulting mixture was stirred at room temperature overnight. Reaction mixture was directly subjected to HPLC purification to afford 109 mg (40%) of the product I-28. LC-MS: Rt 2.56 min, 94.7% pure by area.

4-(4-{[5-(4-Fluoro-phenyl)-2-methylsulfinyl-thiazole-4-carbonyl]-amino}-phenoxy)-pyridine-2-carboxylic acid methylamide—(I-29)

Compound I-29 was prepared from S-26 (90 mg, 0.3 mmol) in the same manner as I-28. A portion of the reaction mixture was HPLC purified to provide 3.6 mg (2%) of the product I-29. LC-MS: Rt 1.94 min, 100% pure by area.

4-(4-{[5-(4-Fluoro-phenyl)-2-methylsulfonyl-thiazole-4-carbonyl]-amino}-phenoxy)-pyridine-2-carboxylic acid methylamide—(I-30)

Compound I-30 was prepared from S-27 (660 mg, 2.2 mmol) in the same manner as I-28. Half of the reaction mixture was purified by HPLC to give 48.4 mg (4%) of 11. LC-MS: Rt 2.12 min, 95.4% pure by area.

4-(4-{[5-(4-Fluoro-phenyl)-2-methylsulfonylamino-thiazole-4-carbonyl]-amino}-phenoxy)-pyridine-2-carboxylic acid methylamide—(I-31)

Compound I-31 was prepared from S-29 (20 mg, 0.063 mmol) in the same manner as I-28. HPLC purification yielded 32 mg (94%) of the product I-31. LC-MS: Rt 1.88 min, 99.4% pure by area.

4-(4-{[5-(4-Fluoro-phenyl)-2-methylthio-oxazole-4-carbonyl]-amino}-phenoxy)-pyridine-2-carboxylic acid methylamide—(I-32)

Compound I-32 was prepared from S-50 (100 mg, 0.4 mmol) following procedure described for the synthesis of I-28. After HPLC purification 158 mg (84%) of I-32 was obtained. LC-MS: Rt 2.59 min, 99.6% pure by area.

4-(4-{[5-(4-Fluoro-phenyl)-2-methylsulfinyl-oxazole-4-carbonyl]-amino}-phenoxy)-pyridine-2-carboxylic acid methylamide—(I-33)

Compound I-33 was prepared from S-51 (60 mg, 0.21 mmol) following procedure described for the synthesis of I-28. After HPLC purification 94 mg (85%) of I-33 was obtained. LC-MS: Rt 1.95 min, 99.8% pure by area.

4-(4-{[5-(4-Fluoro-phenyl)-2-methylsulfonyl-oxazole-4-carbonyl]-amino}-phenoxy)-pyridine-2-carboxylic acid methylamide—(I-34)

Compound I-34 was prepared from S-52 (60 mg, 0.21 mmol) following procedure described for the synthesis of I-28. After HPLC purification 61 mg (57%) of I-34 was obtained. LC-MS: Rt 2.16 min, 92.3% pure by area.

4-(4-{[5-(4-Fluoro-phenyl)-2-methylsulfonyl-1,2-pyrazole-4-carbonyl]-amino}-phenoxy)-pyridine-2-carboxylic acid methylamide—(I-35)

Compound I-35 was prepared from S-60 (156 mg, 0.55 mmol) in the same manner as I-28. A portion of the reaction mixture was purified by HPLC to give 6.4 mg (2%) of I-35. LC-MS: Rt 2.01 min, 98.2% pure by area.

Scheme 24: Synthetic Route to I-36

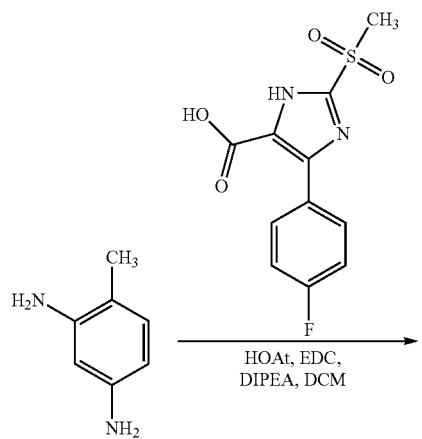

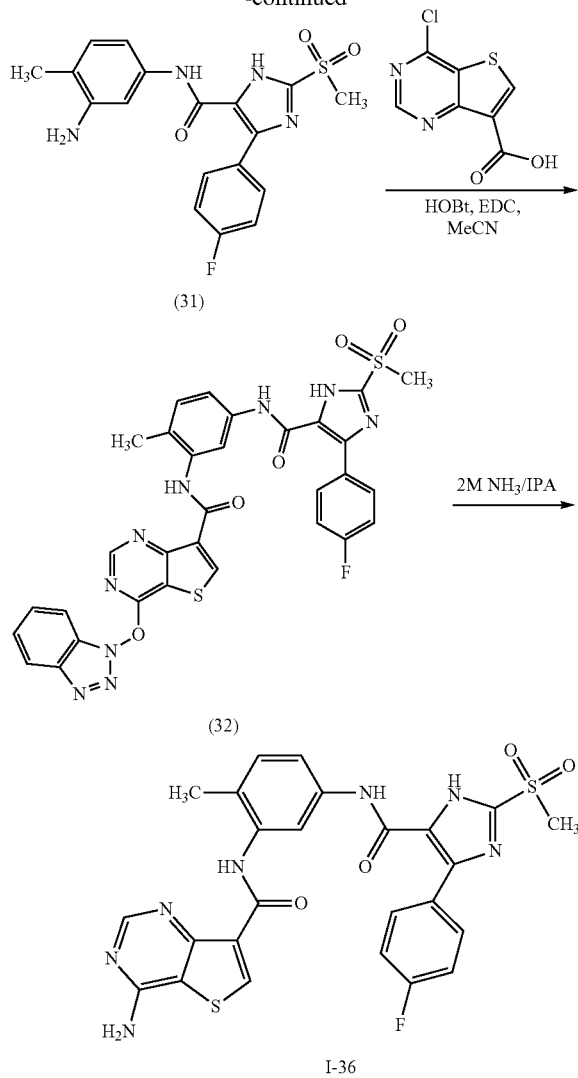

4-amino-N-(5-(4-(4-fluorophenyl)-2-(methylsulfonyl)-1H-imidazole-5-carboxamido)-2-methylphenyl)thieno[3,2-d]pyrimidine-7-carboxamide (I-36)

N-(3-amino-4-methylphenyl)-4-(4-fluorophenyl)-2-(methylsulfonyl)-1H-imidazole-5-carboxamide. (31)

To a flask containing DCM (23.5 mL) on ice was added 4-(4-fluorophenyl)-2-(methylsulfonyl)-1H-imidazole-5-carboxylic acid (665 mg, 2.34 mmol) and to this was added portionwise EDC (545 mg, 3.51 mmol) then stirred for 10 minutes. To this solution was added HOAt (414 mg, 3.04 mmol) followed by DIPEA (1.63 mL, 9.36 mmol). The resulting solution was allowed to react for 1 hr, at which point 4-methylbenzene-1,3-diamine (572 mg, 4.68 mmol) was added and the mixture was then warmed to room temperature and stirred for 18 hours. To the flask was added saturated sodium bicarbonate (75 mL) then extracted with DCM (3×30 mL) and EtOAc (3×20 mL). The organic extracts were washed with brine, combined, dried over Na2SO4, then concentrated under reduced pressure. The crude material was fractionated by SiO2 chromatography (stepwise gradient of DCM to 8% MeOH) and the desired product 30 elutes in 2%

MeOH (189 mg, 20% yield). ¹HNMR (400 MHz, MeOD/CDCl₃): d 7.72 (m, 2H), 7.12 (t, 2H, J=9.2 Hz), 6.94 (d, 1H, J=7.6 Hz), 6.79 (m, 2H), 2.09 (s, 3H), 2.02 (s, 3H). 19FNMR (400 MHz, MeOD/CDCl₃): d −107.7. MS (ESI): 389.0 [M+H]+

4-((1H-benzo[d][1,2,3]triazol-1-yl)oxy)-N-(5-(4-(4-fluorophenyl)-2-(methylsulfonyl)-1H-imidazole-5-carboxamido)-2-methylphenyl)thieno[3,2-d]pyrimidine-7-carboxamide, (32)

To a flask containing MeCN (6.4 mL) and DMF (0.3 mL) on ice was added 4-chlorothieno[3,2-d]pyrimidine-7-carboxylic acid (82.9 mg, 0.39 mmol), HOBt (52.2 mg, 0.39 mmol), and n-(3-amino-4-methylphenyl)-4-(4-fluorophenyl)-2-(methylsulfonyl)-1H-imidazole-5-carboxamide (150 mg, 0.39 mmol). The resulting solution was stirred for 10 min followed by the addition of EDC (180 mg, 1.16 mmol) After 48 hrs, TLC indicates that nearly all of the starting material is consumed. To the solution was added ethyl acetate (10 mL) and water (15 mL) and the solution was made basic (pH-8) with saturated sodium bicarbonate and extracted with ethyl acetate (3×10 mL). The organic fractions were combined, washed with brine, dried over Na2SO4, and concentrated under reduced pressure. The crude material was purified by SiO2 chromatography (DCM to 8% MeOH gradient) and the desired product elutes in 3% MeOH (50 mg, 22% yield). 1HNMR (400 MHz, CDCl₃/MeOD): d 11.07 (s, 1H), 9.07 (s, 1H), 8.89 (s, 1H), 8.69 (s, 1H), 8.14 (s, 1H), 8.01 (d, 1H, J=8.8 Hz), 7.75 (m, 2H), 7.54 (m, 1H), 7.44 (m, 2H), 7.33 (d, 1H, J=7.2 Hz), 7.07 (d, 1H, J=8.0 Hz), 6.94 (m, 2H), 3.20 (s, 3H), 2.34 (s, 3H). 19FNMR (400 MHz, MeOD/CDCl₃): d −110.9. MS (ESI):m/z 683.9 [M+H]+

4-amino-N-(5-(4-(4-fluorophenyl)-2-(methylsulfonyl)-1H-imidazole-5-carboxamido)-2-methylphenyl)thieno[3,2-d]pyrimidine-7-carboxamide (I-36)

Compound 4-chloro-N-(5-(4-(4-fluorophenyl)-2-(methylsulfonyl)-1H-imidazole-5-carboxamido)-2-methylphenyl)thieno[3,2-d]pyrimidine-7-carboxamide (7.0 mg, 0.01 mmol) was dissolved into 2M ammonia in IPA (1.0 mL, 1.99 mmol ammonia). The resulting solution was heated in a sealed vial at 80° C. for 6 hrs. The solvent was removed under reduced pressure and the crude material was purified by SiO₂ chromatography (DCM to 8% MeOH gradient, desired product elutes in 6% MeOH) (4 mg, 59% yield). ¹HNMR (400 MHz, MeOD/CDCl₃): d 8.64 (s, 1H), 8.42 (s, 1H), 8.26 (m, 1H), 7.66 (m, 2H), 7.56 (m, 2H), 7.51 (s, 1H), 7.41 (m, 2H), 7.07 (d, 1H, J=9.2 Hz), 7.01 (t, 2H, J=8.4 Hz), 3.20 (s, 3H), 2.33 (s, 3H). MS (ESI): m/z 565.9 [M+H]+.

Scheme 25: Preparation of N-methylimidazole Inhibitors I-37 and I-38.

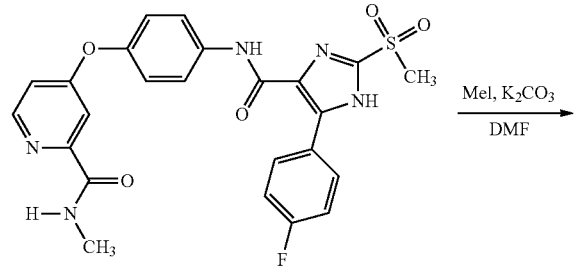

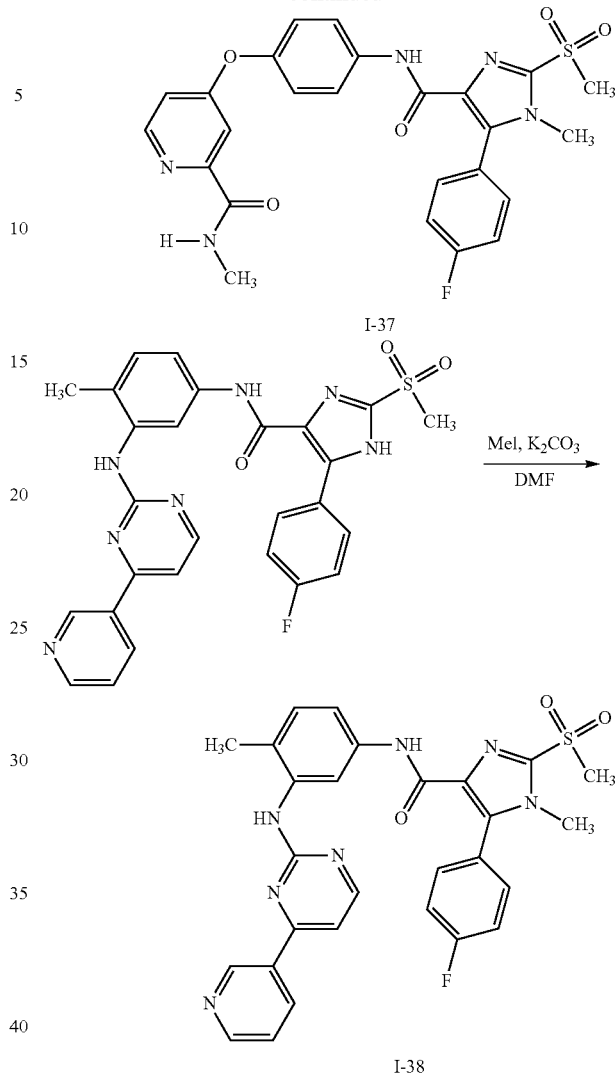

I-37

I-38

Preparation of 4-(4-(5-(4-fluorophenyl)-1-methyl-2-(methylsulfonyl)-1H-imidazole-4-carboxamido)phenoxy)-N-methylpicolinamide (I-37)

To a chilled solution of 4-(4-(5-(4-fluorophenyl)-2-(methylsulfonyl)-1H-imidazole-4-carboxamido)phenoxy)-N-methylpicolinamide (200 mg, 0.39 mmol) and K2CO3 (119 mg, 0.86 mmol) in DMF (3.9 mL), was added methyl iodide (29 μL, 67 mg, 0.47 mmol). The reaction mixture was allowed to warm to room temperature and stirred overnight. TLC indicates completion of reaction with a single major product. Solvent was removed under reduced pressure and the crude material was dissolved in H₂O (20 mL) and extracted with EtOAc (3×10 mL). The organic fractions were dried over Na₂SO₄ and concentrated. The crude material was purified by SiO2 chromatography (DCM/MeOH from 100% DCM to 94% DCM/6% MeOH, the desired product elutes in 97% DCM/3% MeOH) to yield a white solid (149 mg, 72% yield). 1HNMR (400 MHz, CDCl₃): δ 8.88 (s, 1H), 8.33 (d, 1H, J=6.0 Hz), 7.97 (m, 1H), 7.66 (m, 3H), 7.50 (m, 1H), 7.43 (m, 2H), 7.22 (t, 2H, J=8.4 Hz), 7.03 (d, 2H, J=9.2 Hz), 3.79 (s, 3H), 3.50 (s, 3H), 2.98 (d, 3H, J=5.2 Hz). MS (ESI): m/z 524.0 [M+H]+

5-(4-Fluorophenyl)-1-methyl-N-(4-methyl-3-(4-(pyridin-3-yl)pyrimidin-2-yl)amino)phenyl)-2-(methylsulfonyl)-1H-imidazole-4-carboxamide (I-38)

To a chilled solution of 5-(4-fluorophenyl)-N-(4-methyl-3-((4-(pyridin-3-yl)pyrimidin-2-yl)amino)phenyl)-2-(methylsulfonyl)-1H-imidazole-4-carboxamide (200 mg, 0.37 mmol) and K$_2$CO$_3$ (112 mg, 0.81 mmol) in DMF (3.7 mL) was added methyl iodide (27 uL, 63 mg, 0.44 mmol). The reaction mixture was allowed to warm to RT and stirred overnight. Solvent was removed under reduced pressure and the crude material was dissolved in H$_2$O (20 mL) and extracted with EtOAc (3×10 mL). The organic fractions were dried over Na$_2$SO$_4$ and concentrated. The crude material was purified by SiO$_2$ chromatography (DCM/MeOH from 100% DCM to 94% DCM/6% MeOH, the desired product elutes in 97% DCM/3% MeOH) to yield a light yellow solid (26 mg, 13% yield). $^1$HNMR (400 MHz, MeOD/CDCl$_3$): d 9.15 (d, 1H, J=2.4 Hz), 8.56 (m, 2H), 8.43 (d, 1H, J=5.2 Hz), 8.31 (s, 1H), 7.60 (s, 1H), 7.47 (m, 2H), 7.27 (m, 3H), 7.19 (t, 3H, J=8.4 Hz), 3.77 (s, 3H), 3.46 (s, 3H), 2.28 (s, 3H). MS (ESI): m/z 558.0 [M+H]+

Scheme 26: Preparation of 2-Trifluoromethyl oxazole Inhibitors I-39 and I-40.

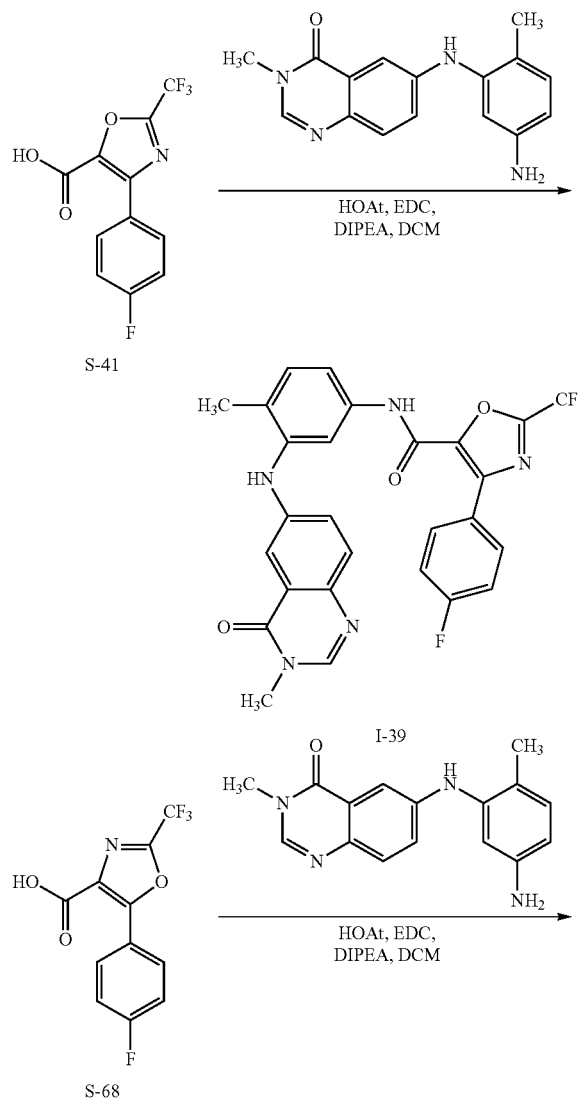

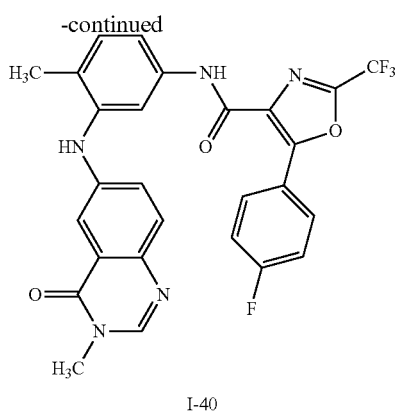

4-(4-Fluorophenyl)-N-(4-methyl-3-((3-methyl-4-oxo-3,4-dihydroquinazolin-6-yl)amino)phenyl)-2-(trifluoromethyl)oxazole-5-carboxamide. (I-39)

To a flask containing DCM (3 mL) on ice was added 4-(4-fluorophenyl)-2-(trifluoromethyl)oxazole-5-carboxylic acid (S-41) (76 mg, 0.28 mmol), EDC (47.2 mg, 0.3 mmol), HOAt (48.9 mg, 0.36 mmol), and DIPEA (0.193 mL, 1.10 mmol). The resulting solution was stirred for 1 hr followed by the addition of 6-((5-amino-2-methylphenyl)amino)-3-methylquinazolin-4(3H)-one (HGM-7) (77.4 mg, 0.28 mmol). The reaction was stirred for 18 hours at ambient temperature at which point the solution was made basic by the addition of saturated sodium bicarbonate (10 mL) which was then extracted with DCM (2×10 mL) and EtOAc (2×10 mL). The organic extracts were washed with brine, combined, dried over Na$_2$SO$_4$, and concentrated. The crude material was fractionated by SiO$_2$ chromatography (stepwise gradient of DCM to 90% DCM/10% MeOH, desired product elutes in 5% MeOH)(101 mg, 67% yield). $^1$HNMR (400 MHz, CDCl$_3$): d 8.9 (s, 1H), 7.82 (m, 2H), 7.80 (s, 1H), 7.55 (d, 1H, J=2.4 Hz), 7.50 (s, 1H), 7.41 (d, 1H, J=8.4 hz), 7.27 (m, 2H), 7.03 (d, 1H, J=8.4 Hz), 6.95 (t, 2H, J=8.8 Hz), 3.44 (s, 3H), 2.12 (s, 3H).

5-(4-fluorophenyl)-N-(4-methyl-3-((3-methyl-4-oxo-3,4-dihydroquinazolin-6-yl)amino)phenyl)-2-(trifluoromethyl)oxazole-4-carboxamide. (I-40)

To a flask containing DCM (3 mL) at 0° C. was added 5-(4-fluorophenyl)-2-(trifluoromethyl)oxazole-4-carboxylic acid (S-68) (17 mg, 0.06 mmol), EDC (10.6 mg, 0.07 mmol), HOAt (10.9 mg, 0.08 mmol), and DIPEA (0.043 mL, 0.25 mmol). The resulting solution was allowed to react at 0° C. for 1 hr, at which point 6-((5-amino-2-methylphenyl)amino)-3-methylquinazolin-4(3H)-one (HGM-7) (17.3 mg, 0.06 mmol) was added. The reaction was allowed to react for 18 hours at ambient temperature at which point saturated sodium bicarbonate (5 mL) was added and extracted with DCM (2×10 mL) then EtOAc (2×10 mL). The organic extracts were washed with brine, combined, dried over Na$_2$SO$_4$, and concentrated. The crude material was fractionated by SiO$_2$ chromatography (stepwise gradient of DCM to 10% MeOH, the desired product elutes in 6% MeOH) (9 mg, 27% yield). $^1$HNMR (400 MHz, CDCl$_3$/MeOD): d 8.29 (m, 2H), 7.98 (s, 1H), 7.62 (d, 1H, J=2.4 Hz), 7.57 (m, 2H), 7.51 (s, 1H), 7.42 (dd, 1H, J=2.8, 9.2 Hz), 7.39 (dd, 1H, J=2.4, 8.4 Hz), 7.24 (d, 1H, J=8.0 Hz), 7.19 (t, 2H, J=8.4 Hz), 3.58 (s, 3H), 2.24 (s, 3H).

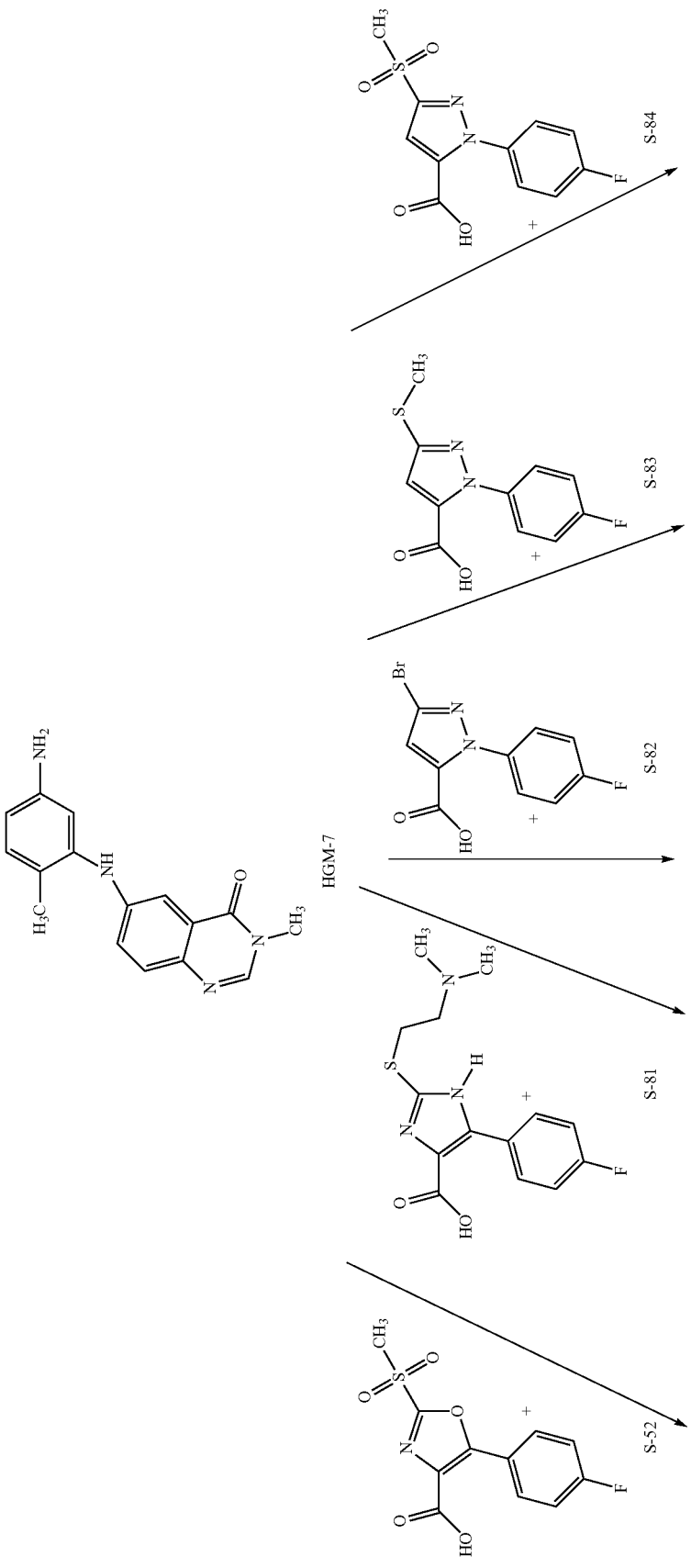
Scheme 27: Preparation of Quinazolinone HGM Inhibitors I-41 and I-47.

-continued
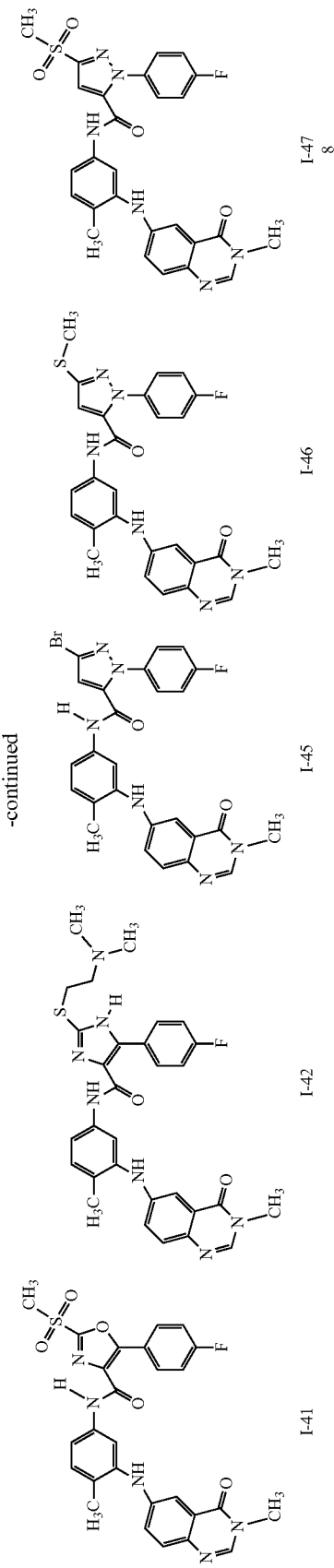
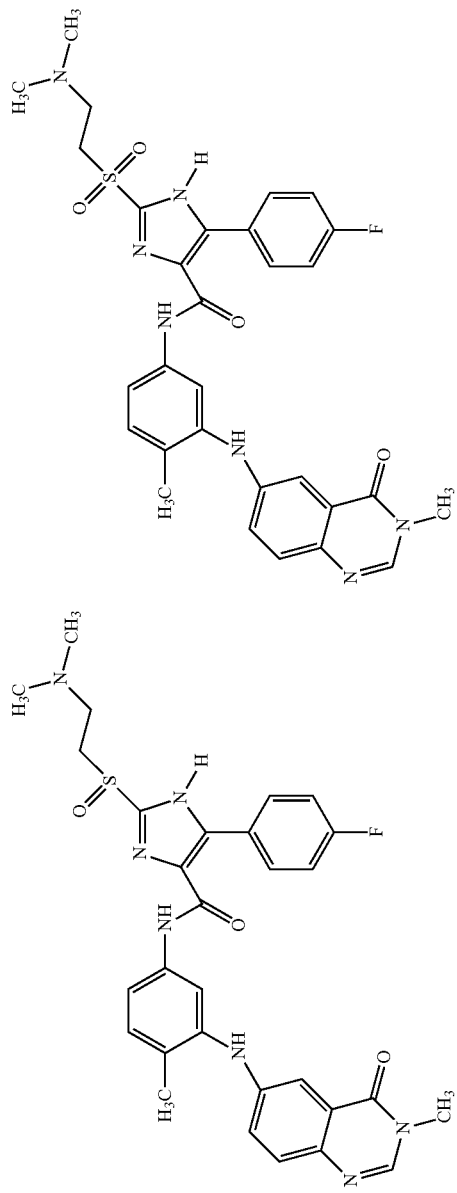

5-(4-fluorophenyl)-N-(4-methyl-3-((3-methyl-4-oxo-3,4-dihydroquinazolin-6-yl)amino)phenyl)-2-(methylsulfonyl)oxazole-4-carboxamide, I-41

6-(5-amino-2-methyl-phenylamino)-3-methyl-3H-quinazolin-4-one HCl salt (110 mg, 0.28 mmol) was dissolved in DMF (5 mL) with 5-(4-fluoro-phenyl)-2-methanesulfonyl-oxazole-4-carboxylic acid (142 mg, 0.5 mmol) at RT. HATU (150 mg, 0.39 mmol) was added, followed by DIEA (0.5 mL, 2.87 mmol). The mixture was stirred for 20 h. Water (20 mL) was added and the mixture was extracted with EtOAc (30 mL). The organic layer was concentrated and the residue was dissolved in minimum amount of DMSO and purified by prep HPLC. 82 mg of title compound was obtained after lyophilization of pure fractions. LC-MS [M+H] 548.1.

2-β2-(dimethylamino)ethyl)thio)-5-(4-fluorophenyl)-N-(4-methyl-3-((3-methyl-4-oxo-3,4-dihydroquinazolin-6-yl)amino)phenyl)-1H-imidazole-4-carboxamide, I-42

6-(5-Amino-2-methyl-phenylamino)-3-methyl-3H-quinazolin-4-one HCl salt (662 mg, 1.7 mmol) was dissolved in DMF (15 mL) with 2-(2-dimethylamino-ethylthio)-5-(4-fluoro-phenyl)-1H-imidazole-4-carboxylic acid (750 mg, 2.55 mmol) at RT. HATU (950 mg, 2.5 mmol) was added, followed by DIEA (1.5 mL, 8.6 mmol). The mixture was stirred for 16 h. Water (100 mL) was added and the mixture was extracted with EtOAc (300 mL). The organic layer was concentrated and the residue was dissolved in minimum amount of DMSO and purified by prep HPLC. 700 mg of title compound was obtained after lyophilization of pure fractions. LC-MS [M+H] 572.2.

2-β2-(dimethylamino)ethyl)sulfinyl)-5-(4-fluorophenyl)-N-(4-methyl-3-((3-methyl-4-oxo-3,4-dihydroquinazolin-6-yl)amino)phenyl)-1H-imidazole-4-carboxamide, I-43

2-(2-Dimethylamino-ethylthio)-5-(4-fluoro-phenyl)-1H-imidazole-4-carboxylic acid [4-methyl-3-(3-methyl-4-oxo-3,4-dihydro-quinazolin-6-ylamino)-phenyl]-amide (150 mg, 0.22 mmol, TFA salt) was dissolved in a mixed solvent of DCM/CH$_3$CN (1.5 mL each) at RT. Oxone (80 mg, 0.13 mmol) was added, followed by MeOH (10 drops). The mixture was heated to 60° C. for 40 mins. It was then cooled and concentrated. The residue was purified by prep HPLC to afford 127 mg of the title compound. LC-MS [M+H] 588.2.

2-β2-(dimethylamino)ethyl)sulfonyl)-5-(4-fluorophenyl)-N-(4-methyl-3-((3-methyl-4-oxo-3,4-dihydroquinazolin-6-yl)amino)phenyl)-1H-imidazole-4-carboxamide, I-44

2-(2-Dimethylamino-ethylthio)-5-(4-fluoro-phenyl)-1H-imidazole-4-carboxylic acid [4-methyl-3-(3-methyl-4-oxo-3,4-dihydro-quinazolin-6-ylamino)-phenyl]-amide (110 mg, 0.26 mmol, TFA salt) was dissolved in a mixed solvent of DCM/CH$_3$CN (1.5 mL each) at RT. Oxone (118 mg, 0.26 mmol) was added, followed by a mixture of MeOH/water (2/1 6 drops). The mixture was heated to 60° C. for 3 h. It was then cooled and concentrated. The residue was purified by prep HPLC to afford 60 mg of the title compound. LC-MS [M+H] 604.2.

3-bromo-1-(4-fluorophenyl)-N-(4-methyl-3-((3-methyl-4-oxo-3,4-dihydroquinazolin-6-yl)amino)phenyl)-1H-pyrazole-5-carboxamide, I-45

6-(5-Amino-2-methyl-phenylamino)-3-methyl-3H-quinazolin-4-one HCl salt (30 mg, 0.08 mmol) was dissolved in DMF (5 mL) with 5-bromo-2-(4-fluoro-phenyl)-2H-pyrazole-3-carboxylic acid (45 mg, 0.16 mmol) at RT. HATU (60 mg, 0.16 mmol) was added, followed by DIEA (0.14 mL, 0.8 mmol). The mixture was stirred for 20 h. Water (10 mL) was added and the mixture was extracted with EtOAc (20 mL). The organic layer was concentrated and the residue was dissolved in minimum amount of DMSO and purified by prep HPLC. 30 mg of title compound was obtained after lyophilization of pure fractions. LC-MS [M+H] 549.0.

1-(4-fluorophenyl)-N-(4-methyl-3-((3-methyl-4-oxo-3,4-dihydroquinazolin-6-yl)amino)phenyl)-3-(methylthio)-1H-pyrazole-5-carboxamide, I-46

6-(5-amino-2-methyl-phenylamino)-3-methyl-3H-quinazolin-4-one HCl salt (110 mg, 0.28 mmol) was dissolved in DMF (5 mL) with 2-(4-fluoro-phenyl)-5-methylthio-2H-pyrazole-3-carboxylic acid (125 mg, 0.5 mmol) at RT. HATU (150 mg, 0.39 mmol) was added, followed by DIEA (0.5 mL, 2.87 mmol). The mixture was stirred for 20 h. Water (20 mL) was added and the mixture was extracted with EtOAc (30 mL). The organic layer was concentrated and the residue was dissolved in minimum amount of DMSO and purified by prep HPLC. 80 mg of title compound was obtained after lyophilization of pure fractions. LC-MS [M+H] 514.2.

1-(4-fluorophenyl)-N-(4-methyl-3-((3-methyl-4-oxo-3,4-dihydroquinazolin-6-yl)amino)phenyl)-3-(methylsulfonyl)-1H-pyrazole-5-carboxamide, I-47

6-(5-Amino-2-methyl-phenylamino)-3-methyl-3H-quinazolin-4-one HCl salt (138 mg, 0.49 mmol) was dissolved in DMF (2 mL) with 2-(4-fluoro-phenyl)-5-methanesulfonyl-2H-pyrazole-3-carboxylic acid (140 mg, 0.49 mmol) at RT. HATU (186 mg, 0.54 mmol) was added, followed by DIEA (0.21 mL, 1.2 mmol). The mixture was stirred for 20 h. Water (10 mL) was added and the mixture was extracted with EtOAc (20 mL). The organic layer was concentrated and the residue was dissolved in minimum amount of DMSO and purified by prep HPLC. 55 mg of title compound was obtained after lyophilization of pure fractions. LC-MS [M+H] 547.2.

Scheme 28: Preparation of Pyrazolopyridine HGM Inhibitors I-48 and I-51.
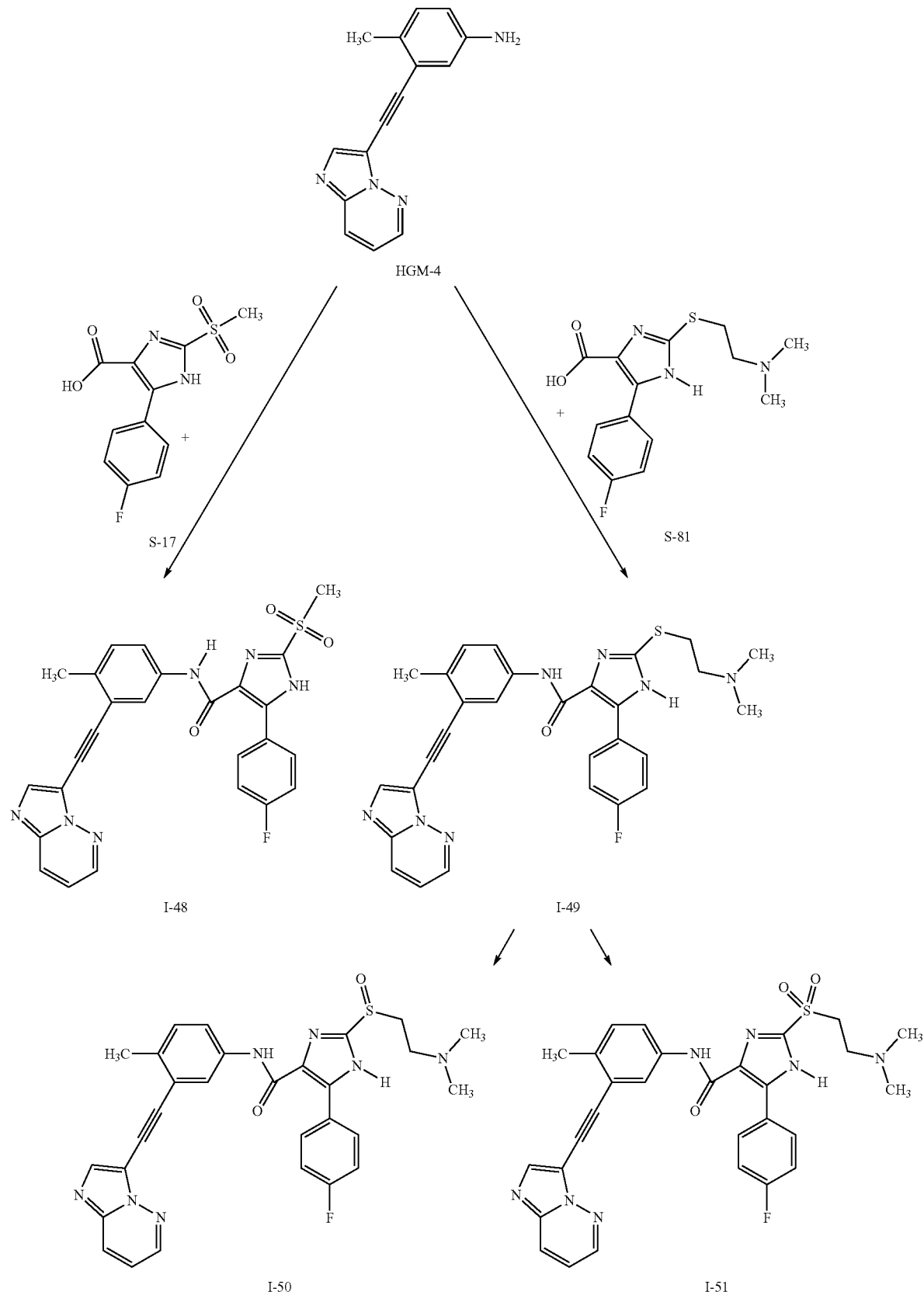

5-(4-fluorophenyl)-N-(3-(imidazo[1,2-b]pyridazin-3-ylethynyl)-4-methylphenyl)-2-(methylsulfonyl)-1H-imidazole-4-carboxamide, I-48

3-Imidazo[1,2-b]pyridazin-3-ylethynyl-4-methyl-phenylamine TFA salt (200 mg, 0.55 mmol) was dissolved in DMF (5 mL) with 5-(4-fluoro-phenyl)-2-methanesulfonyl-1H-imidazole-4-carboxylic acid (204 mg, 0.72 mmol) at RT. HATU (300 mg, 0.79 mmol) was added, followed by DIEA (0.6 mL, 3.44 mmol). The mixture was stirred for 20 h. Water (10 mL) was added and the mixture was extracted with EtOAc (30 mL). The organic layer was concentrated and the residue was dissolved in minimum amount of DMSO and purified by prep HPLC. 140 mg of title compound was obtained after lyophilization of pure fractions. LC-MS [M+H] 515.2.

2-((2-(dimethylamino)ethyl)thio)-5-(4-fluorophenyl)-N-(3-(imidazo[1,2-b]pyridazin-3-ylethynyl)-4-methylphenyl)-1H-imidazole-4-carboxamide, I-49

3-Imidazo[1,2-b]pyridazin-3-ylethynyl-4-methyl-phenylamine TFA salt (450 mg, 1.24 mmol) was dissolved in DMF (10 mL) with 2-(2-Dimethylamino-ethylthio)-5-(4-fluoro-phenyl)-1H-imidazole-4-carboxylic acid (575 mg, 1.86 mmol) at RT. HATU (700 mg, 1.86 mmol) was added, followed by DIEA (1.3 mL, 7.44 mmol). The mixture was stirred for 20 h. Water (80 mL) was added and the mixture was extracted with EtOAc (300 mL). The organic layer was concentrated and the residue was dissolved in minimum amount of DMSO and purified by prep HPLC. 540 mg of title compound was obtained after lyophilization of pure fractions. LC-MS [M+H] 540.3.

2-((2-(dimethylamino)ethylsulfinyl)-5-(4-fluorophenyl)-N-(3-(imidazo[1,2-b]pyridazin-3-ylethynyl)-4-methylphenyl)-1H-imidazole-4-carboxamide, I-50

2-((2-(dimethylamino)ethyl)thio)-5-(4-fluorophenyl)-N-(3-(imidazo[1,2-b]pyridazin-3-ylethynyl)-4-methylphenyl)-1H-imidazole-4-carboxamide (200 mg, 0.31 mmol, TFA salt) was dissolved in a mixed solvent of DCM/CH$_3$CN (1.5 mL each) at RT. Oxone (95 mg, 0.16 mmol) was added, followed by MeOH (10 drops). The mixture was heated to 60° C. for 40 mins. It was then cooled and concentrated. The residue was purified by prep HPLC to afford 121 mg of the title compound. LC-MS [M+H] 556.0.

2-((2-(dimethylamino)ethylsulfonyl)-5-(4-fluorophenyl)-N-(3-(imidazo[1,2-b]pyridazin-3-ylethynyl)-4-methylphenyl)-1H-imidazole-4-carboxamide, I-51

2-((2-(dimethylamino)ethyl)thio)-5-(4-fluorophenyl)-N-(3-(imidazo[1,2-b]pyridazin-3-ylethynyl)-4-methylphenyl)-1H-imidazole-4-carboxamide (200 mg, 0.31 mmol, TFA salt) was dissolved in a mixed solvent of DCM/CH$_3$CN (2.0 mL each) at RT. Oxone (380 mg, 0.62 mmol) was added, followed by a mixture of MeOH/water (2/1, 6 drops). The mixture was heated to 60° C. for 3 h. It was then cooled and concentrated. The residue was purified by prep HPLC to afford 128 mg of the title compound. LC-MS [M+H] 572.2.

New Binding Mode Hypothesis Points to Uniqueness:

The unique properties of this scaffold geometry of compounds of Formula (I) are believed to result from its novel mode of binding to the DFG-out conformation adopted by many kinases. In contrast to the previously proposed binding mode (Dietrich, 2010), FIG. 8A, we herein describe a significantly different binding mode hypothesis, FIG. 8-B.

Figure 8:
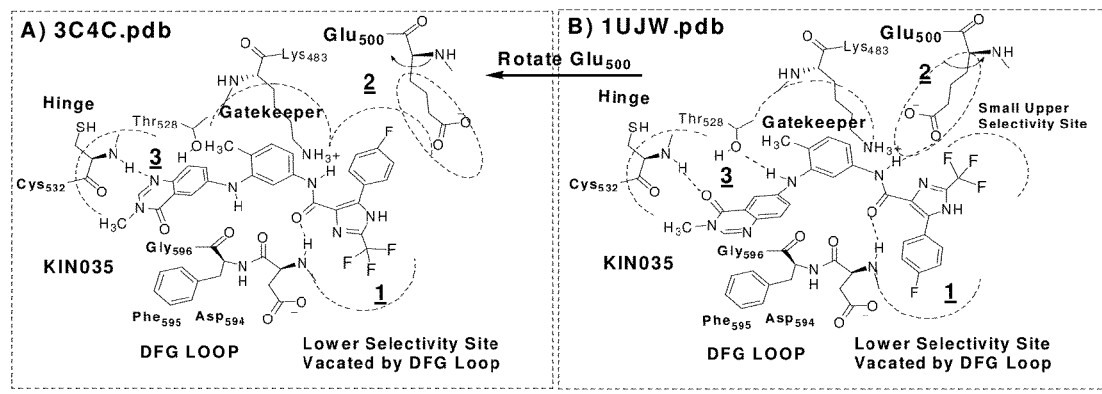
FIG. 8: Illustrates the differences between the previously-described B-Raf binding mode hypothesis for KIN-035. (Panel-A) and the new mode of binding (Panel-B) described herein.

FIG. 8 illustrates differences between the previously-described B-Raf binding mode hypothesis for KIN-035 (Dietrich et. el., 2010), panel-A, and the new binding mode described herein, panel-B which are 1) the lower selectivity site is occupied by the 4-F-phenyl substituent rather than the 2-trifluoromethyl substituent on the imidazole ring, 2) the Glu$^{500}$ side-chain is not required to move and the carboxamide linkage can bridge, in the typical fashion, between the Glu$^{500}$ side chain and the N$\underline{H}$ of Asp$^{593}$. 3) a different orientation of the quinazolinone, thus allows both hydrogen bonding to Cys$^{532}$ and Thr$^{528}$. As indicated in Chart-1, KIN-035, was a potent inhibitor of CSF1R but the other two inhibitors, which varied only slightly in structure, were not. A deeper look into the reported data (Dietrich, 2010) suggested that the additi9.

In particular, addition of a 4-fluoro-substituent on the imidazole phenyl ring, ie. KIN-032 vs KIN-035, improved potency 70-fold. Conversely, replacement of the 4-fluoro substituent on the imidazole phenyl ring with larger R$^3$ and R$^4$ groups dramatically decreases potency for CSF1R.

Figure 9:
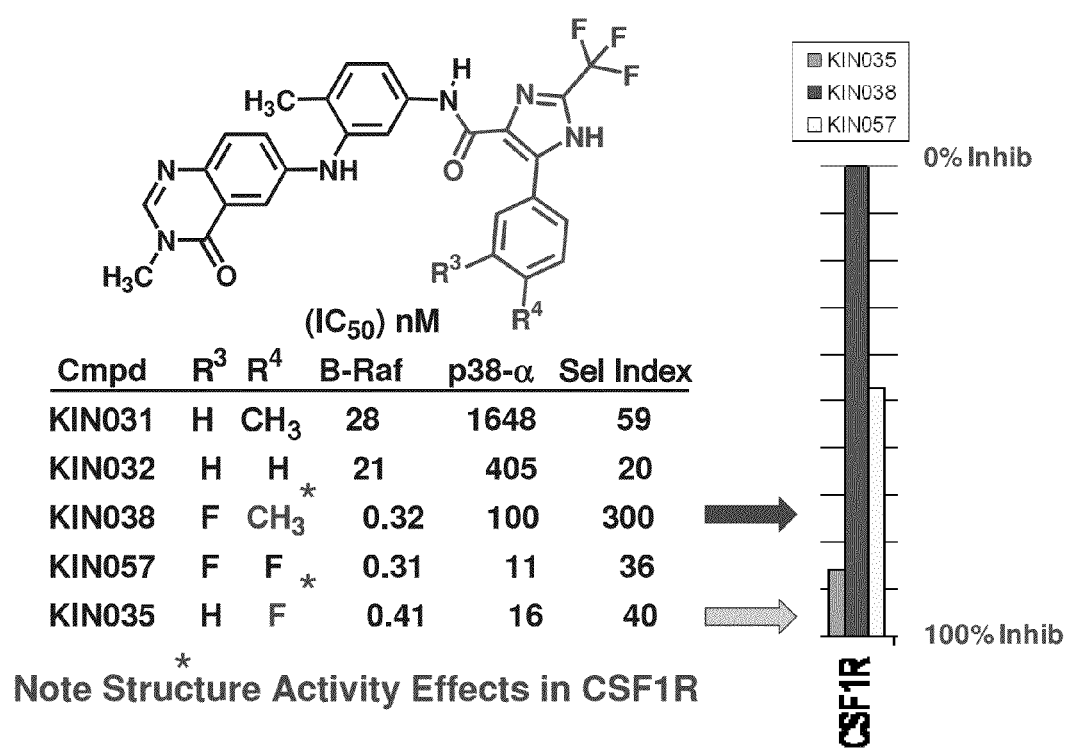
FIG. 9: Graphic of 4JVG.pdb (wild type B-Raf) and 1UWJ.pdb (B-Raf(V600E) mutant and the corresponding cartoon drawings that illustrate the different positioning of Lys$^{601}$ in these two structures.

FIG. 9 provides a summary of SAR data for imidazole quinazolinone inhibitors where there is a dramatic decrease in CSF1 inhibition when R$^3$ and R$^4$ substituents increase in size.

The recent release of the first co-crystal structure of CSF1R with a Type-II inhibitor (3LCO.pdb) provided an opportunity to see if the new binding mode hypothesis described herein accounted for these observations. Modeling of KIN-035 into this crystal structure did indeed indicate an unusually tight fit of the 4-fluoro substituent into an indentation at the bottom of the lower selectivity site, FIG. 9C.

Figure 10:
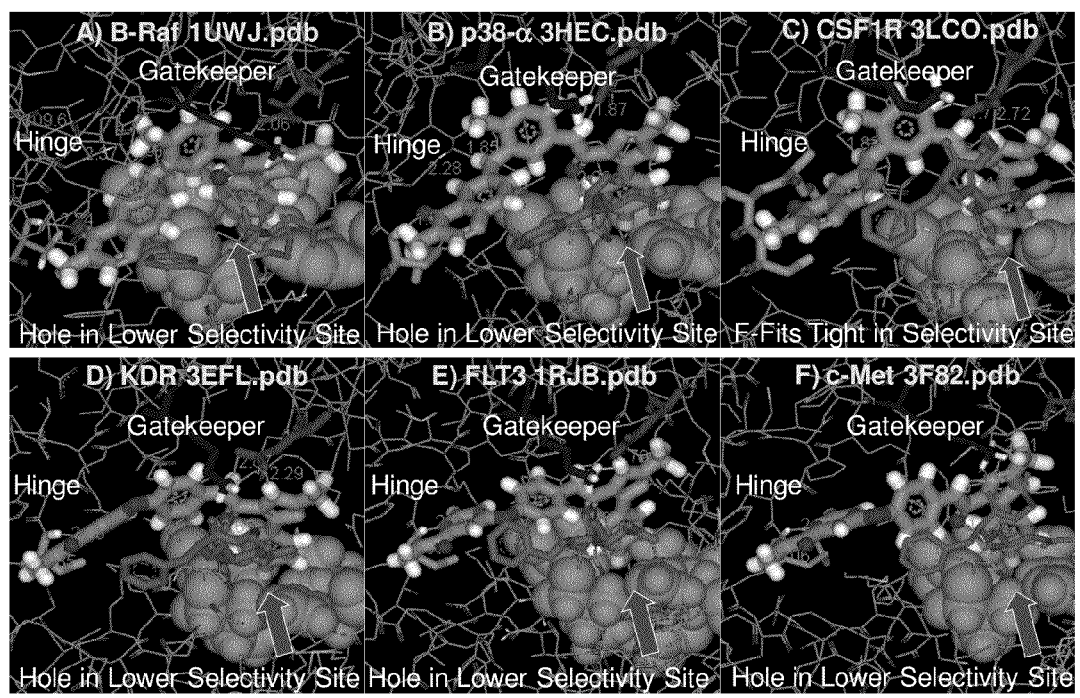
FIG. 10: A graph of real-time kinetic data for SFE-0013 with B-Raf(V600E) that illustrate kinetics consistent with extremely tight or irreversible inhibition.

FIG. 10 shows models of KIN-035 in A) B-Raf, B) p38-α, and C) CSF1R and a new inhibitor, I-6, modeled into D) KDR(VEGFR2), E) FLT3, and F) c-Met. DFG-loops are shown in mauve, conserved lysines and glutamate residues are shown in blue and red, and lower selectivity site residues shown in green CPK form. The arrow illustrates where 4-fluoro substituent fits in indentation.

A similar analysis of other co-crystal structures with Type-II inhibitors, FIG. 10, revealed that an indentation at the bottom of the lower selectivity site, which is typically constructed from 3 to 4 branched aliphatic amino acid side chains shown in green, is a highly conserved feature. It was also observed that variations in the size of this indentation existed between kinase structures and that the unique geometry of the ortho-aryl-imidazole carboxamide scaffold orients the 4-fluoro-aryl substituent ideally to interact with this indentation. For comparison, many c-Met inhibitors contain a 4-F-phenyl substituted phenyl ring that occupies the lower selectivity site, see co-crystal structure of BMS-777607 in 3F82.pdb, (Raeppel S., *Bioorg. Med. Chem. Letts.* (2009), 19:1323-1328; Schroeder G M., *J. Med. Chem.* (2009) 52(5): 1251-1254). However, detailed analysis reveals that the fluorine atom in these compounds are not positioned to interact with the indentation at the bottom of the lower selectivity site of c-Met, FIG. 11.

In spite of structural similarity of these inhibitors, c-Met inhibitors A and B do not penetrate into the indentation at bottom of lower selectivity site, see 3F82.pdb, where as inhibitor 12 can reach this indentation due to its different scaffold geometry (FIG. 11). Conversely, the carbonyl H-bond interactions with the gatekeeper region lysine side-chain exhibited by inhibitors A) and B) is absent in inhibitor I-6 unless mediated by a bridging water.

Implications from Biological Activities:
Broad Applicability of Ortho-Aryl-Imidazole Carboxamide Scaffold:

A total of 15 new inhibitors were designed, prepared, and evaluated against a panel of 29 selected kinases in order to explore the applicability, SAR trends, and the tunability of this scaffold that could be imposed but this unique geometry, Table 21 Inhibitors I-1 to I-12 all retained the 2-$CF_3$-5-(4-F-phenyl) imidazole-4-carboxamide scaffold previously described (Deitrich, 2010), but explored different Hinge-Gatekeeper Motifs (HGM). Predictions from the molecular modeling analysis of KDR, FLT-3, and c-Met, FIG. 10, suggested inhibitors I-6 (Sorafenib HGM) and I-12, should inhibit a broader set of kinases than previously described (Dietrich, 2010).

Inhibitor I-13 was designed to be a direct analog of previously reported KIN-35 (Dietrich et. al., 2010) which incorporates the significantly more polar 2-$CH_3SO_2$-5-(4-F-phenyl) imidazole-4-carboxamide scaffold. Due to the significant shift in polarity compared to the 2-CF3-substituent, a major objective of inhibitor I-13 was to test the proposed new binding mode hypothesis Inhibitor I-14 was designed to evaluate how attachment of this new polar scaffold to the pyridyl-pyrimidine containing HGM of Imatinib would compare to the known profile of activities for this drug Inhibitor I-15 was designed to evaluate how attachment of this polar scaffold would compare with that seen for Inhibitor I-6.

Because molecular modeling studies of the new binding mode, FIG. 8, suggests a tight fit of the ortho-4-fluorophenyl-5-membered heteraryl carboxamide scaffold into the lower selectivity site, it was suspected that the HGM variations could display unique SAR and unexpected selectivity profiles due to severely limited active site dynamics. Molecular modeling studies also suggested that replacement of the 2-trifluoromethyl group on the imidazole scaffold by the methylsulfonyl moiety would be a good test of the proposed new binding mode hypothesis. The results from this limited kinase profiling are summarized in Table-21.

TABLE 21

Comparison of % inhibition profiles of KIN035 at 1 μM and Inhibitors 1-13 at 5 μM.

| Inhibitor # | Structure | DCAMKL2 | JNK2 | MAPK1 | P38α | PI3Kα | AURORA | MEK1 | ABL1 | BTK | DDR2 | EGFR | EPH-A2 | FLT-1 | FLT-3 | FLT-4 | FMS (CSF1R) |
|---|---|---|---|---|---|---|---|---|---|---|---|---|---|---|---|---|---|
| KIN-035 | 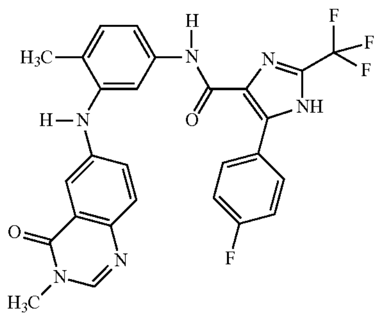 [SMILES: Cc1ccc(NC(=O)c2nc(C(F)(F)F)[nH]c2-c2ccc(F)cc2)cc1Nc1ccc2ncn(C)c(=O)c2c1] | X | | | | | | | | | | | | | | | |
| | | Ambit Biosciences % Inhibition at 1 μM inhibitor concentration without prolonged preincubation | | | | | | | | | | | | | | | |
| | | | | X | | | | | | | | X | X | | | | X |
| | | | | X | | | | | | | | | X | | | | X |
| | | | | X | | | | | | | | | | | | | X |
| | | | | X | | | | | | | | | | | | | |
| I-1 | 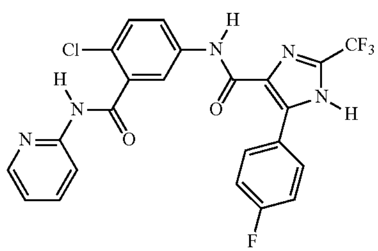 [SMILES: O=C(Nc1ccccn1)c1cc(NC(=O)c2nc(C(F)(F)F)[nH]c2-c2ccc(F)cc2)ccc1Cl] | Nanosyn Inc. % Inhibition at 10 μM inhibitor concentration without prolonged preincubation | | | | | | | | | | | | | | | |
| | | X | | | | | | | | | | | | | | | |

TABLE 21-continued

Comparison of % inhibition profiles of KIN035 at 1 μM and Inhibitors 1-13 at 5 μM.

| | | |
|---|---|---|
| I-2 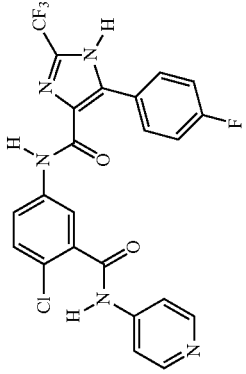 | Nanosyn Inc. % Inhibition at 10 μM inhibitor concentration without prolonged preincubation | X X |
| I-3 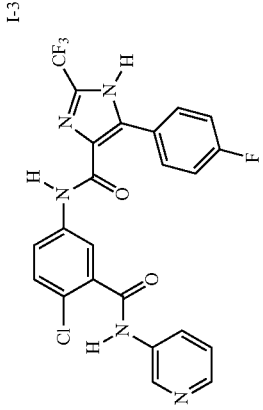 | Nanosyn Inc. % Inhibition at 10 μM inhibitor concentration without prolonged preincubation<br>X<br>X<br>X | X |
| I-4 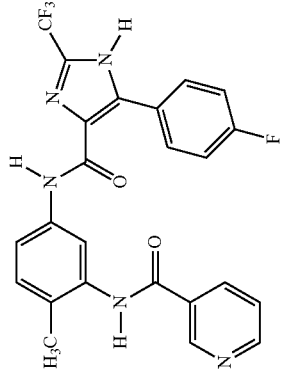 | Nanosyn Inc. % Inhibition at 10 μM inhibitor concentration without prolonged preincubation<br>X<br>X<br>X | |

TABLE 21-continued
Comparison of % inhibition profiles of KIN035 at 1 μM and Inhibitors 1-13 at 5 μM.
| | | Nanosyn Inc. % Inhibition at 10 μM inhibitor concentration without prolonged preincubation |
|---|---|---|
| I-5 | 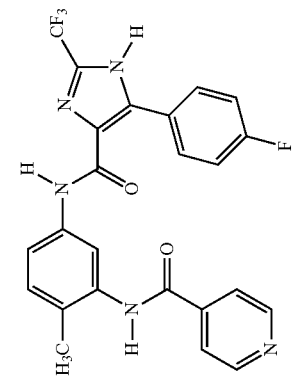 | X X X |
| I-6 | 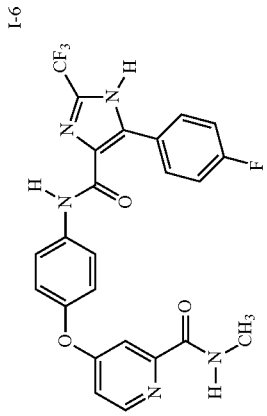 | X X X<br>X X X<br>X X X<br>X X |
| I-7 | 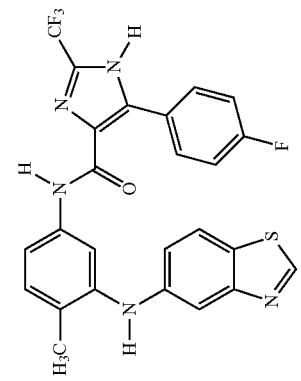 | X X<br>X X X<br>X X X<br>X X X |

TABLE 21-continued

Comparison of % inhibition profiles of KIN035 at 1 μM and Inhibitors 1-13 at 5 μM.

| | Nanosyn Inc. % Inhibition at 10 μM inhibitor concentration without prolonged preincubation | | | | | |
|---|---|---|---|---|---|---|
| I-8 | X | X | X | X | X | X |
| | X | | | | | |
| | X | | | | | |
| I-9 | Nanosyn Inc. % Inhibition at 10 μM inhibitor concentration without prolonged preincubation | | | | | |
| | X | X | X | | | |
| | X | | | | | |
| | X | | | | | |
| I-10 | Nanosyn Inc. % Inhibition at 10 μM inhibitor concentration without prolonged preincubation | | | | | |
| | X | | | | | |
| | X | | | | | |
| | X | | | | | |
| | X | | | | | |

TABLE 21-continued
Comparison of % inhibition profiles of KIN035 at 1 μM and Inhibitors 1-13 at 5 μM.
| | Nanosyn Inc. % Inhibition at 10 μM inhibitor concentration without prolonged preincubation |
|---|---|
| I-11 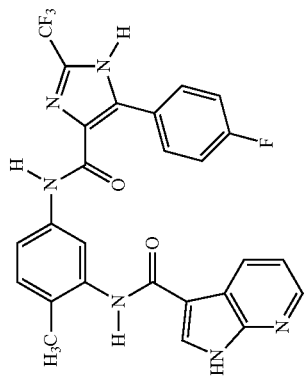 | X X<br>X<br>X<br>X |
| I-12 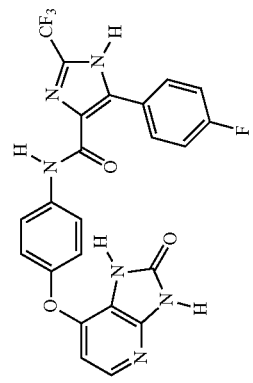 | X X<br>X X<br>X X<br>X X X<br>X X<br>X X X X<br>X X<br>X X X |
| I-13 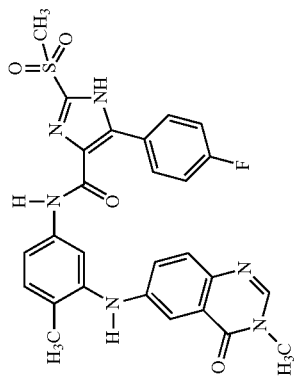 | X X<br>X X<br>X |

TABLE 21-continued

Comparison of % inhibition profiles of KIN035 at 1 μM and Inhibitors 1-13 at 5 μM.

| Inhibitor # | Structure | Kinases Profiled | | | | | | | | | | | | >25% Inhib. | >50% Inhib. | >75% Inhib. | >90% Inhib. |
|---|---|---|---|---|---|---|---|---|---|---|---|---|---|---|---|---|---|
| | | IGF1R | KDR | KIT | MET | PDGFRα | PDGFRβ | RET | RON | TIE2 | TYK2 | BRAF | BRAF-V599E | CRAF | | | | |
| KIN-035 | | Ambit Biosciences % Inhibition at 1 μM inhibitor concentration without prolonged preincubation | | | | | | | | | | | | | | | | |
| | | X | X | X | X | X | X | | | | | X | X | X | X | | | |
| | | | X | X | X | X | X | | | | | X | X | X | | X | X | X |
| | | | X | X | X | X | X | | | | | X | X | X | | | X | X |
| | | | X | | | | | | | | | X | X | X | | | | X |
| I-1 | | Nanosyn Inc. % Inhibition at 10 μM inhibitor concentration without prolonged preincubation | | | | | | | | | | | | | | | | |
| | | | X | | | | | | | | | | | | X | | | |
| | | | | | | | | | | | | | | | | X | X | X |
| | | | | | | | | | | | | | | | | X | X | X |
| | | | | | | | | | | | | | | | | | | X |
| I-2 | | Nanosyn Inc. % Inhibition at 10 μM inhibitor concentration without prolonged preincubation | | | | | | | | | | | | | | | | |
| | | | | | | | | | | | | | | | X | X | X | X |
| | | | | | | | | | | | | | | | | X | X | X |
| | | | | | | | | | | | | | | | | | | X |

TABLE 21-continued

Comparison of % inhibition profiles of KIN035 at 1 μM and Inhibitors 1-13 at 5 μM.

| | | Nanosyn Inc. % Inhibition at 10 μM inhibitor concentration without prolonged preincubation | | | | | | | | | | |
|---|---|---|---|---|---|---|---|---|---|---|---|---|
| I-3 | | X | X | X | X | | | X | X | X | X | X |
| | | X | X | X | | | | | X | X | X | |
| | | X | | | | | | | | | | |
| I-4 | | X | X | X | X | | | X | X | X | X | X |
| | | X | X | X | | | | | X | X | X | |
| | | X | | | | | | | | | | |
| I-5 | | X | X | X | X | | | X | X | X | X | X |
| | | X | X | X | | | | | X | X | X | |
| | | X | | | | | | | | | | |

TABLE 21-continued

Comparison of % inhibition profiles of KIN035 at 1 µM and Inhibitors 1-13 at 5 µM.

| | Nanosyn Inc. % Inhibition at 10 µM inhibitor concentration without prolonged preincubation | | | | | | | | |
|---|---|---|---|---|---|---|---|---|---|
| I-6 | X | X | X | X | X | X | X | | |
| | X | X | X | X | X | X | X | X | |
| | X | X | X | X | | X | X | X | X |
| | X | | | | | | | X | X |
| I-7 | | X | X | | | | X | X | X |
| | | X | X | | | | X | X | X |
| | | X | X | | | | | X | X |
| | | | | | | | | | X |
| I-8 | X | X | X | | | X | X | X | X |
| | | X | X | | | | X | X | X |
| | | X | | | | | | X | X |
| | | | | | | | | | X |

TABLE 21-continued

Comparison of % inhibition profiles of KIN035 at 1 μM and Inhibitors 1-13 at 5 μM.

| | Nanosyn Inc. % Inhibition at 10 μM inhibitor concentration without prolonged preincubation |
|---|---|
| I-9 | X X X X X X X X X X X X X X X |
| I-10 | X X X X X X X X X X X X X X X |
| I-11 | X X X X X X X X X X X X X X X X X |

TABLE 21-continued
Comparison of % inhibition profiles of KIN035 at 1 μM and Inhibitors 1-13 at 5 μM.
| | | Nanosyn Inc. % Inhibition at 10 μM inhibitor concentration without prolonged preincubation | | | | | | | | | | | | | | | | | |
|---|---|---|---|---|---|---|---|---|---|---|---|---|---|---|---|---|---|---|---|
| I-12 | 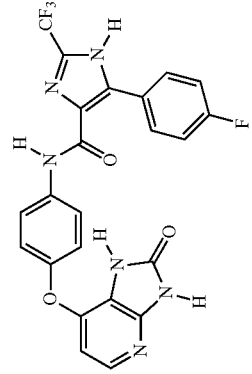 | X | X | X | X | X | X | X | X | X | X | X | X | | X | X | X | X | X | |
| | | X | X | | | | | | | X | | | | | | | | | | |
| | | Nanosyn Inc. % Inhibition at 10 μM inhibitor concentration without prolonged preincubation | | | | | | | | | | | | | | | | | |
| I-13 | | X | X | X | | | X | | | X | X | X | | X | X | X | X | X | | |
| | | X | X | | | | | | | X | | | | | | | | | | |

As anticipated, inhibitor I-6, which incorporated the HGM of Sorafenib, displayed a significantly expanded selectivity profile compared to KIN-035 (Deitrich et. al., 2010), which, with some exceptions, resembled that of Sorafenib itself. Compared to the activity profile reported for Sorafenib (DDR2, FLTs(1,3,4), FMS, KDR, KIT, PDGFR-α, PDGFR-β, and RET with some ABL1, B-Raf, C-Raf, and TIE2, but not c-MET or RON activities (Karaman, 2008; Kumar, 2009), inhibitor I-6 most potently inhibited DDR2, FLTs(1,3,4), FMS, KDR, KIT, PDGFR-α, PDGFR-β, and TIE2 with some ABL1, B-Raf, C-Raf, and RET with the addition of c-MET and RON activities. While these modeling studies predicted that KDR and FLT-3, as well as many other kinases, should be inhibited, it was not expected that c-Met inhibition be observed owning to the lack of an appropriate group to interact with Lys 1110, see 3F82.pdb (Schroeder G. M., *J. Med. Chem.* (2009) 52(5):1251-1254).

The related inhibitor I-12 also inhibited many of the same kinases as inhibitor I-6 with the best inhibition seen for DDR2, FLT-3, FMS, and TIE2. More modest activity for Aurora-A, FLT-1/4, KDR, KIT, PDGFRs was accompanied by better activity for B-Raf mutant and wild-type forms, Modest inhibition of MEK-1, BTK, c-Met, RET, and RON was also observed. These data support our new binding hypothesis and demonstrates that this ortho-(4-F-phenyl)-5-membered heteroaryl carboxamide scaffold has broad applicability. Moreover, the observed inhibition of MEK-1 with I-12 and TYK2 with I-6 represents additional activities against kinases for which no type-II inhibitors have been reported to date. These data suggests that this unique scaffold geometry may better stabilize the DFG-out conformation of kinases and could be useful to probe kinases for this conformational change. To further evaluate the scope of inhibition, I-6 was evaluated against a larger panel of 230 kinases, Table-22. These data better illustrate the potential applicability of the scaffold geometry to inhibitor design.

TABLE 22

Kinases inhibited at least 50% by I-6 when evaluated at 5 uM against a panel of 230 kinases. Kinases are listed in alphabeticalorder.

| ABL1 | EPH-B1 | KIT | P38-α | TIE2 |
|---|---|---|---|---|
| ABL-T315I | EPH-B2 | LCK | PAK1 | TRKA |
| ARG | EPH-B4 | LOK | PDGFR-α | TRKB |
| AXL | FLT1 | LYNA | PDGFR-β | TRKC |
| BLK | FLT3 | LYNB | PRKD3 | TYK2 |
| BRAF | FLT4 | MAP4K2 | PTK5 | TYRO3 |
| CRAF | FGR | MAP4K5 | RET | YES |
| DDR2 | FER | MEK2 | RON | |
| EPH-A1 | FMS | MER | SIK | |
| EPH-A2 | HCK | MET | SPHK1 | |
| EPH-A3 | HIPK3 | MKNK1 | SPHK2 | |
| EPH-A4 | HIPK4 | MNK2 | SRC | |
| EPH-A5 | JAK2 | MUSK | SRMS | |
| EPH-A8 | KDR | | | |

The reverse amide series of inhibitors I-1 to 15 was prepared because compounds with these HGMs had displayed good activity against FMS (Lyne P. D., *Bioorg. Med/Chem. Letts.* (2009), 19(3): 1026-1029). Surprisingly, of these five compounds only I-3 demonstrated significant inhibition of FMS while I-1 and I-2 showed no significant activity against for any of the kinases tested. This poor activity is thought to result from the rigid anchoring of the trisubstituted imidazole scaffold described in the new binding mode hypothesis described herein. In addition, several noteworthy combinations of activities awere observed. Noteworthy among these are:

1) Inhibitor 6: Inhibition, albeit modest, of TYK2.
2) Inhibitor 11: High selectivity for p38α.
3) Inhibitor 11: Observation of PI3K-α inhibition.
4) Inhibitor 12: Inhibition, albeit modest, of MEK1, a kinase for which no Type-II inhibitors have been reported.
5) Inhibitor 13: Observation of PI3K-α inhibition with the 2-methylsulfone analog of KIN-035.
6) Inhibitor 13: The unique combination of p38-α, B-Raf, C-Raf, and PI3K activities.

Figure 2:
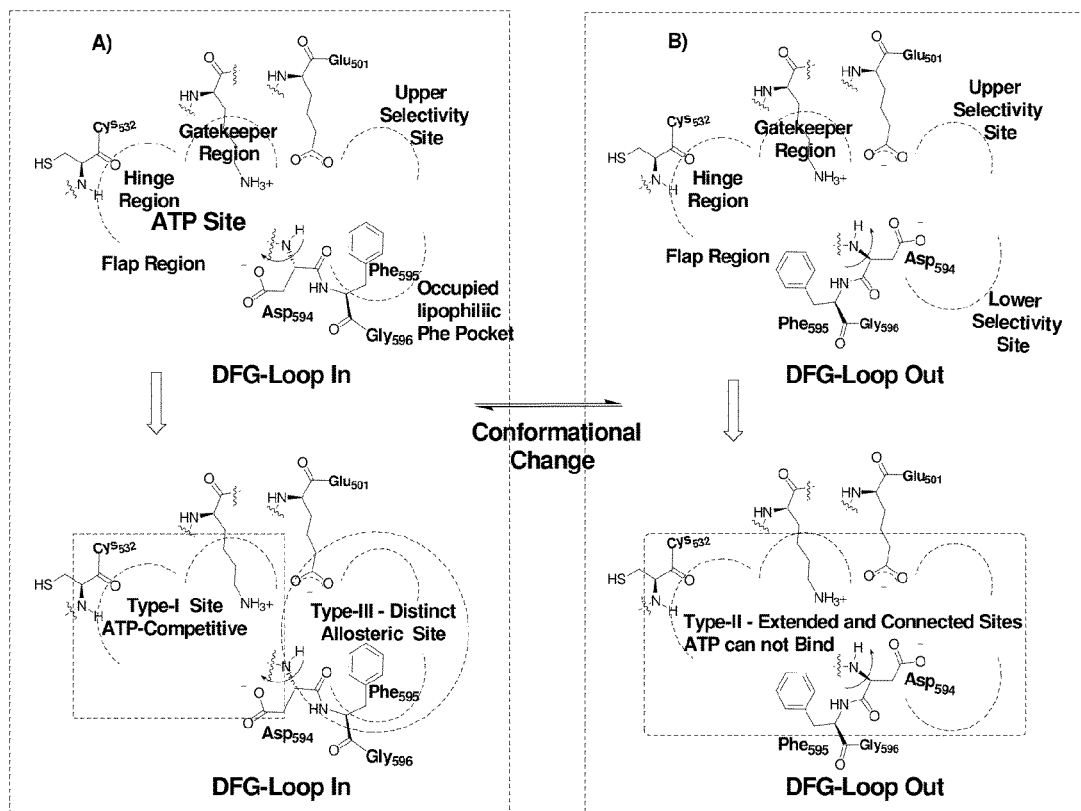
FIG. 2: Illustrates the conformational change for B-Raf (V600E) between A) DFG-In and B) DFG-Out populations and where Type-I, Type-II, and Type-III inhibitors interact.
Figure 4:
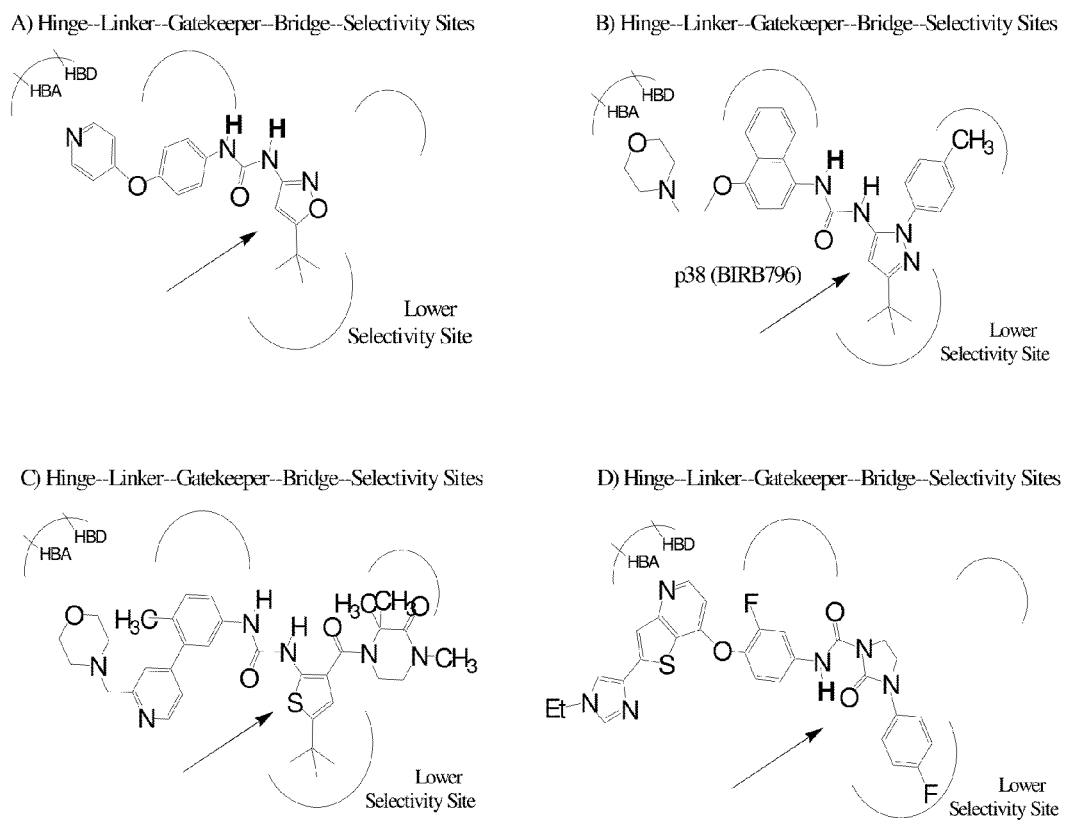
FIG. 4: Illustrates urea linked aryl-substituted 5-membered heteroaryl kinase inhibitors.
Figure 5:
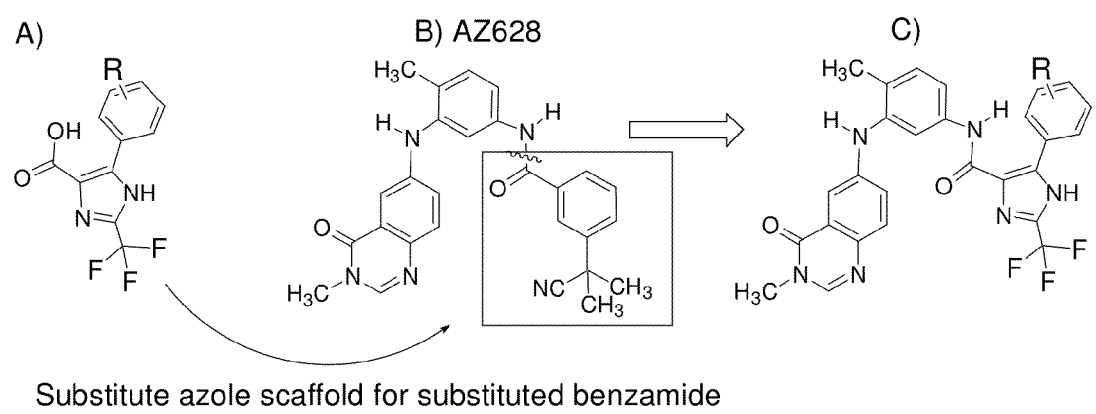
FIG. 5: Proposed retrosynthesis of disclosed imidazole containing B-Raf inhibitors.
Figure 6:
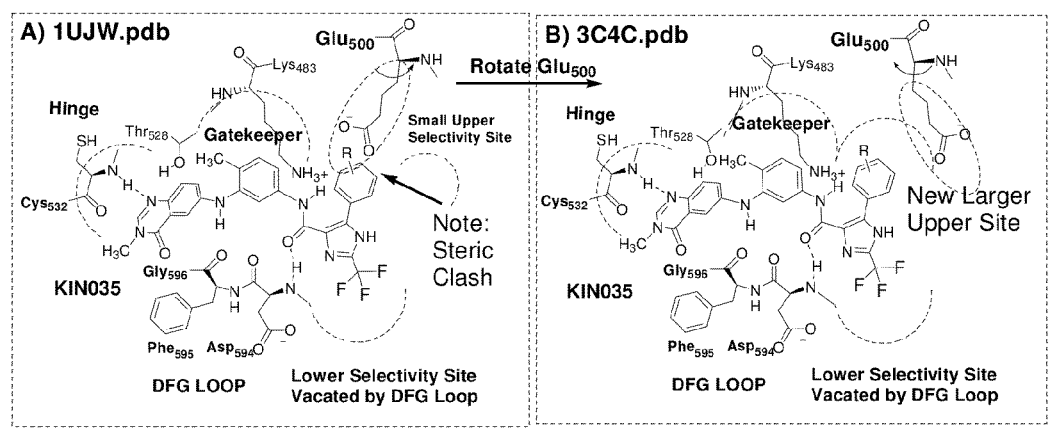
FIG. 6: Illustrates the published binding mode of quinazolinone containing inhibitors with B-Raf.
Figure 7:
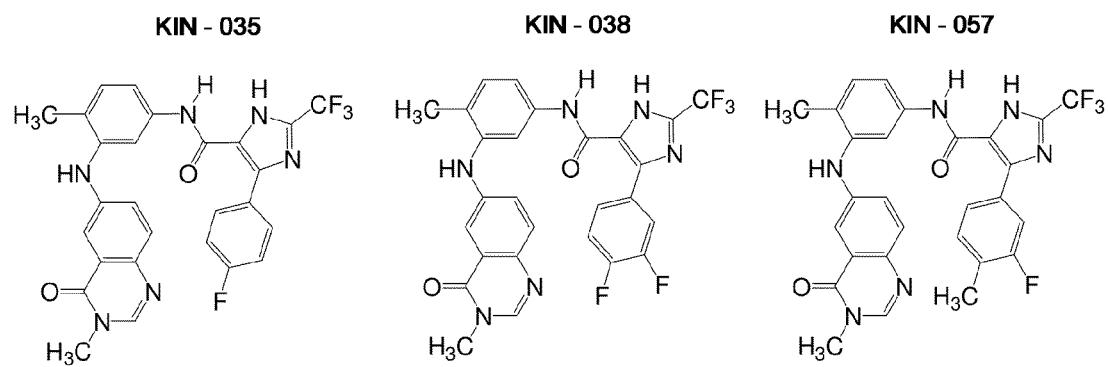
FIG. 7: Shows 2-CF3-imidazole quinazolinone inhibitors previously profiled (Deitrich, et al. 2010).

Considerations Specific to B-Raf(V600) Activity:

As previously stated, type-II kinase inhibitors bind to a minor conformation some kinases exhibit in which a DFG-loop vacates a lipophilic pocket immediately adjacent to the ATP binding site. This loop movement is illustrated in Figure-2.

In contrast to the previously reported binding mode utilizing 3C4C.pdb, FIG. 12A, our molecular modeling studies were based on the co-crystal structures (1UWJ.pdb) of B-Raf (V600E) with Sorafenib and the more recent co-crystal structure (4G9R.pdb) of B-Raf(V600E) with the quinazolinone inhibitor AZ628. These studies provided an alternative mode of binding depicted in FIG. 12B. Detailed examination of the potential interactions available to this scaffold that are unique to the V600E mutant structures compared to structures of the wild type kinase, suggested a strategy for the development of selective inhibitors of B-Raf(V600E). A key difference between wild type B-Raf and the valine to gluatate (V600E) mutant in various co-crystal structures is the positioning of the adjacent Lys601 residue. In the wild type kinase structure 4JGV.pdb, this residue is solvent exposed and on the surface of the protein, FIG. 13A, whereas in the two B-RafV600E structures (1UWJ.pdb and 4G9R.pdb) this residue is flipped in toward the inhibitor, FIG. 13B.

To test both our binding mode hypothesis and to see if these structural differences could be taken exploited to impart selectivity and potency improvements, I-13, in which the lipophilic 2-trifluoromethy substituent on imidazole ring of inhibitor KIN-035, was replaced by the polar 2-methylsulfonyl substitutent. In a side by side $IC_{50}$ comparison using a LanthaScreen assay, a 10 fold increase in potency ($IC_{50}$=6.6 nM for I-13 vs. 67 nM with KIN-0035) was observe. In addition, I-13 was approximately 80 fold more potent against the mutant verses wild type B-Raf ($IC_{50}$ ~500 nM). Interestingly, it was observed that the $IC_{50}$ value for I-13 appeared to decrease over a several hour preincubation period. To address this issue, real time kinetic experiments were performed. These kinetic data, FIG. 13, are consistent with either extremely tight binding or irreversible inhibition.

The kinetic data with I-13 are consistent with the reported long disassociation half life for AZ-628 with which it shares the quinazolinone Hinge Interacting motif (Hatzivassiliou G. et al, *Nature*(2010) 464: 431-435. It is feasible that, with a minor movement of the Lys[601] sidechain, FIG. 14A, the terminal amino group can be positioned for favorable electrostatic interactyions with the 2-methylsulfonyl group of I-13. Furthermore, it is mechanistically feasible for the side-chain amino group of this residue to attack the imidazole ring displacing the methylsulfonyl group in order to form a covalent adduct, FIG. 14B. The nucleophilic aromatic substitution of methyl sulfonyl groups adjacent to pyridine or pyrimidine nitrogens is well known and the reaction of 2-methylsulfonyl-benzimidazole with amines has been reported, albeit with strong base, at elevated temperatures (140 deg.C), and in the absence of a solvent. (Ping L. et al, *Tetrahedron Lett.* (2008) 49(12): 1910-1914). If such a displacement were to take place, it would likely require a specific geometry, prolonged contact time, and catalytic assistance from neighboring groups at the active site. FIG. 13 illustrates how such a convergence might be achieved with B-Raf (V600E). Regardless of mechanism, exploitation of these differences between wild type and V600E B-Raf could lead to inhibitors for the treatment of cancers with improved potency and selectivity.

Because c-Raf, PI3K-α and MEK1 are kinases reported to enable the escape of B-Raf mutant addicted cancers from B-Raf(V600E) inhibition, discovery of a B-Raf inhibitor with these additional activities represents a very attractive and unique opportunity for anti-cancer therapy. Taken together, these data illustrate that, even within a limited number of analogs, unexpected and unique activities can be obtained using this novel scaffold geometry.

To further test the breadth of applicability and ability to achieve selectivity with inhibitors that share this scaffold geometry, I-11 and I-12 were evaluated against a larger panel of 220 high interest kinases, Table-23.

TABLE 23

Summary of profiling data for I-11, 1-12, 1-14 and 1-15 assayed in duplicate against a panel of 220 kinases. Kinases listed in table were inhibited better than 50% at the profiling concentration of 5 μM.

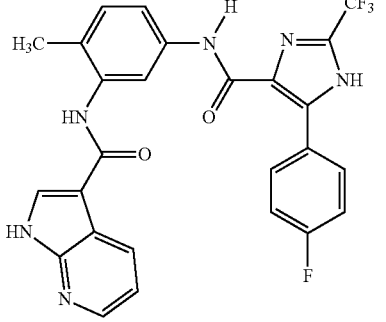

Inhibitor 11

| Cmpd Conc. (μM) | Kinase Target |
|---|---|
| 5 | KIT-V560G |
| 5 | P38-α |

Inhibitor 12

| Cmpd Conc. (μM) | Kinase Target |
|---|---|
| 5 | ABL-M361T |
| 5 | ABL-Q252H |
| 5 | ABL-H396P |
| 5 | ARG |
| 5 | AURORA-A |
| 5 | AURORA-C |
| 5 | BRK |
| 5 | BLK |
| 5 | CDK2 |
| 5 | DDR2 |
| 5 | EPH-A4 |
| 5 | EPH-B2 |
| 5 | EPH-B4 |
| 5 | FER |
| 5 | FGR |
| 5 | FLT-1 |
| 5 | FLT-3 |

TABLE 23-continued

Summary of profiling data for I-11, 1-12, 1-14 and 1-15 assayed in duplicate against a panel of 220 kinases. Kinases listed in table were inhibited better than 50% at the profiling concentration of 5 μM.

| 5 | FMS |
|---|---|
| 5 | HIPK4 |
| 5 | KDR |
| 5 | KIT |
| 5 | KIT-V560G |
| 5 | LCK |
| 5 | LOK |
| 5 | LYNA |
| 5 | LYNB |
| 5 | MAP4K2 |
| 5 | MER |
| 5 | MET |
| 5 | MKNK1 |
| 5 | MNK2 |
| 5 | MUSK |
| 5 | P38-α |
| 5 | PDGFR-α |
| 5 | PDGFR-α-V561D |
| 5 | PTK5 |
| 5 | RON |
| 5 | SRMS |
| 5 | SRC |
| 5 | TIE2 |
| 5 | TNK1 |
| 5 | TRKA |
| 5 | TRKB |
| 5 | TRKC |
| 5 | TRYO3 |

Inhibitor 14

| Cmpd Conc. (μM) | Kinase Target |
|---|---|
| 5 | ABL-Q252H |
| 5 | ABL-M351T |
| 5 | ARG |
| 5 | BRAF-V599E |
| 5 | CRAF |
| 5 | DDR2 |
| 5 | FMS |
| 5 | KIT |
| 5 | KIT-V560G |
| 5 | PI3-KINASE-α |
| 5 | TNK1 |
| 5 | PI3-KINASE-δ |
| 5 | P38-α |
| 5 | PDGFR-α-V561D |
| 5 | PDGFR-α |
| 5 | PDGFR-β |

TABLE 23-continued

Summary of profiling data for I-11, I-12, I-14 and I-15 assayed in duplicate against a panel of 220 kinases. Kinases listed in table were inhibited better than 50% at the profiling concentration of 5 μM.

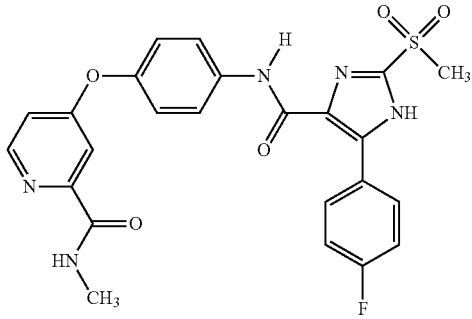 [SMILES: CNC(=O)c1cc(Oc2ccc(NC(=O)c3nc(S(C)(=O)=O)[nH]c3-c3ccc(F)cc3)cc2)ccn1]

Inhibitor 15

| Cmpd Conc. (μM) | Kinase Target |
|---|---|
| 5 | ABL-Q252H |
| 5 | ABL-M351T |
| 5 | ABL-H386P |
| 5 | BLK |
| 5 | BRK |
| 5 | DDR2 |
| 5 | FMS |
| 5 | EPH-A4 |
| 5 | EPH-B2 |
| 5 | MUSK |
| 5 | HIPK4 |
| 5 | LOK |
| 5 | MER |
| 5 | MNK2 |
| 5 | MUSK |
| 5 | SRMS |
| 5 | TIE2 |
| 5 | TRKA |
| 5 | TRKB |
| 5 | TRKC |
| 5 | TRYO3 |

While I-11 remained extremely selective for p38-α, I-12 displayed greater that 50% inhibition for 45 of the panel kinases and 72 kinases at >25% inhibition. These data illustrate that, by modifying the HGM, both a wide range of kinases can be inhibited and high degrees of selectivity can be obtained Inhibitors, I-14 and I-15 were also tested against this panel, Table-22. These two inhibitors illustrate that attractive profiles can be obtained using a wider range of HGMs.

Because the inhibition profile of I-14 included members of both the MAPK and PI3K pathways, $IC_{50}$ determinations were performed on the most significantly inhibited kinases with the inclusion of all the PI3K isoforms. These data, Table-24 which were intended to explore both potency and mechanism of inhibition, revealed the most significant time dependence with all the PI3K isoforms. The observation of potency and isoform selectivity with time-dependency for PI3K-γ appears to be unprecedented in the literature. In addition, these activities combined with inhibition of p38-α, Raf-1, DDR and CSF-1R, would be complimentary and potentially synergistic activities for both the treatment of certain inflammation based conditions and cancers.

TABLE 24

Determination of time dependence and IC50 values for I-14 for selected kinases. Due to the low ATP concentration used (10 uM), the effects of preincubation may be attenuated for some kinases.

| Inhibitor I-14 | Compound IC50* (nM): | Compound IC50* (nM): | Time Dependence |
|---|---|---|---|
| Preincubation | 15 Min | 60 Min | |
| Lipid Kinase | 1-14 | 1-14 | Observed? |
| PI3K-γ | 126.60 | 57.82 | Yes |
| PI3K-α | 898.90 | 386.60 | Yes |
| PI3K-δ | 3177.00 | 1121.00 | Yes |
| PI3K-β | 12620.00 | 2908.00 | Yes |
| Protein Kinases | | | |
| RAF1 | 96.55 | 81.35 | Yes |
| P38a/MAPK14 | 149.70 | 150.10 | No |
| BRAF (V599E) | 194.40 | 194.00 | No |
| DDR2 | 222.30 | 221.10 | No |
| FMS | 219.90 | 239.60 | No |
| TNK1 | 210.00 | 241.00 | No |
| BRAF | 388.30 | 323.10 | Yes |
| PDGFR-α | 177.70 | 342.00 | No |
| c-Kit | 772.10 | 986.90 | No |
| P38b/MAPK11 | 1018.00 | 1084.00 | No |
| ROS/ROS1 | 1248.00 | 1284.00 | No |
| ARAF | 1394.00 | 1296.00 | Yes |
| PDGFR-β | 2014.00 | 2512.00 | No |
| Aurora A | 2738.00 | 2633.00 | No |

Based on the interesting activity data for I-14 I and I-15, a small library of 20 analogs was prepared, ie. 10 new scaffolds coupled to the Imatinib and Sorafenib HGMs (HGM-1 and HGM-17), to explore the effects of scaffold alterations on activity profiles, Table 25. A summary of these activity profiles compared to those of I-14 and I-15 is presented in Table 26 and Table 27.

TABLE 25

Construction of the Expanded Library of 20 New Inhibitors based on inhibitors 1-14 and 1-15.

| Scaffold # | Scaffold Structure | HGM-1 Inhibitor Structure | | HGM-35 Inhibitor Structure | |
|---|---|---|---|---|---|
| S-15 | (4-fluorophenyl, 2-methylthio imidazole-5-carboxylic acid) | I-16 | I-26 | | |
| S-16 | (4-fluorophenyl, 2-methylsulfinyl imidazole-5-carboxylic acid) | I-17 | I-27 | | |
| S-17 | (4-fluorophenyl, 2-methylsulfonyl imidazole-5-carboxylic acid) | I-14 | I-15 | | |

TABLE 25-continued

Construction of the Expanded Library of 20 New Inhibitors based on inhibitors 1-14 and 1-15.

| Scaffold # | Scaffold Structure | | HGM-1 Inhibitor Structure | | HGM-35 Inhibitor Structure |
|---|---|---|---|---|---|
| S-25 | [4-fluorophenyl-thiazole-carboxylic acid with H₃C-S-] | I-18 | [HGM-1 scaffold with methylthio thiazole] | I-28 | [HGM-35 scaffold with methylthio thiazole] |
| S-26 | [4-fluorophenyl-thiazole-carboxylic acid with H₃C-S(O)-] | I-19 | [HGM-1 scaffold with methylsulfinyl thiazole] | I-29 | [HGM-35 scaffold with methylsulfinyl thiazole] |
| S-27 | [4-fluorophenyl-thiazole-carboxylic acid with H₃C-S(O)₂-] | I-20 | [HGM-1 scaffold with methylsulfonyl thiazole] | I-30 | [HGM-35 scaffold with methylsulfonyl thiazole] |

TABLE 25-continued

Construction of the Expanded Library of 20 New Inhibitors based on inhibitors 1-14 and 1-15.

| Scaffold # | Scaffold Structure | HGM-1 Inhibitor Structure | HGM-35 Inhibitor Structure |
|---|---|---|---|
| S-29 | (structure) | I-21 | I-31 |
| S-50 | (structure) | I-22 | I-32 |
| S-51 | (structure) | I-23 | I-33 |

TABLE 25-continued

Construction of the Expanded Library of 20 New Inhibitors based on inhibitors 1-14 and 1-15.

| Scaffold # | Scaffold Structure | | HGM-1 Inhibitor Structure | HGM-35 Inhibitor Structure |
|---|---|---|---|---|
| S-52 | (structure) | I-24 (HGM-1 amine) / I-34 (HGM-35 amine) | I-24 | I-34 |
| S-60 | (structure) | | I-25 | I-35 |

TABLE 26

Kinase Inhibition Profiles of the 20 new compounds defined in Table 25 against a panel of 230 kinaes when assayed at 5 uM. The inhibiton profiles for inhibitor I-15 is included for comparison.

| Scafffold # | 15 | 16 | 17 | 25 | 26 | 27 | 29 | 50 | 51 | 52 | 60 |
|---|---|---|---|---|---|---|---|---|---|---|---|
| HGM# | 1 | 1 | 1 | 1 | 1 | 1 | 1 | 1 | 1 | 1 | 1 |
| Cpd # | I-16 | I-17 | I-14 | I-18 | I-19 | I-20 | I-21 | I-22 | I-23 | I-24 | I-25 |
|  | ABL1 | ARG | ARG | ARG | ABL1 | ABL1 | ARG | ABL1 | ABL1 | ABL1 | ABL1 |
|  | ARG | AURORA-A | CRAF | CRAF | ARG | ARG | CRAF | ARG | ARG | ARG | ARG |
|  | CRAF | AURORA-B | DDR2 | DDR2 | ARK5 | CLK4 | DDR2 | CRAF | ARK5 | ARK5 | ARK5 |
|  | DDR2 | AXL | FMS | EPH-A5 | AXL | CRAF | FMS | DDR2 | AXL | BTK | CRAF |
|  | EPH-A2 | CLK4 | KIT | EPH-A8 | CDK2-Cy | DDR2 | KIT | EPH-A2 | CDK2-Cy | CRAF | DDR2 |
|  | EPH-A4 | CRAF | P38-α | EPH-B2 | CK2 | EPH-A2 | P38-α | EPH-A3 | CK2 | DDR2 | EPH-A2 |
|  | EPH-A5 | DDR2 | PDGFR-α | KIT | CLK4 | EPH-A4 | P38-β | EPH-A4 | CLK4 | EPH-A2 | EPH-A4 |
|  | EPH-A8 | EPH-A2 | PDGFR-β | PDGFR-α | CRAF | EPH-A5 | PDGFR-α | EPH-A5 | CRAF | EPH-A5 | EPH-A5 |
|  | EPH-B1 | EPH-A4 | PI3K-α | PDGFR-β | DDR2 | EPH-A8 | ROS | EPH-A8 | DDR2 | EPH-A8 | EPH-A8 |
|  | EPH-B2 | EPH-A5 | TNK1 |  | EPH-A1 | EPH-B1 | TNK1 | EPH-B1 | EPH-A1 | EPH-B1 | EPH-B1 |
|  | EPH-B4 | EPH-A8 |  |  | EPH-A2 | EPH-B2 |  | EPH-B2 | EPH-A2 | EPH-B2 | EPH-B2 |
|  | FMS | EPH-B1 |  |  | EPH-A3 | FMS |  | EPH-B3 | EPH-A3 | EPH-B4 | EPH-B4 |
|  | HIPK4 | EPH-B2 |  |  | EPH-A4 | KIT |  | EPH-B4 | EPH-A4 | ITK | FMS |
|  | KIT | EPH-B3 |  |  | EPH-A5 | LYNA |  | FMS | EPH-A5 | JNK1 | KIT |
|  | KIT-D816V | FMS |  |  | EPH-A8 | LYNB |  | KIT | EPH-A8 | JNK2 | LYNA |
|  | LCK | KIT |  |  | EPH-B1 | PDGFR-α |  | P38-α | EPH-B1 | JNK3 | LYNB |
|  | LYNA | LYNA |  |  | EPH-B2 | PDGFR-β |  | P38-β | EPH-B2 | KIT | P38-α |
|  | MNK2 | LYNB |  |  | EPH-B3 | ROS |  | PDGFR-α | EPH-B3 | LYNA | P38-β |
|  | P38-α | P38-α |  |  | EPH-B4 | TNK1 |  | PDGFR-α | EPH-B4 | LYNB | PDGFR-α |
|  | P38-β | P38-β |  |  | FER |  |  |  | FER | P38-α | PDGFR-β |
|  | PDGFR-α | PDGFR-α |  |  | FES |  |  |  | FES | P38-β | ROS |
|  | PDGFR-β | PDGFR-β |  |  | FMS |  |  |  | FMS | PDGFR-α | TNIK |
|  | PI3K-α | PI3K-α |  |  | HCK |  |  |  | HCK | PDGFR-α | TNK1 |
|  | TNIK | PLK1 |  |  | HIPK4 |  |  |  | HIPK4 | PI3K-α |  |
|  | TNK1 | ROS |  |  | JNK1 |  |  |  | JNK1 | TEC |  |
|  |  | TNIK |  |  | JNK2 |  |  |  | JNK2 | TNK1 |  |
|  |  | TNK1 |  |  | JNK3 |  |  |  | JNK3 | TXK |  |
|  |  |  |  |  | KIT |  |  |  | KIT |  |  |
|  |  |  |  |  | LCK |  |  |  | LCK |  |  |
|  |  |  |  |  | LTK |  |  |  | LTK |  |  |
|  |  |  |  |  | LYNA |  |  |  | LYNA |  |  |
|  |  |  |  |  | LYNB |  |  |  | LYNB |  |  |
|  |  |  |  |  | MUSK |  |  |  | MUSK |  |  |
|  |  |  |  |  | P38-α |  |  |  | P38-α |  |  |
|  |  |  |  |  | P38-β |  |  |  | P38-β |  |  |
|  |  |  |  |  | PDGFR-α |  |  |  | PDGFR-α |  |  |
|  |  |  |  |  | PDGFR-β |  |  |  | PDGFR-β |  |  |
|  |  |  |  |  | PYK2 |  |  |  | PYK2 |  |  |
|  |  |  |  |  | ROS |  |  |  | ROS |  |  |
|  |  |  |  |  | TAOK3 |  |  |  | TAOK3 |  |  |
|  |  |  |  |  | TIE2 |  |  |  | TIE2 |  |  |
|  |  |  |  |  | TNIK |  |  |  | TNIK |  |  |
|  |  |  |  |  | TNK1 |  |  |  | TNK1 |  |  |

TABLE 27

Kinase Inhibition Profiles of the 20 new compounds defined in Table 25, continued. Inhibitors were profiled against a panel of 230 kinaes when assayed at 5 uM.

| Scafffold # | 15 | 16 | 17 | 25 | 26 | 27 | 29 | 50 | 51 | 52 | 60 |
|---|---|---|---|---|---|---|---|---|---|---|---|
| HGM# | 35 | 35 | 35 | 35 | 35 | 35 | 35 | 35 | 35 | 35 | 35 |
| Cpd # | I-26 | I-27 | I-15 | I-28 | I-29 | I-30 | I-31 | I-32 | I-33 | I-34 | I-35 |
|  | AXL | AXL | BLK | ABL1 | AXL | AXL | BRK | AXL | AXL | AXL | CRAF |
|  | BRK | BLK | BRK | ARG | BRK | BLK | CRAF | BLK | BLK | DDR2 | DDR2 |
|  | CRAF | BRK | DDR2 | AXL | CRAF | BRK | DDR2 | BRK | DDR2 | EPH-A4 | EPH-A1 |
|  | DDR2 | CRAF | EPH-A4 | BLK | DDR2 | DDR2 | HIPK4 | DDR2 | EPH-A2 | EPH-A5 | EPH-A4 |
|  | EPH-A4 | DDR2 | EPH-B2 | BRK | EPH-A1 | EPH-A4 | MER | EPH-A2 | EPH-A3 | EPH-B4 | EPH-A5 |
|  | EPH-A5 | EPH-A3 | FMS | CRAF | EPH-A2 | EPH-A5 | MKNK1 | EPH-A3 | EPH-A4 | FLT3 | EPH-A8 |
|  | EPH-A8 | EPH-A4 | HIPK4 | DDR2 | EPH-A4 | EPH-A8 | MNK2 | EPH-A4 | EPH-A5 | HIPK4 | EPH-B2 |
|  | EPH-B1 | EPH-A5 | MER | EPH-A1 | EPH-A5 | EPH-B2 | MUSK | EPH-A5 | EPH-A8 | KDR | FGFR2 |
|  | EPH-B2 | EPH-A8 | MNK2 | EPH-A2 | EPH-A8 | EPH-B4 | TIE2 | EPH-A8 | EPH-B1 | KIT | FLT3 |
|  | EPH-B4 | EPH-B1 | MUSK | EPH-A3 | EPH-B2 | FLT3 | TRKA | EPH-B2 | EPH-B2 | LCK | FMS |
|  | FER | EPH-B2 | SRMS | EPH-A4 | EPH-B4 | FMS | TRKC | EPH-B4 | EPH-B4 | LOK | HIPK4 |
|  | FGR | EPH-B4 | TIE2 | EPH-A5 | EPH-B4 | HCK | TYRO3 | FLT3 | FLT3 | MNK2 | KDR |

TABLE 27-continued

Kinase Inhibition Profiles of the 20 new compounds defined in Table 25, continued.
Inhibitors were profiled against a panel of 230 kinaes when assayed at 5 uM.

| Scafffold # | 15 | 16 | 17 | 25 | 26 | 27 | 29 | 50 | 51 | 52 | 60 |
|---|---|---|---|---|---|---|---|---|---|---|---|
| HGM# | 35 | 35 | 35 | 35 | 35 | 35 | 35 | 35 | 35 | 35 | 35 |
| Cpd # | I-26 | I-27 | I-15 | I-28 | I-29 | I-30 | I-31 | I-32 | I-33 | I-34 | I-35 |
| | FLT3 | FER | TRKA | EPH-A8 | FGFR1 | HIPK3 | | FMS | HIPK4 | MUSK | KIT |
| | FMS | FLT3 | TRKB | EPH-B2 | FGFR2 | HIPK4 | | HIPK3 | JAK2 | P38-α | P38-α |
| | HIPK4 | FMS | TRKC | EPH-B4 | FGFR4 | JAK2 | | HIPK4 | KDR | P38-β | P38-β |
| | JAK2 | HIPK4 | TYRO3 | FGR | FLT1 | KDR | | KDR | KIT | RET | RET |
| | KDR | JAK2 | | FLT1 | FLT3 | LCK | | KIT | LCK | SRC | TAOK3 |
| | KIT | KDR | | FLT3 | FLT4 | LOK | | LCK | LOK | TAOK2 | TIE2 |
| | LCK | KIT | | FLT4 | FMS | LYNA | | LOK | LYNA | TAOK3 | |
| | LOK | LCK | | FMS | HIPK4 | LYNB | | MAP4K5 | LYNB | TIE2 | |
| | LYNA | LOK | | HCK | JAK2 | MAP4K5 | | MER | MAP4K5 | TRKA | |
| | MAP4K5 | MAP4K5 | | HIPK3 | KDR | MER | | MNK2 | MER | TYRO3 | |
| | MEK2 | MER | | HIPK4 | KIT | MET | | MUSK | MNK2 | YES | |
| | MER | MKNK1 | | JAK2 | LCK | MNK2 | | P38-α | MUSK | | |
| | MKNK1 | MNK2 | | KDR | LYNA | MUSK | | P38-β | P38-α | | |
| | MNK2 | MUSK | | KIT | LYNB | PDGFR-α | | PDGFR-α | P38-β | | |
| | MUSK | P38-α | | LCK | MAP4K5 | PI3K-α | | SRC | PI3K-α | | |
| | PDGFR-α | PDGFR-α | | LOK | MER | RON | | TAOK3 | RET | | |
| | RON | TIE2 | | LYNA | MKNK1 | TIE2 | | TIE2 | TAOK2 | | |
| | TIE2 | TRKA | | LYNB | MNK2 | TRKB | | TRKA | TAOK3 | | |
| | TRKA | TRKB | | MAP4K5 | MUSK | TRKC | | TRKB | TIE2 | | |
| | TRKB | TRKC | | MER | P38-α | TYRO3 | | TRKC | TRKA | | |
| | TRKC | TYRO3 | | MET | PDGFR-α | YES | | TYRO3 | TRKB | | |
| | TYRO3 | | | MKNK1 | PDGFR-β | | | | TRKC | | |
| | | | | MNK2 | RET | | | | TYRO3 | | |
| | | | | MUSK | RON | | | | | | |
| | | | | P38-α | TIE2 | | | | | | |
| | | | | PDGFR-α | TRKA | | | | | | |
| | | | | PDGFR-β | TRKB | | | | | | |
| | | | | PTK5 | TRKC | | | | | | |
| | | | | RON | TYRO3 | | | | | | |
| | | | | SRC | | | | | | | |
| | | | | TIE2 | | | | | | | |
| | | | | TRKA | | | | | | | |
| | | | | TRKB | | | | | | | |
| | | | | TRKC | | | | | | | |
| | | | | TAOK3 | | | | | | | |
| | | | | YES | | | | | | | |

TABLE 28

Kinase Inhibition Profiles of Inhibitors I-36, I-37, and I-38 against a panel of 250 kinaes when assayed at 5 uM.

| Scaffold # | | |
|---|---|---|
| S-17 | N-Methyl S-17 | N-Methyl S-17 |
| HGM # | | |
| HGM-11 | HGM-35 | HGM-1 |
| Cpd ID# | | |
| I-36 | I-37 | I-38 |
| ABL | ARG | ARG |
| ARG | AXL | CRAF |
| BRAF | BLK | DDR2 |
| CLK4 | BRAF | FMS |
| CRAF | CRAF | KIT |
| CSK | DDR2 | MRCK-α |
| DDR2 | EPH-A3 | PDGFR-α |
| EPH-A2 | EPH-A4 | PDGFR-β |
| EPH-A3 | EPH-A5 | ROS |
| EPH-A4 | EPH-A8 | TNK1 |
| EPH-A5 | EPH-B2 | |
| EPH-A8 | EPH-B4 | |
| EPH-B2 | FER | |
| FLT-1 | FGR | |
| FLT-2 | FLT-2 | |
| FLT-3 | FMS | |
| FMS | HIPK4 | |
| KDR | JAK2 | |
| KIT | KDR | |
| LOK | KIT | |
| LYNA | LCK | |
| LYNB | LOK | |
| MAP4K4 | LYNA | |
| p38-α | LYNB | |
| p38-β | MKNK1 | |
| PDGFR-α | MNK2 | |
| PDGFR-β | MUSK | |
| PI3K-α | PDGFR-α | |
| RET | RON | |
| PIPK2 | TIE2 | |
| TAOK2 | TRKB | |
| TAOK3 | TRKC | |
| TIE2 | TYRO3 | |

TABLE 29

Kinase Inhibition Profiles of Inhibitors I-41 to I-51 against a panel of 250 kinaes when assayed at 5 uM.

| Scaffold # | S-52 | S-84 | S-84 Sulfoxide | S-84 Sulfone | S-81 | S-82 | S-83 | S-17 | S-84 | S-84 Sulfoxide | S-84 Sulfone |
|---|---|---|---|---|---|---|---|---|---|---|---|
| HGM # | HGM-7 | HGM-7 | HGM-7 | HGM-7 | HGM-7 | HGM-7 | HGM-7 | HMG-4 | HMG-4 | HMG-4 | HMG-4 |
| Cpd ID# | I-41 | I-42 | I-43 | I-44 | I-45 | I-46 | I-47 | I-48 | I-49 | I-50 | I-51 |
| | BRAF | ARG | BRAF | CRAF | BRAF | BRAF | ABL | ARG | ABL1 | ABL1 | ARG |
| | CRAF | BLK | CRAF | DDR2 | CRAF | CRAF | ARG | CRAF | ARG | ARG | BRAF |
| | DDR2 | BMX | DDR2 | EPH-A8 | DDR2 | DDR2 | BRAF | DDR2 | AURORA-A | AURORA-A | CRAF |
| | EPH-A2 | BRAF | EPH-A2 | FMS | EPH-A2 | EPH-A2 | CRAF | EPH-A2 | BLK | BLK | DDR2 |
| | EPH-A3 | BRK | EPH-A3 | p38-α | EPH-A4 | EPH-A4 | CSK | EPH-A3 | BMX | BMX | EPH-A2 |
| | EPH-A4 | CRAF | EPH-A4 | PDGFR-α | EPH-A5 | EPH-A5 | DDR2 | EPH-A4 | BRAF | BRAF | EPH-A3 |
| | EPH-A5 | CSK | EPH-A5 | PDGFR-β | EPH-A8 | EPH-A8 | EPH-A2 | EPH-A5 | BRK | CRAF | EPH-A4 |
| | EPH-A8 | DDR2 | EPH-A8 | | EPH-B2 | EPH-B2 | EPH-A4 | EPH-A8 | BTK | DDR2 | EPH-A5 |
| | EPH-B1 | EPH-A1 | EPH-B2 | | FLT-1 | KIT | EPH-A5 | EPH-B2 | CAMK1A | EPH-A2 | EPH-A8 |
| | EPH-B2 | EPH-A2 | EPH-B4 | | FLT-3 | LCK | EPH-A8 | KDR | CLK4 | EPH-A3 | EPH-B2 |
| | EPH-B4 | EPH-A3 | FLT-1 | | FMS | LYNA | EPH-B2 | KIT | CRAF | EPH-A4 | FER |
| | FLT-1 | EPH-A4 | FLT-3 | | KDR | LYNB | FMS | LYNB | CSK | EPH-A5 | FLT-1 |
| | FLT-3 | EPH-A5 | FMS | | KIT | p38-α | FYN | p38-α | DDR2 | EPH-A8 | FLT-3 |
| | FMS | EPH-A8 | KDR | | LYNA | p38-β | HCK | PDGFR-α | EPH-A1 | EPH-B1 | FMS |
| | KDR | EPH-B1 | KIT | | LYNB | PDGFR-α | KDR | PDGFR-β | EPH-A2 | EPH-B2 | KDR |
| | KIT | EPH-B2 | LYNB | | p38-α | PDGFR-β | KIT | PI3K-α | EPH-A3 | EPH-B3 | KIT |
| | LYNA | EPH-B3 | p38-α | | p38-β | RET | LCK | PI3K-γ | EPH-A4 | EPH-B4 | LYNA |
| | LYNB | EPH-B4 | p38-β | | PDGFR-α | | LYNA | | EPH-A5 | FER | LYNB |
| | p38-α | FGFR1 | PDGFR-α | | | | LYNB | | EPH-A8 | FGFR4 | MAP4K2 |
| | p38-β | FGR | PDGFR-β | | | | p38-α | | EPH-B1 | FGR | MAP4K5 |
| | PDGFR-α | FLT-1 | | | | | p38-β | | EPH-B2 | FLT-1 | NEK1 |
| | PDGFR-β | FLT-3 | | | | | PAK4 | | EPH-B3 | FLT-3 | p38-α |
| | | FMS | | | | | PDGFR-α | | EPH-B4 | FMS | p38-β |
| | | FYN | | | | | PDGFR-β | | ERB-B4 | FYN | PDGFR-α |
| | | HCK | | | | | RET | | FAX | HCK | PDGFR-β |
| | | KDR | | | | | PIPK2 | | FER | KDR | PI3K-α |
| | | KIT | | | | | SRC | | FGFR1 | KIT | TAOK3 |
| | | LCK | | | | | YES | | FGFR2 | LCK | TIE2 |
| | | LYNA | | | | | | | FGFR3 | LOK | |
| | | LYNB | | | | | | | FGFR4 | LYNA | |
| | | MAP4K2 | | | | | | | FGR | LYNB | |
| | | MAP4K5 | | | | | | | FLT-1 | MAP4K2 | |
| | | NEK1 | | | | | | | FLT-2 | MAP4K5 | |
| | | p38-α | | | | | | | FLT-3 | MUSK | |
| | | p38-β | | | | | | | FMS | NEK1 | |
| | | PDGFR-α | | | | | | | FYN | p38-α | |
| | | PDGFR-β | | | | | | | HCK | p38-β | |
| | | RET | | | | | | | HIPK4 | PDGFR-α | |
| | | PIPK2 | | | | | | | KDR | PDGFR-β | |
| | | SRC | | | | | | | KIT | RET | |
| | | TAOK2 | | | | | | | LCK | TAOK3 | |
| | | TAOK3 | | | | | | | LOK | TIE2 | |
| | | TIE2 | | | | | | | LYNA | | |
| | | TNK1 | | | | | | | LYNB | | |
| | | YES | | | | | | | MAP4K2 | | |
| | | | | | | | | | MAP4K4 | | |
| | | | | | | | | | MAP4K5 | | |
| | | | | | | | | | MELK | | |
| | | | | | | | | | MINK | | |
| | | | | | | | | | MUSK | | |
| | | | | | | | | | NEK1 | | |
| | | | | | | | | | p38-α | | |
| | | | | | | | | | p38-β | | |
| | | | | | | | | | PDGFR-α | | |
| | | | | | | | | | PDGFR-β | | |
| | | | | | | | | | PIM3 | | |
| | | | | | | | | | PTK5 | | |
| | | | | | | | | | PYK2 | | |
| | | | | | | | | | RET | | |
| | | | | | | | | | PIPK2 | | |
| | | | | | | | | | ROS | | |
| | | | | | | | | | SRC | | |
| | | | | | | | | | SRMS | | |
| | | | | | | | | | TAK1-TAB1 | | |
| | | | | | | | | | TAOK2 | | |
| | | | | | | | | | TAOK3 | | |
| | | | | | | | | | TIE2 | | |
| | | | | | | | | | TNIK | | |
| | | | | | | | | | TNK1 | | |
| | | | | | | | | | TRKB | | |

TABLE 29-continued

Kinase Inhibition Profiles of Inhibitors I-41 to I-51 against a panel of 250 kinaes when assayed at 5 uM.

| Scaffold # | S-52 | S-84 | S-84 Sulfoxide | S-84 Sulfone | S-81 | S-82 | S-83 | S-17 | S-84 | S-84 Sulfoxide | S-84 Sulfone |
|---|---|---|---|---|---|---|---|---|---|---|---|
| HGM # | HGM-7 | HGM-7 | HGM-7 | HGM-7 | HGM-7 | HGM-7 | HGM-7 | HMG-4 | HMG-4 | HMG-4 | HMG-4 |
| Cpd ID# | I-41 | I-42 | I-43 | I-44 | I-45 | I-46 | I-47 | I-48 | I-49 | I-50 | I-51 |
| | | | | | | | | | TRKC | | |
| | | | | | | | | | TXK | | |
| | | | | | | | | | YES | | |

Additional Uses for Kinase inhibitors with this Scaffold Geometry:

New Tools to Identify Kinases Capable of Atypical Conformations:

Taken together, these data demonstrate the broad applicability and utility of this scaffold geometry for the targeted inhibition of a large number of kinases. Therefore, because this scaffold geometry is believed to be highly complementary to the conserved topography of lower selectivity sites created by movements of a kinase's DFG loop, compounds based on this generic geometry may be expected to induce or stabilize these conformational changes particularly well. Indeed, kinases that have been previously not been known to adopt these conformations may prove amenable to inhibition by or association with inhibitors built on this scaffold concept. For example, affinity reagents that target a specific inactive form of protein kinases have been described and used to access if a kinase can adopt this inactive conformation, (Ranjitkar, 2010).

Figure 15:
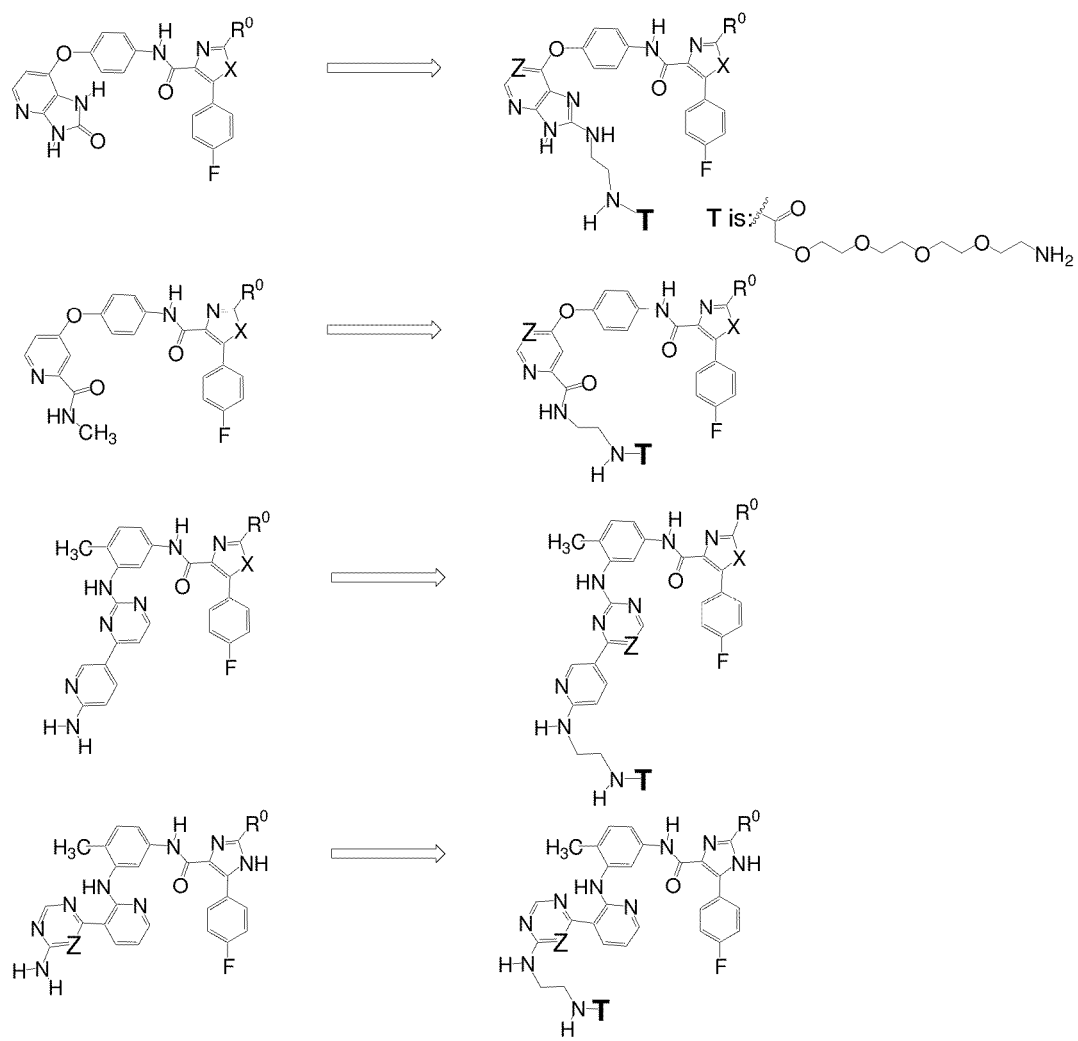
FIG. 15: Illustrates certain inhibitors and affinity probes for the indentification of new atypical kinase conformations.

Similarly, inhibitors and affinity agents derived from molecules that share the specific scaffold geometry described herein; such as Inhibitors I-12, I-14, I-15 and the like; will have applications as novel tools for the identification of kinases that can adopt inactive or other atypical conformations. Once selected, the specific structural information could then be confirmed by X-ray co-crystal structure determination. Examples of such inhibitors and their corresponding affinity probes are illustrated in FIG. 15, which shows representative inhibitors and analogous affinity probes useful for the identification of atypical kinase conformations where $R_0$ is as definded above.

Figure 16:
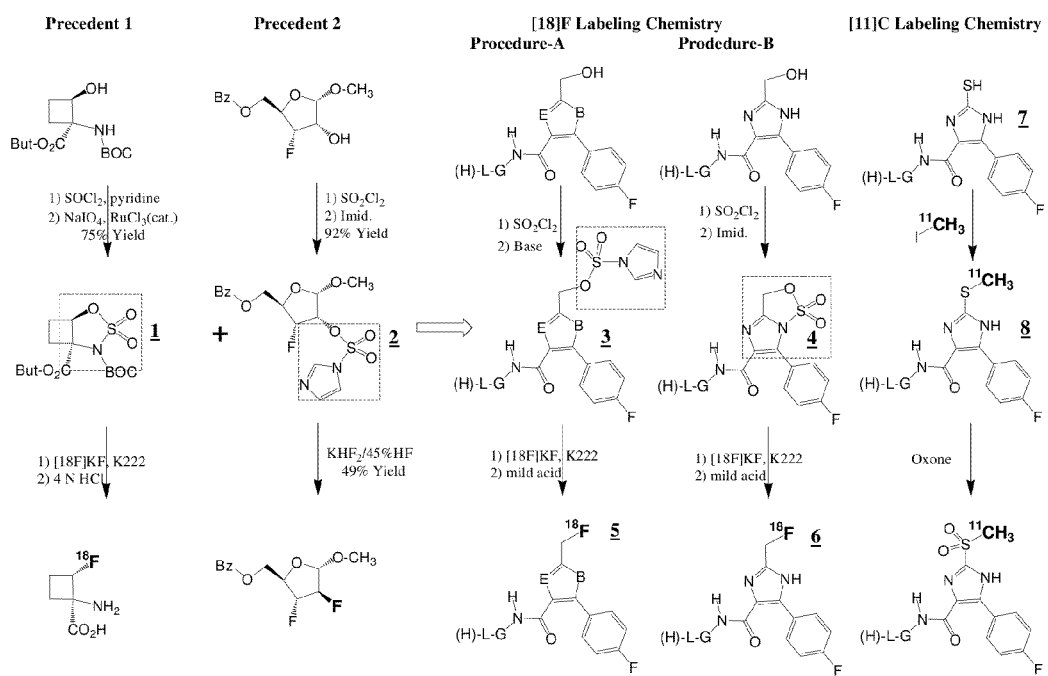
FIG. 16: Represents an exemplary method for the incorporation of $^{18}$F or $^{11}$C labels for PET probe preparation.

The interesting profiles and a wide range of selectivity demonstrated by these few early compounds support many utilities for kinase inhibitors that share this scaffold geometry. These data suggest that incorporation of Hinge-Gatekeeper Motifs from either known type-II inhibitors or from ATP competitive inhibitors are expected to provide novel kinase inhibition profiles that may have therapeutic potential. Another potential utility for compounds sharing this scaffold geometry is for the evaluation and identification of the potential for a given kinase to assume an atypical or DFG-out conformation. A third utility for kinase inhibitors that share this scaffold geometry is their adaptation for incorporation of radio labels for positron emission tomography, Adaptation of this Scaffold to the Preparation Kinase-Targeted PET Imaging Agents:

In contrast to recently reported cumbersome methods described for the introduction of $^{18}F$ into kinase inhibitors (Griffiths, 2010), we herein describe several novel, generally applicable, and highly practical synthetic strategies for the incorporation of $^{18}F$ or $^{11}C$ labels in the last step(s) of PET probe preparation FIG. 16.

Two precedents are illustrated for the introduction of fluoride in FIG. 16. In the first, a cyclic sulfamate 1 is used as the activated intermediate for fluoride displacement. In the second an imidazoyl sulfonate 2 provides the necessary activation. Application of the second precedent to an appropriate 2-hydroxymethyl scaffold should provide the radiolabeled derivative 5 via imidazoyl-sulfonate 3, procedure-A. Procedure-B is a special case for selected imidazole scaffolds in which addition of imidazole is not required as formation of an intramolecular cyclic imidazoly sulfonate 4 should be formed. Intermediate 4 could be formed and used immediately for introduction of [1,8]F label or stored for later use. Due to the 110 minute half-life of [18]F (http://www.iem-inc.com/toolhalf.html), the strength of this strategy is that it occurs at the end of the synthesis and allows production of the [1,8]F probes 5 and 6 in a single step just prior to utilization.

Due to the even shorter 20 minute half life of $^{11}$C, utilization of this radio-isotope is more challenging. Nevertheless, our observation that inhibitors that incorporate the 2-methylsulfonyl 5-membered heteroaryl carboxamide scaffold display attractive selectivity profiles provides a viable alternative for the rapid introduction of [1,1]C radio-label. Using a fully elaborated 2-mercapto-thiazole precursor 7, alkylation with [1,1]C methyl iodide or bromide would quickly provide the 2-methyl mercapto imidazole 8 in good yield (Garcia, 2005; Tang, 2011). If required, the corresponding sulfoxide or sulfone analogs could be optionally prepared or, depending on metabolism, in vivo oxidation may provide these oxidation states Due to the short half lives of both [1,8]F and $^{11}$C, introduction of the radiolabel as the end of the synthesis offers a clear advantage.

Figure 17:
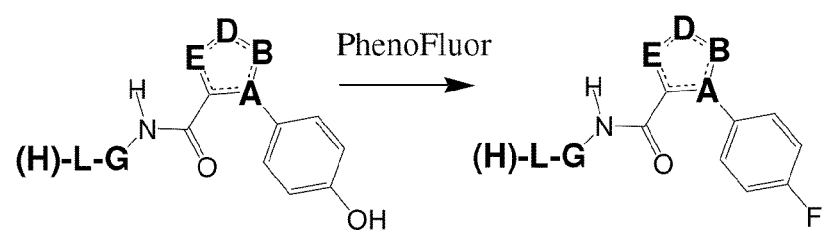
FIG. 17: Illustrates a strategic route for [1,8]F incorporation with (1,3-Bis(2,6-diisopropylphenyl)-2,2-difluoro-2,3-dihydro-1H-imidazole).

Alternate strategies for the introduction of [1,8]F into an ary ring such as PhenoFluor™ (1,3-Bis(2,6-diisopropylphenyl)-2,2-difluoro-2,3-dihydro-1H-imidazole) is commercially available (Sigma-Aldrich product directory as catalog number SFL0001) and could be exploited using an appropriate phenolic intermediate (see http://www.scifluor.com), FIG. 17.

Uniqueness as a Platform Technology:

Based on our recent findings, Tables 3 and 4, the 2-substituted ortho-aryl-imidazole carboxamide scaffold is broadly recognized, albeit modestly in some cases, by a wide variety of kinases. Although co-crystal structure determinations will be needed to confirm the mode of binding for each kinases, many of the inhibited kinases are thought to be capable of adopting the DGF-out conformation. In addition to being widely accepted, this scaffold is proposed to adopt a novel mode of binding within the conserved topography of the lower selectivity-site produced by movement of the DFG loop from its pocket, FIG. 10. In so doing, a highly complementary fit provides a uniquely rigid anchor point against which distances between affinity and selectivity elements are defined. The selectivity for p38-α observed for Inhibitor 11, Table-3, may be an example of this rigid anchoring function.

Taken together, this invention describes a new platform technology that can be useful for both the discovery of new targeted therapeutics as well as the development of highly selective PET imaging agents. The capability to achieve both broad applicability and to dial in exceptional selectivity with a single scaffold is highly unusual. Moreover, because the scaffolds and the chemistries described herein can, in principle, also be adapted to the preparation of structurally similar PET imaging probes, this invention offers unique opportunities for synergy and cost savings, FIG. 18. For example, the ability to develop selective imaging agents for kinase targets will be particularly useful to establish proof of concept from preclinical animal studies through clinical evaluation. In addition, selection of the most appropriate patient populations for efficacy studies will likely result in significant cost savings (de Vries, 2010). Eventually, application of imaging agents based on this generic technology will be used for the diagnosis, characterization, and monitoring of diseases characterized by the over expression, up-regulation, mutation, and aberrant activity of kinases.

The 2-substituted 5-aryl-imidazole carboxamide scaffold has been shown to be both unique and broadly applicable to the design of multi-targeted type-II kinase inhibitors. The unique geometry defined by this scaffold is believed to be particularly well suited to establish novel interactions at the bottom of the lower selectivity site that can be exploited to increase binding affinity, rigidity, and selectivity. FIG. 18 illustrates various strategies for construction of penultimate intermediates or final kinase inhibitors and imaging agents using the scaffold platform described herein. Scaffold acids can be coupled to a suitably protected HGM amine (Route-1); to a suitably protected gatekeeper residue followed by deprotection and coupling of and appropriately protected hinge-linger group (Route-2); or to a suitably protected linker-gatekeeper fragment followed by deprotection and coupling to a suitably protected hinge interacting group.

It is proposed that the aryl ring of the 5-membered heteroaryl carboxamide scaffold is ideally positioned to closely mimic interactions normally made by the phenylalanine side-chain of the DFG-loop. Therefore, when an appropriate Hinge-Gatekeeper interacting substitutent (H)-L-G- is attached to an appropriate ortho-aryl 5-membered heteroaryl carboxamide scaffold as in Formula-1, the unique geometry defined by this scaffold results in a highly complementary and tight fit with the new lipophilic pocket (lower selectivity site) generated as a result of the DFG-loop movement. This invention describes a previously unappreciated common feature of the bottom of the lower selectivity site that can be exploited by an appropriate substituent on the Ar group in Formula-1 to provide both affinity and selectivity enhancements. This conserved feature or indentation results from the common method of construction of this lipophilic pocket in many kinases.

Because we have demonstrated that a scaffold with this combination of functionality and scaffold geometry can both yield broad applicability and yet, with simple modification, lead to a highly selective inhibitor, this scaffold geometry is considered a general platform technology for the stabilization or inducement of the inactive DFG-out conformation of kinases capable of adopting it. Molecular modeling studies suggest that the binding mode described herein is consistent with both the observed SAR and the observed broad applicability conferred by an imidazole scaffold that shares this general geometry.

Our observation that the indentation formed by convergence of aliphatic amino acid side chains is a general feature at the bottom of the lower selectivity site of many kinases is new. However, interactions described in these models need not be the only mode of binding by which kinase inhibition can result nor is the inactive DFG-out conformation, necessarily, the only kinase conformation that these inhibitors may bind to.

Compounds that target a combination of tyrosine kinases that are associated with oncogene addiction that also block escape or compensatory mechanisms shown to lead to tyrosine kinase inhibitor (TKI) drug resistance would be of high value. We have demonstrated that access to unique selectivity profiles can be achieved using the scaffold concepts described herein. For example, compounds SFE-00013 and SFE-0014 inhibit PI3Ks in addition to Raf (including B-Raf, B-Raf mutant V600E), C-Raf, p38-α and PDGFR-α, thereby simultaneously inhibiting both the critical Ras/Raf/MEK/ERK and PI3K/AKT/mTOR pathways. On the other hand, SFE-0011 is very selective for p38-α but with modest PI3K activity. Optimization of this lead may lead to a novel approach for the treatment of chronic inflammation. It is expected that these and other unique profiles resulting from this invention will provide both novel therapeutic agents for the treatment of cancers, pain, infectious and neurodegenerative diseases, and inflammation related conditions.

The variety of kinases inhibited and the variations in the inhibition profiles produced by both variation of the HGM and the scaffold functionality illustrates the utility of this new scaffold geometry for the identification of novel agents usefull for the treatment of diseases where the mutation, over expression, or aberrant activity of kinases through loss of phosphatase activities play a contributory role.

In general, PET imaging agents with targeted kinase inhibitor activity will be allow the study of roles kinase targets play in disease related physiology. In a special case, compounds the represent the subset of Formula I where $R_0$ is defined as $-CH_2[18]F$ or $-SO_m[11]CH_3$ provide unique utilities as positron emission tomography (PET) imaging agents for the study, diagnosis, characterization, and monitoring of diseases and conditions resulting from the aberrant expression, activation, or activity of the kinases for which they inhibit. Moreover, the technologies for the general introduction of radio label described herein, constitute a generic technology for the preparation and routine production of selective multi-target kinase inhibitor-based imaging agents.

It is anticipated that the combination of appropriately targeted PET imaging agents combined with the availability of either closely related inhibitors or structurally different inhibitors with equivalent selectivity profiles offers an innovative and useful strategy for the identification and development of patient specific therapies for conditions where the aberrant expression, activation, or mutation of a kinase or profile of kinases is indicated.

What is claimed is:

1. A compound represented by structural Formulae (VII) to (XIV):

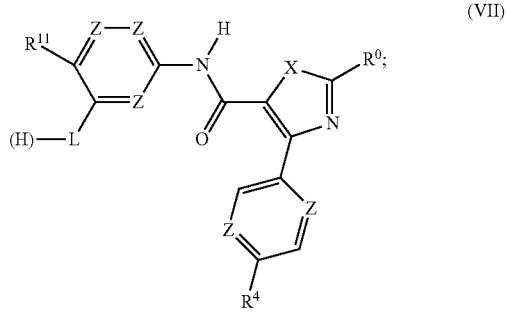

(VII)

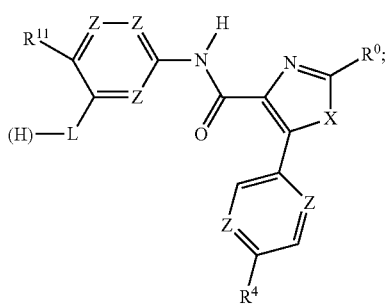
(VIII)
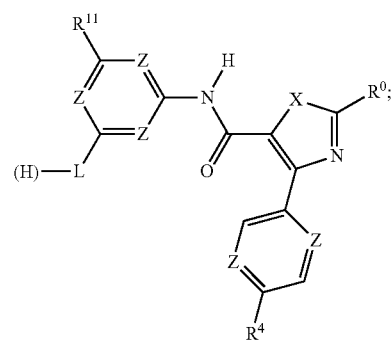
(IX)
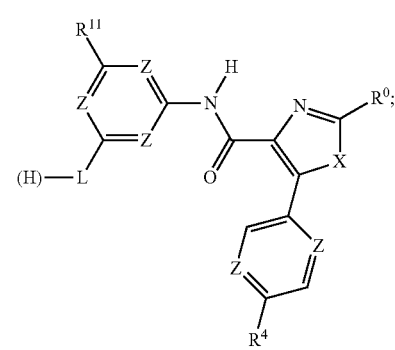
(X)
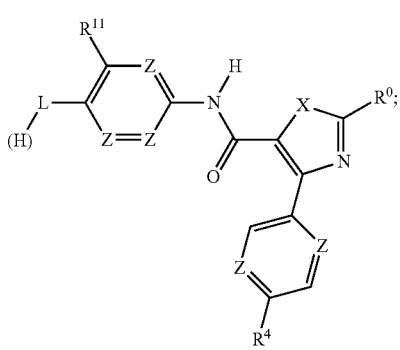
(XI)
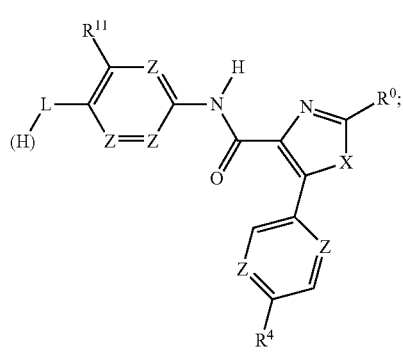
(XII)
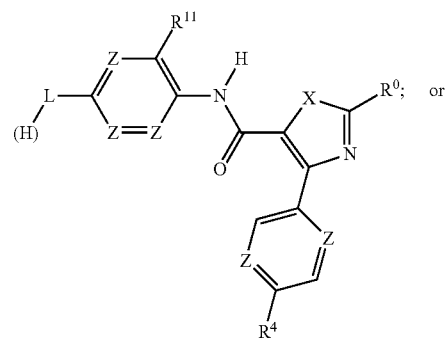
(XIII)
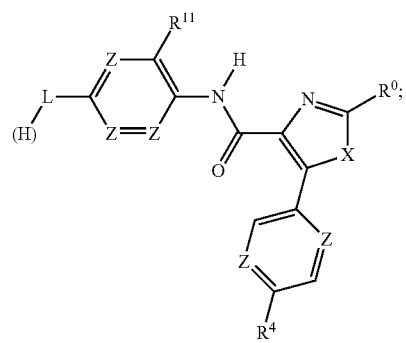
(XIV)
or a pharmaceutically acceptable salt, wherein:
1) L is —O—, —S—, —NH— or —C(O)NR¹; and (H) is of the structural formulae
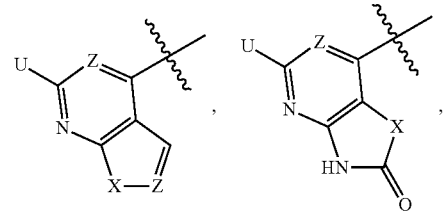
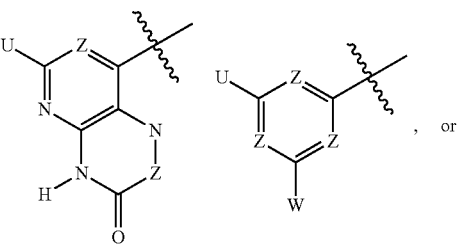
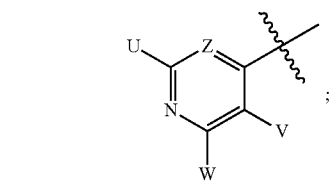

or
2) L is —O—, —NH—, —CC—, or —C(O)NR¹; and (H) is of the structural formulae

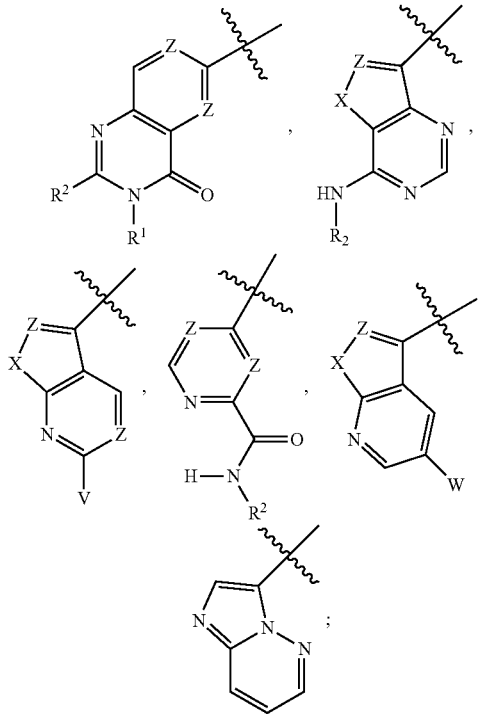

$R_{11}$ is selected from H, —CH$_3$, —CH$_2$CH$_3$, cyclopropyl, —F, —Cl, —CN, —OCH$_3$, and —S—CH$_3$;
$R_0$ is selected from —F, —C$_2$-C$_4$ alkenyl, —C$_2$-C$_4$ alkynyl, —CO(CH$_2$)$_n$Y, —(CH$_2$)$_n$—NR$^A$R$^B$, —[O—(CH$_2$)$_2$]$_n$Y, —(CH$_2$)$_n$SO$_2$NR$^A$R$^B$, —S(O)$_m$—(CH$_2$)$_m$—R¹, —S(O)$_m$R¹, —OR², —CH$_2$—F, —CH$_2$[18]F, —CHF$_2$, —CHF[18]F, —CH[18]F$_2$, —CF$_3$, —CF$_2$[18]F, —CF[18]F$_2$, and —C[18]F$_3$;
provided that R⁰ is not CF$_3$ when the ring to which it is attached is a 1H-imidazole ring;
R¹ is independently H, CH$_3$, —CH$_2$CH$_3$, or cyclopropyl;
R² is independently H, —CH$_3$, —(CH$_2$)$_n$—CH$_3$, or —(CH$_2$)$_n$—NR$^A$R$^B$;
R$^A$ and R$^B$ are each independently H, CH$_3$, —CH$_2$CH$_3$, or cyclopropyl; or R$^A$ and R$^B$ taken together form a 3-6 membered carbocyclic ring system or 5-7 membered saturated heterocyclic ring system;
Y is —CHR¹R², —CN, —COR¹, —CONR$^A$R$^B$, —OR¹, —NR$^A$R$^B$, —NR¹COR², —S(O)$_m$R¹, —SO$_2$NR$^A$R$^B$, —[O—(CH$_2$)$_2$]$_n$—CH$_2$F, —S(O)$_m$[11]CH$_3$, —[O—(CH$_2$)$_2$]$_n$—CH$_2$$^{18}$F, —CH$_2$—F; —CH$_2$[18]F, —CHF$_2$, —CHF[18]F, —CH[18]F$_2$, —CF$_3$, —CF$_2$[18]F, —CF[18]F$_2$, or —C[18]F$_3$;
m is 0, 1, or 2;
n is 1, 2, or 3;
U is —H, F, Cl, —OR¹, or —NHR¹;
V and W are each independently selected from —H, —F, —Cl, —CF$_3$, —CONHR², —X—R¹, —X—(CH$_2$)$_n$CN, —X—(CH$_2$)$_m$COR¹, X—(CH$_2$)$_m$CONR¹R², —X—CH$_2$—(CH$_2$)$_n$OR¹, —X—CH$_2$—(CH$_2$)$_n$NR¹R², —X—CH$_2$—(CH$_2$)$_n$S(O)$_m$R¹, —X—(CH$_2$)$_n$S(O)$_m$NR¹R², —O—(CH$_2$)$_2$NR¹R², —O—(CH$_2$)$_3$NR¹R², —O—(CH$_2$)$_n$CONR¹R², —O$_5$—C$_6$heteroaryl, —COCH=CH—(CH$_2$)$_n$NR¹R², and T;

T is:

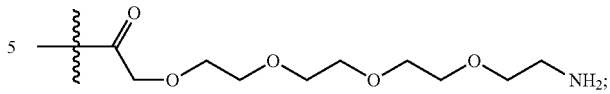

Z is independently selected from —CH—, —CF—, and —N—;
R$_4$ is selected from H, —CH$_3$, —CH$_2$CH$_3$, cyclopropyl, —F; -$^{18}$F, —Cl, —Br, —CH$_2$F, —CH$_2$[18]F, —CHF$_2$, —CF$_3$, —HC=CHR¹, —CCR¹; —CN, —OCF$_3$, —NHR¹—OR¹, and —S(O)$_m$R¹; and
X is —O—, —NR²—, or —S—.

2. A compound represented by structural Formulae (XX) to (XXVIV):

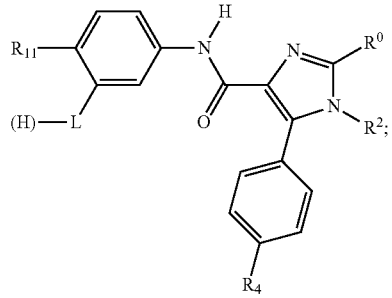

XX

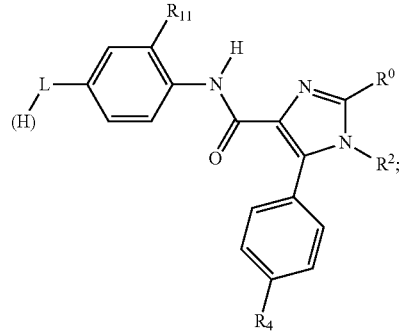

XXI

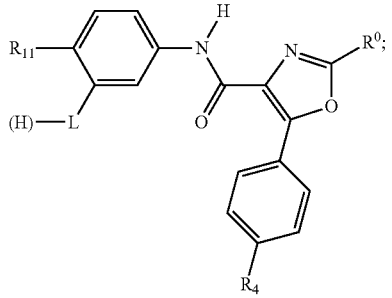

XXII

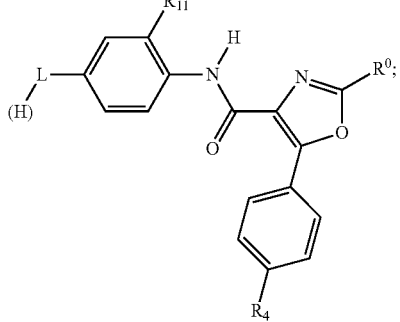

XXIII

XXIV 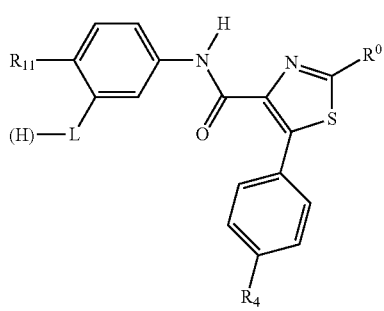
XXV 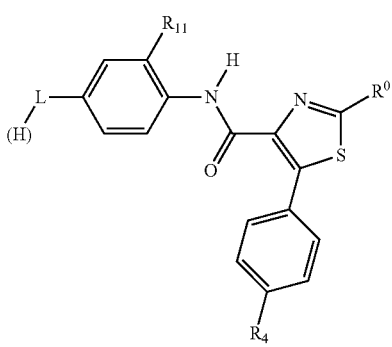
XXVI 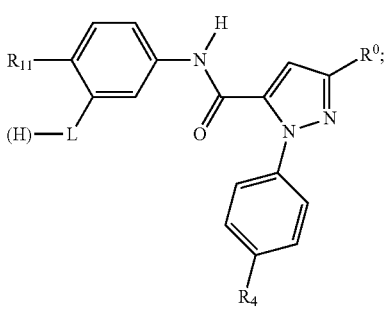
XXVII 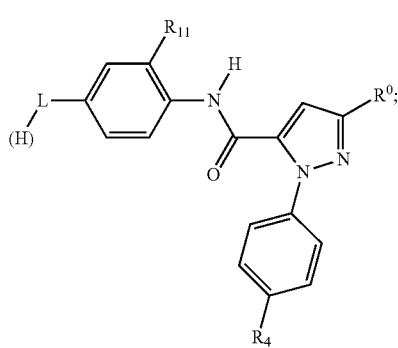
XXVIII 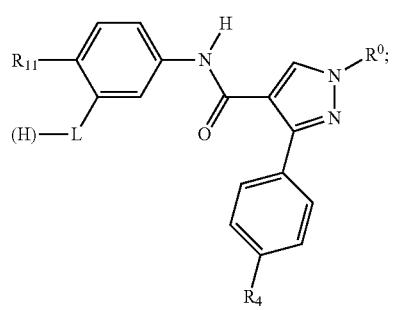
XXVIV 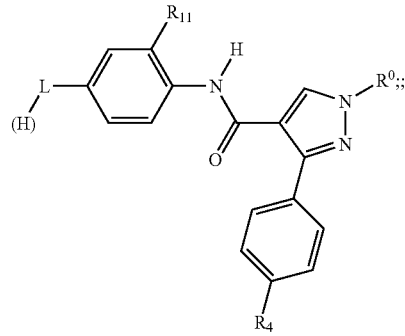
or a pharmaceutically acceptable salt thereof, wherein:
1) L is —O—, —S—, —NH— or —C(O)NR¹; and (H) is of the structural formulae
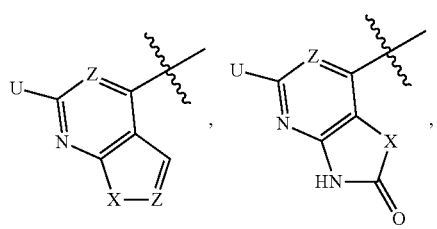
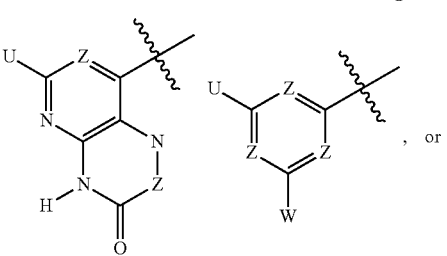
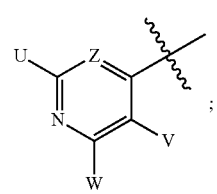
or
2) L is —O—, —NH—, —CC—, or —C(O)NR¹; and (H) is of the structural formulae
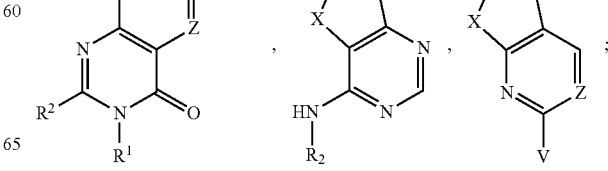

-continued

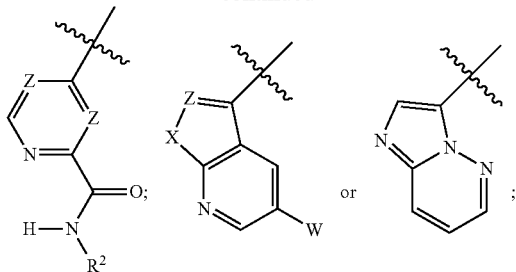

$R_{11}$ is selected from H, —$CH_3$, —$CH_2CH_3$, cyclopropyl, —F, —Cl, —CN, —$OCH_3$, and —S—$CH_3$;

$R_0$ is selected from —F, —$C_2$-$C_4$ alkenyl, —$C_2$-$C_4$ alkenyl, —$CO(CH_2)_nY$, —$(CH_2)_n$—$NR^AR^B$, —[O—$(CH_2)_2]_nY$, —$(CH_2)_nSO_2NR^AR^B$, —$S(O)_m$—$(CH_2)_m$—$R^1$, —$S(O)_mR^1$, —$OR^2$, —$CH_2$—F, —$CH_2[18]F$, —$CHF_2$, —$CHF[18]F$, —$CH[18]F_2$, —$CF_3$, —$CF_2[18]F$, —$CF[18]F_2$, and —$C[8]F_3$; provided that $R^0$ is not $CF_3$ when the ring to which it is attached is a 1H-imidazole ring;

$R^1$ is independently H, $CH_3$, —$CH_2CH_3$, or cyclopropyl;

$R^2$ is independently H, —$CH_3$, —$(CH_2)_n$—$CH_3$, or —$(CH_2)_n$—$NR^AR^B$;

$R^A$ and $R^B$ are each independently H, $CH_3$, —$CH_2CH_3$, or cyclopropyl; or $R^A$ and $R^B$ taken together form a 3-6 membered carbocyclic ring system or 5-7 membered saturated heterocyclic ring system;

Y is —$CHR^1R^2$, —CN, —$COR^1$, —$CONR^AR^B$, —$OR^1$, —$NR^AR^B$, —$NR^1COR^2$, —$S(O)_mR^1$, —$SO_2NR^AR^B$, —[O—$(CH_2)_2]_n$—$CH_2F$, —$S(O)_m[11]CH_3$, —[O—$(CH_2)_2]_n$—$CH_2^{18}F$, —$CH_2$—F; —$CH_2[18]F$, —$CHF_2$, —$CHF[18]F$, —$CH[18]F_2$, —$CF_3$, —$CF_2[18]F$, —$CF[18]F_2$, or —$C[18]F_3$;

m is 0, 1, or 2;

n is 1, 2, or 3;

U is —H, F, Cl, —$OR^1$, or —$NHR^1$;

V and W are each independently selected from —H, —F, —Cl, —$CF_3$, —$CONHR^2$, —X—$R^1$, —X—$(CH_2)_nCN$, —X—$(CH_2)_mCOR^1$, X—$(CH_2)_mCONR^1R^2$, —X—$CH_2$—$(CH_2)_nOR^1$, —X—$CH_2$—$(CH_2)_nNR^1R^2$, —X—$CH_2$—$(CH_2)_nS(O)_mR^1$, —X—$(CH_2)_nS(O)_mNR^1R^2$, —O—$(CH_2)_2NR^1R^2$, —O—$(CH_2)_3NR^1R^2$, —O—$(CH_2)_nCONR^1R^2$, —$C_5$-$C_6$heteroaryl, —COCH=CH—$(CH_2)_nNR^1R^2$, and T;

T is:

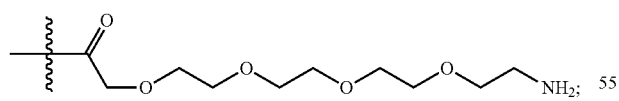

Z is independently selected from —CH—, —CF—, and —N—;

$R_4$ is selected from H, —$CH_3$, —$CH_2CH_3$, cyclopropyl, —F; —[18]F, —Cl, —Br, —$CH_2F$, —$CH_2[18]F$, —$CHF_2$, —$CF_3$, —HC=$CHR^1$, —$CCR^1$; —CN, —$OCF_3$, —$NHR^1$ —$OR^1$, and —$S(O)_mR^1$; and X is —O—, —$NR^2$—, or —S—.

3. A compound represented by structural Formulae (VII) to (XIV):

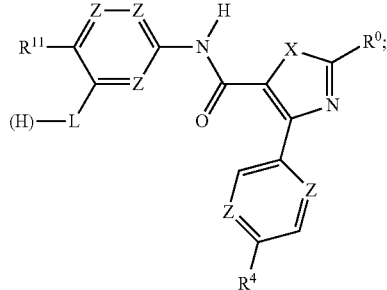

(VII)

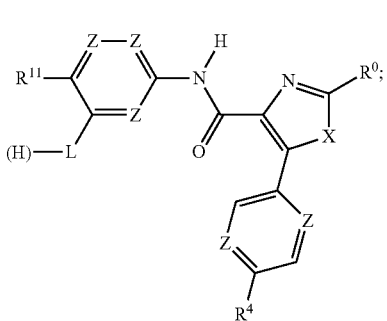

(VIII)

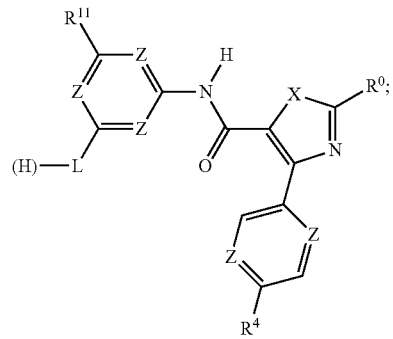

(IX)

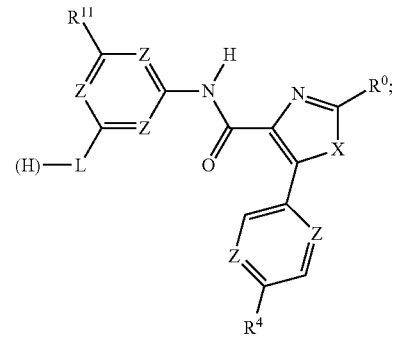

(X)

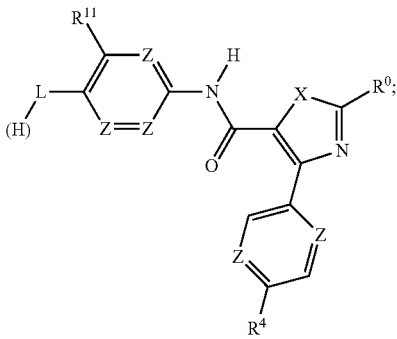

(XI)

-continued (XII)
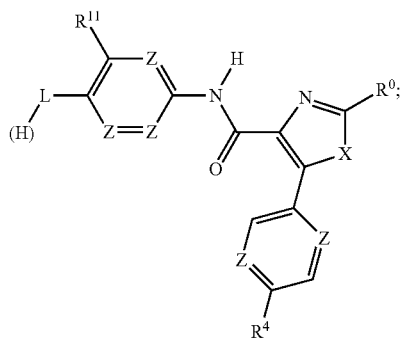

(XIII)
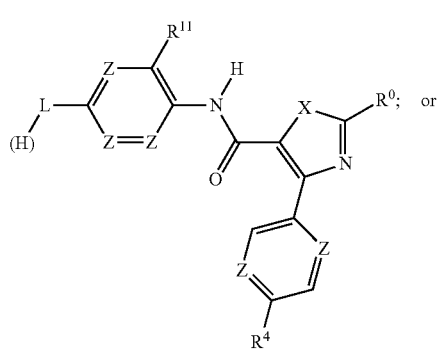

(XIV)
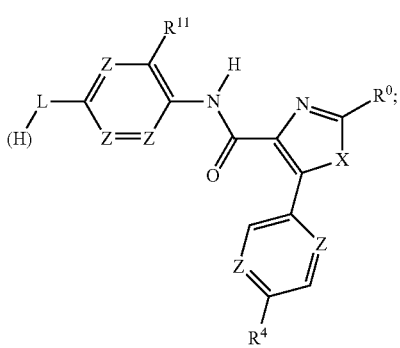

or a pharmaceutically acceptable salt, wherein:
L is of the structural formulae

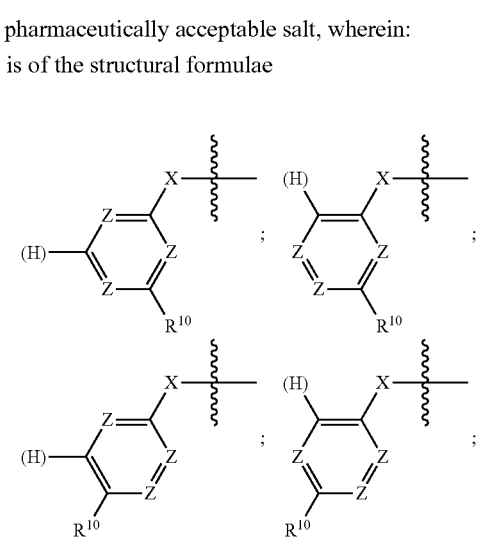

-continued
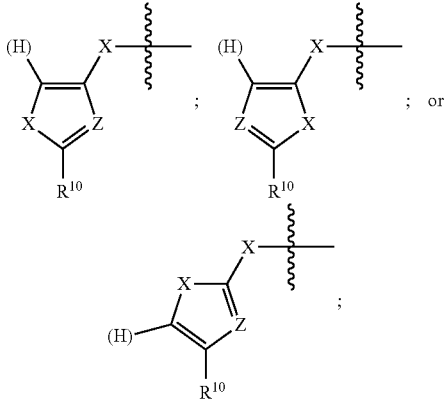

(H) is of the structural formulae

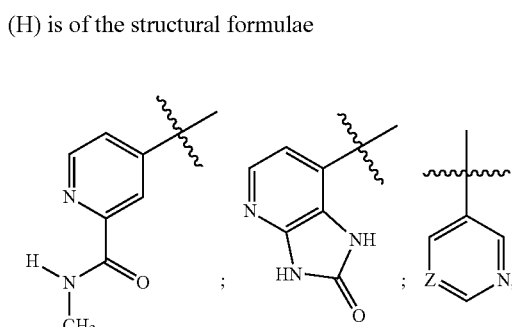

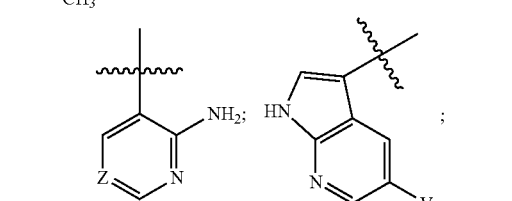

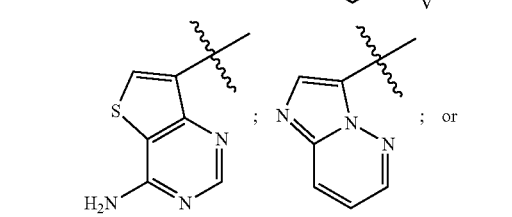

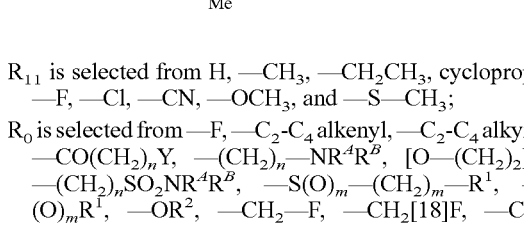

$R_{11}$ is selected from H, —CH$_3$, —CH$_2$CH$_3$, cyclopropyl, —F, —Cl, —CN, —OCH$_3$, and —S—CH$_3$;

$R_0$ is selected from —F, —C$_2$-C$_4$ alkenyl, —C$_2$-C$_4$ alkynyl, —CO(CH$_2$)$_n$Y, —(CH$_2$)$_n$—NR$^A$R$^B$, [O—(CH$_2$)$_2$]$_n$Y, —(CH$_2$)$_n$SO$_2$NR$^A$R$^B$, —S(O)$_m$—(CH$_2$)$_m$—R$^1$, —S(O)$_m$R$^1$, —OR$^2$, —CH$_2$—F, —CH$_2$[18]F, —CHF, —CHF[18]F, —CH[18]F$_2$, —CF$_3$, —CF$_2$[18]F, —CF[18]F$_2$, and —C[18]F$_3$;

provided that R$^0$ is not CF$_3$ when the ring to which it is attached is a 1H-imidazole ring;

R$^1$ is independently H, CH$_3$, —CH$_2$CH$_3$, or cyclopropyl;

$R^2$ is independently H, —$CH_3$, —$(CH_2)_n$—$CH_3$, or —$(CH_2)_n$—$NR^AR^B$;

$R^A$ and $R^B$ are each independently H, $CH_3$, —$CH_2CH_3$, or cyclopropyl; or $R^A$ and $R^B$ taken together form a 3-6 membered carbocyclic ring system or 5-7 membered saturated heterocyclic ring system;

Y is —$CHR^1R^2$, —CN, —$COR^1$, —$CONR^AR^B$, —$OR^1$, —$NR^AR^B$, —$NR^1COR^2$, —$S(O)_mR^1$, —$SO_2NR^AR^B$, [O—$(CH_2)_2]_n$—$CH_2F$, —$S(O)_m[11]CH_3$, [O—$(CH_2)_2]_n$—$CH_2{}^{18}F$, —$CH_2$—F; —$CH_2[18]F$, —$CHF_2$, —$CHF[18]F$, —$CH[18]F_2$, —$CF_3$, —$CF_2[18]F$, —$CF[18]F_2$, or —$C[18]F_3$;

m is 0, 1, or 2;
n is 1, 2, or 3;

V is selected from —H, —F, —Cl, —$CF_3$, —$CONHR^2$, —X—$R^1$, —X—$(CH_2)_n$CN, —X—$(CH_2)_mCOR^1$, X—$(CH_2)_mCONR^1R^2$, —X—$(CH_2)_mOR^1$, —X—$CH_2$—$(CH_2)_nNR^1R^2$, —X—$CH_2$—$(CH_2)_nS(O)_mR^1$, —X—$(CH_2)_nS(O)_mNR^1R^2$, —O—$(CH_2)_2NR^1R^2$, —O—$(CH_2)_3NR^1R^2$, —O—$(CH_2)_nCONR^1R^2$, —$C_5$-$C_6$heteroaryl, —COCH=CH—$(CH_2)_nNR^1R^2$, and T;

T is:

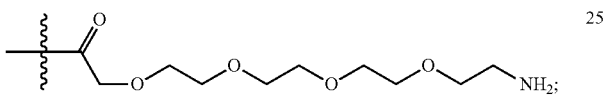

Z is independently selected from —CH—, —CF—, and —N—;

$R_4$ is selected from H, —$CH_3$, —$CH_2CH_3$, cyclopropyl, —F; -$^{18}$F, —Cl, —Br, —$CH_2F$, —$CH_2[18]F$, —$CHF_2$, —$CF_3$, —HC=$CHR^1$, —$CCR^1$; —CN, —$OCF_3$, —$NHR^1$—$OR^1$, and —$S(O)_mR^1$;

$R^{10}$ is hydrogen; and
X is —O—, —$NR^2$—, or —S—.

4. A compound represented by structural Formulae (XX) to (XXVIV):

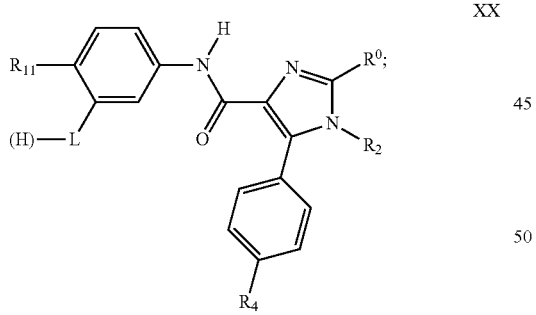

XX

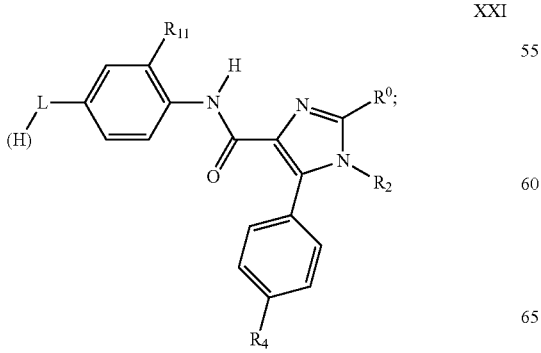

XXI

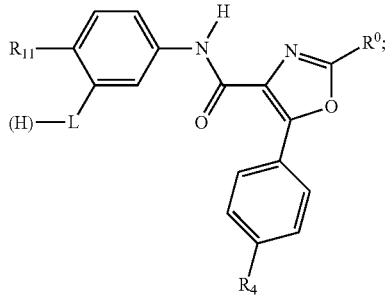

XXII

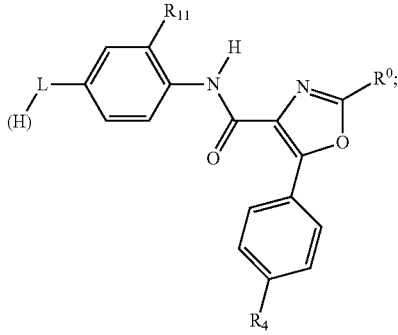

XXIII

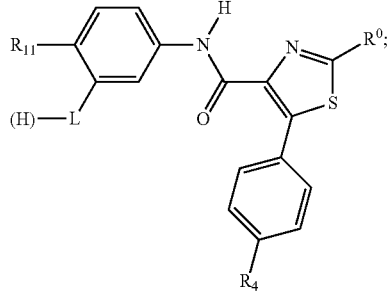

XXIV

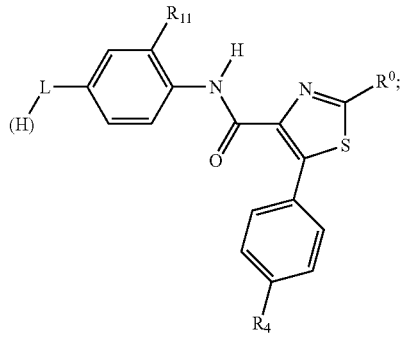

XXV

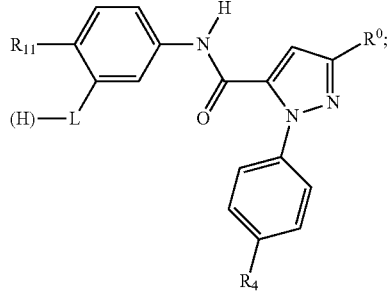

XXVI

-continued

XXVII
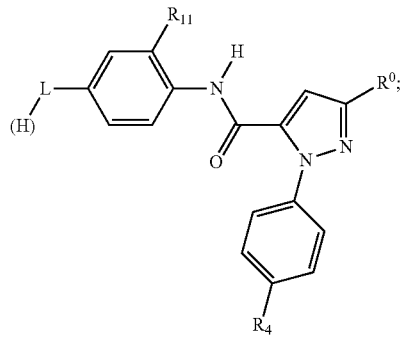

XXVIII
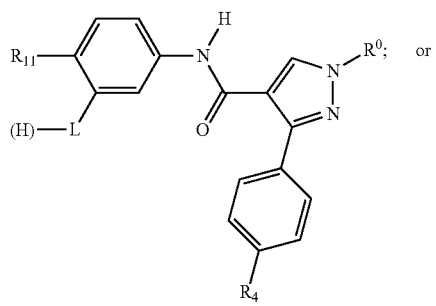
or

XXVIV
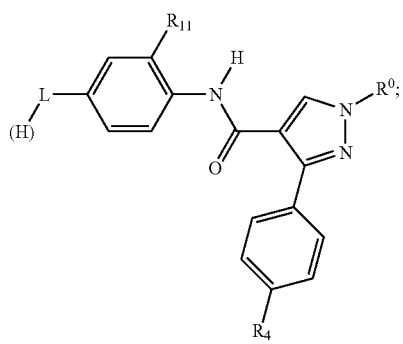

or a pharmaceutically acceptable salt thereof, wherein:
L is of the structural formulae

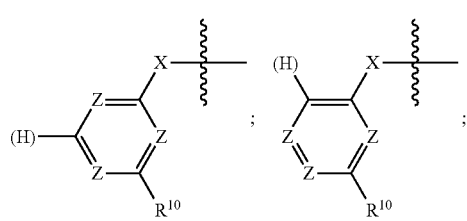
;
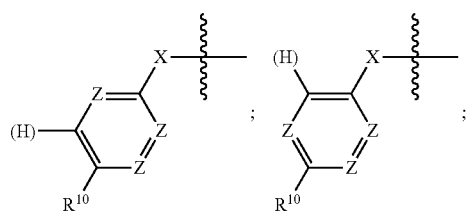
;

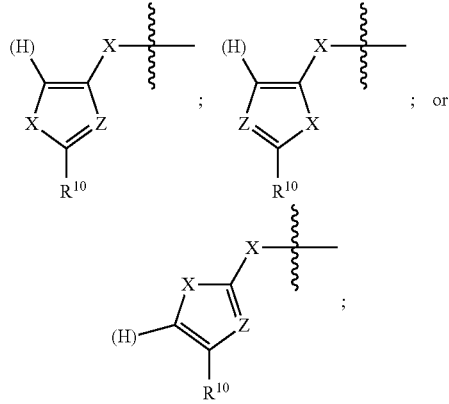

(H) is of the structural formulae

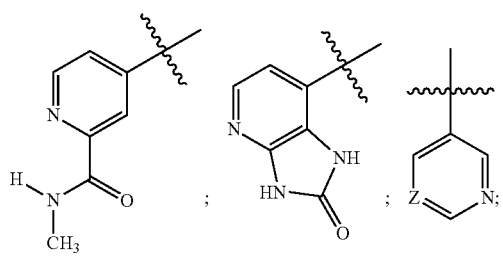

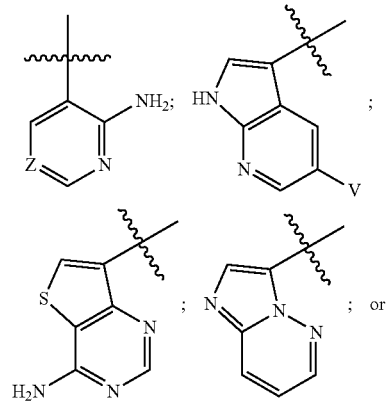

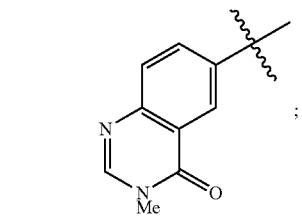
;

$R_{11}$ is selected from H, —CH$_3$, —CH$_2$CH$_3$, cyclopropyl, —F, —Cl, —CN, —OCH$_3$, and —S—CH$_3$;
$R_0$ is selected from —F, —C$_2$-C$_4$ alkenyl, —C$_2$-C$_4$ alkynyl, —CO(CH$_2$)$_n$Y, —(CH$_2$)$_n$—NR$^A$R$^B$, —[O—(CH$_2$)$_2$]$_n$Y, —(CH$_2$)$_n$SO$_2$NR$^A$R$^B$, —S(O)$_m$—(CH$_2$)$_m$R$^1$, —S(O)$_m$R$^1$, —OR$^2$, —CH$_2$—F, —CH$_2$[18]F, —CHF$_2$, —CHF[18]F, —CH[18]F$_2$, —CF$_3$, —CF$_2$[18]F, —CF[18]F$_2$, and —C[18]F$_3$; provided that R$^0$ is not CF$_3$ when the ring to which it is attached is a 1H-imidazole ring;
$R^1$ is independently H, CH$_3$, —CH$_2$CH$_3$, or cyclopropyl;
$R^2$ is independently H, —CH$_3$, —(CH$_2$)$_n$—CH$_3$, or —(CH$_2$)$_n$—NR$^A$R$^B$;

$R^A$ and $R^B$ are each independently H, $CH_3$, —$CH_2CH_3$, or cyclopropyl; or $R^A$ and $R^B$ taken together form a 3-6 membered carbocyclic ring system or 5-7 membered saturated heterocyclic ring system;

Y is —$CHR^1R^2$, —CN, —$COR^1$, —$CONR^AR^B$, —$OR^1$, —$NR^AR^B$, —$NR^1COR^2$, —$S(O)_mR^1$, —$SO_2NR^AR^B$, —$[O—(CH_2)_2]_n$—$CH_2F$, —$S(O)_m[11]CH_3$, —$[O—(CH_2)_2]_n$—$CH_2^{18}F$, —$CH_2$—F; —$CH_2[18]F$, —$CHF_2$, —$CHF[18]F$, —$CH[18]F_2$, —$CF_3$, —$CF_2[18]F$, —$CF[18]F_2$, or —$C[18]F_3$;

m is 0, 1, or 2;

n is 1, 2, or 3;

V is selected from —H, —F, —Cl, —$CF_3$, —$CONHR^2$, —X—$R^1$, —X—$(CH_2)_n CN$, —X—$(CH_2)_m COR^1$, X—$(CH_2)_m CONR^1R^2$, —X—$CH_2$—$(CH_2)_n OR^1$, —X—$CH_2$—$(CH_2)_n NR^1R^2$, —X—$CH_2$—$(CH_2)_n S(O)_m R^1$, —X—$(CH_2)_n S(O)_m NR^1R^2$, —O—$(CH_2)_2 NR^1R^2$, —O—$(CH_2)_3 NR^1R^2$, —O—$(CH_2) CONR^1R^2$, —$C_5$-$C_6$heteroaryl, —$COCH=CH$—$(CH_2)_n NR^1R^2$, and T;

T is:

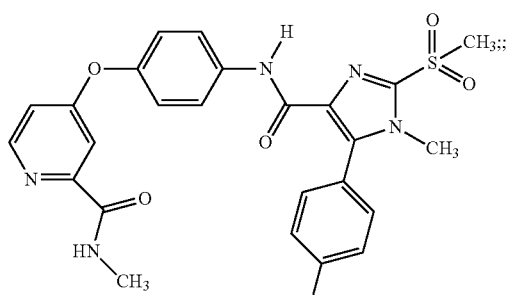

Z is independently selected from —CH—, —CF—, and —N—;

$R_4$ is selected from H, —$CH_3$, —$CH_2CH_3$, cyclopropyl, —F; -$^{18}$F, —Cl, —Br, —$CH_2F$, —$CH_2[18]F$, —$CHF_2$, —$CF_3$, —HC=$CHR^1$, —$CCR^1$; —CN, —$OCF_3$, —$NHR^1$—$OR^1$, and —$S(O)_m R^1$;

$R^{10}$ is hydrogen; and

X is —O—, —$NR^2$—, or —S—.

5. A compound selected from the formulae:

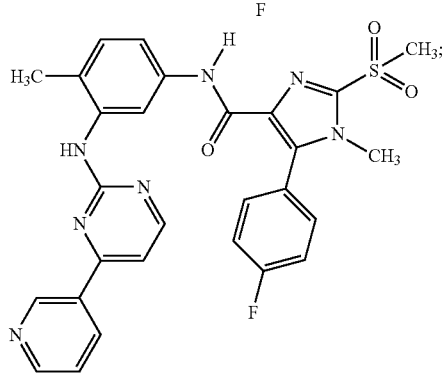

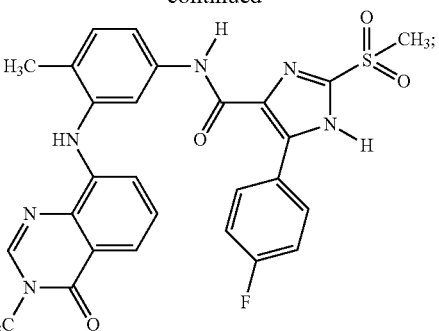

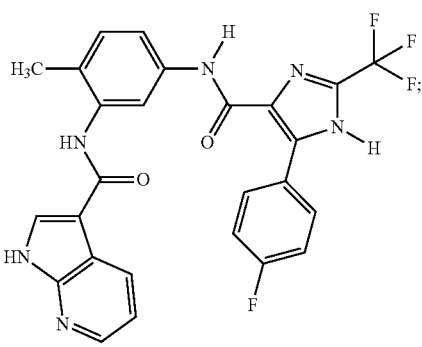

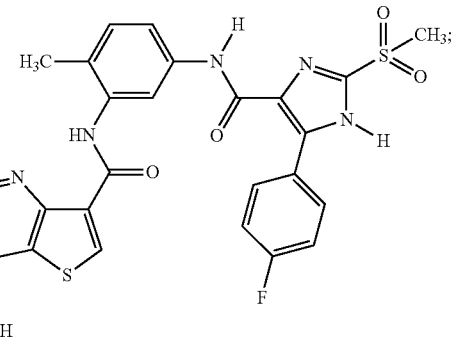

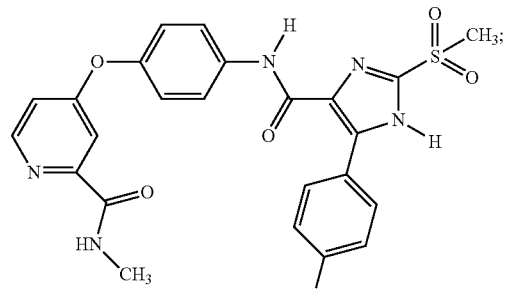

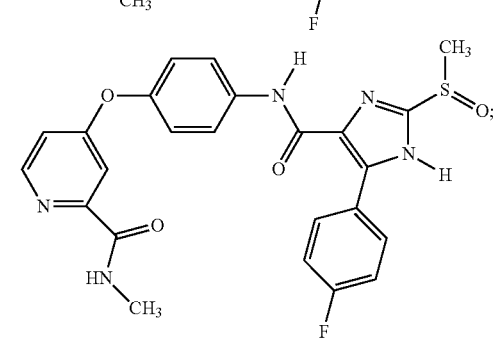

275
-continued
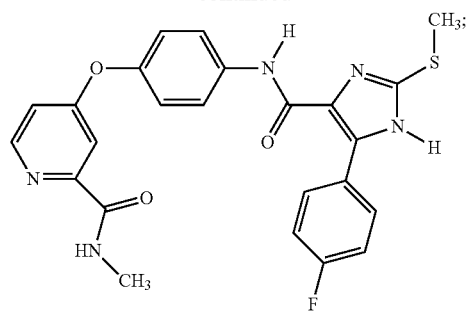
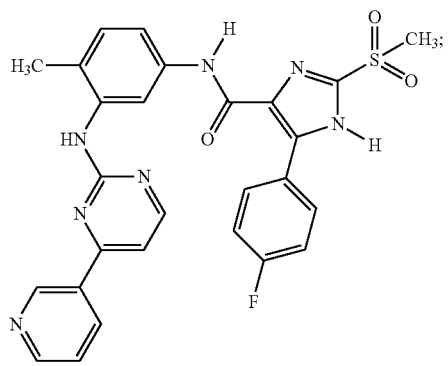
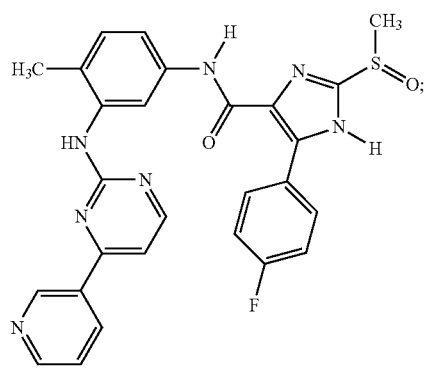
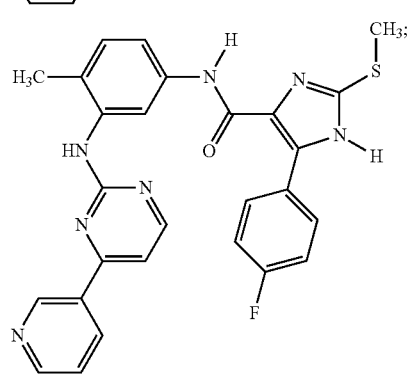
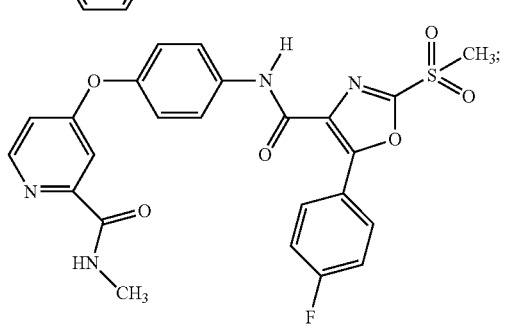
276
-continued
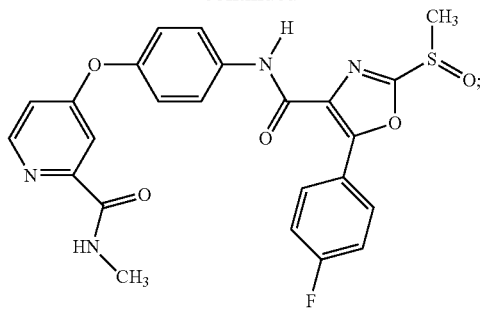
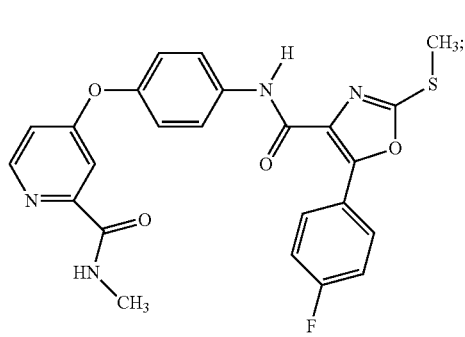
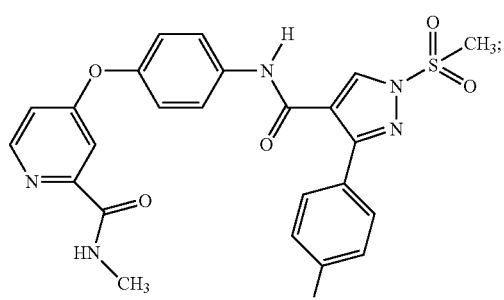
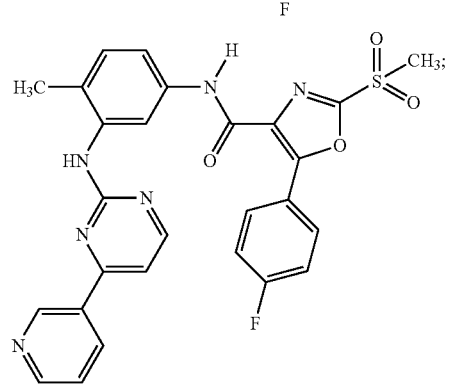
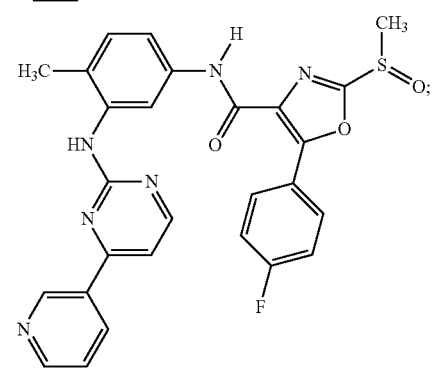

-continued
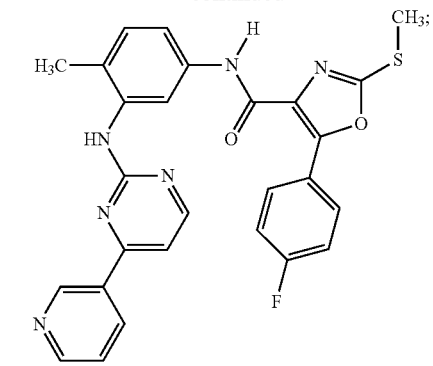
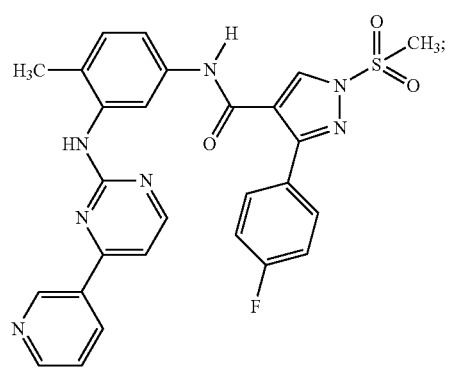
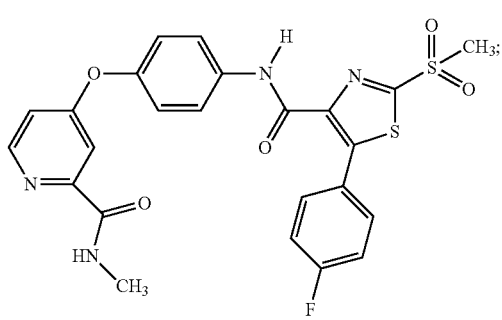
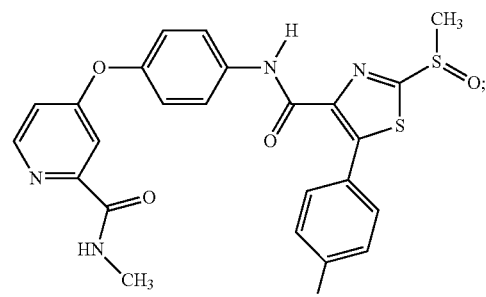
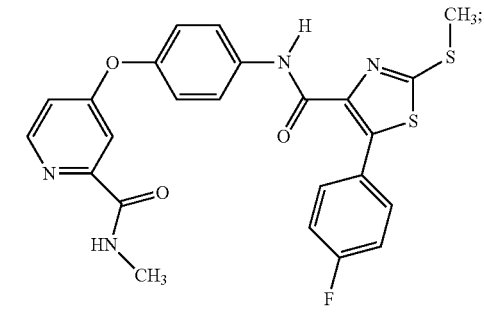
-continued
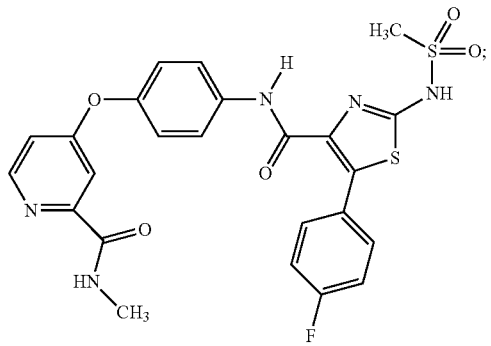
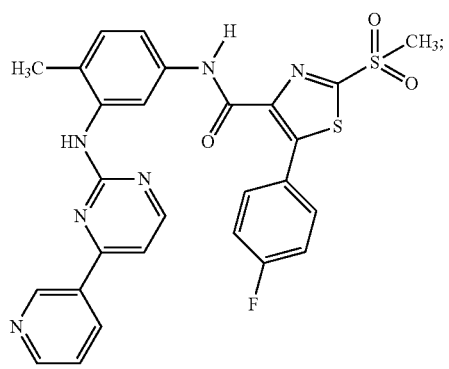
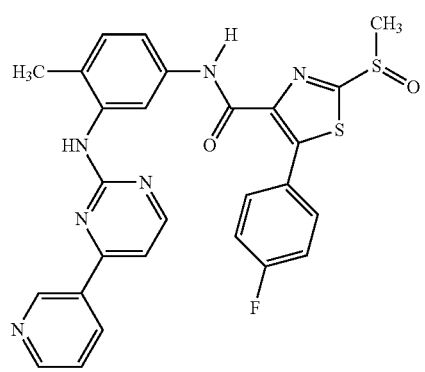
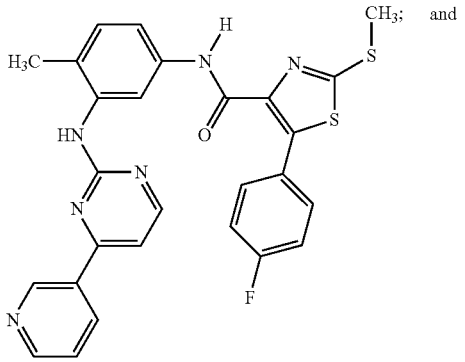

279
-continued
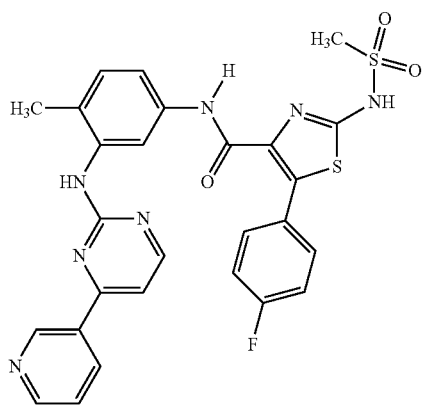
or a pharmaceutically acceptable salt thereof.
6. A compound selected from the formulae:
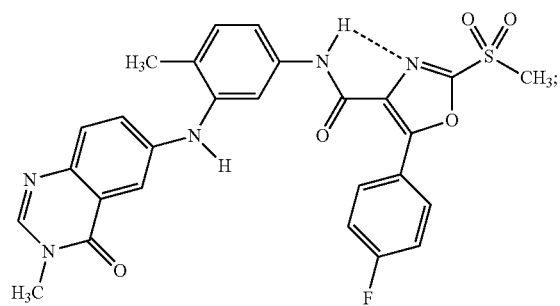
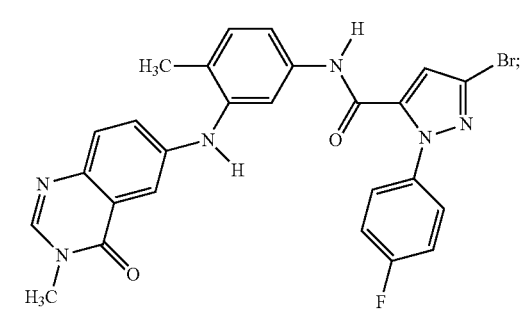
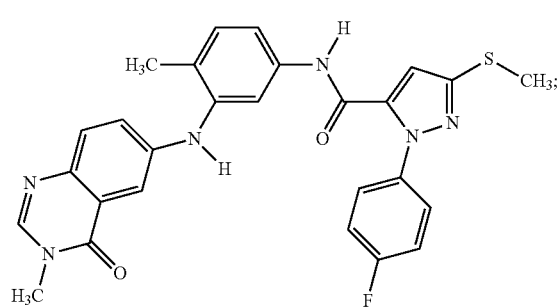
280
-continued
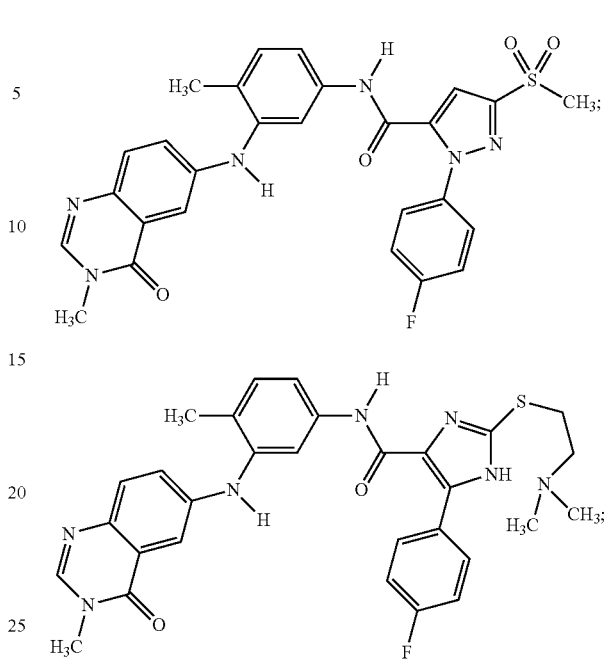
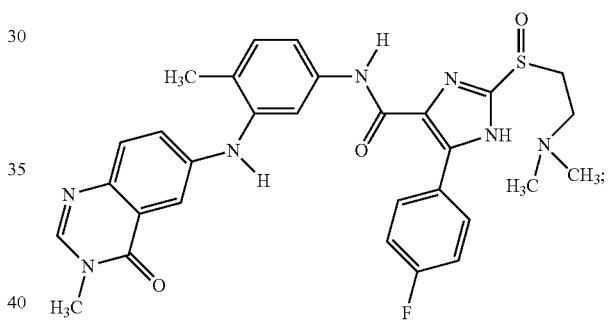
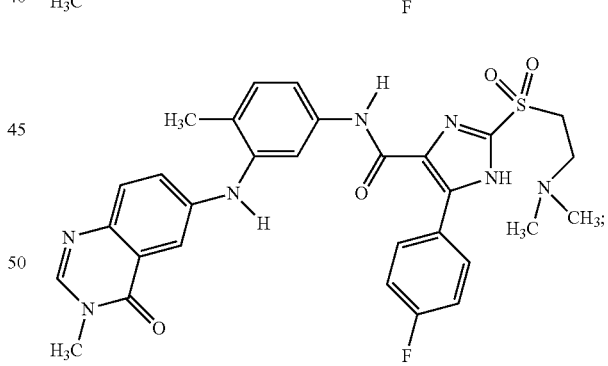
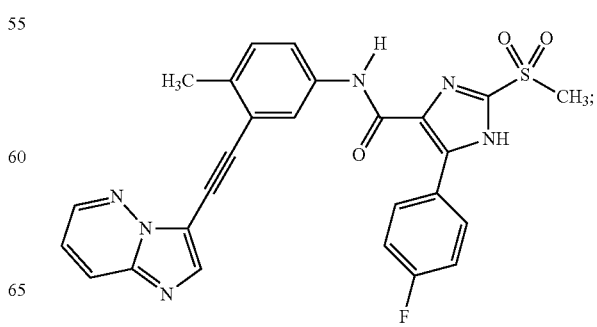

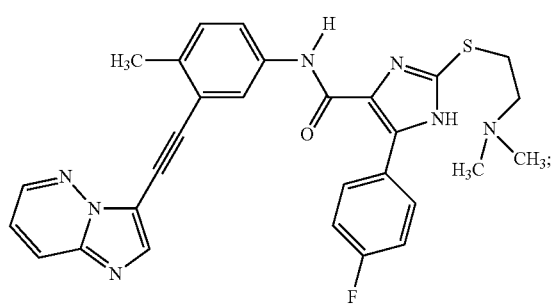

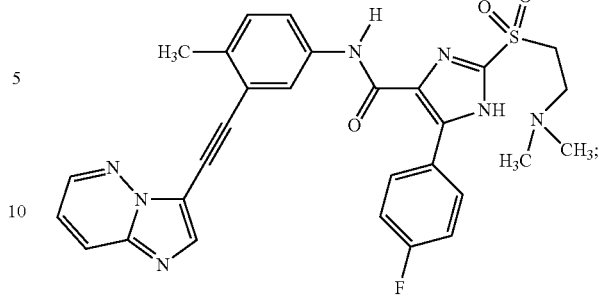

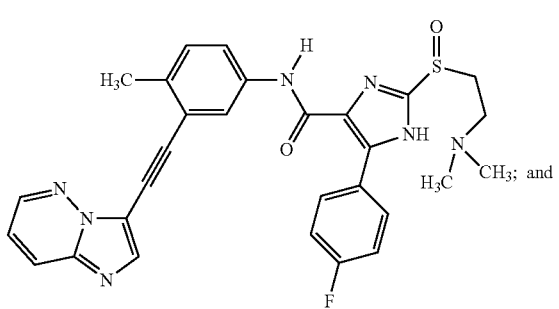

or a pharmaceutically acceptable salt thereof.

7. A pharmaceutical composition comprising a compound of claim 1, or a pharmaceutically acceptable salt thereof, and a pharmaceutically acceptable carrier or diluent.

8. A pharmaceutical composition comprising a compound of claim 3, or a pharmaceutically acceptable salt thereof, and a pharmaceutically acceptable carrier or diluent.

9. A pharmaceutical composition comprising a compound of claim 2, or a pharmaceutically acceptable salt thereof, and a pharmaceutically acceptable carrier or diluent.

10. A pharmaceutical composition comprising a compound of claim 4, or a pharmaceutically acceptable salt thereof, and a pharmaceutically acceptable carrier or diluent.

* * * * *